(12) United States Patent
Slusher et al.

(10) Patent No.: US 11,427,590 B2
(45) Date of Patent: Aug. 30, 2022

(54) SMALL MOLECULE INHIBITORS OF NEUTRAL SPHINGOMYELINASE 2 (NSMASE2) FOR THE TREATMENT OF NEURODEGENERATIVE DISEASES

(71) Applicants: The Johns Hopkins University, Baltimore, MD (US); Institute of Organic Chemistry and Biochemistry AS CR V.V.I., Prague (CZ)

(72) Inventors: Barbara Slusher, Kingsville, MD (US); Camilo Rojas, Baltimore, MD (US); Ajit G. Thomas, Baltimore, MD (US); Radim Nencka, Roztoky (CZ); Michal Sala, Kladno (CZ); Hubert Hrebabecky, Prague (CZ); Norman Haughey, Baltimore, MD (US)

(73) Assignees: The Johns Hopkins University, Baltimore, MD (US); Institute of Organic Chemistry & Biochemistry, Prague (CZ)

( * ) Notice: Subject to any disclaimer, the term of this patent is extended or adjusted under 35 U.S.C. 154(b) by 0 days.

(21) Appl. No.: 16/475,433

(22) PCT Filed: Jan. 5, 2018

(86) PCT No.: PCT/US2018/012699
§ 371 (c)(1),
(2) Date: Jul. 2, 2019

(87) PCT Pub. No.: WO2018/129405
PCT Pub. Date: Jul. 12, 2018

(65) Prior Publication Data
US 2020/0190089 A1    Jun. 18, 2020

Related U.S. Application Data

(60) Provisional application No. 62/443,324, filed on Jan. 16, 2017.

(51) Int. Cl.
*A61P 25/28* (2006.01)
*A61P 25/00* (2006.01)
*A61P 35/00* (2006.01)
*C07D 487/04* (2006.01)

(52) U.S. Cl.
CPC ................ *C07D 487/04* (2013.01)

(58) Field of Classification Search
CPC .......... A61P 25/28; A61P 25/00; A61P 35/00; C07D 487/04
See application file for complete search history.

(56) References Cited

U.S. PATENT DOCUMENTS 9,193,736 B2 * 11/2015 Player ............... A61P 25/00
2008/0045536 A1    2/2008 Vaccaro et al.
2012/0059162 A1    3/2012 Kusakabe et al.
2012/0220581 A1    8/2012 Pastor-Fernandez et al.
2013/0109661 A1*   5/2013 Hermann ........... A61P 25/00
                                                514/233.2
2014/0364413 A1   12/2014 Player et al.
2015/0232472 A1    8/2015 Flohr et al.

FOREIGN PATENT DOCUMENTS

CN      103360399 A      10/2013
WO      WO 2002/066447    8/2002
WO      WO 2015/086501 A1  6/2015

OTHER PUBLICATIONS

Flohr et al., 2014, cap0lus an 2014:790644.*
RN1348425, registry database compound, entry date Dec. 4, 2011.*
CancerPrevention, 2021, https://www.cancerresearchuk.org/about-cancer/causes-of-cancer/can-cancer-be-prevented-0.*
ADPrevention, 20201, https://www.alz.org/alzheimers-dementia/research_progress/prevention.*
Sala et al., 2020, J. Med. Chem., 63 (11), 6028-6056.*
Zhang et al., 2020, Journal of Enzyme Inhibition and Medicinal Chemistry, 35, 1322-1330.*
Claus et al., Inhibition of Sphingomyelin Hydrolysis: Targeting the Lipid Mediator Ceramide as a Key Regulator of Cellular Fate. Curr Med Chem. 2009;16:1978-2000.
Extended EP Search Report for EP 18736683, dated May 25, 2020, 9 pages.
Asai et al., Depletion of microglia and inhibition of exosome synthesis halt tau propagation. Nat Neurosci. Nov. 2015;18(11):1584-93.
Berge et al., Pharmaceutical salts. J Pharm Sci. Jan. 1977;66(1):1-19.
Bowes et al., ,Reducing safety-related drug attrition: the use of in vitro pharmacological profiling. Nat Rev Drug Discov. Dec. 2012;11(12):909-22.
Chemical Abstract compound, STN express. RN 1348425-65-9 (Entered STN: Dec. 4, 2011) see the compound.
Cutler et al., Evidence that accumulation of ceramides and cholesterol esters mediates oxidative stress-induced death of motor neurons in amyotrophic lateral sclerosis. Ann Neurol. Oct. 2002;52(4):448-57.
Dickens et al., Astrocyte-shed extracellular vesicles regulate the peripheral leukocyte response to inflammatory brain lesions. Sci Signal. Apr. 4, 2017;10(473):eaai7696. 28 pages.
Figuera-Losada et al., Cambinol, a novel inhibitor of neutral sphingomyelinase 2 shows neuroprotective properties. PLoS One. May 26, 2015;10(5):e0124481. 18 pages.

(Continued)

*Primary Examiner* — Sun Jae Yoo
(74) *Attorney, Agent, or Firm* — Casimir Jones, S.C.; Jeffrey W. Childers

(57) ABSTRACT

Small molecule inhibitors of neutral sphingomyelinase 2 (nSMase2) and their use for treating neurodegenerative diseases, such as, neurodegenerative diseases associated with high levels of ceramide, including, but not limited to Alzheimer's disease (AD), HIV-associated neurocognitive disorder (HAND), multiple sclerosis (MS), and amyotrophic lateral sclerosis (ALS), and, in other aspects, for treating cancer, are provided.

17 Claims, 8 Drawing Sheets

(56) References Cited

OTHER PUBLICATIONS

Greene, Wuts, Protective Groups in Organic Synthesis, 3rd ed. John Wiley & Sons. 1999. TOC only. 3 pages.

Haughey et al., Perturbation of sphingolipid metabolism and ceramide production in HIV-dementia. Ann Neurol. Feb. 2004;55(2):257-67.

Horres et al., The roles of neutral sphingomyelinases in neurological pathologies. Neurochem Res. Jun. 2012;37(6):1137-49.

Jana et al., Human immunodeficiency virus type 1 gp120 induces apoptosis in human primary neurons through redox-regulated activation of neutral sphingomyelinase. J Neurosci. Oct. 27, 2004;24(43):9531-40.

Jana et al., Ceramide and neurodegeneration: susceptibility of neurons and oligodendrocytes to cell damage and death. J Neurol Sci. Mar. 15, 2009;278(1-2):5-15.

Jana et al., Fibrillar amyloid-beta-activated human astroglia kill primary human neurons via neutral sphingomyelinase: implications for Alzheimer's diseas. J Neurosci. Sep. 22, 2010;30(38):12676-89.

Jana et al., Sphingolipids in multiple sclerosis. Neuromolecular Med. Dec. 2010;12(4):351-61.

Kosaka et al., Neutral sphingomyelinase 2 (nSMase2)-dependent exosomal transfer of angiogenic microRNAs regulate cancer cell metastasis. J Biol Chem. Apr. 12, 2013;288(15):10849-59.

Kull et al., Mixturs of quaternary ammonium compounds and long-chain fatty acids as antifungal agents. Appl Microbiol. Nov. 1961;9(6):538-41.

Luberto et al., Inhibition of tumor necrosis factor-induced cell death in MCF7 by a novel inhibitor of neutral sphingomyelinase. J Biol Chem. Oct. 25, 2002;277(43):41128-39.

McCluskey et al., Inflammatory responses in the rat brain in response to different methods of intra-cerebral administration. J Neuroimmunol. Feb. 2008;194(1-2):27-33.

Mejdrova et al., Highly Selective Phosphatidylinositol 4-Kinase IIIβ Inhibitors and Structural Insight into Their Mode of Action. J Med Chem. May 14, 2015;58(9):3767-93.

Rais et al., Discovery of 6-Diazo-5-oxo-l-norleucine (DON) Prodrugs with Enhanced CSF Delivery in Monkeys: A Potential Treatment for Glioblastoma. J Med Chem. Sep. 22, 2016;59(18):8621-33.

Sala et al., Purine analogs as phosphatidylinositol 4-kinase IIIβ inhibitors. Bioorg Med Chem Lett. Jun. 1, 2016;26(11):2706-12.

Stanovnik et al., Synthesen und Reaktivitat von 2,3,6,7,8-Pentachlorimidazo-[1,2-b]pyridazin und 3,6,7,8-tetrachlor-s-triazolo-[4,3-b]pyridazin. Monatshefte fur Chemie, 1972, vol. 103, No. 6, pp. 1624-1631.

Van Echten-Deckert et al., Sphingolipids: critical players in Alzheimer's disease. Prog Lipid Res. Oct. 2012;51(4):378-93.

International Search Report and Written Opinion for PCT/US2018/012699, dated Apr. 30, 2018. 16 pages.

* cited by examiner

FIG. 4A
FIG. 4B
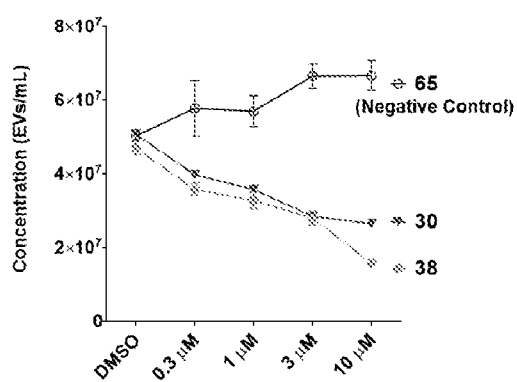
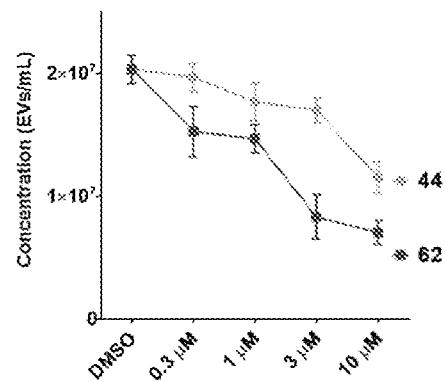
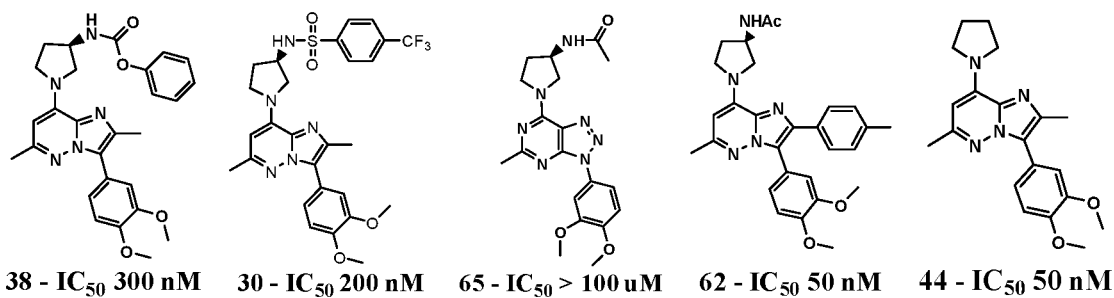
38 - IC$_{50}$ 300 nM    30 - IC$_{50}$ 200 nM    65 - IC$_{50}$ > 100 uM    62 - IC$_{50}$ 50 nM    44 - IC$_{50}$ 50 nM

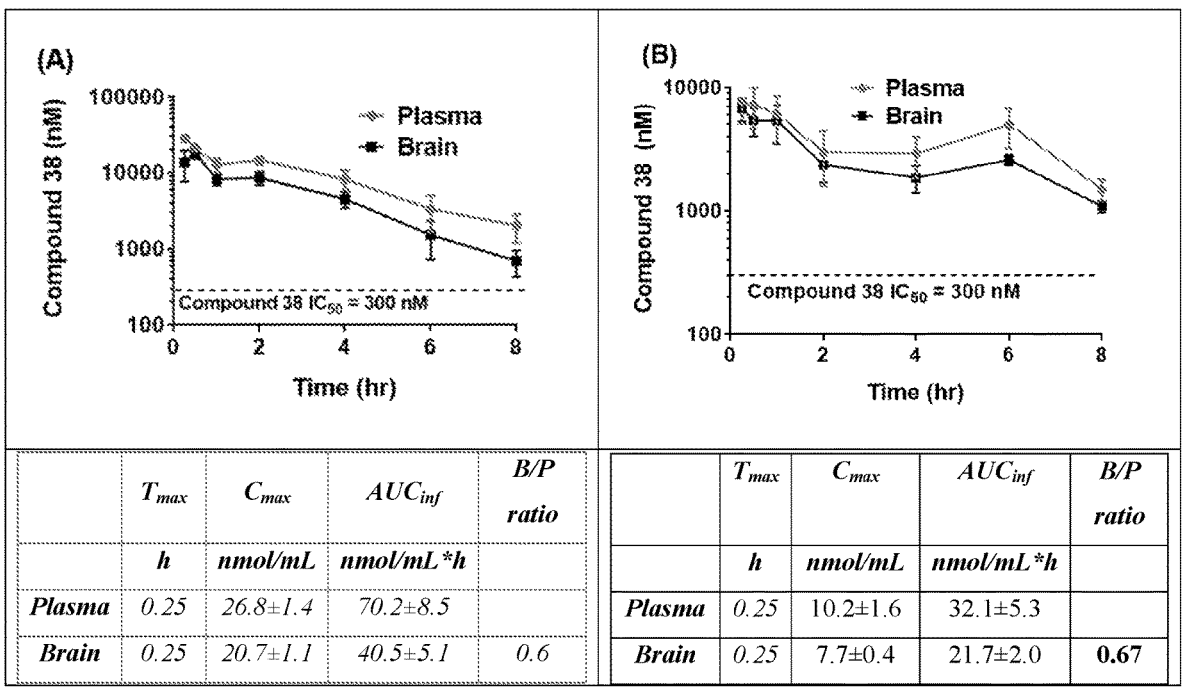
*FIG. 7A*  *FIG. 7B*

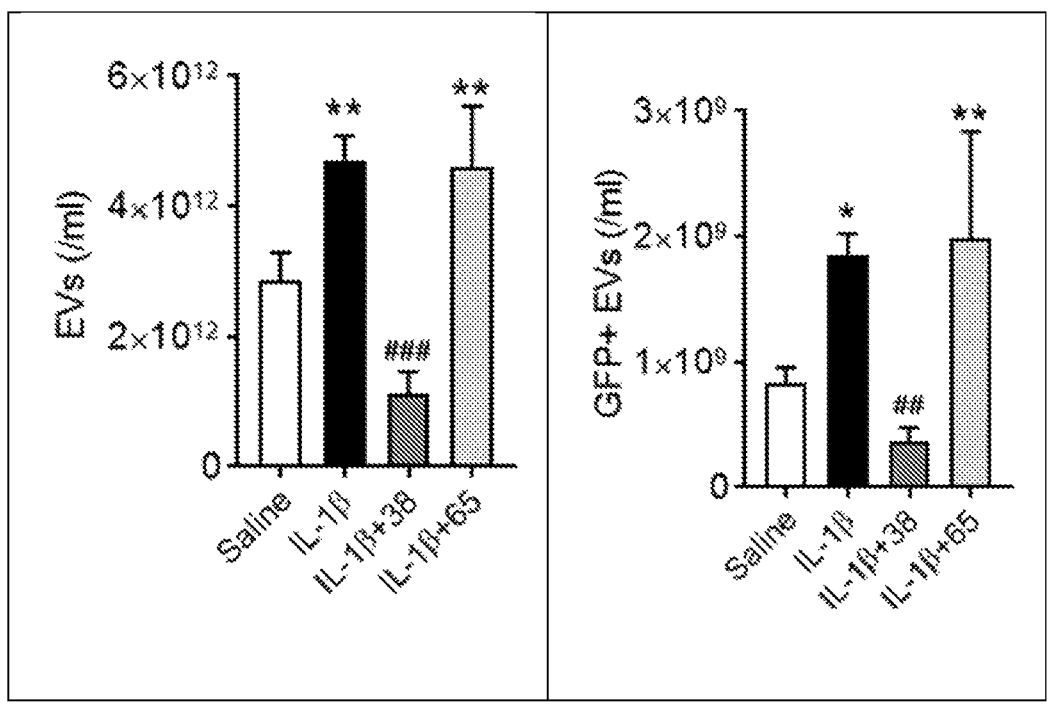
*FIG. 8A*  *FIG. 8B*

SMALL MOLECULE INHIBITORS OF NEUTRAL SPHINGOMYELINASE 2 (NSMASE2) FOR THE TREATMENT OF NEURODEGENERATIVE DISEASES

CROSS-REFERENCE TO RELATED APPLICATION

This application claims the benefit and priority to U.S. Patent Application No. 62/443,324, filed Jan. 6, 2017, the entire content of which is hereby incorporated by reference.

FEDERALLY SPONSORED RESEARCH OR DEVELOPMENT

This invention was made with government support under MH107659 and MH075673, awarded by the National Institutes of Health. The government has certain rights in the invention.

BACKGROUND

Ceramide is a bioactive lipid that plays an important role in stress responses leading to apoptosis, cell growth arrest, and differentiation. Ceramide production is due in part to sphingomyelin hydrolysis by sphingomyelinases. In brain, neutral sphingomyelinase 2 (nSMase2) is expressed in neurons and increases in its activity and expression have been associated with pro-inflammatory conditions observed in patients afflicted with Alzheimer's disease, multiple sclerosis, and human immunodeficiency virus (HIV-1). Increased nSMase2 activity translates into higher ceramide levels and neuronal cell death, which can be prevented by chemical or genetic inhibition of nSMase2 activity or expression.

To date, however, there are no soluble, specific and potent small molecule inhibitor tool compounds for use in vivo studies or as a starting point for medicinal chemistry optimization. Moreover, the majority of the known inhibitors were identified using bacterial, bovine, or rat nSMase2. Thus, until now, there have been no known drug-like inhibitors of human neutral sphingomyelinase 2 (nSMase2). The most widely used inhibitor, i.e., GW4869, was identified from an early screen using rat neutral sphingomyelinase over 14 years ago (J Biol Chem 277, 41128 (2002)). GW4869, however, exhibits poor solubility and consequently has very limited ability to serve as pharmacological tool or as starting point for clinical development.

SUMMARY

The presently disclosed subject matter provides small molecule inhibitors of neutral sphingomyelinase 2 (nSMase2) and their use, in some aspects, for treating neurodegenerative diseases, such as, neurodegenerative diseases associated with high levels of ceramide, including, but not limited to Alzheimer's disease (AD), HIV-associated neurocognitive disorder (HAND), multiple sclerosis (MS), and amyotrophic lateral sclerosis (ALS), and, in other aspects, for treating cancer.

Accordingly, in some aspects, the presently disclosed subject matter provides a compound of formula (I):

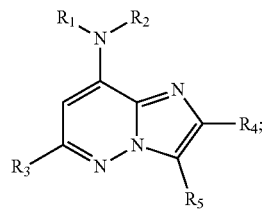

wherein:
$R_1$ and $R_2$ are each independently selected from substituted or unsubstituted alkyl or together with the nitrogen atom to which they are bound form a substituted or unsubstituted 5- or 6-membered heterocyclic ring;

$R_3$ is selected from the group consisting of H, substituted or unsubstituted alkyl, substituted or unsubstituted alkoxyl, substituted or unsubstituted thioalkyl, substituted or unsubstituted aryl, and halogen;

$R_4$ is selected from the group consisting of H, substituted or unsubstituted alkyl, and substituted or unsubstituted aryl;

$R_5$ is selected from the group consisting of H, halogen, substituted or unsubstituted alkyl, substituted or unsubstituted aryl, substituted or unsubstituted heteroaryl, and a substituted or unsubstituted multicyclic aryl or multicyclic heteroaryl ring;

under the proviso that if $R_1$ and $R_2$ together with the nitrogen atom to which they are bound are pyridinyl or morpholinyl, then $R_5$ cannot be H, halogen, or substituted or unsubstituted heteroaryl; and pharmaceutically acceptable salts thereof.

In particular aspects, the compound of formula (I) is:

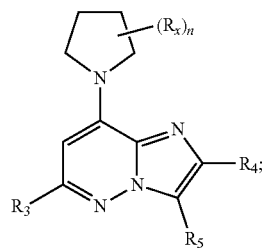

wherein:
n is an integer selected from the group consisting of 0, 1, 2, 3, 4, 5, 6, 7, and 8;

$R_x$ is selected from the group consisting of halogen, hydroxyl, substituted or unsubstituted alkoxyl, substituted or unsubstituted thioalkyl, cyano, amino, —$N_3$, substituted or unsubstituted aryl, substituted or unsubstituted cycloheteroalkyl, substituted or unsubstituted heteroaryl, —X—(C=O)—$C_{1-6}$ alkyl, wherein X is O or S, and —$NR_6R_7$, wherein $R_6$ is selected from the group consisting of H or substituted or unsubstituted $C_{1-6}$ alkyl; and $R_7$ is selected from the group consisting of —C(=O)—$(CR_yR_z)_m$—$R_8$, —C(=O)—$(CR_yR_z)_m$—O—$R_8$, —C(=O)—O—$(CR_yR_z)_m$—$R_8$, and —S(=O)$_2$—$R_9$, wherein each m is an integer selected from the group consisting of 0, 1, 2, 3, 4, 5, and 6, $R_y$ and $R_z$ are each independently H, alkoxyl, or halogen, $R_8$ and $R_9$ are each independently selected from the group consisting of substituted or unsubstituted alkyl, —$CF_3$, substituted or unsubstituted cycloalkyl, substituted or unsubstituted aryl, substituted or unsubstituted cycloheteroaryl, substituted or unsubstituted multicyclic aryl or heteroaryl ring, and $NR_{10}R_{11}$, wherein $R_{10}$ and $R_{11}$ are each independently selected from the group consisting of H, substituted or unsubstituted $C_{1-6}$ alkyl, and substituted or unsubstituted aryl.

In more particular aspects, the compound of formula (I) is:

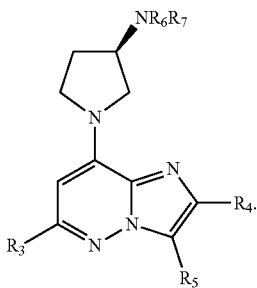

In yet more particular aspects, the compound of formula (I) is:

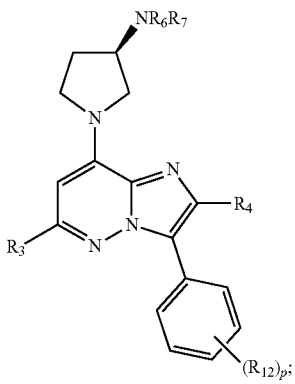

wherein:

p is an integer selected from the group consisting of 0, 1, 2, 3, 4, and 5;

each $R_{12}$ is independently selected from the group consisting of substituted or unsubstituted alkyl, hydroxyl, alkoxyl, halogen, cyano, amino, —$CF_3$, —O—$CF_3$, substituted or unsubstituted cycloheteroakyl, —$NR_{13}(C=O)R_{14}$, —S(=O)$_2$—$R_{15}$, —S(=O)$_2$—$NR_{15}R_{16}$, —$SR_{16}$, —C(=O)—$R_{17}$, —C(=O)—O—$R_{18}$, and —C(=O)—$NR_{19}R_{20}$, wherein $R_{13}$ is selected from the group consisting of H or substituted or unsubstituted $C_{1-6}$ alkyl, $R_{14}$ is substituted or unsubstituted $C_{1-6}$ alkyl or —O—$R_{21}$, and $R_{15}$, $R_{16}$, $R_{17}$, $R_{18}$, $R_{19}$, $R_{20}$, $R_{21}$ are each independently H or substituted or unsubstituted $C_{1-6}$ alkyl.

In other aspects, the presently disclosed subject matter provides a method for treating a condition, disease, or disorder associated with an increased neutral sphingomyelinase 2 (nSMase2) activity or expression, the method comprising administering to a subject in need of treatment thereof an effective amount of an nSMase2 inhibitor of formula (I).

In certain aspects, the condition, disease, or disorder comprises a neurodegenerative disease. In particular aspects, the neurodegenerative disease is selected from the group consisting of Alzheimer's disease (AD), HIV-associated neurocognitive disorder (HAND), multiple sclerosis (MS), and amyotrophic lateral sclerosis (ALS). In other aspects, the condition, disease, or disorder is a cancer.

In yet other aspects, the presently disclosed subject matter provides a method for inhibiting neutral sphingomyelinase 2 (nSMase2), the method comprising administering to a subject, cell, or tissue an amount of a compound of formula (I) effective to inhibit nSMase2.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1:
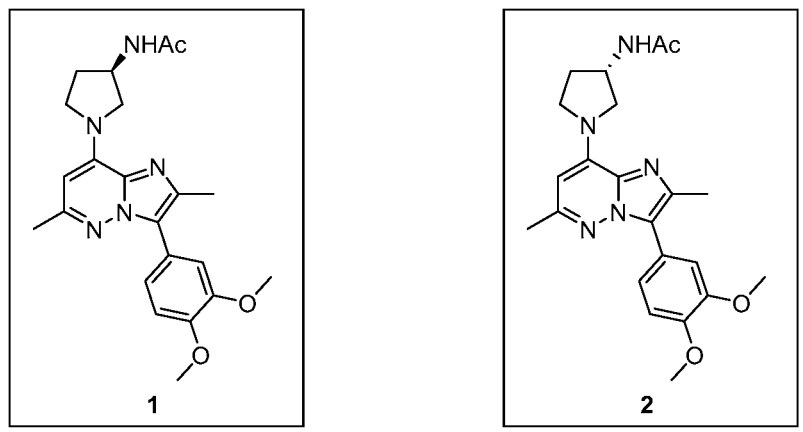
Figure 2:
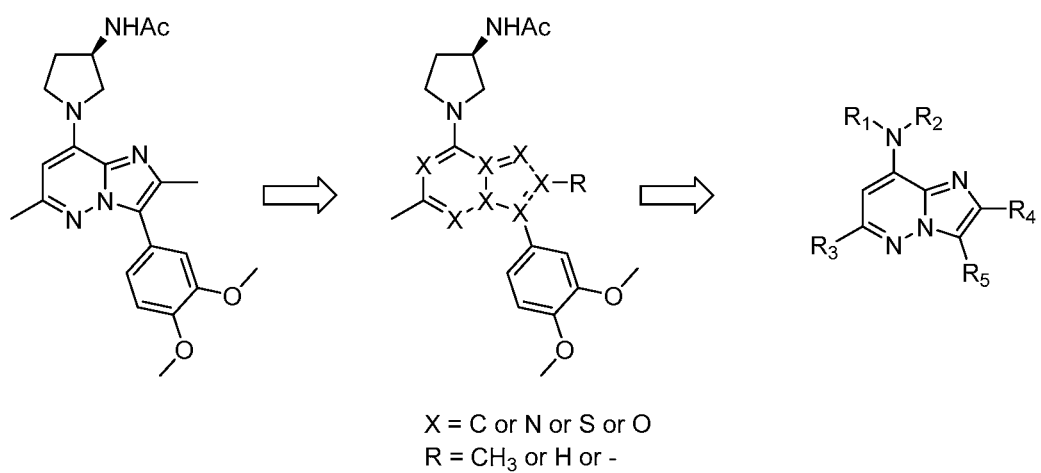
Figure 3A:
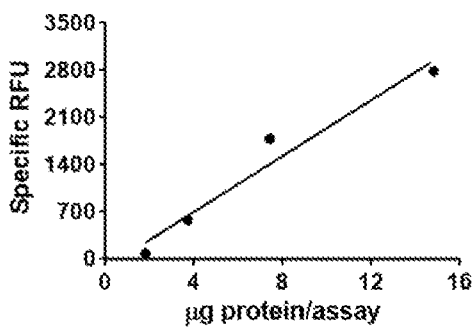
Figure 3B:
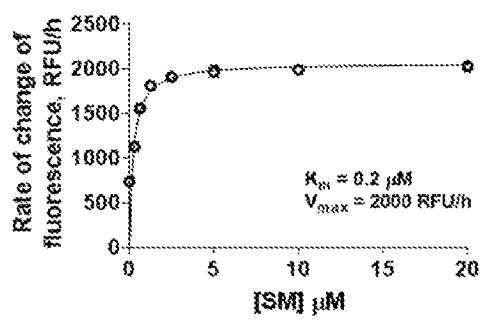
Figure 3C:
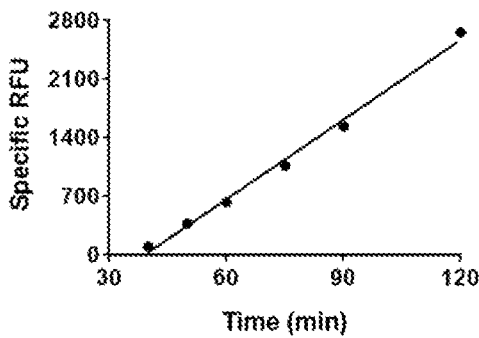
Figure 5:
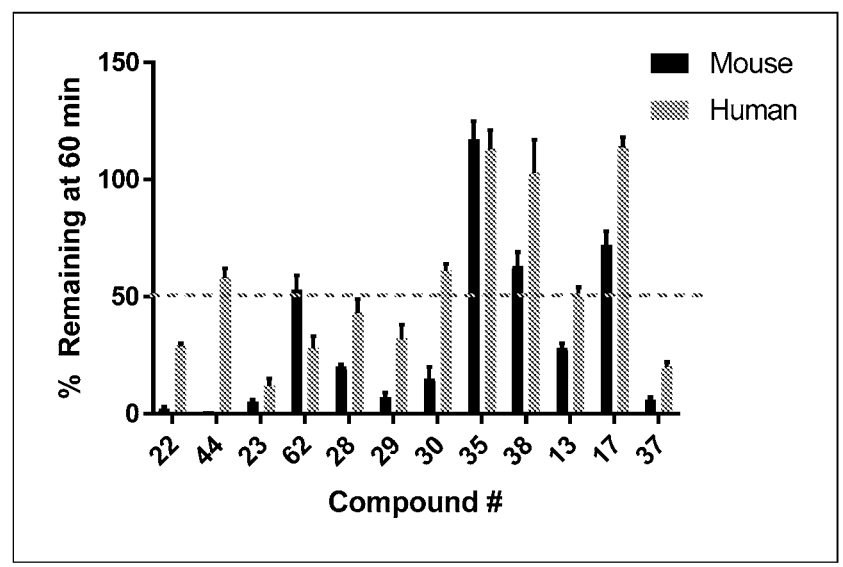
Figure 6:
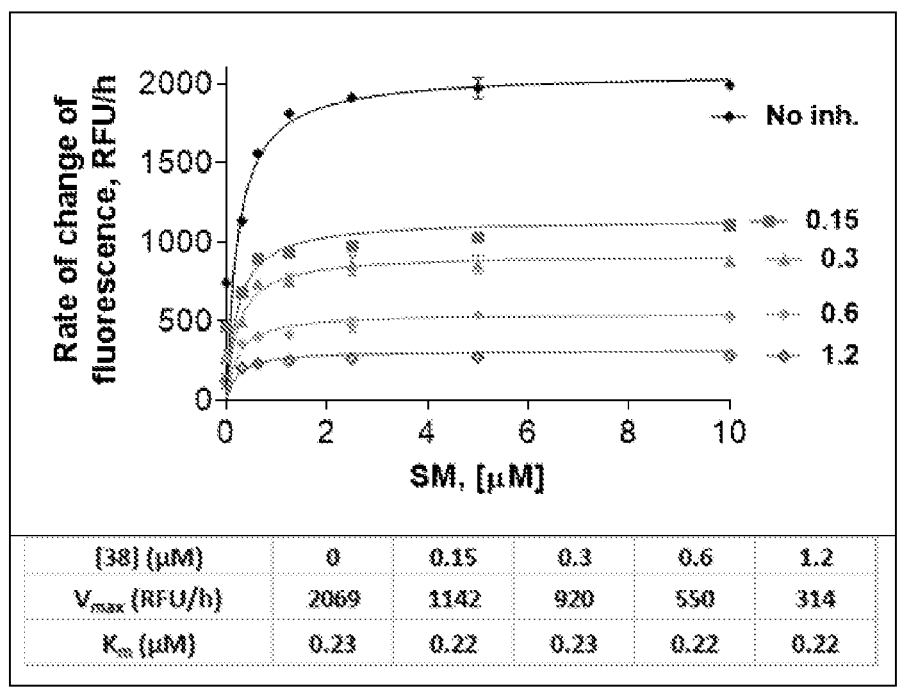

Having thus described the presently disclosed subject matter in general terms, reference will now be made to the accompanying Figures, which are not necessarily drawn to scale, and wherein:

FIG. 1 shows two compounds, 1 (I35MCK380) and 2 (I35MCK388), identified in an unbiased screening of the Institute of Organic Chemistry and Biochemistry (IOCB) compound library against human neutral sphingomyelinase 2 (hnSMase2);

FIG. 2 shows an imidazo[1,2-b]pyridazine scaffold from which modification of various positions on the imidazo[1,2-b]pyridazine core was carried out to obtain a library of potential inhibitors of hnSMase2;

FIG. 3A, FIG. 3B, and FIG. 3C show the characterization of fluorescence-based activity assay using human nSMase2;

FIG. 4A and FIG. 4B show the inhibition of exosome release in vitro by compounds 38, 30 and 65 (upper row, left panel, FIG. 4A) and 44 and 62 (upper row, right panel, FIG. 4B);

FIG. 5 shows the Phase I metabolic stability of selected nSMase2 inhibitors;

FIG. 6 shows the mechanism of inhibition of compound 38;

FIG. 7A and FIG. 7B show pharmacokinetics of compound 38 following 10 mg/kg i.p. (FIG. 7A) and 10 mg/kg peroral (FIG. 7B) administrations in mice; and FIG. 8 shows the inhibition of exosome release in vivo by compound 38.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Small Molecule Inhibitors of Neutral Sphingomyelinase 2 (nSMase2) for the Treatment of Neurodegenerative Diseases Unbiased screening of the chemical library from the Institute of Organic Chemistry and Biochemistry (IOCB) using a newly developed human neutral sphingomyelinase assay identified previously undisclosed I35MCK380 and I35MCK388 as potent inhibitors of nSMase2 ($IC_{50}=1$ μM). Subsequent structure-activity relationship (SAR) studies provided additional novel analogues with submicromolar potencies and improved solubility over known inhibitors and lead to an understanding of the chemical features necessary for neutral sphingomyelinase 2 inhibition. As there are no known potent and drug-like nSMase 2 inhibitors identified to date, these inhibitors could serve as critical tool compounds for the field and/or to be developed clinically.

Accordingly, in some embodiments, the presently disclosed subject matter provides small molecule inhibitors of neutral sphingomyelinase 2 (nSMase2) for the treatment of neurodegenerative diseases, such as, neurodegenerative diseases associated with high levels of ceramide, including, but not limited to, Alzheimer's disease (AD), multiple sclerosis (MS), amyotrophic lateral sclerosis (ALS) and HIV-associated neurocognitive disorders (HAND). The presently disclosed nSMase2 inhibitors also could be used for the treatment of cancer.

A. Representative Compounds of Formula (I)

In some embodiments, the presently disclosed subject matter provides a compound of formula (I):

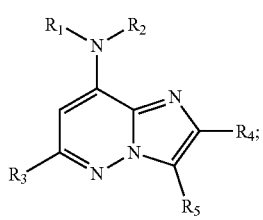

(I)

wherein:

$R_1$ and $R_2$ are each independently selected from substituted or unsubstituted alkyl or together with the nitrogen atom to which they are bound form a substituted or unsubstituted 5- or 6-membered heterocyclic ring;

$R_3$ is selected from the group consisting of H, substituted or unsubstituted alkyl, substituted or unsubstituted alkoxyl, substituted or unsubstituted thioalkyl, substituted or unsubstituted aryl, and halogen;

$R_4$ is selected from the group consisting of H, substituted or unsubstituted alkyl, and substituted or unsubstituted aryl;

$R_5$ is selected from the group consisting of H, halogen, substituted or unsubstituted alkyl, substituted or unsubstituted aryl, substituted or unsubstituted heteroaryl, and a substituted or unsubstituted multicyclic aryl or multicyclic heteroaryl ring;

under the proviso that if $R_1$ and $R_2$ together with the nitrogen atom to which they are bound are pyridinyl or morpholinyl, then $R_5$ cannot be H, halogen, or substituted or unsubstituted heteroaryl; and pharmaceutically acceptable salts thereof.

One of ordinary skill in the art upon review of the presently disclosed subject matter would appreciate that compounds disclosed in U.S. patent application publication no. US20120220581A1 for Imidazo[1,2-b]pyridazine Derivatives and their use as PDE10 Inhibitors, to Pastor-Fernandez, published Aug. 30, 2012, are not included in the presently disclosed compounds.

In particular embodiments, the substituted alkyl or unsubstituted alkyl represented by $R_1$, $R_2$, $R_3$, $R_4$, and $R_5$ of formula (I) can be a $C_1$, $C_2$, $C_3$, $C_4$, $C_5$, $C_6$, $C_7$, or $C_8$ linear or branched alkyl, in some embodiments, $C_{1-4}$ substituted or unsubstituted alkyl, in some embodiments, $C_{1-6}$ substituted or unsubstituted alkyl, in some embodiments, $C_{1-8}$ alkyl substituted or unsubstituted alkyl, including, but not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, and the like, each of which can include one or more substitutents. Representative substituent groups include, but are not limited to, alkyl, substituted alkyl, halogen, aryl, substituted aryl, alkoxyl, hydroxyl, nitro, amino, alkylamino, dialkylamino, sulfate, cyano, mercapto, and alkylthio.

In further embodiments, the 5- to 6-membered heterocyclic ring formed from $R_1$ and $R_2$ together with the nitrogen to which they are bound includes, but is not limited to, pyrrolidinyl, imidazolidinyl, imidazolinyl, pyrazolidinyl, pyrazolinyl, piperidinyl, piperazinyl, indolinyl, 3-pyrrolinyl, morpholinyl, and the like.

In certain embodiments, the substituted or unsubstituted alkyl, substituted or unsubstituted aryl, substituted or unsubstituted heteroaryl, and a substituted or unsubstituted multicyclic aryl or multicyclic heteroaryl ring represented by $R_5$ of formula (I) includes phenyl, thiophen-2-yl, furanyl, thiazolyl, pyridinyl, indolyl, benzo[d][1,3]dioxolyl, and the like.

In some embodiments, the compound of formula (I) is:

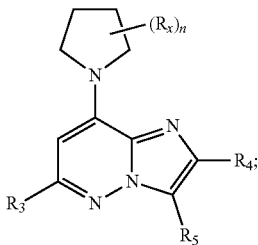

wherein:

n is an integer selected from the group consisting of 0, 1, 2, 3, 4, 5, 6, 7, and 8;

$R_x$ is selected from the group consisting of halogen, hydroxyl, alkoxyl, thioalkyl, cyano, amino, —$N_3$, substituted or unsubstituted aryl, substituted or unsubstituted cycloheteroalkyl, substituted or unsubstituted heteroaryl, —X—C(=O)—$C_{1-6}$ alkyl, wherein X is O or S, and —$NR_6R_7$, wherein $R_6$ is selected from the group consisting of H or substituted or unsubstituted $C_{1-6}$ alkyl; and $R_7$ is selected from the group consisting of —C(=O)—$(CR_yR_z)_m$—$R_8$, —C(=O)—$(CR_yR_z)_m$—O—$R_8$, —C(=O)—O—$(CR_yR_z)_m$—$R_8$, and —S(=O)$_2$—$R_9$, wherein each m is an integer selected from the group consisting of 0, 1, 2, 3, 4, 5, and 6, $R_y$ and $R_z$ are each independently H, alkoxyl, or halogen, $R_8$ and $R_9$ are each independently selected from the group consisting of substituted or unsubstituted alkyl, —$CF_3$, substituted or unsubstituted cycloalkyl, substituted or unsubstituted aryl, substituted or unsubstituted cycloheteroaryl, substituted or unsubstituted multicyclic aryl or heteroaryl ring, and NR$_{10}$R$_{11}$, wherein R$_{10}$ and R$_{11}$ are each independently selected from the group consisting of H, substituted or unsubstituted C$_{1-6}$ alkyl, and substituted or unsubstituted aryl.

In particular embodiments, the compound of formula (I) is:

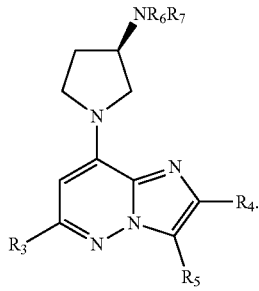

In yet more particular embodiments, the compound of formula (I) is:

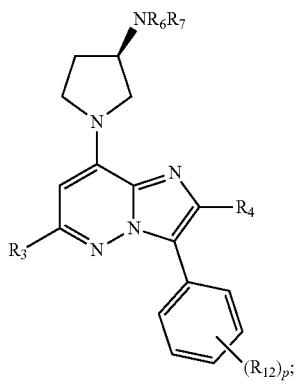

wherein:

p is an integer selected from the group consisting of 0, 1, 2, 3, 4, and 5;

each R$_{12}$ is independently selected from the group consisting of substituted or unsubstituted alkyl, hydroxyl, alkoxyl, halogen, cyano, amino, —CF$_3$, —O—CF$_3$, substituted or unsubstituted cycloheteroaklyl, —NR$_{13}$(C═O)R$_{14}$, —S(═O)$_2$—R$_{15}$, —S(═O)$_2$—NR$_{15}$R$_{16}$, —SR$_{16}$, —C(═O)—R$_{17}$, —C(═O)—O—R$_{18}$, and —C(═O)—NR$_{19}$R$_{20}$, wherein R$_{13}$ is selected from the group consisting of H or substituted or unsubstituted C$_{1-6}$ alkyl, R$_{14}$ is substituted or unsubstituted C$_{1-6}$ alkyl or —O—R$_{21}$, and R$_{15}$, R$_{16}$, R$_{17}$, R$_{18}$, R$_{19}$, R$_{20}$, R$_{21}$ are each independently H or substituted or unsubstituted C$_{1-6}$ alkyl.

In certain embodiments, R$_6$ is H and R$_7$ is —C(═O)—(CR$_y$R$_z$)$_m$—R$_8$, wherein m is 0 and R$_8$ is C$_{1-6}$ alkyl. In particular embodiments, the compound of formula (I) is selected from the group consisting of:

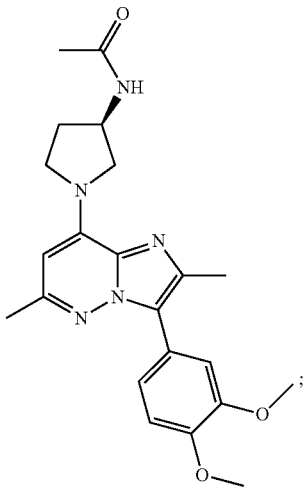

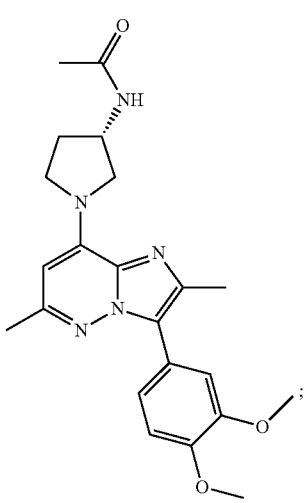

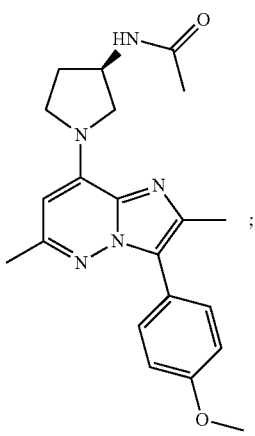

-continued
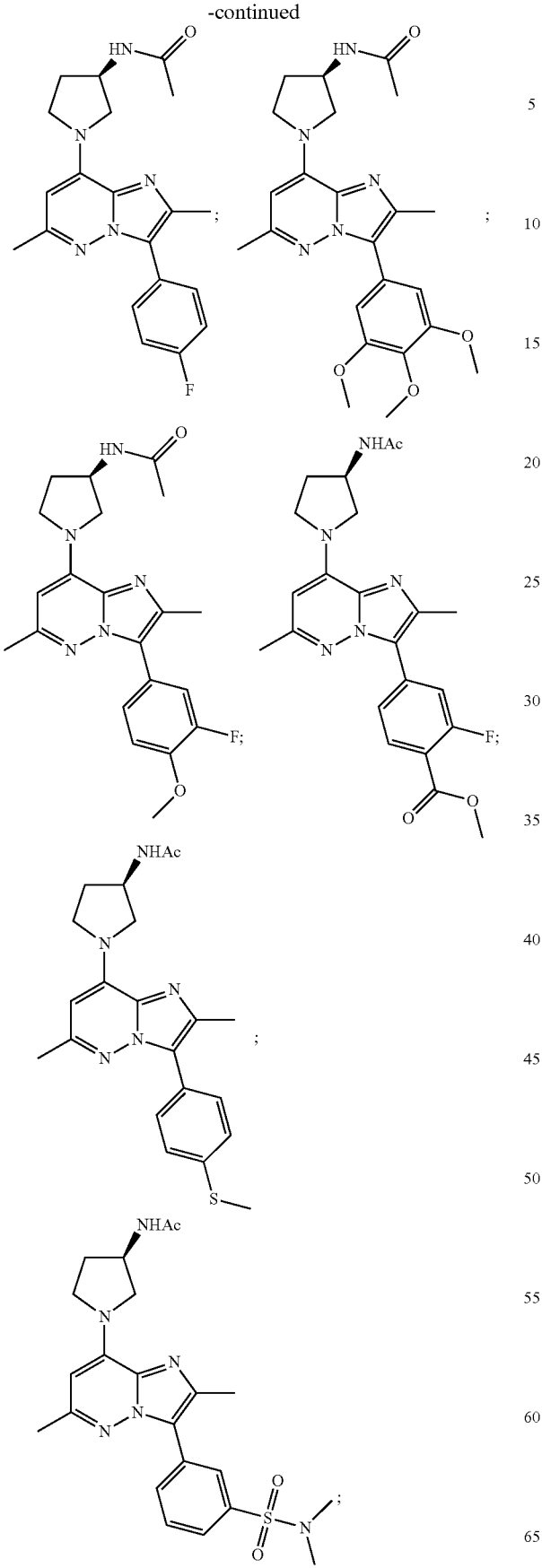
-continued
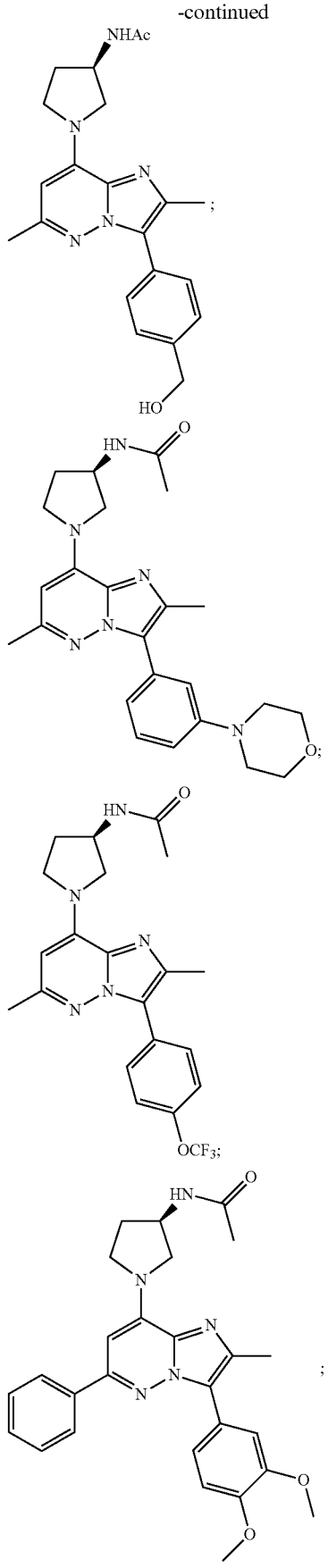

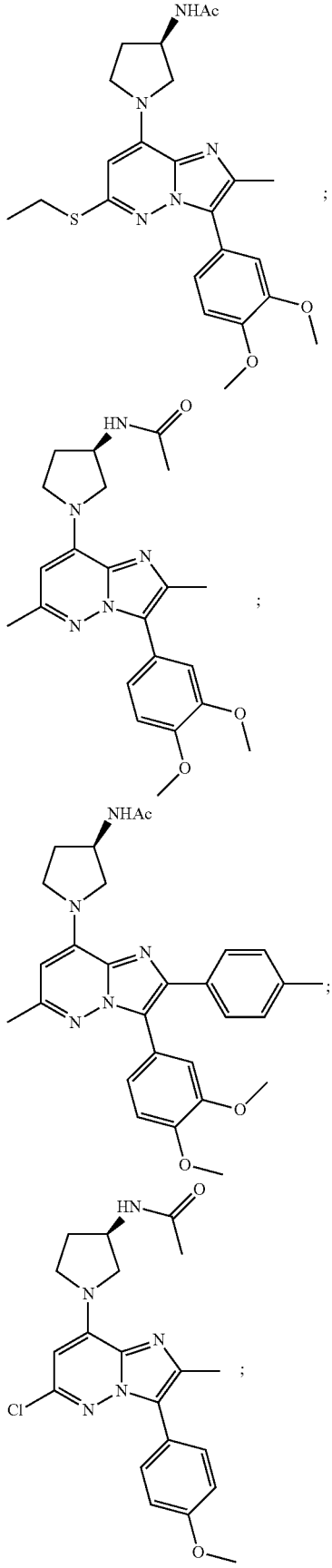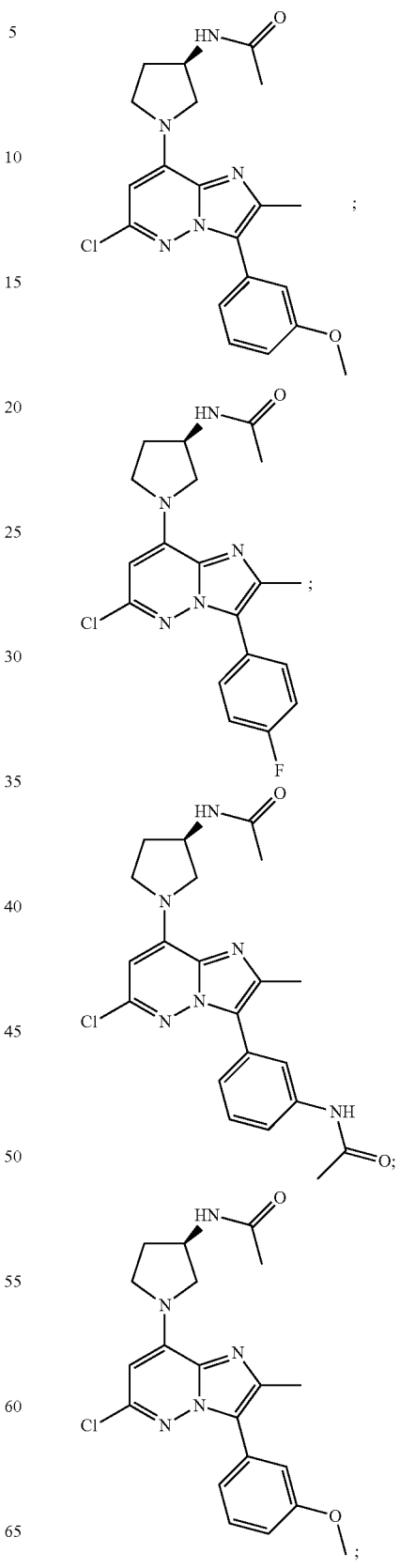

-continued

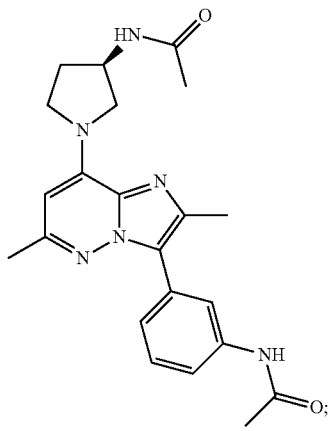

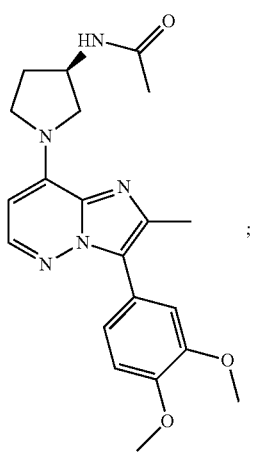

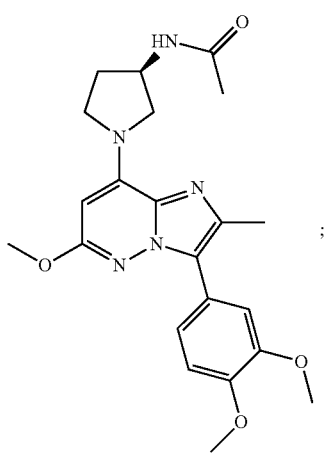

-continued

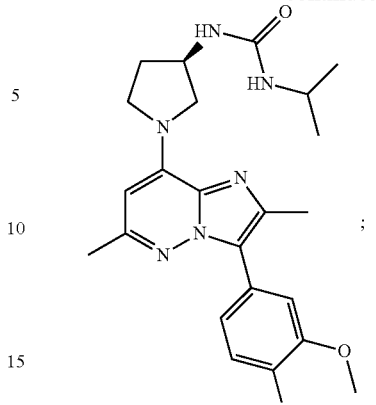

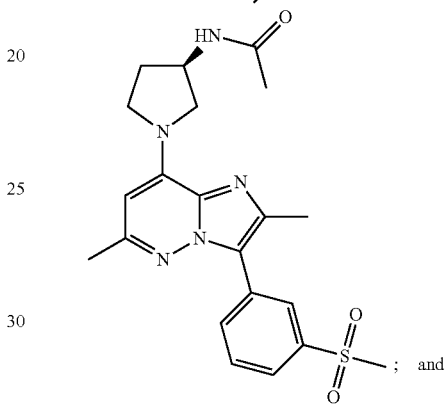

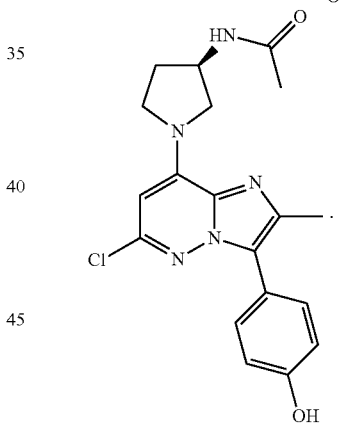

In certain embodiments, $R_6$ is H and $R_7$ is selected from the group consisting of —C(=O)—(CR$_y$R$_z$)$_m$—R$_8$, —C(=O)—(CR$_y$R$_z$)$_m$—O—R$_8$, —C(=O)—O—(CR$_y$R$_z$)$_m$—R$_8$, wherein each m is an integer selected from the group consisting of 0, 1, 2, 3, 4, 5, and 6, $R_y$ and $R_z$ are each independently H, alkoxyl, or halogen, $R_8$ is selected from the group consisting of substituted or unsubstituted alkyl, —CF$_3$, substituted or unsubstituted cycloalkyl, substituted or unsubstituted aryl, substituted or unsubstituted cycloheteroaryl, substituted or unsubstituted multicyclic aryl or heteroaryl ring, and NR$_{10}$R$_{11}$, wherein R$_{10}$ and R$_{11}$ are each independently selected from the group consisting of H, substituted or unsubstituted C$_{1-6}$ alkyl, and substituted or unsubstituted aryl. In particular embodiments, the compound of formula (I) is selected from the group consisting of:

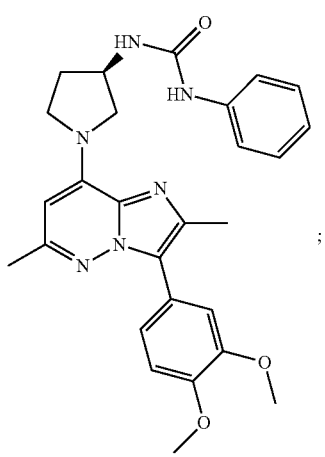
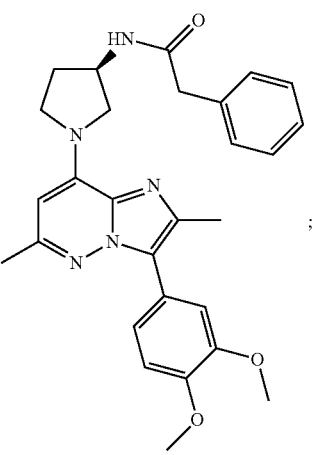
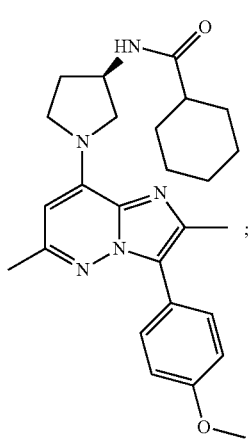
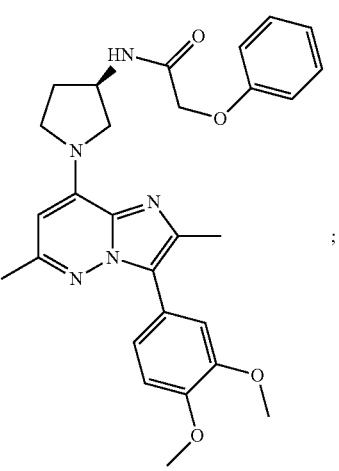
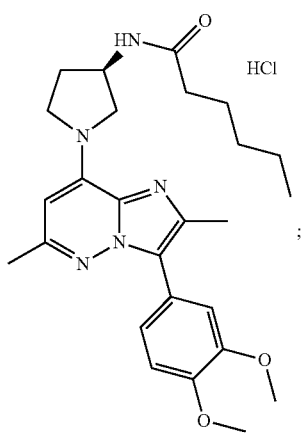
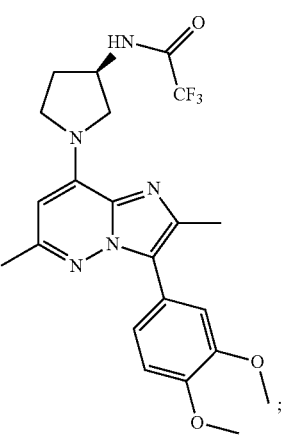

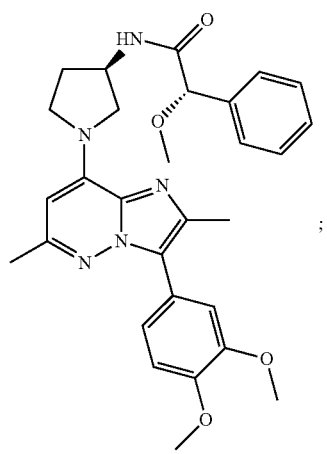
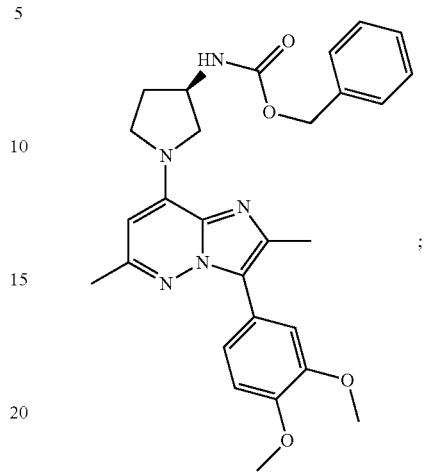
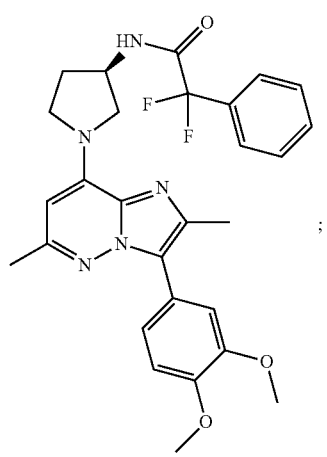
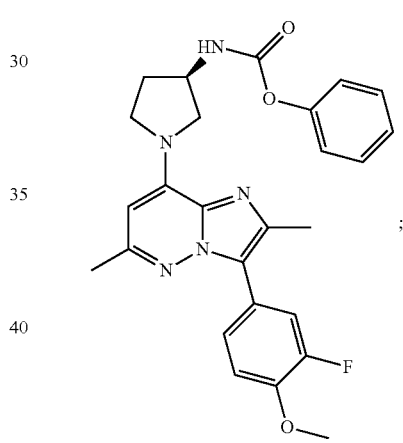
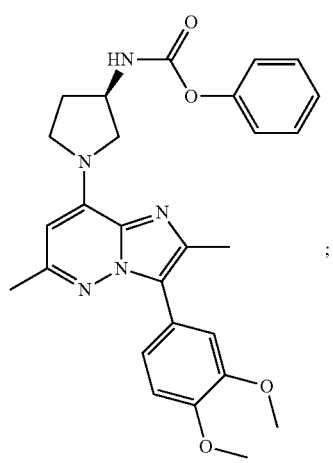
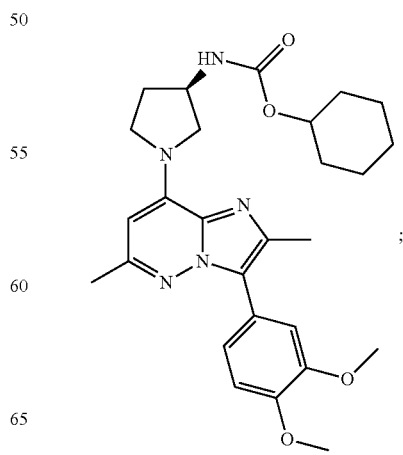

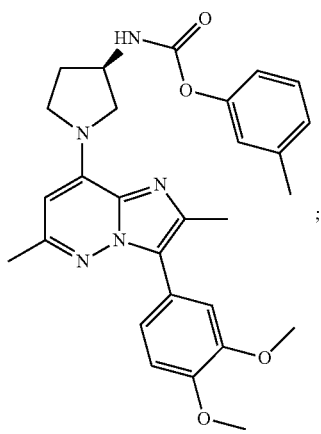
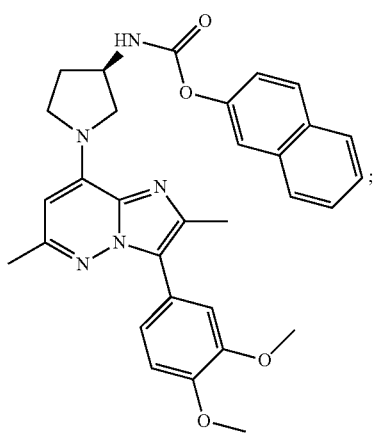
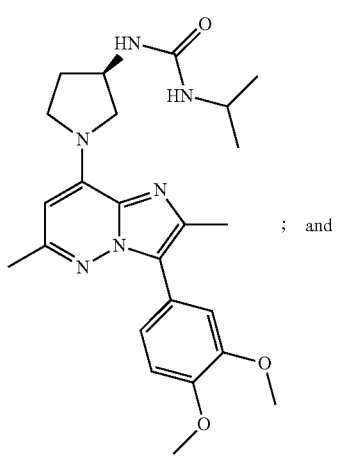
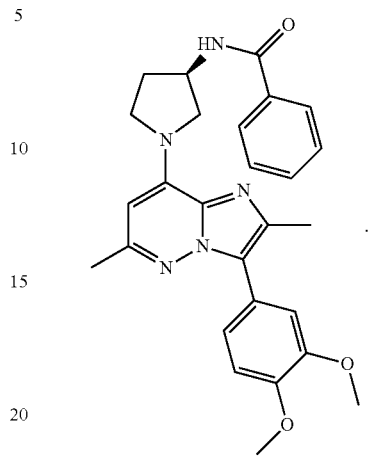
In certain embodiments, R$_6$ is H and R$_7$ is —S(=O)$_2$—R$_9$. In particular embodiments, the compound of formula (I) is selected from the group consisting of:
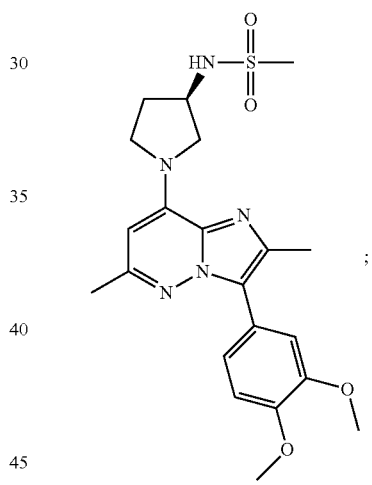
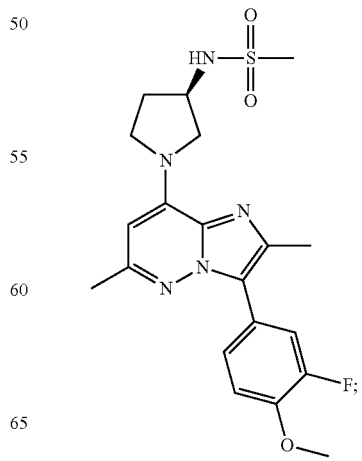

-continued
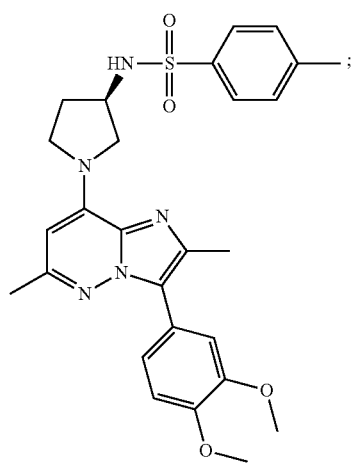
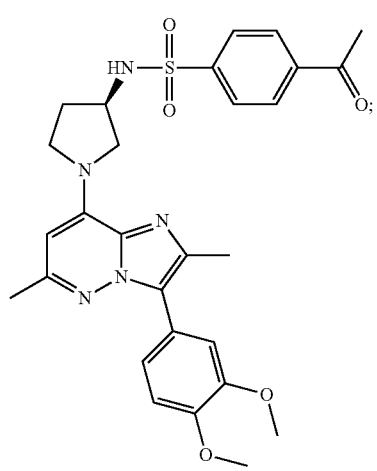
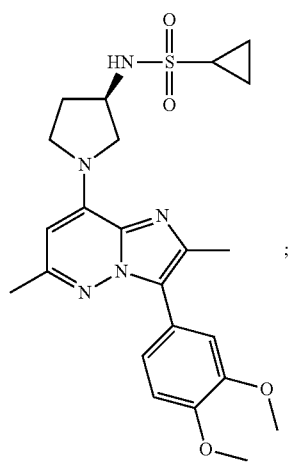
-continued
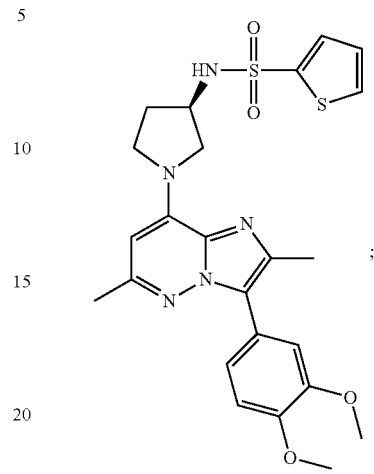
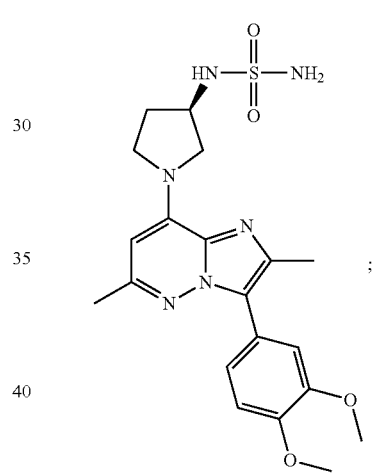
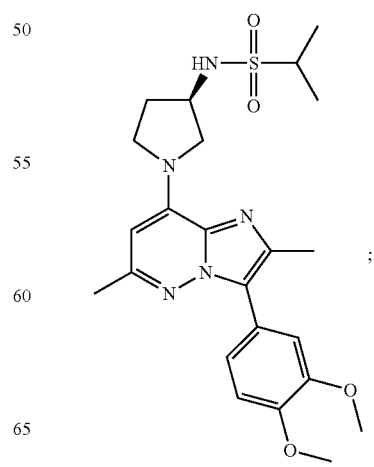

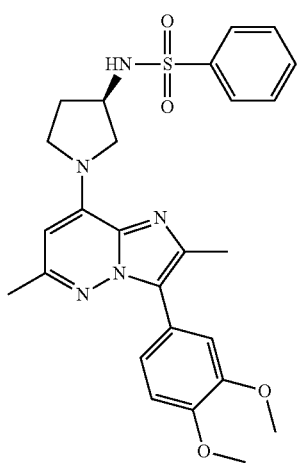
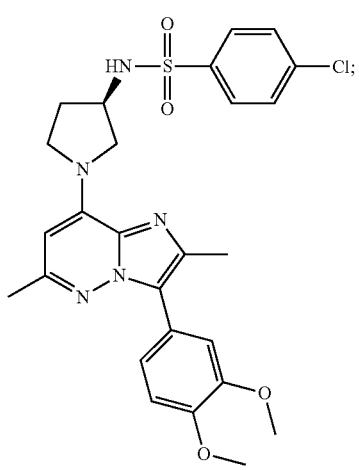
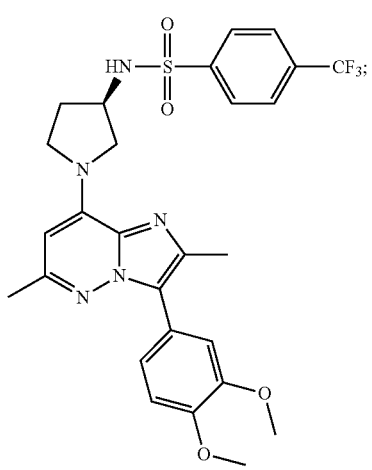
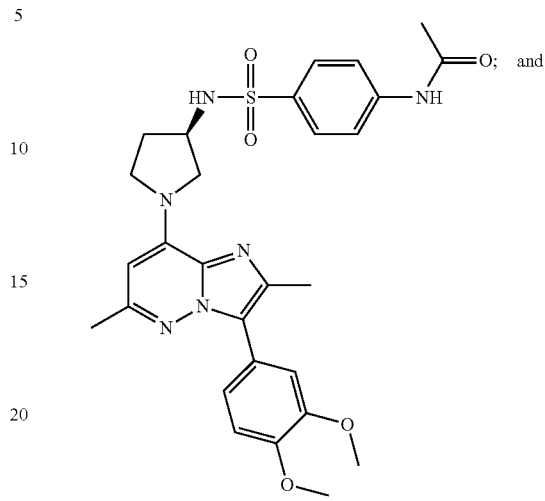
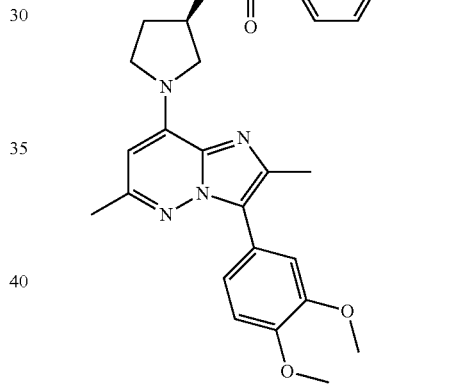
In certain embodiments, R$_5$ is selected from the group consisting of H, halogen, and substituted or unsubstituted alkyl. In particular embodiments, the compound of formula (I) is selected from the group consisting of:
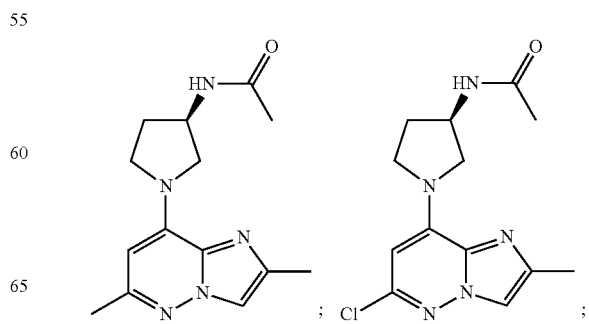

-continued

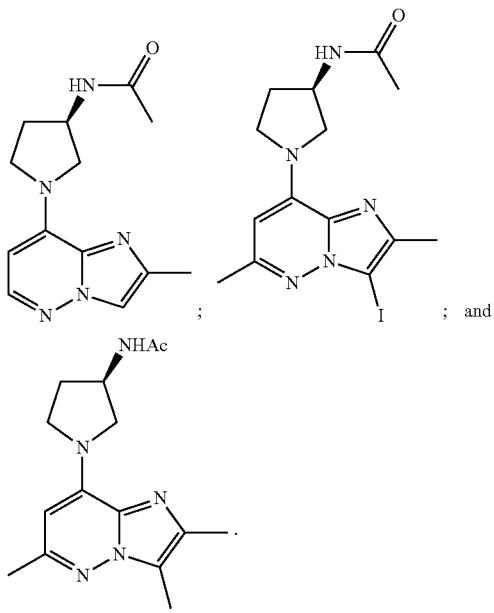

In certain embodiments, R$_5$ is a substituted or unsubstituted multicyclic aryl or multicyclic heteroaryl ring. In particular embodiments, the compound of formula (I) is selected from the group consisting of:

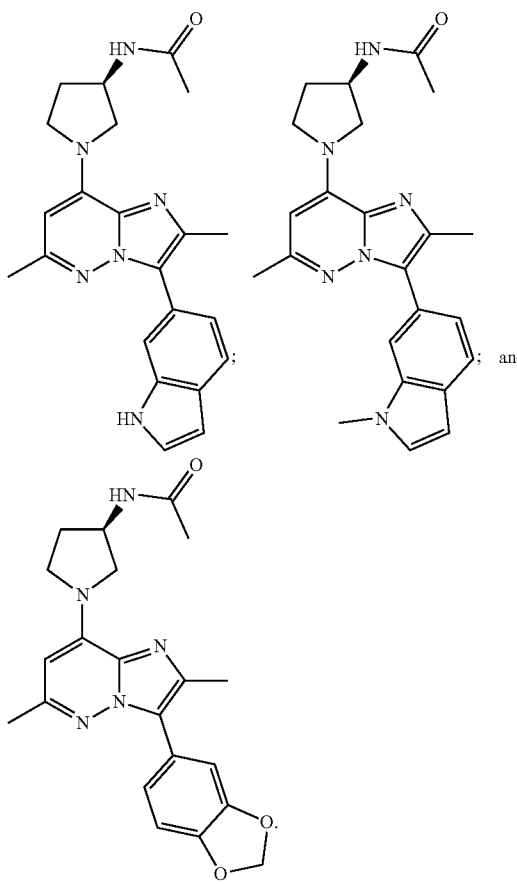

In certain embodiments, R$_5$ is a substituted or unsubstituted heteroaryl. In particular embodiments, the compound of formula (I) is selected from the group consisting of:

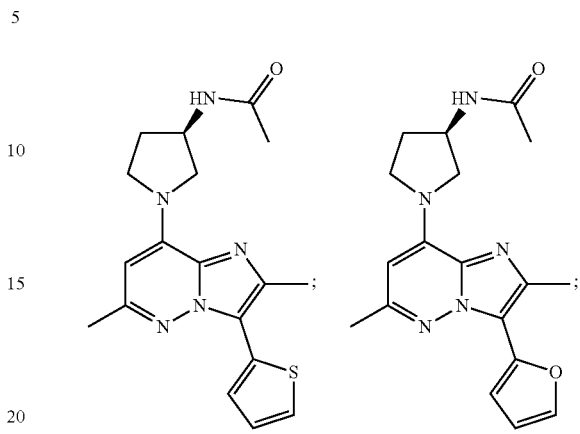

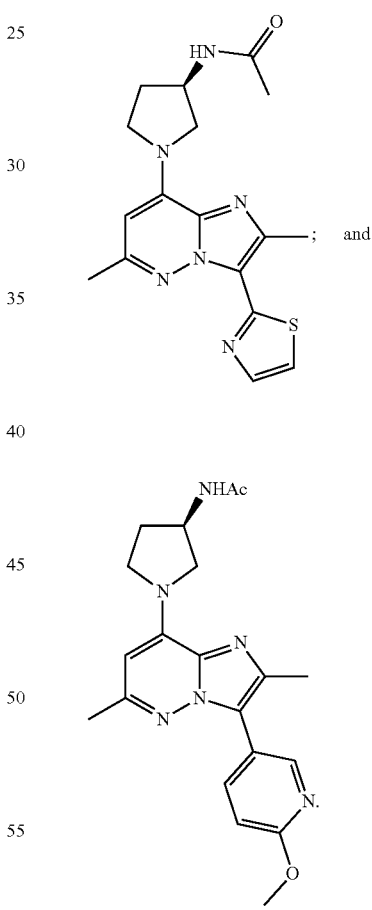

In certain embodiments, n is 0, 1, or 2 and R$_x$ is selected from the group consisting of halogen, hydroxyl, alkoxyl, thioalkyl, cyano, amino, —N$_3$, substituted or unsubstituted aryl, substituted or unsubstituted cycloheteroalkyl, substituted or unsubstituted heteroaryl, and —X—(C=O)—C$_{1-6}$ alkyl, wherein X is O or S. In particular embodiments, the compound of formula (I) is selected from the group consisting of:

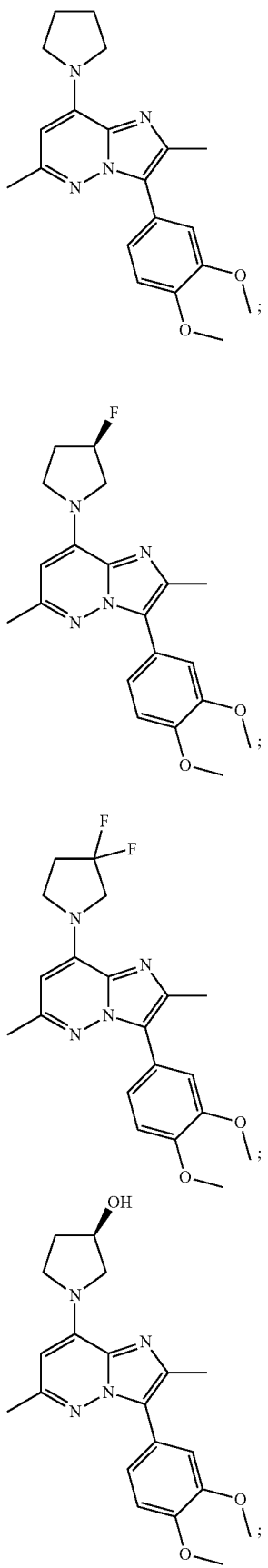
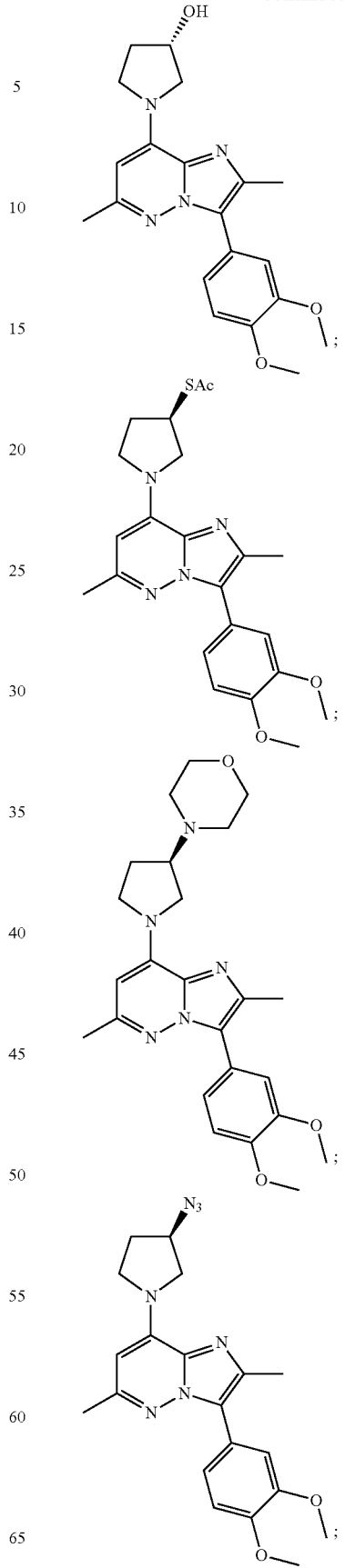

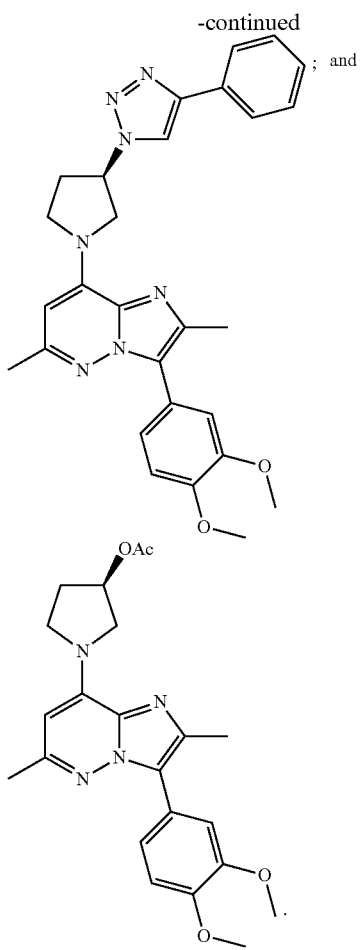

In certain embodiments, $R_1$ and $R_2$ together with the nitrogen atom to which they are bound form a substituted or unsubstituted 5- or 6-membered heterocyclic ring selected from the group consisting of:

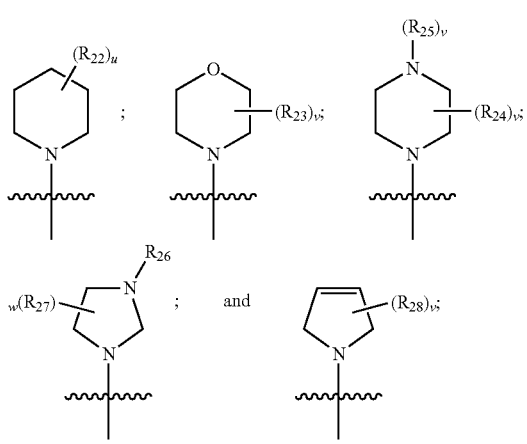

wherein:

u is an integer selected from the group consisting of 0, 1, 2, 3, 4, and 5;

each v is independently an integer selected from the group consisting of 0, 1, 2, 3, and 4;

w is an integer selected from the group consisting of 0, 1, 2, and 3; and $R_{22}$, $R_{23}$, $R_{24}$, $R_{25}$, $R_{26}$, $R_{27}$, and $R_{28}$ are each independently selected from the group consisting of H, —(C═O)—$R_{29}$, —(C═O)—O—$R_{30}$, —S(═O)$_2$—$R_{31}$, and —N$R_{32}$—C(═O)—$R_{33}$, wherein $R_{29}$, $R_{30}$, $R_{31}$, $R_{32}$, and $R_{33}$ are each independently selected from the group consisting of H, substituted or unsubstituted alkyl, and substituted or unsubstituted cycloalkyl. In particular embodiments, the compound of formula (I) is selected from the group consisting of:

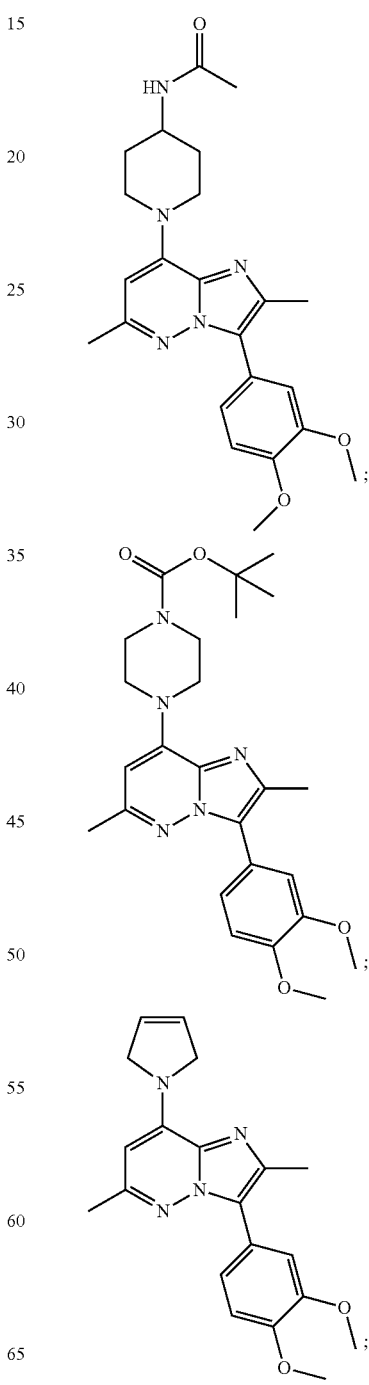

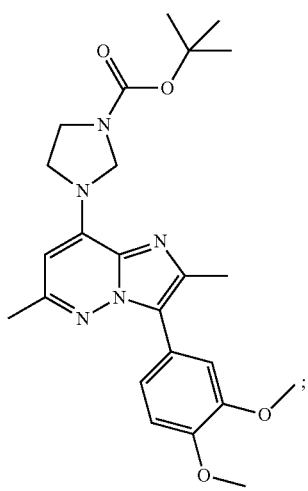
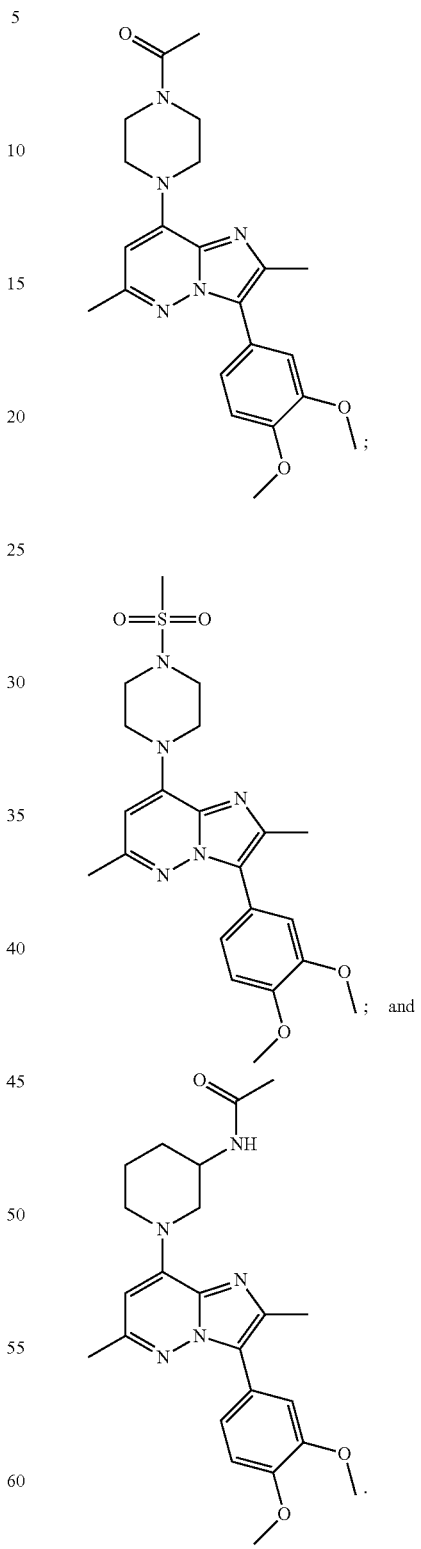
In certain embodiments, $R_1$ and $R_2$ are each independently selected from substituted or unsubstituted alkyl. In particular embodiments, the compound of formula (I) is:

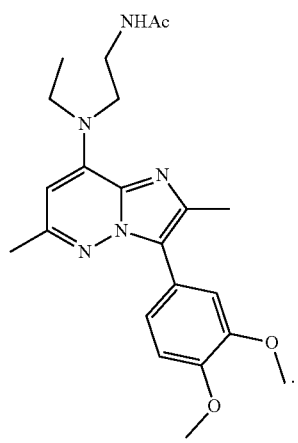
Representative compounds of formula (I) and their activities are summarized in Table 1A.
TABLE 1A
| Representative Inhibitors of nSMase2 of Formula (I) | | |
|---|---|---|
| Entry | Structure | IC$_{50}$ (μM) |
| 1 | 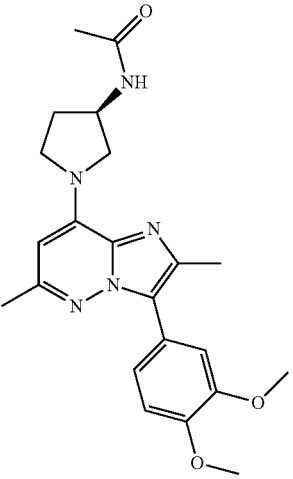 | 1 |
| 2 | 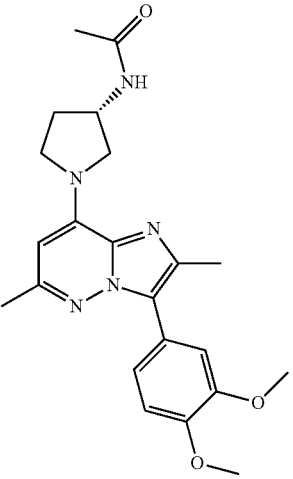 | 2 |
TABLE 1A-continued
| Representative Inhibitors of nSMase2 of Formula (I) | | |
|---|---|---|
| Entry | Structure | IC$_{50}$ (μM) |
| 3 | 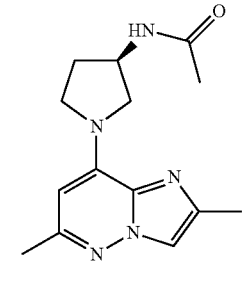 | 8 |
| 4 | 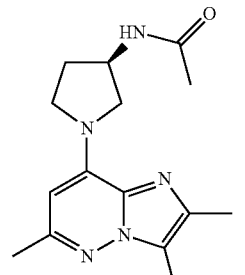 | 1 |
| 5 | 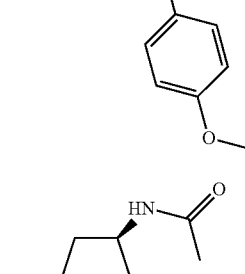 | 2 |
| 6 | 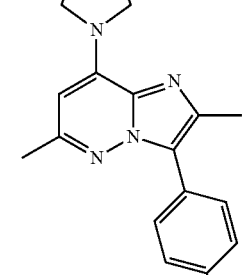 | 1 |

TABLE 1A-continued

Representative Inhibitors of nSMase2 of Formula (I)

| Entry | Structure | IC$_{50}$ (μM) |
|---|---|---|
| 7 | 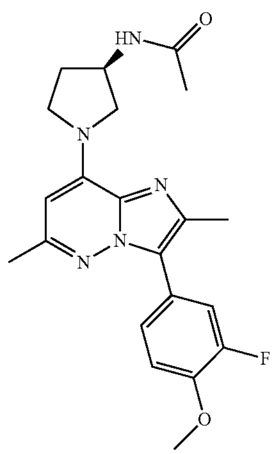 [SMILES: COc1ccc(-c2c(C)nc3c(N4CC[C@@H](NC(C)=O)C4)cc(C)nn23)cc1F] | 0.6 |
| 8 | 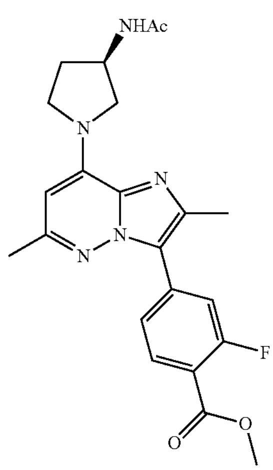 [SMILES: COC(=O)c1ccc(-c2c(C)nc3c(N4CC[C@@H](NC(C)=O)C4)cc(C)nn23)cc1F] | 0.4 |
| 9 | 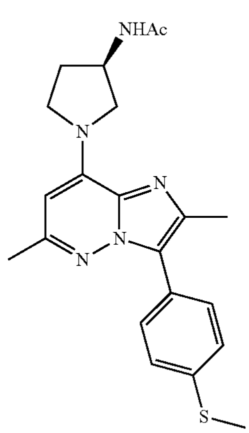 | 0.2 |
| 10 | | 0.5 |
| 11 | | 0.5 |
| 12 | | 0.4 |

TABLE 1A-continued

Representative Inhibitors of nSMase2 of Formula (I)

| Entry | Structure | IC$_{50}$ (μM) |
|---|---|---|
| 13 | 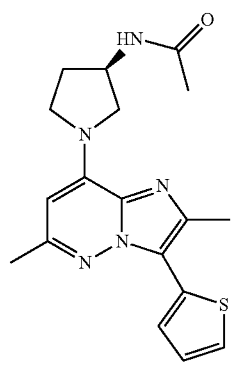 | 0.3 |
| 14 | 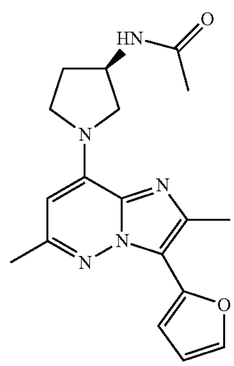 | 0.9 |
| 15 | 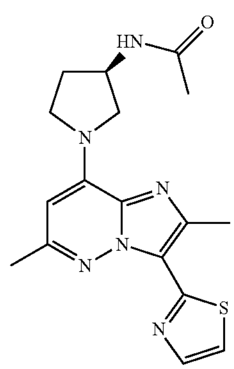 | 1 |
| 16 | 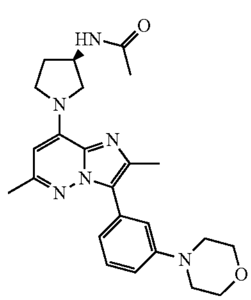 [SMILES: CC(=O)N[C@@H]1CCN(c2cc(C)nn3c(-c4cccc(N5CCOCC5)c4)c(C)nc23)C1] | 0.8 |
| 17 | 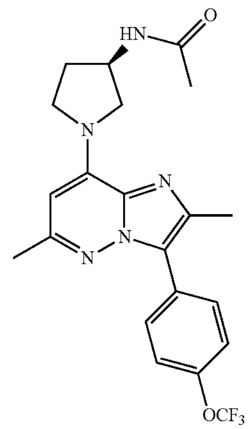 | 0.2 |
| 18 | 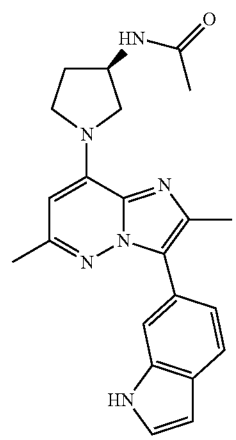 | 0.7 |
| 19 | 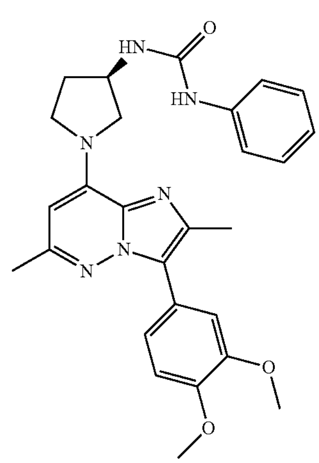 [SMILES: COc1ccc(-c2c(C)nc3c(N4CC[C@@H](NC(=O)Nc5ccccc5)C4)cc(C)nn23)cc1OC] | 0.2 |

TABLE 1A-continued

Representative Inhibitors of nSMase2 of Formula (I)

| Entry | Structure | IC$_{50}$ (μM) |
|---|---|---|
| 20 | 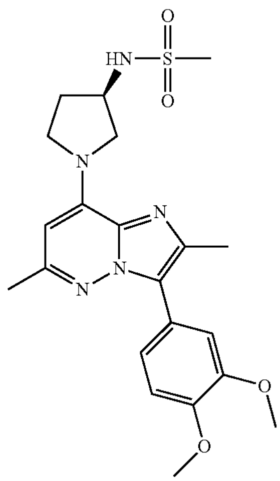 | 1 |
| 21 | 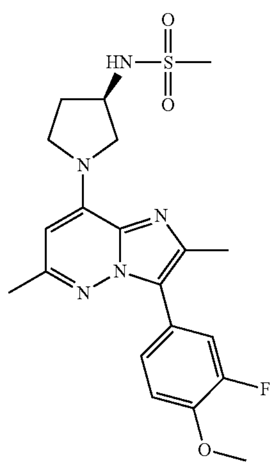 [SMILES: COc1ccc(-c2c(C)nc3c(N4CC[C@@H](NS(C)(=O)=O)C4)cc(C)nn23)cc1F] | 0.1 |
| 22 | 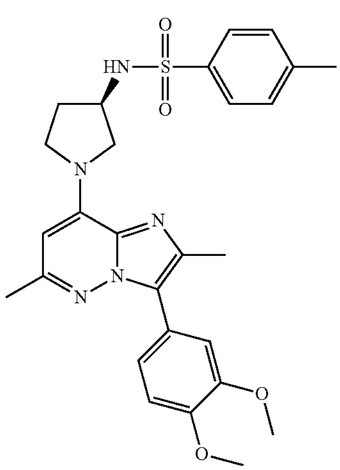 | 0.09 |
| 23 | 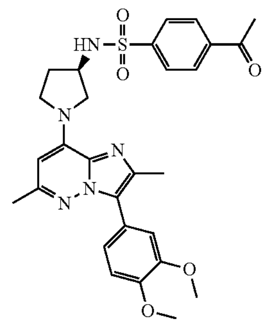 [SMILES: COc1ccc(-c2c(C)nc3c(N4CC[C@@H](NS(=O)(=O)c5ccc(C(C)=O)cc5)C4)cc(C)nn23)cc1OC] | 0.2 |
| 24 | 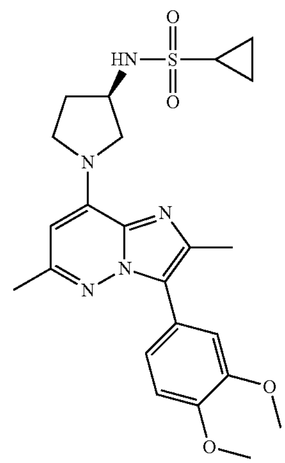 | 0.1 |
| 25 | 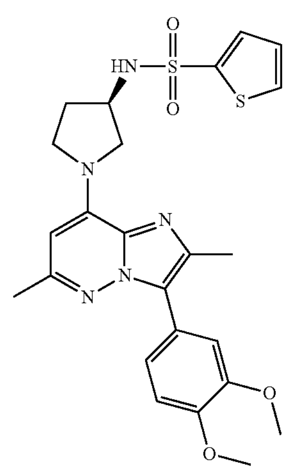 [SMILES: COc1ccc(-c2c(C)nc3c(N4CC[C@@H](NS(=O)(=O)c5cccs5)C4)cc(C)nn23)cc1OC] | 0.1 |

TABLE 1A-continued

Representative Inhibitors of nSMase2 of Formula (I)

| Entry | Structure | IC$_{50}$ (μM) |
|---|---|---|
| 26 | | 0.3 |
| 27 | | 0.3 |
| 28 | | 0.5 |
| 29 | 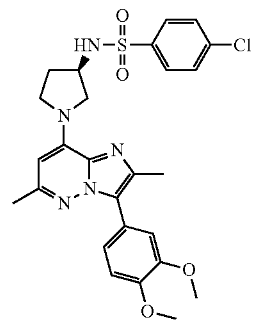 [SMILES: COc1ccc(-c2c(C)nc3c(N4CC[C@@H](NS(=O)(=O)c5ccc(Cl)cc5)C4)cc(C)nn23)cc1OC] | 0.4 |
| 30 | 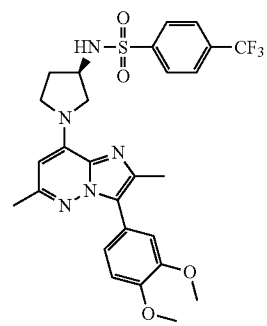 [SMILES: COc1ccc(-c2c(C)nc3c(N4CC[C@@H](NS(=O)(=O)c5ccc(C(F)(F)F)cc5)C4)cc(C)nn23)cc1OC] | 0.2 |
| 31 | 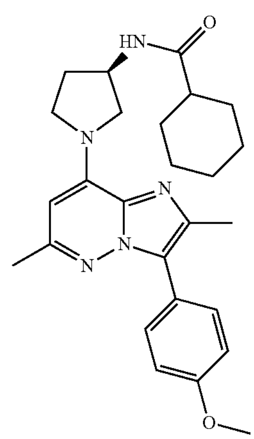 | 0.7 |
| 32 | 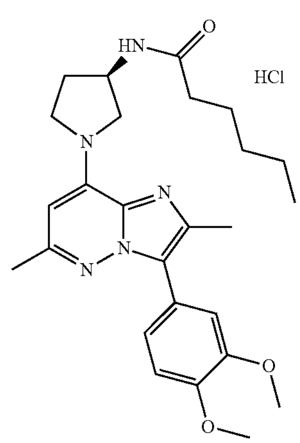 [SMILES: CCCCCC(=O)N[C@@H]1CCN(c2cc(C)nn3c(-c4ccc(OC)c(OC)c4)c(C)nc23)C1 ; Cl] | 0.1 |

TABLE 1A-continued
Representative Inhibitors of nSMase2 of Formula (I)
| Entry | Structure | IC$_{50}$ (µM) |
|---|---|---|
| 33 | 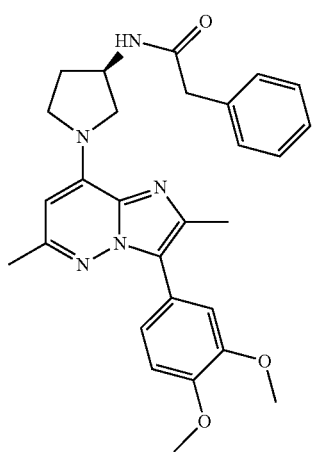 [SMILES: COc1ccc(-c2c(C)nc3c(N4CC[C@@H](NC(=O)Cc5ccccc5)C4)cc(C)nn23)cc1OC] | 0.4 |
| 34 | 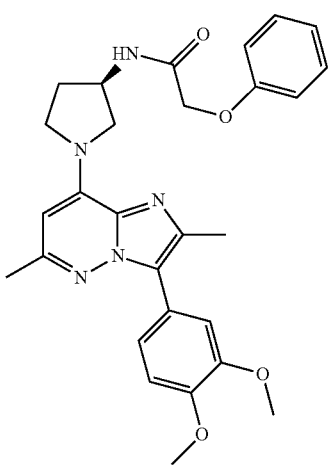 [SMILES: COc1ccc(-c2c(C)nc3c(N4CC[C@@H](NC(=O)COc5ccccc5)C4)cc(C)nn23)cc1OC] | 0.2 |
| 35 | 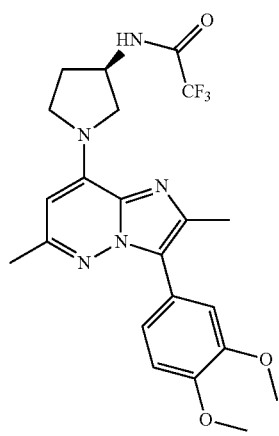 | 0.9 |
| 36 | 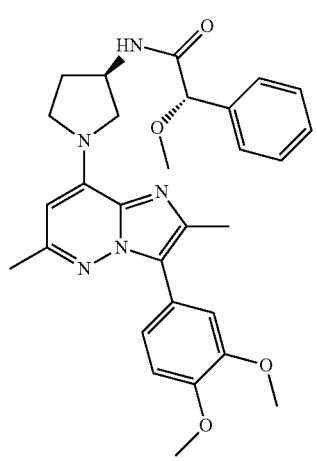 [SMILES: COc1ccc(-c2c(C)nc3c(N4CC[C@@H](NC(=O)[C@@H](OC)c5ccccc5)C4)cc(C)nn23)cc1OC] | 0.4 |
| 37 | 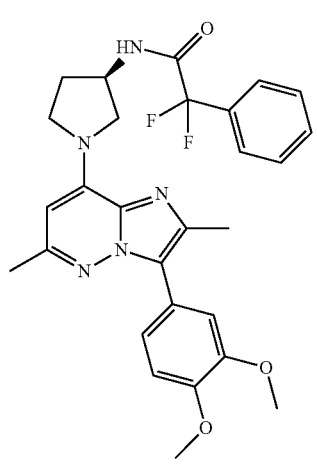 [SMILES: COc1ccc(-c2c(C)nc3c(N4CC[C@@H](NC(=O)C(F)(F)c5ccccc5)C4)cc(C)nn23)cc1OC] | 0.1 |
| 38 | 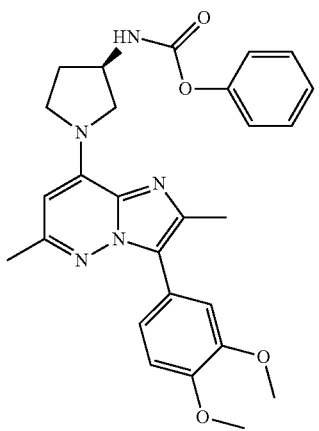 [SMILES: COc1ccc(-c2c(C)nc3c(N4CC[C@@H](NC(=O)Oc5ccccc5)C4)cc(C)nn23)cc1OC] | 0.3 |

TABLE 1A-continued
Representative Inhibitors of nSMase2 of Formula (I)
| Entry | Structure | IC$_{50}$ (μM) |
|---|---|---|
| 39 | 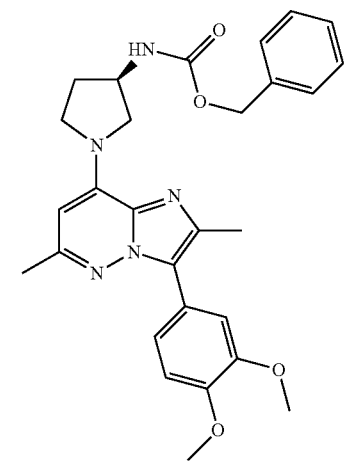 | 0.3 |
| 40 | 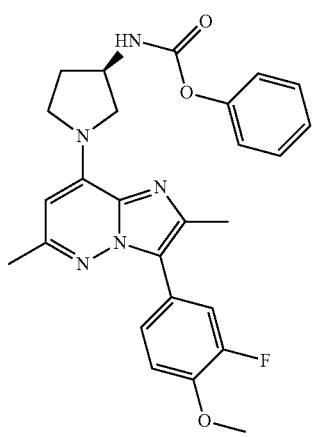 [SMILES: COc1ccc(-c2c(C)nc3c(N4CC[C@@H](NC(=O)Oc5ccccc5)C4)cc(C)nn23)cc1F] | 0.3 |
| 41 | 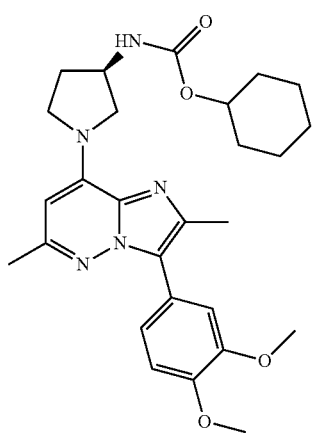 [SMILES: COc1ccc(-c2c(C)nc3c(N4CC[C@@H](NC(=O)OC5CCCCC5)C4)cc(C)nn23)cc1OC] | 0.3 |
TABLE 1A-continued
Representative Inhibitors of nSMase2 of Formula (I)
| Entry | Structure | IC$_{50}$ (μM) |
|---|---|---|
| 42 | 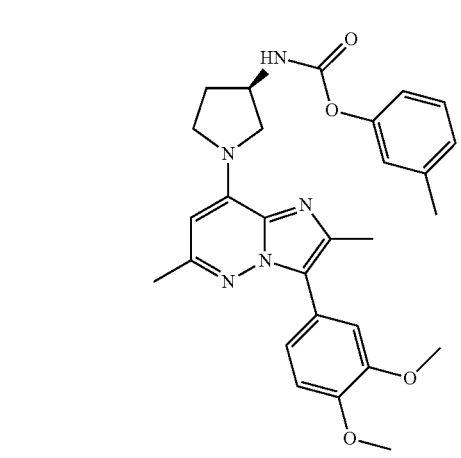 [SMILES: COc1ccc(-c2c(C)nc3c(N4CC[C@@H](NC(=O)Oc5cccc(C)c5)C4)cc(C)nn23)cc1OC] | 0.2 |
| 43 | 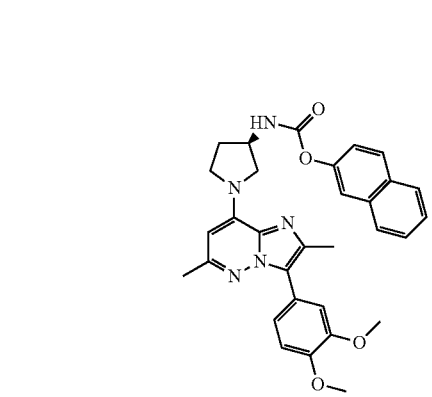 [SMILES: COc1ccc(-c2c(C)nc3c(N4CC[C@@H](NC(=O)Oc5ccc6ccccc6c5)C4)cc(C)nn23)cc1OC] | 0.3 |
| 44 | 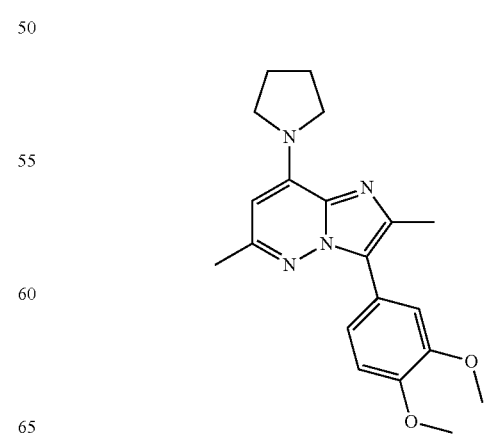 | 0.05 |

TABLE 1A-continued
Representative Inhibitors of nSMase2 of Formula (I)
| Entry | Structure | IC$_{50}$ (μM) |
|---|---|---|
| 45 | 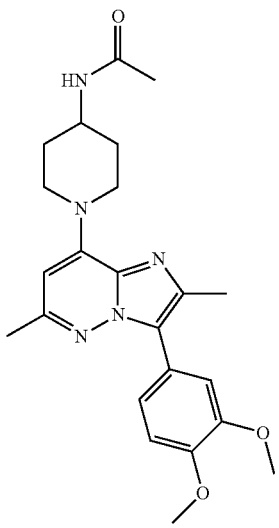 | 1 |
| 46 | 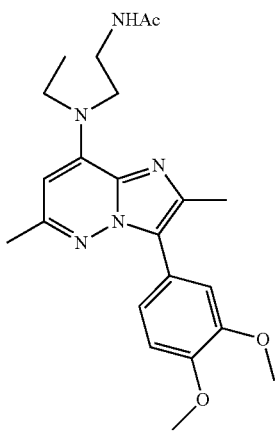 | 5 |
| 47 | 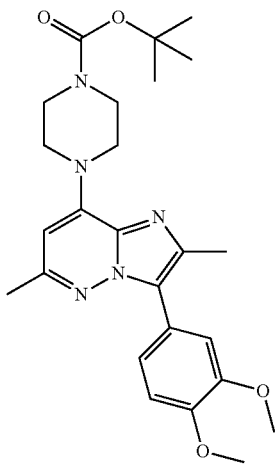 | 2 |
TABLE 1A-continued
Representative Inhibitors of nSMase2 of Formula (I)
| Entry | Structure | IC$_{50}$ (μM) |
|---|---|---|
| 48 | 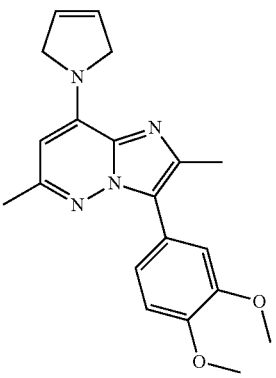 | 1 |
| 49 | 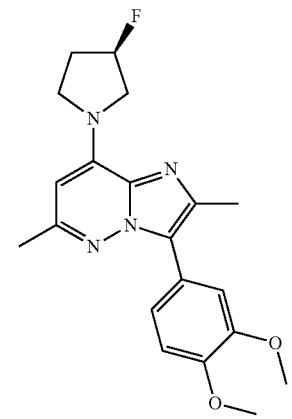 | 0.7 |
| 50 | 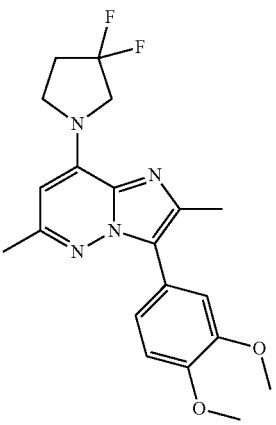 | 1 |

TABLE 1A-continued

Representative Inhibitors of nSMase2 of Formula (I)

| Entry | Structure | IC$_{50}$ (μM) |
|---|---|---|
| 51 | 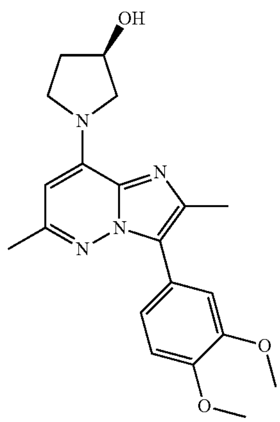 | 0.6 |
| 52 | 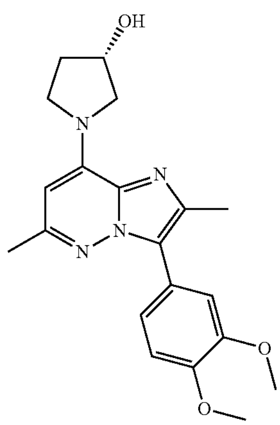 | 0.5 |
| 53 | 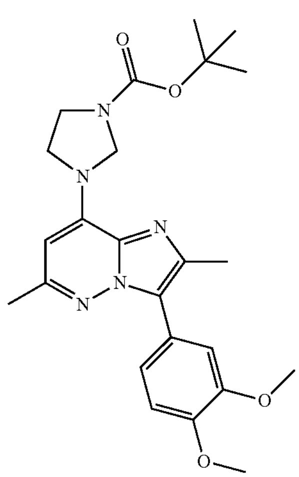 | 0.9 |
| 54 | 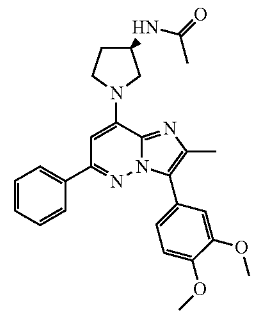 [SMILES: COc1ccc(-c2c(C)nc3c(N4CC[C@@H](NC(C)=O)C4)cc(-c4ccccc4)nn23)cc1OC] | 0.7 |
| 55 | 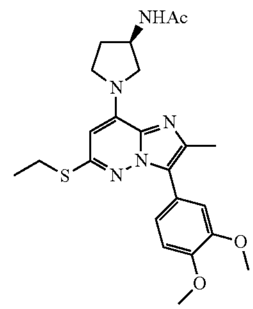 [SMILES: CCSc1cc(N2CC[C@@H](NC(C)=O)C2)c2nc(C)c(-c3ccc(OC)c(OC)c3)n2n1] | 1 |
| 56 | 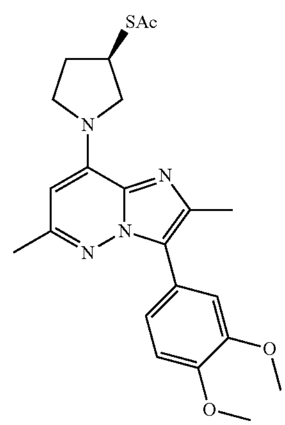 | 0.3 |
| 57 | 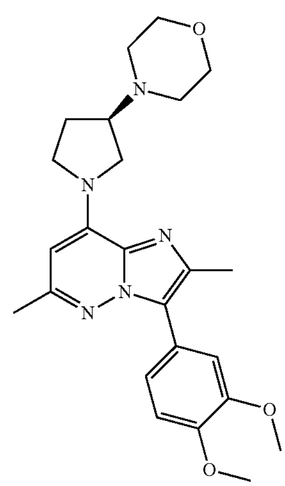 | 0.7 |

TABLE 1A-continued
Representative Inhibitors of nSMase2 of Formula (I)
| Entry | Structure | IC$_{50}$ (μM) |
|---|---|---|
| 58 | 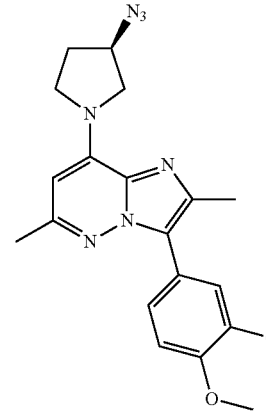 | 0.7 |
| 59 | 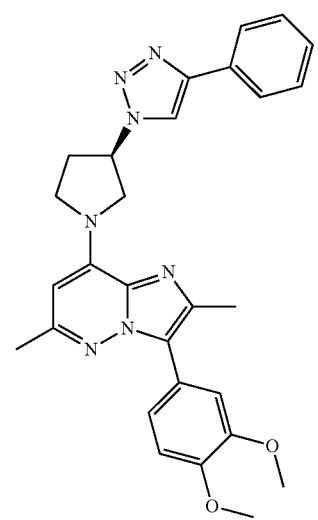 [SMILES: COc1ccc(-c2c(C)nc3c(N4CC[C@@H](n5cc(-c6ccccc6)nn5)C4)cc(C)nn23)cc1OC] | 0.3 |
| 60 | 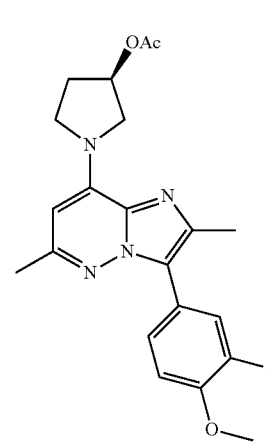 | 0.4 |
| 61 | 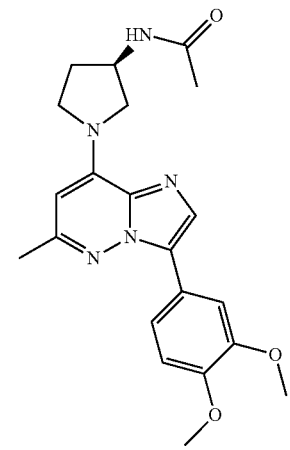 | 0.9 |
| 62 | 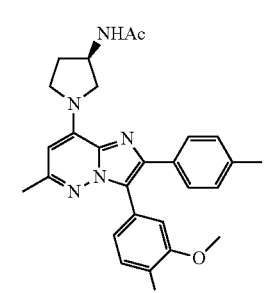 | 0.05 |
| 63 | 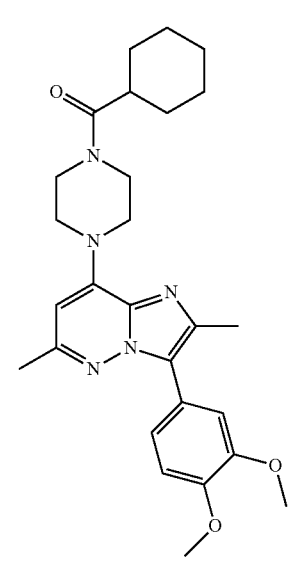 | 2 |

TABLE 1A-continued
Representative Inhibitors of nSMase2 of Formula (I)
| Entry | Structure | IC$_{50}$ (μM) |
|---|---|---|
| 64 | 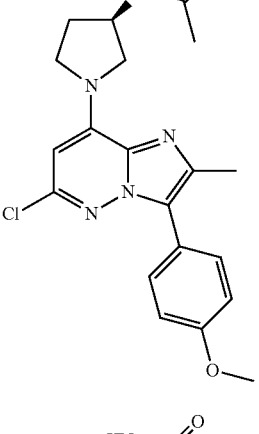 | 1 |
| 65 | 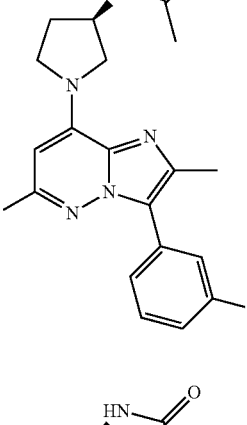 | 100 |
| 9-PROV | 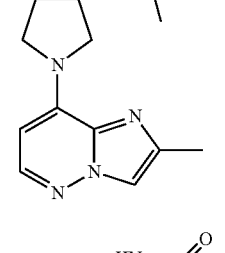 | >100 |
| 11-PROV | 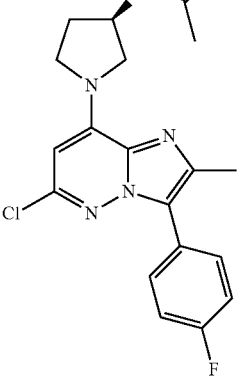 | >100 |
| 14-PROV | 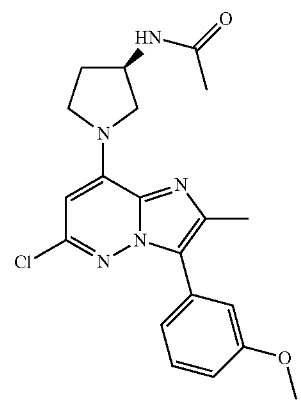 [SMILES: COc1cccc(-c2c(C)nc3c(N4CC[C@@H](NC(C)=O)C4)cc(Cl)nn23)c1] | >100 |
| 15-PROV | 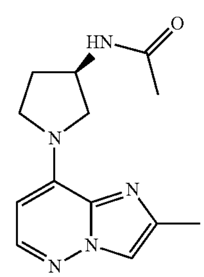 [SMILES: CC(=O)N[C@@H]1CCN(c2ccnn3cc(C)nc23)C1] | >10 |
| 18-PROV | 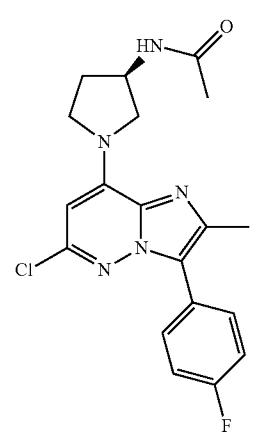 [SMILES: CC(=O)N[C@@H]1CCN(c2cc(Cl)nn3c(-c4ccc(F)cc4)c(C)nc23)C1] | >100 |

TABLE 1A-continued
Representative Inhibitors of nSMase2 of Formula (I)
| Entry | Structure | IC$_{50}$ (μM) |
|---|---|---|
| 19-PROV | 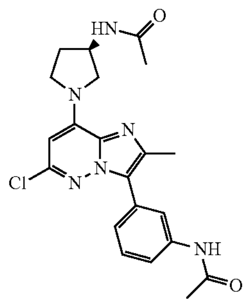 [SMILES: CC(=O)Nc1cccc(-c2c(C)nc3c(N4CC[C@@H](NC(C)=O)C4)cc(Cl)nn23)c1] | >100 |
| 20-PROV | 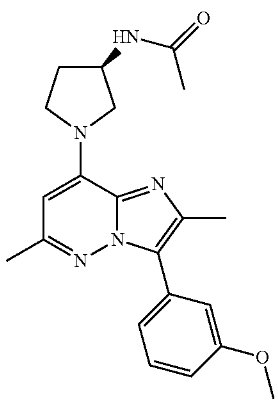 | >1 |
| 22-PROV | 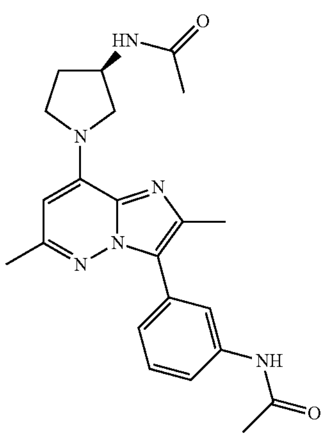 [SMILES: CC(=O)Nc1cccc(-c2c(C)nc3c(N4CC[C@@H](NC(C)=O)C4)cc(C)nn23)c1] | >1 |
| 23-PROV | 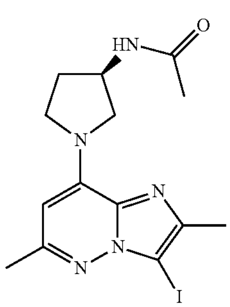 | >10 |
| 33-PROV | | >1 |
| 38-PROV | | >1 |
| 39b-PROV | | ≤1 |
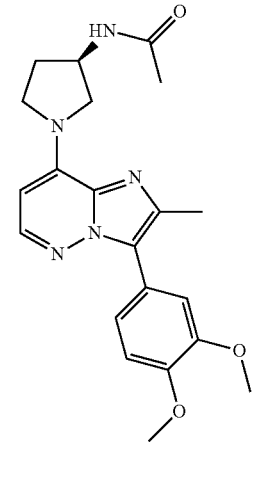 [SMILES: COc1ccc(-c2c(C)nc3c(N4CC[C@@H](NC(C)=O)C4)ccnn23)cc1OC]
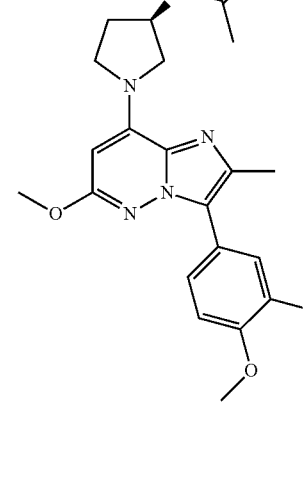
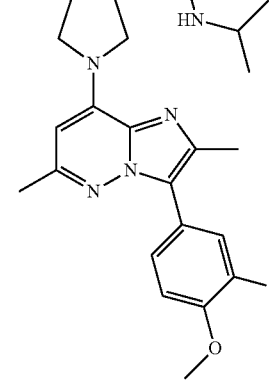

TABLE 1A-continued
Representative Inhibitors of nSMase2 of Formula (I)
| Entry | Structure | IC$_{50}$ (μM) |
|---|---|---|
| 40-PROV | 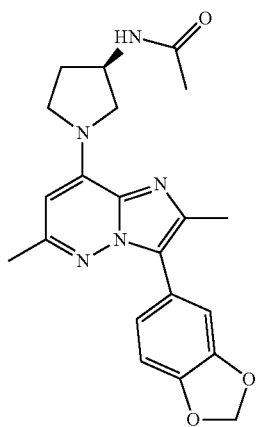 [SMILES: CC(=O)N[C@@H]1CCN(c2cc(C)nn3c(-c4ccc5c(c4)OCO5)c(C)nc23)C1] | ≤1 |
| 42-PROV | 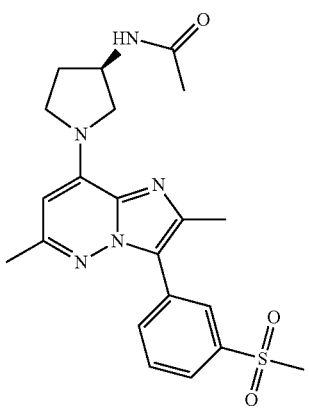 | >1 |
| 43-PROV | 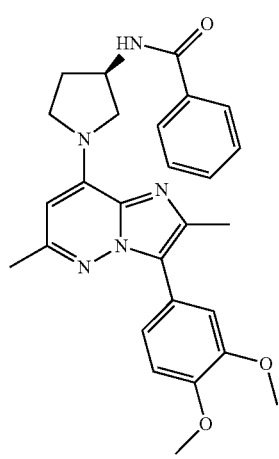 | ≤1 |
| 44-PROV | 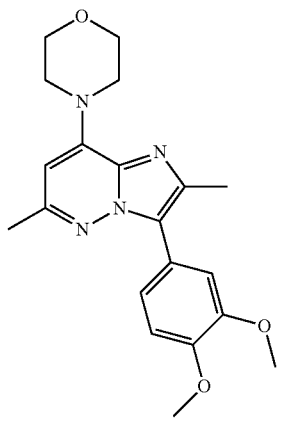 | >1 |
| 46-PROV | 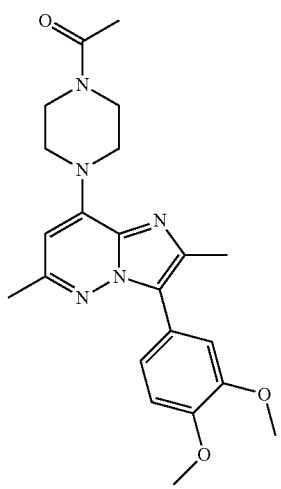 | >1 |
| 47-PROV | 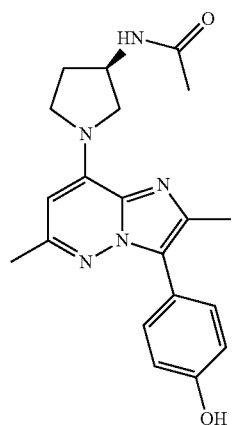 | ≤1 |

TABLE 1A-continued

Representative Inhibitors of nSMase2 of Formula (I)

| Entry | Structure | IC$_{50}$ (µM) |
|---|---|---|
| 48-PROV | 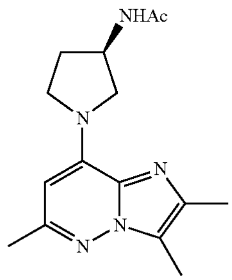 | >1 |
| 50-PROV | 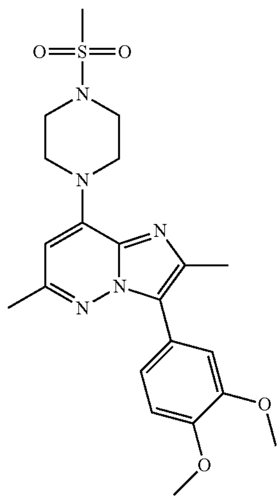 | — |
| 54-PROV | 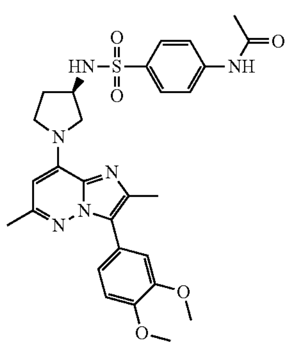 [SMILES: COc1ccc(-c2c(C)nc3c(N4CC[C@@H](NS(=O)(=O)c5ccc(NC(C)=O)cc5)C4)cc(C)nn23)cc1OC] | — |
| 56-PROV | 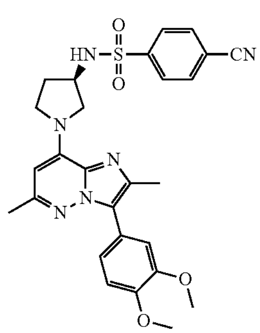 [SMILES: COc1ccc(-c2c(C)nc3c(N4CC[C@@H](NS(=O)(=O)c5ccc(C#N)cc5)C4)cc(C)nn23)cc1OC] | — |
| 59-PROV | 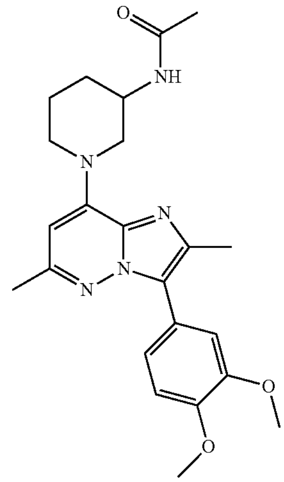 | — |

In other embodiments, the presently disclosed subject matter provides a compound of formula (II):

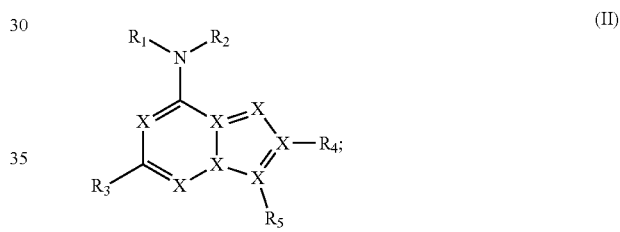

(II)

wherein: each X is independently selected from the group consisting of C(H)$_{0-1}$, N, O, and S; R$_1$ and R$_2$ together with the nitrogen atom to which they are bound form a substituted or unsubstituted 5- or 6-membered heterocyclic ring; R$_3$ is selected from the group consisting of H, substituted or unsubstituted alkyl, substituted or unsubstituted alkoxyl, substituted or unsubstituted thioalkyl, substituted or unsubstituted aryl, and halogen; R$_4$ can be present or absent and when present is selected from the group consisting of H, substituted or unsubstituted alkyl; R$_5$ is selected from the group consisting of H, halogen, substituted or unsubstituted aryl, substituted or unsubstituted heteroaryl, and a substituted or unsubstituted multicyclic aryl or heteroaryl ring; and pharmaceutically acceptable salts thereof.

In such embodiments, the compound of formula (II) can be selected from the group consisting of:

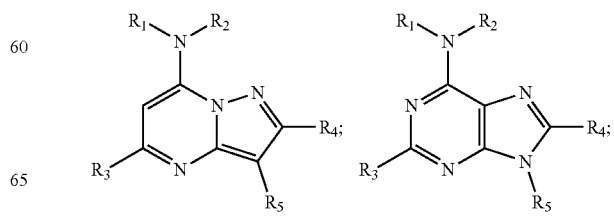

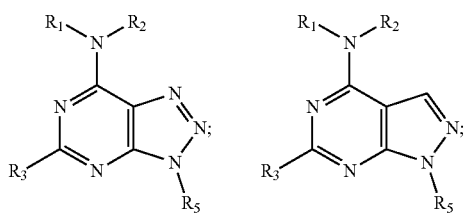
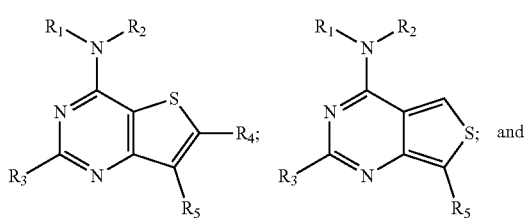
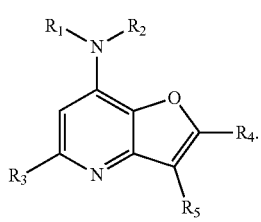
Representative compounds of formula (II) and their activities are summarized in Table 1B.
TABLE 1B
| | | Representative Inhibitors of nSMase2 of Formula (II) | | |
|---|---|---|---|---|
| No | Code | Structure | Activity* | MW |
| 1-PROV | MS 796 | | D | 397.43 |
| 2-PROV | MS 797 | | D | 396.44 |
| 3-PROV | MS 798 | | D | 410.47 |
| 4-PROV | MS 799 | | D | 409.48 |

TABLE 1B-continued
Representative Inhibitors of nSMase2 of Formula (II)
| No | Code | Structure | Activity* | MW |
|---|---|---|---|---|
| 5-PROV | MS 800 | 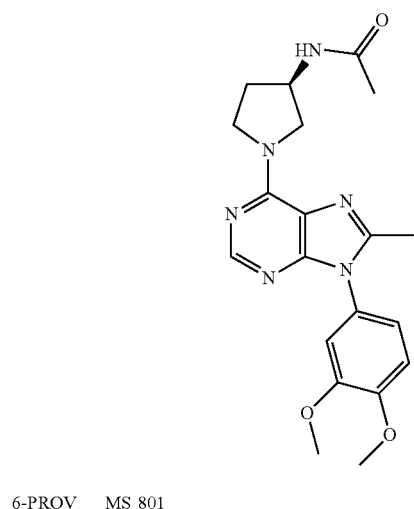 | D | 396.44 |
| 6-PROV | MS 801 | 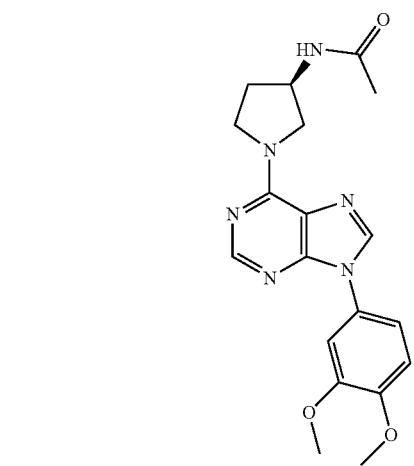 | D | 382.42 |
| 7-PROV | MS 799A | 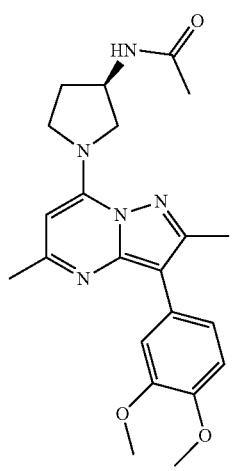 | D | 409.48 |
| 8-PROV | MS 803 | 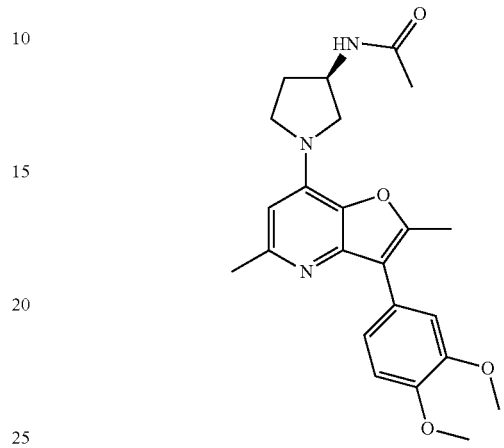 | D | 409.48 |
| 10-PROV | MS 805 | 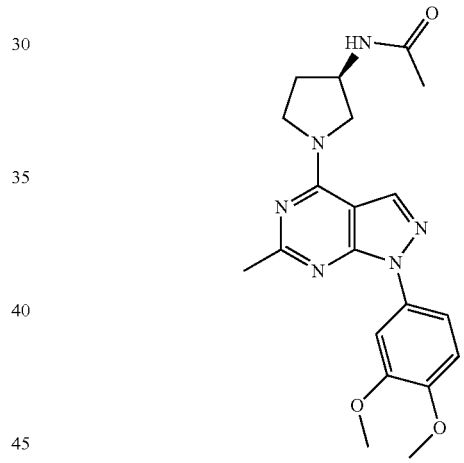 | D | 396.44 |
| 12-PROV | MS 807 | 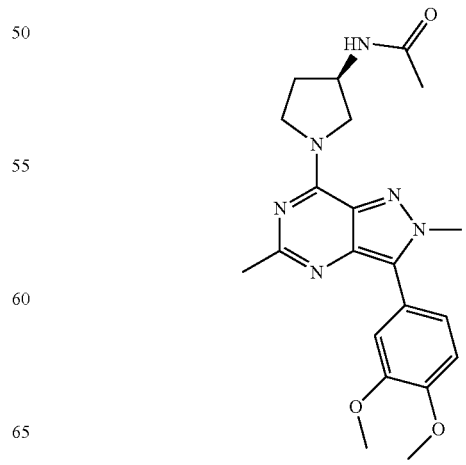 | D | 410.47 |

TABLE 1B-continued
Representative Inhibitors of nSMase2 of Formula (II)
| No | Code | Structure | Activity* | MW |
|---|---|---|---|---|
| 13-PROV | MS 808 | 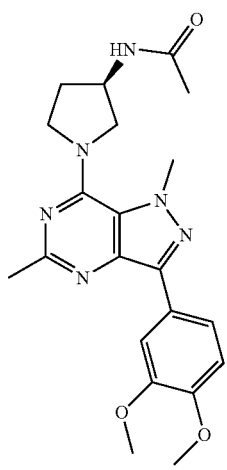 [SMILES: COc1ccc(-c2nn(C)c3c(N4CC[C@@H](NC(C)=O)C4)nc(C)nc23)cc1OC] | D | 410.47 |
| 24-PROV | HH 1280 | 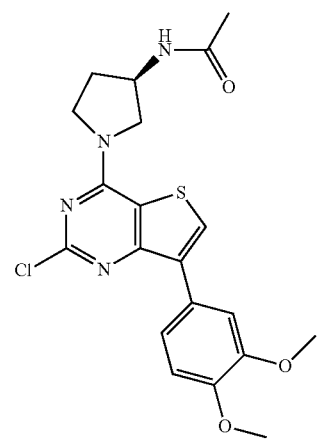 [SMILES: COc1ccc(-c2csc3c(N4CC[C@@H](NC(C)=O)C4)nc(Cl)nc23)cc1OC] | D | 432.92 |
| 25-PROV | HH 1281 | 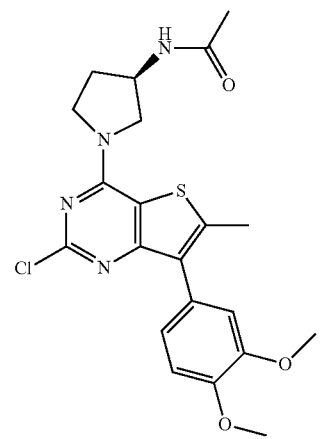 [SMILES: COc1ccc(-c2c(C)sc3c(N4CC[C@@H](NC(C)=O)C4)nc(Cl)nc23)cc1OC] | D | 446.95 |
| 26-PROV | HH 1283 | 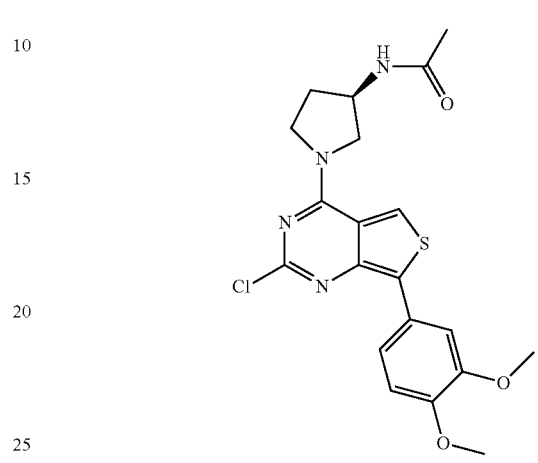 | D | 432.92 |
| 27-PROV | HH 1284 | 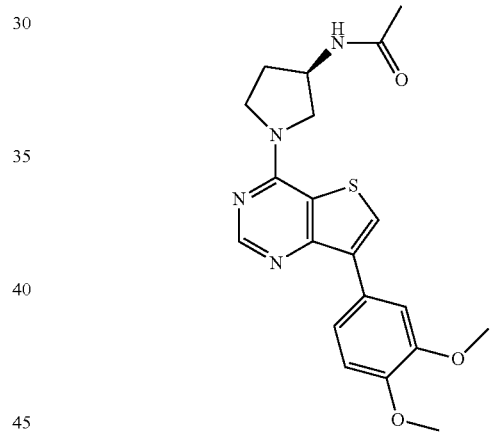 | D | 398.48 |
| 28-PROV | HH 1287 | 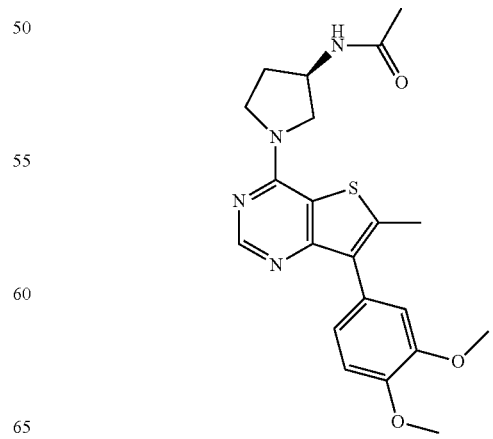 | D | 412.51 |

TABLE 1B-continued

Representative Inhibitors of nSMase2 of Formula (II)

| No | Code | Structure | Activity* | MW |
|---|---|---|---|---|
| 29a-PROV | HH 1288 | 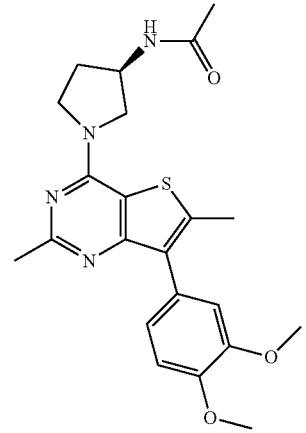 | D | 426.54 |
| 29b-PROV | HH 1289 | 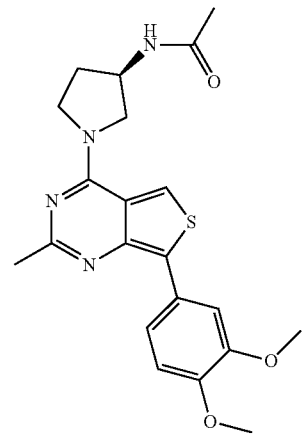 | D | 412.51 |
| 30-PROV | HH 1290 | 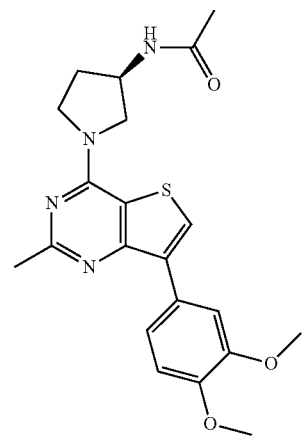 | D | 412.51 |
| 36-PROV | MS 824 | 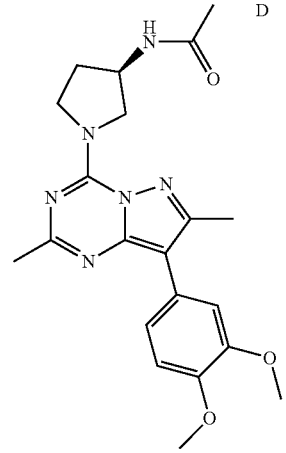 | D | 410.47 |

*The activities of the compounds are scaled into four groups (A-D) as follows: Category D $IC_{50} > 100$ μM; Category C $IC_{50} > 10$ μM; Category B $IC_{50} > 1$ μM; Category A $IC_{50} \leq 1$ μM.

B. Methods for Treating a Condition, Disease, or Disorder Associated with an Increased Neutral Sphingomyelinase 2 (Nsmase2) Activity or Expression In some embodiments, the presently disclosed subject matter provides a method for treating a condition, disease, or disorder associated with an increased neutral sphingomyelinase 2 (nSMase2) activity or expression, the method comprising administering to a subject in need of treatment thereof an effective amount of an nSMase2 inhibitor of formula (I):

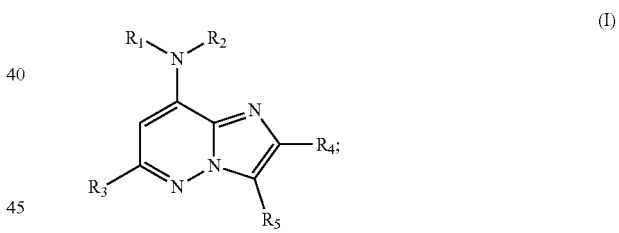

wherein:

$R_1$ and $R_2$ are each independently selected from substituted or unsubstituted alkyl or together with the nitrogen atom to which they are bound form a substituted or unsubstituted 5- or 6-membered heterocyclic ring;

$R_3$ is selected from the group consisting of H, substituted or unsubstituted alkyl, substituted or unsubstituted alkoxyl, substituted or unsubstituted thioalkyl, substituted or unsubstituted aryl, and halogen;

$R_4$ is selected from the group consisting of H, substituted or unsubstituted alkyl, and substituted or unsubstituted aryl;

$R_5$ is selected from the group consisting of H, halogen, substituted or unsubstituted alkyl, substituted or unsubstituted aryl, substituted or unsubstituted heteroaryl, and a substituted or unsubstituted multicyclic aryl or multicyclic heteroaryl ring;

under the proviso that if $R_1$ and $R_2$ together with the nitrogen atom to which they are bound are pyridinyl or morpholinyl, then $R_5$ cannot be H, halogen, or substituted or unsubstituted heteroaryl; and pharmaceutically acceptable salts thereof.

In other embodiments, the presently disclosed subject matter provides a method for treating a condition, disease, or disorder associated with an increased neutral sphingomyelinase 2 (nSMase2) activity or expression, the method comprising administering to a subject in need of treatment thereof an effective amount of an nSMase2 inhibitor of formula (II):

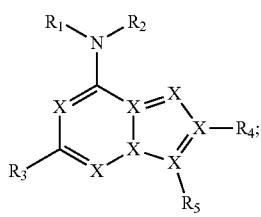

(II)

wherein: each X is independently selected from the group consisting of $C(H)_{0-1}$, N, O, and S; $R_1$ and $R_2$ together with the nitrogen atom to which they are bound form a substituted or unsubstituted 5- or 6-membered heterocyclic ring; $R_3$ is selected from the group consisting of H, substituted or unsubstituted alkyl, substituted or unsubstituted alkoxyl, substituted or unsubstituted thioalkyl, substituted or unsubstituted aryl, and halogen; $R_4$ can be present or absent and when present is selected from the group consisting of H, substituted or unsubstituted alkyl; $R_5$ is selected from the group consisting of H, halogen, substituted or unsubstituted aryl, substituted or unsubstituted heteroaryl, and a substituted or unsubstituted multicyclic aryl or heteroaryl ring; and pharmaceutically acceptable salts thereof.

In some embodiments, the compound of formula (II) is selected from the group consisting of:

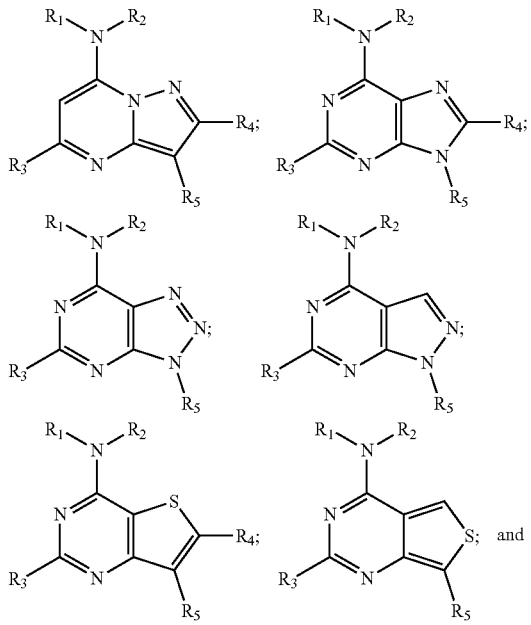

-continued

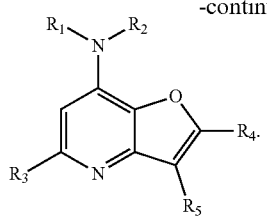

In some embodiments, the condition, disease, or disorder is associated with an elevated level of ceramide in the subject in need of treatment compared to a control subject not afflicted with the condition, disease, or disorder.

In some embodiments, the condition, disease, or disorder comprises a neurodegenerative disease. In particular embodiments, the neurodegenerative disease is selected from the group consisting of Alzheimer's disease (AD), HIV-associated neurocognitive disorder (HAND), multiple sclerosis (MS), and amyotrophic lateral sclerosis (ALS).

In yet other embodiments, the condition, disease, or disorder is a cancer.

In particular embodiments, the administration of an effective amount of a compound of formula (I) to the subject decreases the (nSMase2) activity or expression or decreases a level of ceramide in the subject.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

The term "combination" is used in its broadest sense and means that a subject is administered at least two agents, more particularly a compound of formula (I) and at least one beta-lactam antibiotic and, optionally, one or more antibacterial agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the compounds of formula (I) described herein can be administered alone or in combination with adjuvants that enhance stability of the compounds of formula (I), alone or in combination with one or more antibacterial agents, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of a compound of formula (I) and at least one additional therapeutic agent can be varied so long as the beneficial effects of the combination of these agents are achieved. Accordingly, the phrase "in combination with" refers to the administration of a compound of formula (I) and at least one additional therapeutic agent either simultaneously, sequentially, or a combination thereof. Therefore, a subject administered a combination of a compound of formula (I) and at least one additional therapeutic agent can receive compound of formula (I) and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of formula (I) and at least one additional therapeutic agent are administered simultaneously, they can be administered to the subject as separate pharmaceutical compositions, each comprising either a compound of formula (I) or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound of formula (I) and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A + Q_b/Q_B = \text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

C. Methods for Inhibiting Neutral Sphingomyelinase 2 (nSMase2)

In some embodiments, the presently disclosed subject matter provides a method for inhibiting neutral sphingomyelinase 2 (nSMase2), the method comprising administering to a subject, cell, or tissue an amount of a compound of formula (I) effective to inhibit nSMase2:

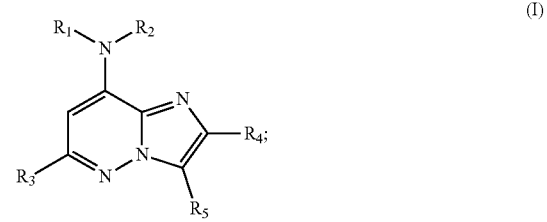

(I)

wherein:

$R_1$ and $R_2$ are each independently selected from substituted or unsubstituted alkyl or together with the nitrogen atom to which they are bound form a substituted or unsubstituted 5- or 6-membered heterocyclic ring;

R₃ is selected from the group consisting of H, substituted or unsubstituted alkyl, substituted or unsubstituted alkoxyl, substituted or unsubstituted thioalkyl, substituted or unsubstituted aryl, and halogen;

R₄ is selected from the group consisting of H, substituted or unsubstituted alkyl, and substituted or unsubstituted aryl;

R₅ is selected from the group consisting of H, halogen, substituted or unsubstituted alkyl, substituted or unsubstituted aryl, substituted or unsubstituted heteroaryl, and a substituted or unsubstituted multicyclic aryl or multicyclic heteroaryl ring;

under the proviso that if R₁ and R₂ together with the nitrogen atom to which they are bound are pyridinyl or morpholinyl, then R₅ cannot be H, halogen, or substituted or unsubstituted heteroaryl; and pharmaceutically acceptable salts thereof.

In other embodiments, the presently disclosed subject matter provides a method for inhibiting neutral sphingomyelinase 2 (nSMase2), the method comprising administering to a subject, cell, or tissue an amount of a compound of formula (II) effective to inhibit nSMase2:

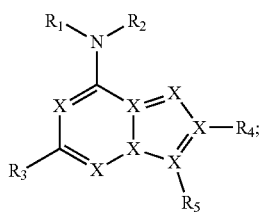

(II)

wherein: each X is independently selected from the group consisting of $C(H)_{0-1}$, N, O, and S; R₁ and R₂ together with the nitrogen atom to which they are bound form a substituted or unsubstituted 5- or 6-membered heterocyclic ring; R₃ is selected from the group consisting of H, substituted or unsubstituted alkyl, substituted or unsubstituted alkoxyl, substituted or unsubstituted thioalkyl, substituted or unsubstituted aryl, and halogen; R₄ can be present or absent and when present is selected from the group consisting of H, substituted or unsubstituted alkyl; R₅ is selected from the group consisting of H, halogen, substituted or unsubstituted aryl, substituted or unsubstituted heteroaryl, and a substituted or unsubstituted multicyclic aryl or heteroaryl ring; and pharmaceutically acceptable salts thereof.

In some embodiments, the compound of formula (I) is selected from the group consisting of:

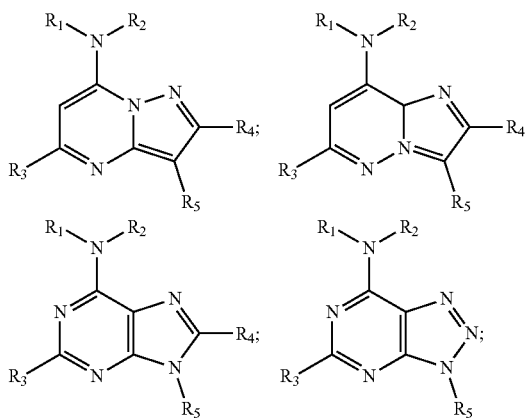

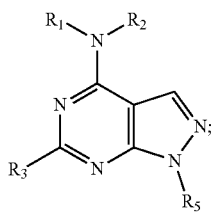 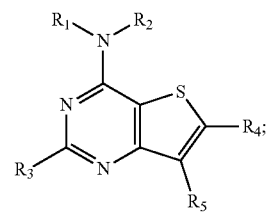

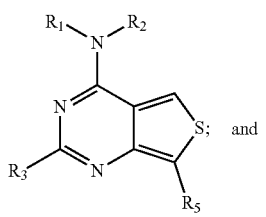 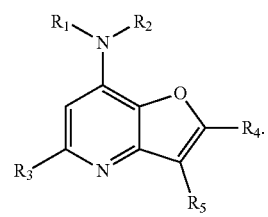

In particular embodiments, the compound of formula (I) is:

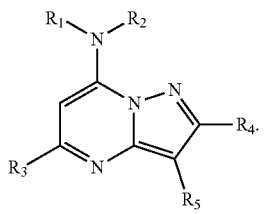

In yet more particular embodiments, the compound of formula (I) is:

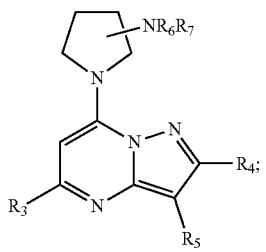

wherein: R₆ is selected from the group consisting of H or $C_{1-6}$ substituted or unsubstituted alkyl; and R₇ is selected from the group consisting of —C(=O)—R₈, —S(=O)₂—R₉, wherein R₈ and R₉ are each independently selected from the group consisting of substituted or unsubstituted alkyl, substituted or unsubstituted cycloalkyl, substituted or unsubstituted aryl, substituted or unsubstituted heteroaryl, and NR₁₀R₁₁, wherein R₁₀ and R₁₁ are each independently selected from the group consisting of H or substituted or unsubstituted $C_{1-6}$ alkyl.

In certain embodiments, the compound of formula (I) is:

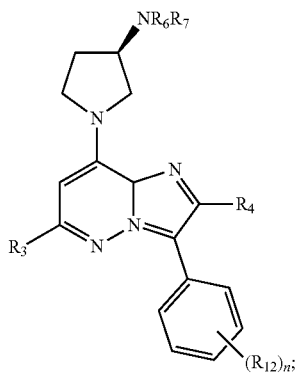

wherein: n is an integer selected from the group consisting of 0, 1, 2, 3, 4, and 5; each each $R_{12}$ is independently selected from the group consisting of substituted or unsubstituted alkyl, hydroxyl, alkoxyl, halogen, cyano, amino, —$CF_3$, —O—$CF_3$, substituted or unsubstituted cycloheteroaklyl, —$NR_{13}$(C═O)$R_{14}$, —S(═O)$_2$—$R_{15}$, —S(═O)$_2$—$NR_{15}R_{16}$, —$SR_{16}$, —C(═O)—$R_{17}$, —C(═O)—O—$R_{18}$, and —C(═O)—$NR_{19}R_{20}$, wherein $R_{13}$ is selected from the group consisting of H or substituted or unsubstituted $C_{1-6}$ alkyl, $R_{14}$ is substituted or unsubstituted $C_{1-6}$ alkyl or —O—$R_{21}$, and $R_{15}$, $R_{16}$, $R_{17}$, $R_{18}$, $R_{19}$, $R_{20}$, $R_{21}$ are each independently H or substituted or unsubstituted $C_{1-6}$ alkyl.

As used herein, the term "inhibit," and grammatical derivations thereof, refers to the ability of a presently disclosed compound, e.g., a presently disclosed compound of formula (I), to block, partially block, interfere, decrease, or reduce the growth of bacteria or a bacterial infection. Thus, one of ordinary skill in the art would appreciate that the term "inhibit" encompasses a complete and/or partial decrease in the growth of bacteria or a bacterial infection, e.g., a decrease by at least 10%, in some embodiments, a decrease by at least 20%, 30%, 50%, 75%, 95%, 98%, and up to and including 100%.

D. Pharmaceutical Compositions and Administration

In another aspect, the present disclosure provides a pharmaceutical composition including one compound of formula (I) alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_{1-10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, acylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, cyano, and mercapto.

The term "heteroalkyl," by itself or in combination with another term, means, unless otherwise stated, a stable straight or branched chain having from 1 to 20 carbon atoms or heteroatoms or a cyclic hydrocarbon group having from 3 to 10 carbon atoms or heteroatoms, or combinations thereof, consisting of at least one carbon atom and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O)$_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkylene moiety, also as defined above, e.g., a $C_{1-20}$ alkylene moiety. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidinyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated hydrocarbon has one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{2-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{2-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—($CH_2$)$_3$—); cyclohexylene (—$C_6H_{10}$—); —CH=CH—CH=CH—; —CH=CH—$CH_2$—; —$CH_2CH_2CH_2CH_2$—, —$CH_2$CH=CHCH$_2$—, —$CH_2$C≡CCH$_2$—, —$CH_2CH_2$CH($CH_2CH_2CH_3$)$CH_2$—, —($CH_2$)$_q$—N(R)—($CH_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—($CH_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

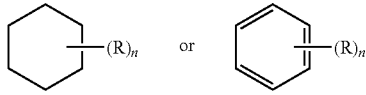

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

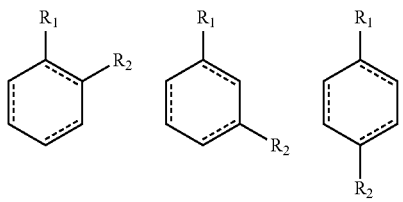

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⁓⁓⁓ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN, CF$_3$, fluorinated C$_{1-4}$ alkyl, and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)$_2$R', —S(O)$_2$NR'R", —NRSO$_2$R', —CN and —NO$_2$, —R', —N$_3$, —CH(Ph)$_2$, fluoro(C$_{1-4}$)alkoxo, and fluoro(C$_{1-4}$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., C$_6$H$_5$—CH$_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The term "cyano" refers to the —C≡N group.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_{1-4}$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —$S(O_2)R$.

The term "sulfoxide" refers to a compound having a sulfinyl group —S(O)R

The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P.G.M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

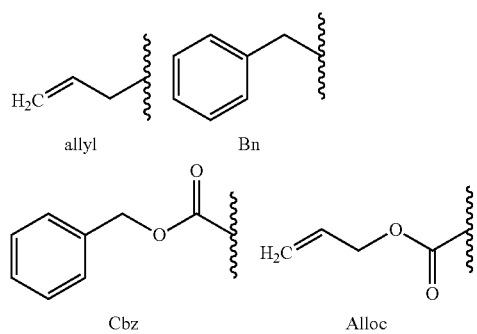
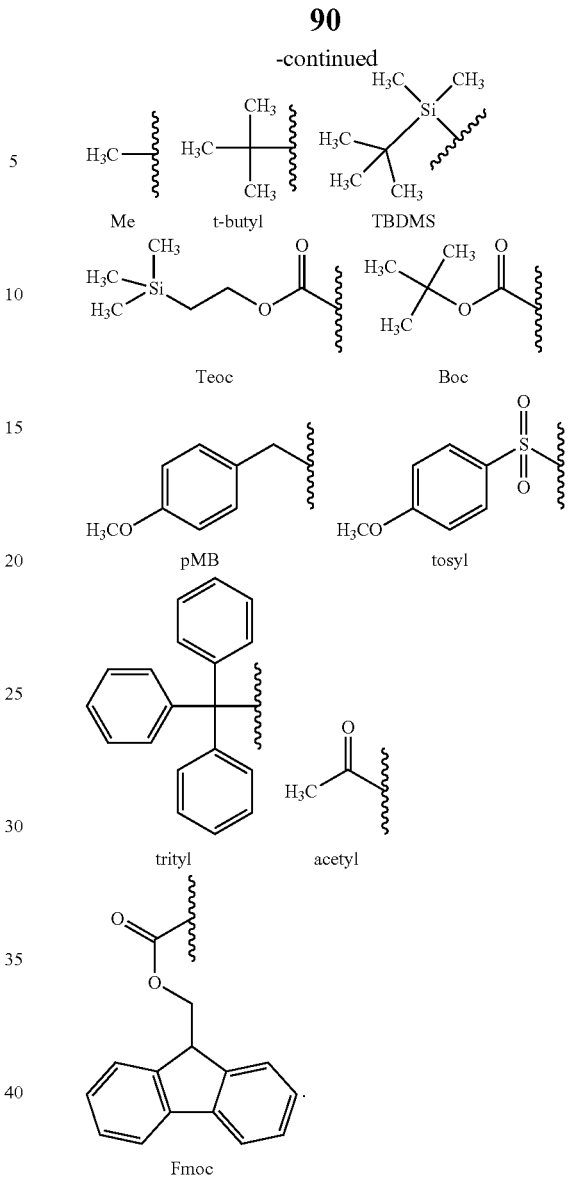

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

High Throughput Screening and SAR

The presently disclosed subject matter provides a library of bicyclic heterocyclic compounds having an imidazo[1,2-b]pyridazine scaffold as a central core, which may act as inhibitors of human neutral sphingomyelinase 2 (hnSMase2).

The initial screening of the IOCB compound library against hnSMase2 resulted in the discovery of two compounds with a closely related structures—compounds 1 (I35MCK380) and 2 (I35MCK388) (see FIG. 1).

The SAR study consisted of several steps. Firstly, the central imidazo[1,2-b]pyridazine core was substituted by numerous other bicyclic heterocycles including [1,2,3]triazolo[4,5-d]pyrimidine, purine, pyrazolo[1,5-a]pyrimidine, furo[3,2-b]pyridine, pyrazolo[5,4-d]pyrimidine, thieno[3,2-d]pyrimidine, thieno[3,4-d]pyrimidine and others. Since imidazo[1,2-b]pyridazine proved to be the only effective scaffold, the study was continued by gradual modification of various positions on this core to obtain a library of potential inhibitors of hnSMase2 (FIG. 2).

The synthetic strategy was generally as follows: Dichloroderivative SM-1 was used as a starting material (J. Med. Chem, 2015, 58, 3767). Halogen atom in position 8 was replaced by (R)—N-(pyrrolidin-3-yl)acetamide to give derivative SM-2. Second chlorine atom in position 6 was then converted to a methyl by treatment with trimethylaluminum-DABCO complex to afford compound 3, which was in the last step iodinated by NIS in dichloromethane. Compound SM-4 served as a starting material for synthesis of majority of the final compounds. Alternative starting material SM-6 bearing chlorine in position 6 and iodine in position 3 was prepared from derivative SM-5 (J. Med. Chem, 2015, 58, 3767) using same conditions as in the preparation of SM-2.

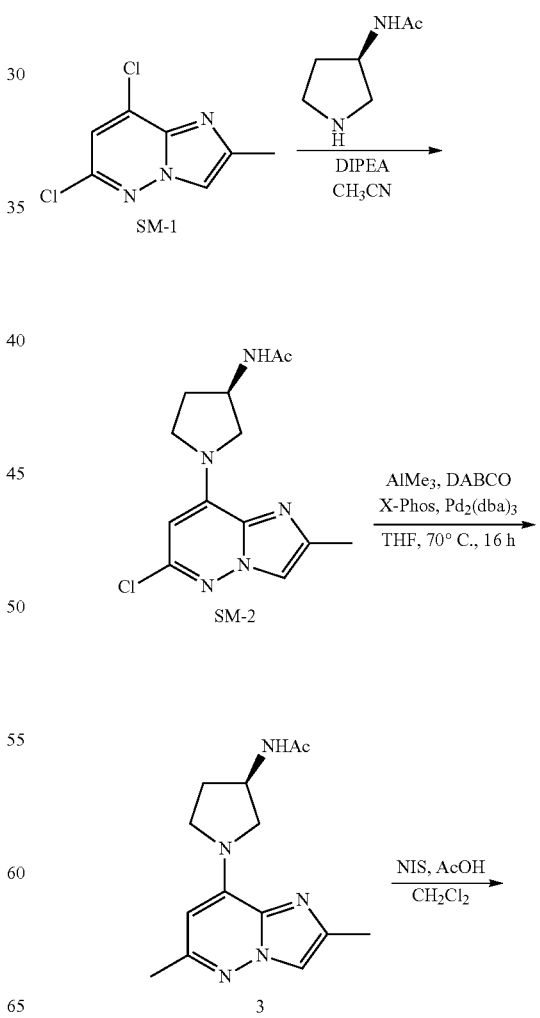

Scheme 1

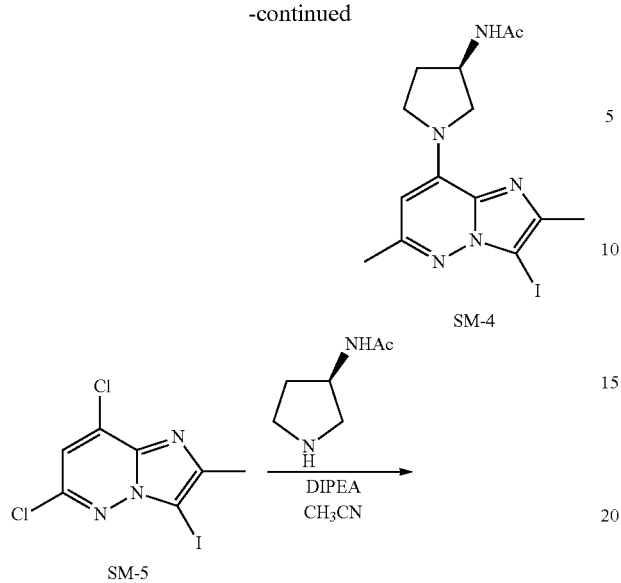

SM-4

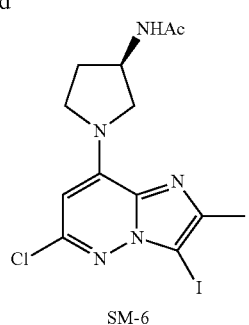

SM-6

Methods for introducing aryl or hetaryl substituents to position 3 on the central core are depicted in Scheme 2. Using method A (Suzuki coupling) or method C (Stille coupling) on SM-4 led to a set of final compounds 1 and 4-18. For preparation of the chloro derivative SM-7 method B was used. Compound SM-7 then served as a starting material for preparation of derivatives with modified position 6.

Scheme 2

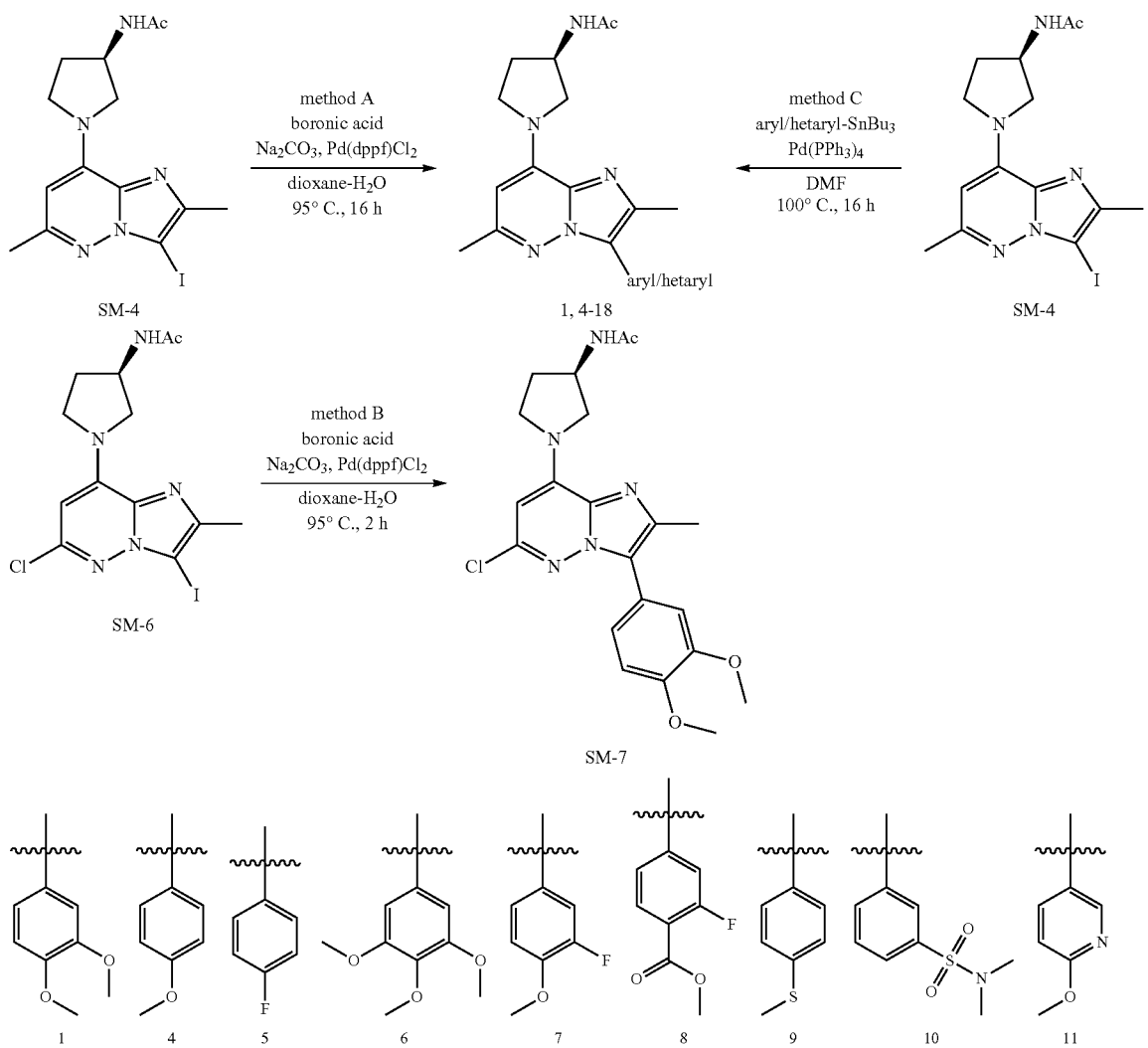

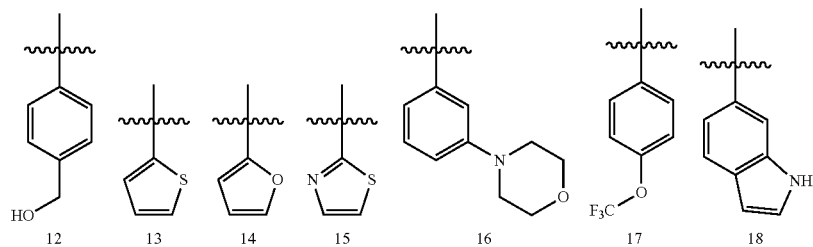

Compound 2, the opposite enantiomer to compound 1, was synthesized using the same reaction conditions, only (S)—N-(pyrrolidin-3-yl)acetamide was used instead of (R)-enantiomer (Scheme 3).

Scheme 3

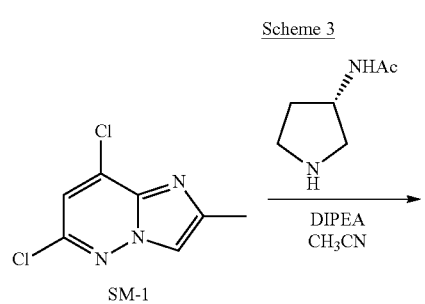

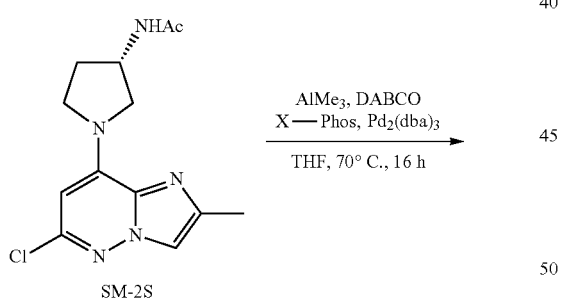

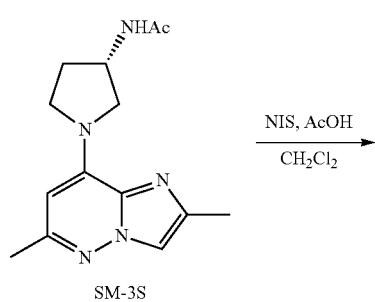

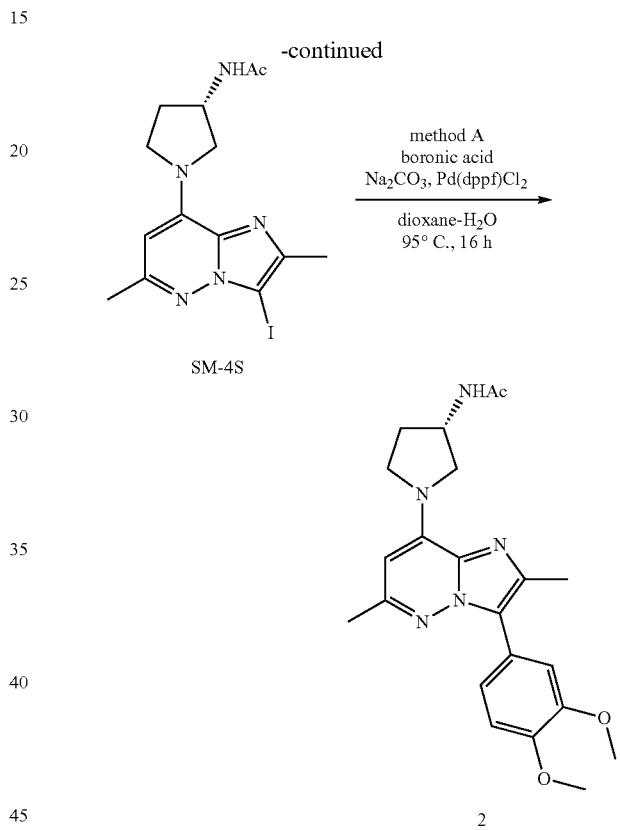

Since the initial studies suggested that the substituent at position 8 of the central core can significantly influence the activity, derivatives of compounds 1 and 7 bearing various substituents on the amino group of the pyrrolidine ring (Scheme 4) also were prepared using the following methods.

Firstly, the acetyl group was removed under acidic conditions, furnishing hydrochlorides of compounds 1a and 7a, which served as a starting material for subsequent derivatizations. Four different modifications were chosen, phenyl urea (19), sulfonyl derivatives (20-30), acyl derivatives (31-37) and carbamates (39-43), which were then easily accessible by reaction of the compounds 1a or 7a, respectively, with phenylisocyanate, variously substituted sulfonyl chlorides, acyl chlorides and carbamates, respectively, under basic conditions. In some specific cases, the HATU coupling agent and carboxylic acids were used. Compounds 40-42 were prepared by slightly modified method. Firstly, p-nitrophenylcarbamate was prepared and this intermediate was immediately treated with appropriate alcohol or phenol.

Scheme 4

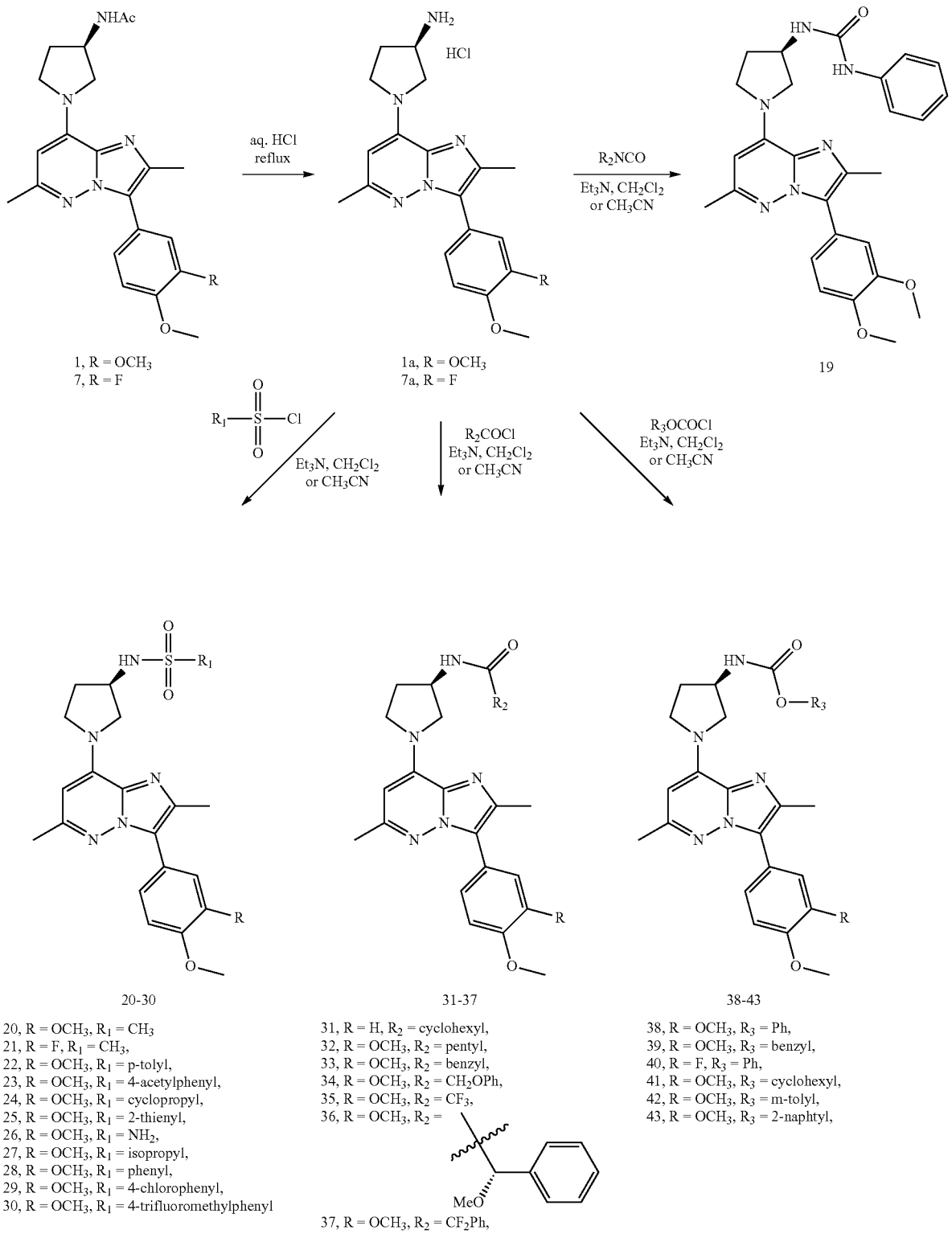

20-30
20, R = OCH₃, R₁ = CH₃
21, R = F, R₁ = CH₃,
22, R = OCH₃, R₁ = p-tolyl,
23, R = OCH₃, R₁ = 4-acetylphenyl,
24, R = OCH₃, R₁ = cyclopropyl,
25, R = OCH₃, R₁ = 2-thienyl,
26, R = OCH₃, R₁ = NH₂,
27, R = OCH₃, R₁ = isopropyl,
28, R = OCH₃, R₁ = phenyl,
29, R = OCH₃, R₁ = 4-chlorophenyl,
30, R = OCH₃, R₁ = 4-trifluoromethylphenyl 31-37
31, R = H, R₂ = cyclohexyl,
32, R = OCH₃, R₂ = pentyl,
33, R = OCH₃, R₂ = benzyl,
34, R = OCH₃, R₂ = CH₂OPh,
35, R = OCH₃, R₂ = CF₃,
36, R = OCH₃, R₂ =

37, R = OCH₃, R₂ = CF₂Ph, 38-43
38, R = OCH₃, R₃ = Ph,
39, R = OCH₃, R₃ = benzyl,
40, R = F, R₃ = Ph,
41, R = OCH₃, R₃ = cyclohexyl,
42, R = OCH₃, R₃ = m-tolyl,
43, R = OCH₃, R₃ = 2-naphtyl,

Compounds with Modified Position 8

Derivatives bearing differently modified amines were prepared as depicted in scheme 5. Firstly the chlorine atom in position 8 was exchanged under $S_NAr$ conditions (DIPEA, $CH_3CN$ or ethanol). Dimethoxyphenyl substituent was then introduced to position 3 by Suzuki coupling, according to the general method B, which was followed by methylation using trimethylaluminum-DABCO complex as a methylation reagent.

Scheme 5

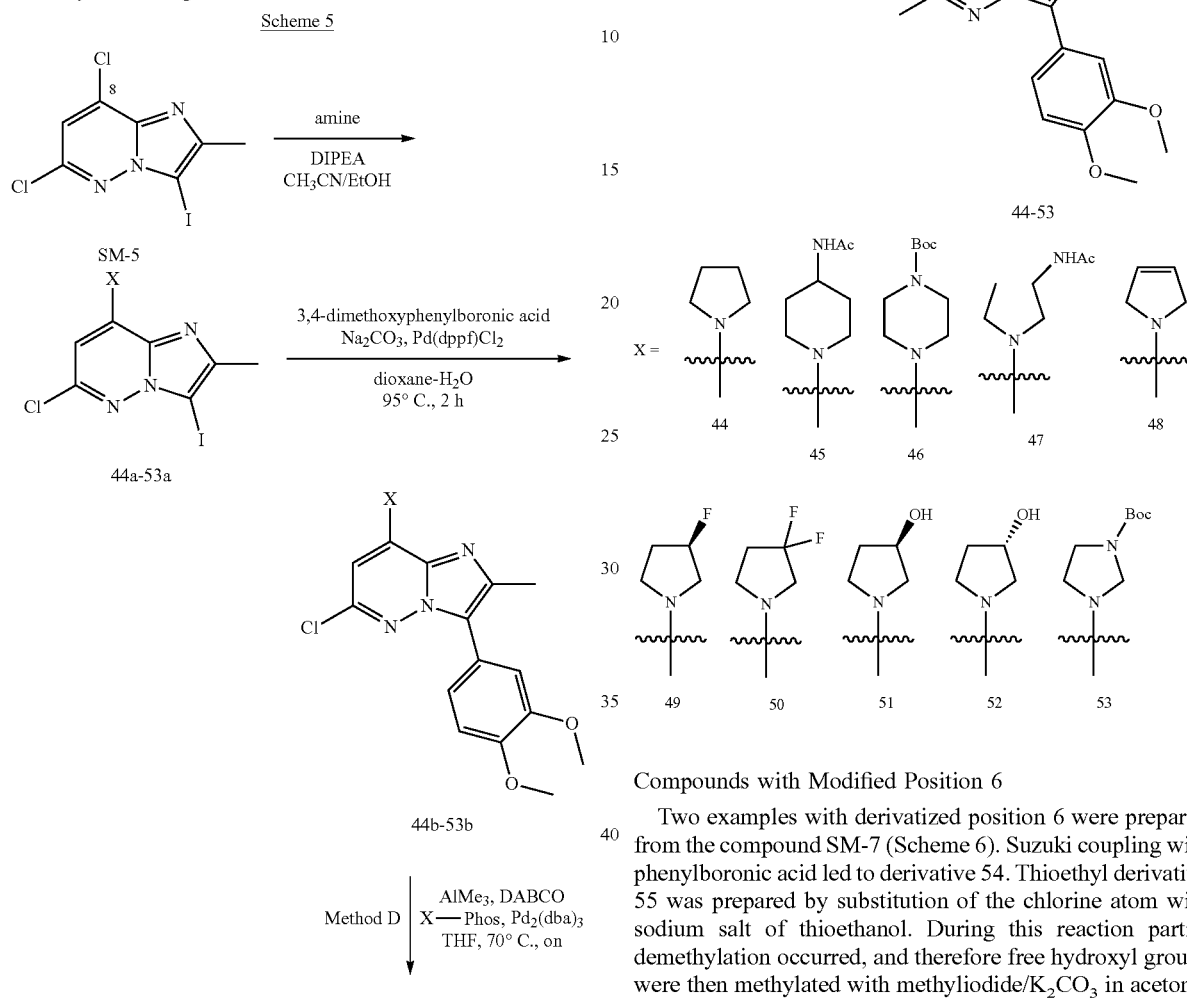

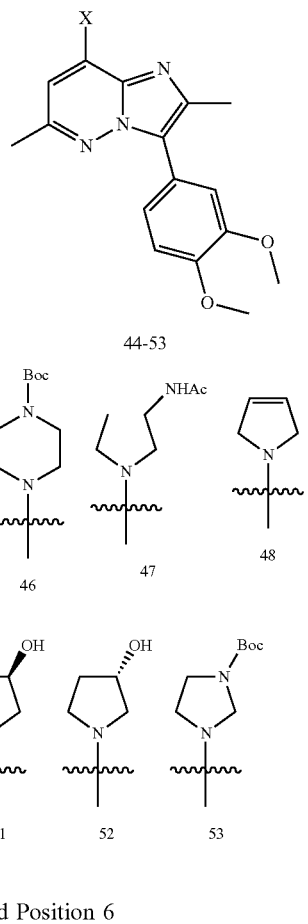

Compounds with Modified Position 6

Two examples with derivatized position 6 were prepared from the compound SM-7 (Scheme 6). Suzuki coupling with phenylboronic acid led to derivative 54. Thioethyl derivative 55 was prepared by substitution of the chlorine atom with sodium salt of thioethanol. During this reaction partial demethylation occurred, and therefore free hydroxyl groups were then methylated with methyliodide/$K_2CO_3$ in acetone.

Scheme 6

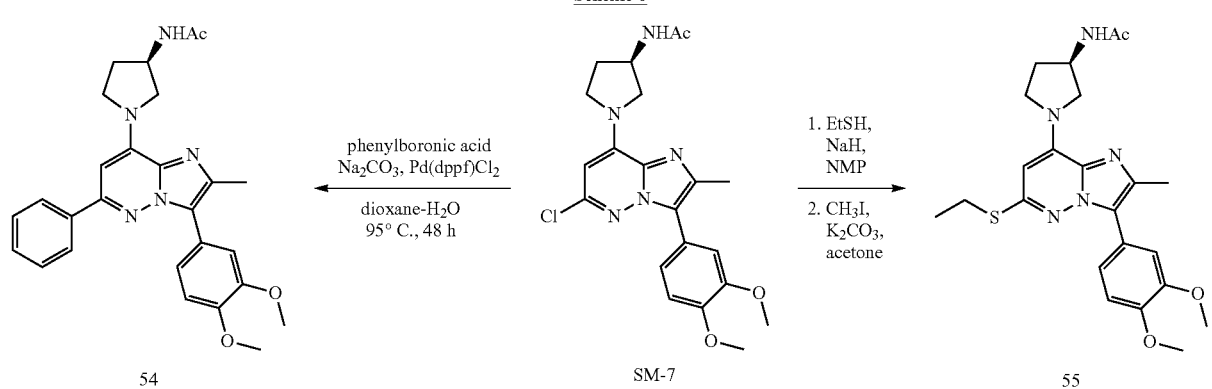

Compounds with Further Modified Position 3 on Pyrrolidine Ring

Further modifications on pyrrolidine ring were achieved under Mitsunobu conditions applied on the hydroxy derivative 52 (Scheme 7). S-acetyl derivative 56 and azido compound 58 were prepared. Huisgen cycloaddition of the azido compound 58 with phenylacetylene afforded triazolo derivative 59 under standard conditions (copper sulphate/sodium ascorbate). Morpholino derivative 57 was prepared by closing the morpholino ring on an amino group of 1a using bis 2,2'-dichloroethylether. Acetylation (Ac$_2$O) of the hydroxy group in compound 51 afforded O-acetyl derivative 60.

Scheme 7

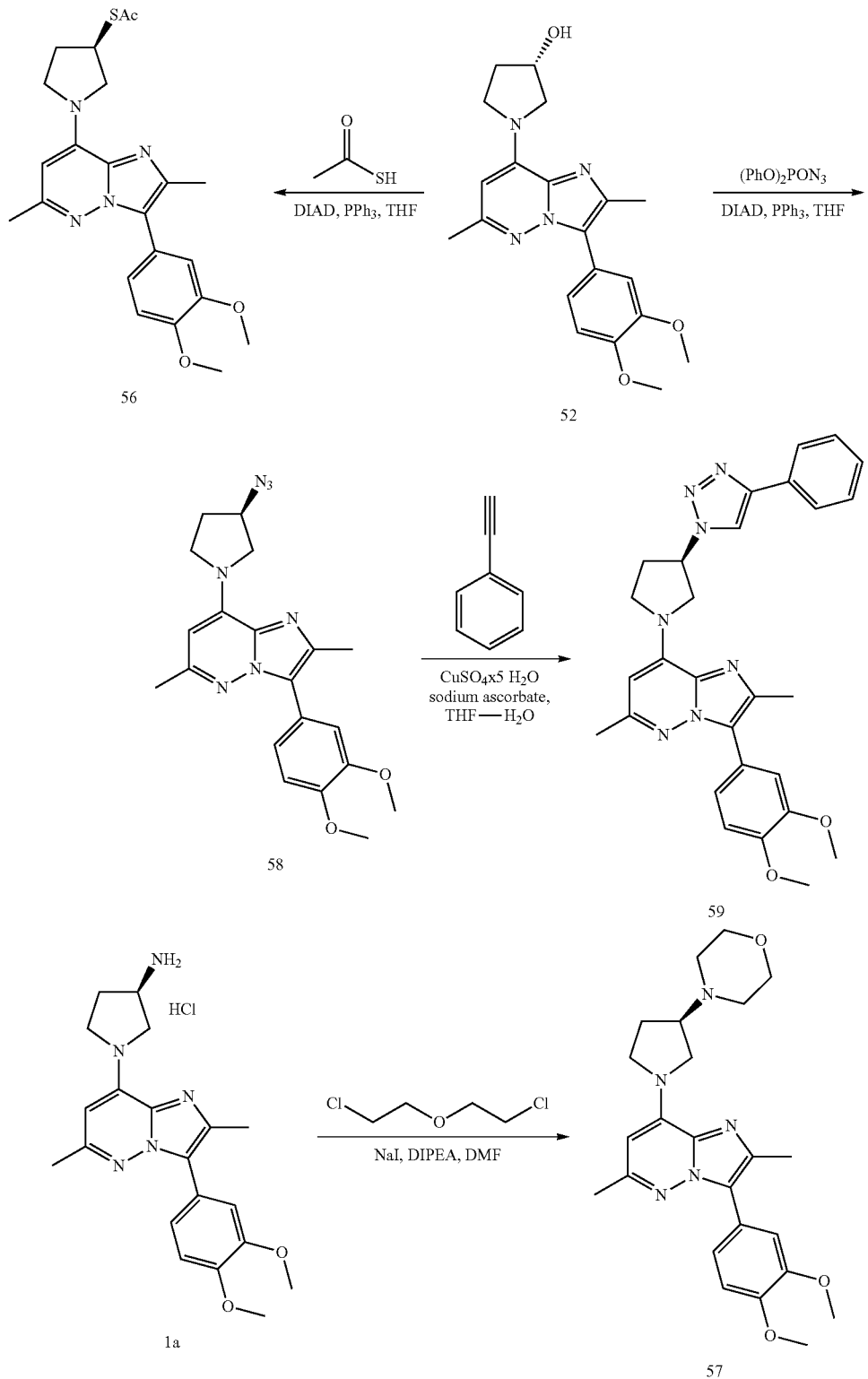

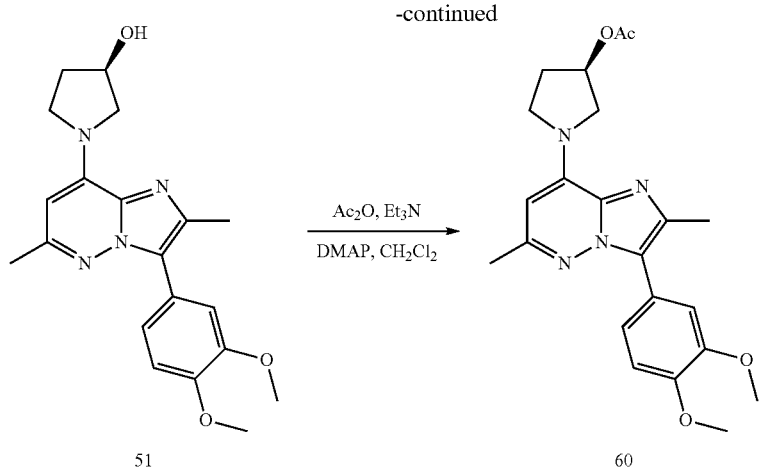

Compound (61) with no substituent in position 2 was prepared by following the synthetic route described in Scheme 8. Firstly, chlorine in position 8 in compound 60b (prepared by condensation of 60a with aq. chloroacetaldehyde) was replaced by (R)—N-(pyrrolidin-3-yl)acetamide and obtained substrate 60c was then converted to chloro intermediate 60d by Suzuki coupling (method A). Position 6 was then methylated with trimethylaluminum-DABCO complex (method D).

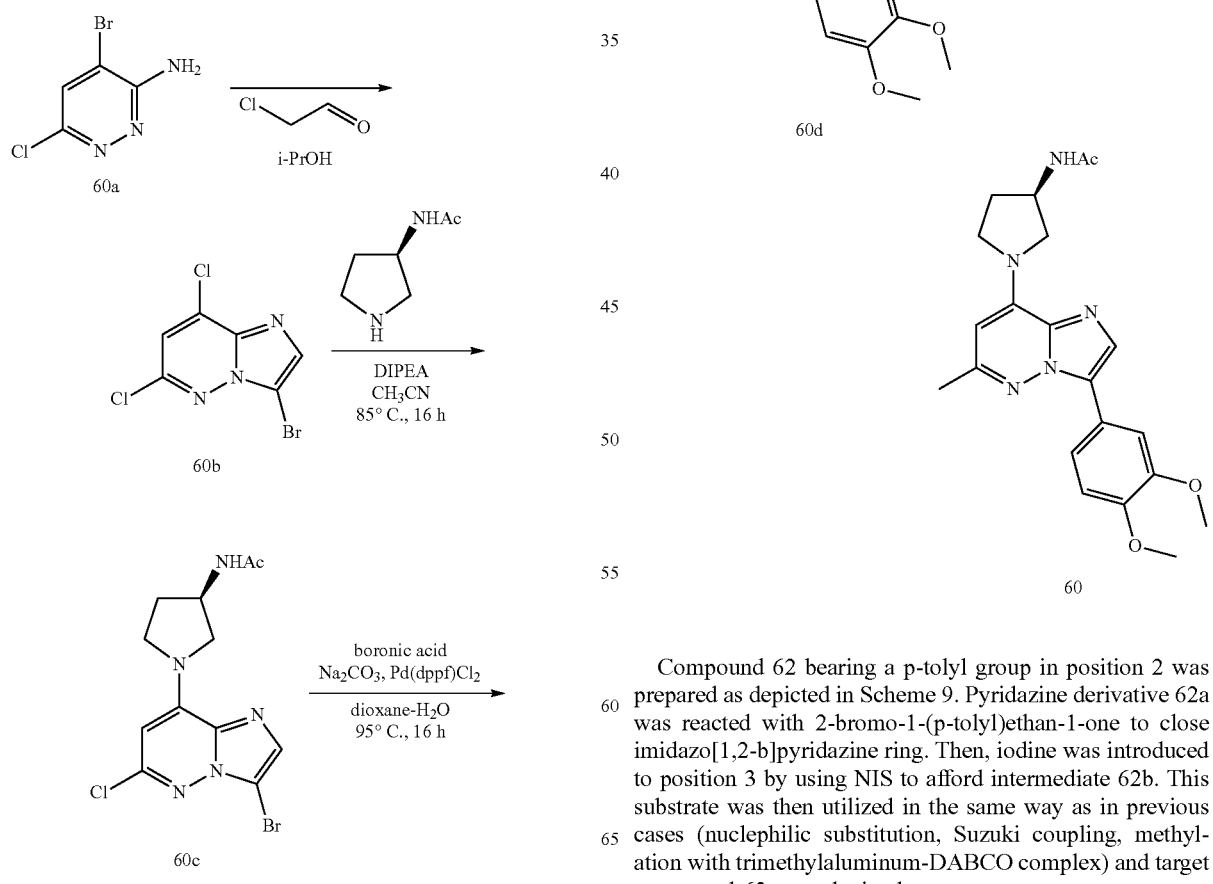

Compound 62 bearing a p-tolyl group in position 2 was prepared as depicted in Scheme 9. Pyridazine derivative 62a was reacted with 2-bromo-1-(p-tolyl)ethan-1-one to close imidazo[1,2-b]pyridazine ring. Then, iodine was introduced to position 3 by using NIS to afford intermediate 62b. This substrate was then utilized in the same way as in previous cases (nuclephilic substitution, Suzuki coupling, methylation with trimethylaluminum-DABCO complex) and target compound 62 was obtained.

Scheme 9
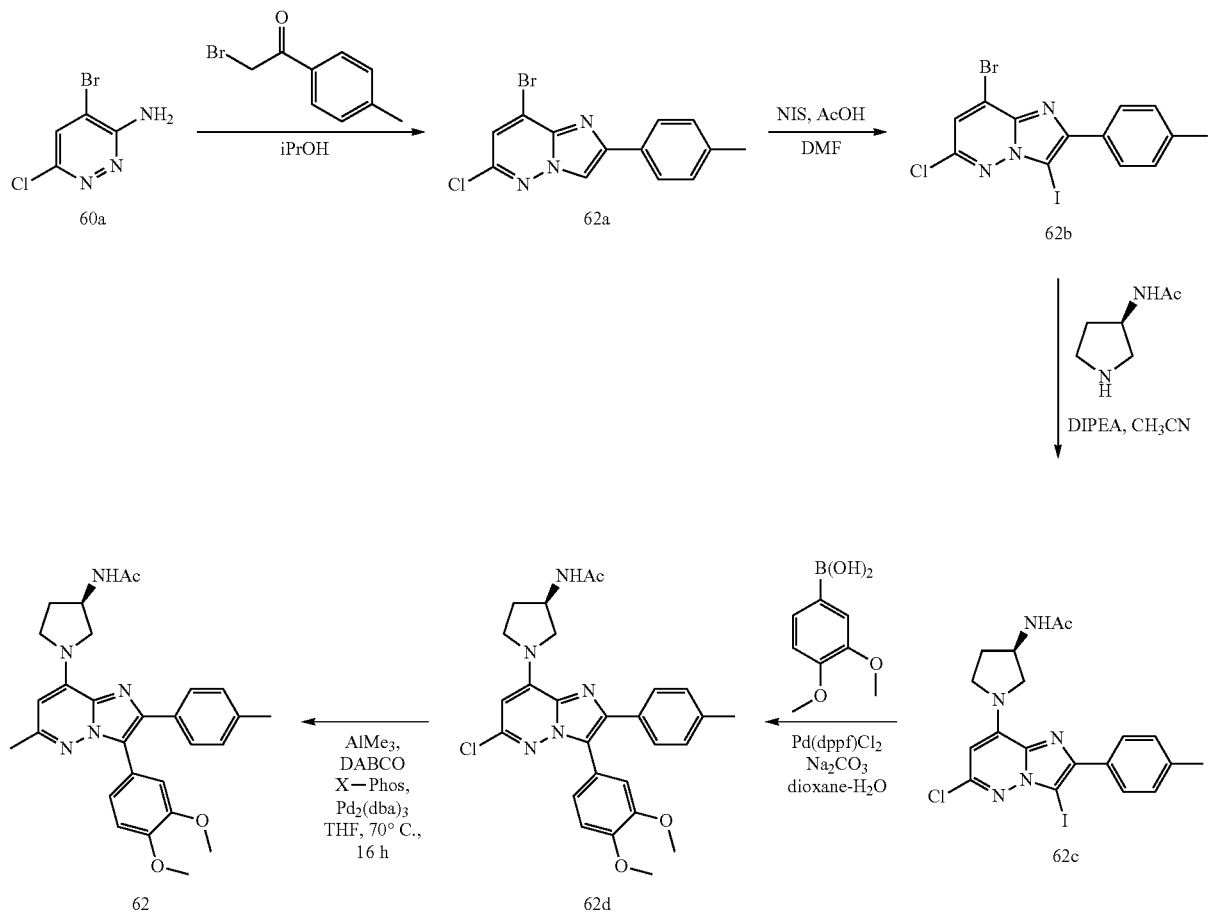
Two more modifiactions were prepared (Scheme 10). Boc-protected derivative 46 was converted to cyclohexanoyl derivative 63. To increase solubility of compound 18, the NH group was methylated to obtain derivative 64.
Scheme 10
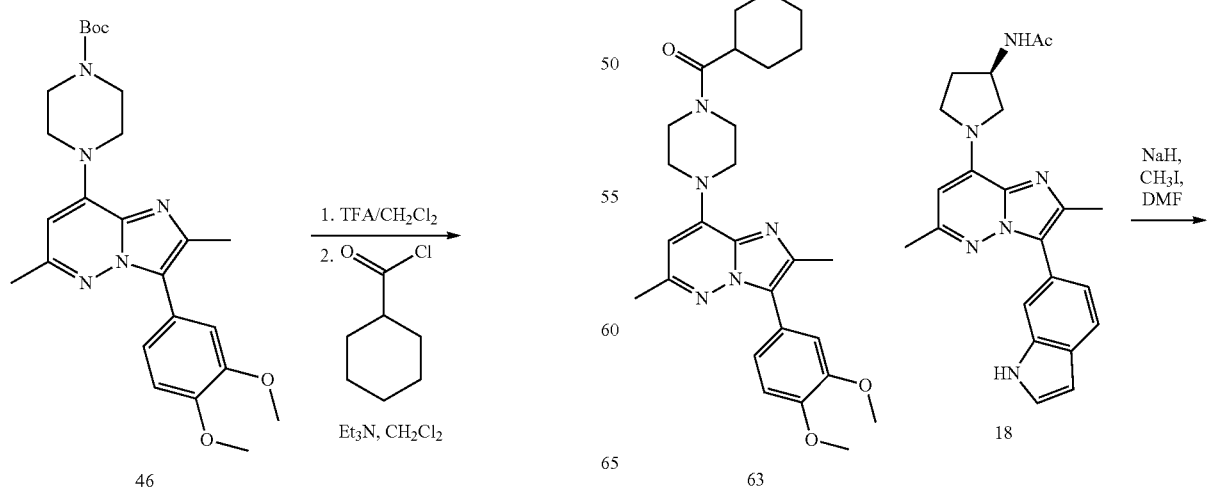
-continued

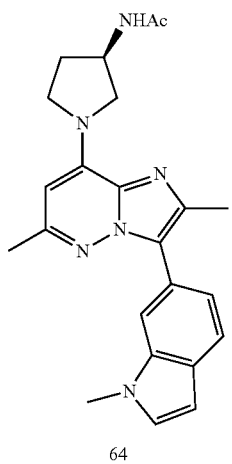

64

8-azapurine derivative 65 (Scheme 11) as a model compound with similar PK characteristic and also as a negative control for the experiments. Pyrrolidine substituent was introduced to the scaffold by nucleophilic substitution of the chlorine in 6-chloro-8-azapurine derivative (*Bioorg. Med. Chem. Lett.*, 2016, 26, 2706). Boc protecting group was then cleaved under acidic conditions and free amino group was acetylated to afford the target molecule.

Example 2

Chemical Syntheses and Characterization

NMR spectra (δ, ppm; J, Hz) were measured on a Bruker Avance 11-400 instrument (400.0 MHz for $^1$H and 101 MHz for $^{13}$C) in hexadeuterated dimethyl sulfoxide or $CDCl_3$ and referenced to the solvent signal (δ 2.50 and 39.70, respectively, 7.26 and 77.16). Mass spectra were measured on a LTQ Orbitrap XL (Thermo Fisher Scientific) using electrospray ionization (ESI). Column chromatography was performed on Silica gel 60 (Fluka) and thin-layer chromatography (TLC) on Silica gel 60 F254 foils (Merck). Solvents were evaporated at 2 kPa and bath temperature 30-60° C.; the compounds were dried at 13 Pa and 50° C. For all the tested compounds satisfactory elemental analysis was obtained supporting >95% purity. Optical rotation was measured on polarimeter Autopol IV (Rudolph Research Analytical) at 589 nm wavelength in chloroform or DMSO. UPLC samples were measured on Waters UPLC H-Class Core System, (column Waters Acquity UPLC BEH C18 1.7 μm, 2.1×100 mm), Waters Acquity UPLC PDA detector, Mass spectrometer Waters SQD2 and MassLynx Mass Spectrometry Software. For reverse-phase flash column chromatography, C-18 RediSep Rf column Teledyne ISCO (50 g) were used.

Synthesis of Intermediates SM-4, SM-6

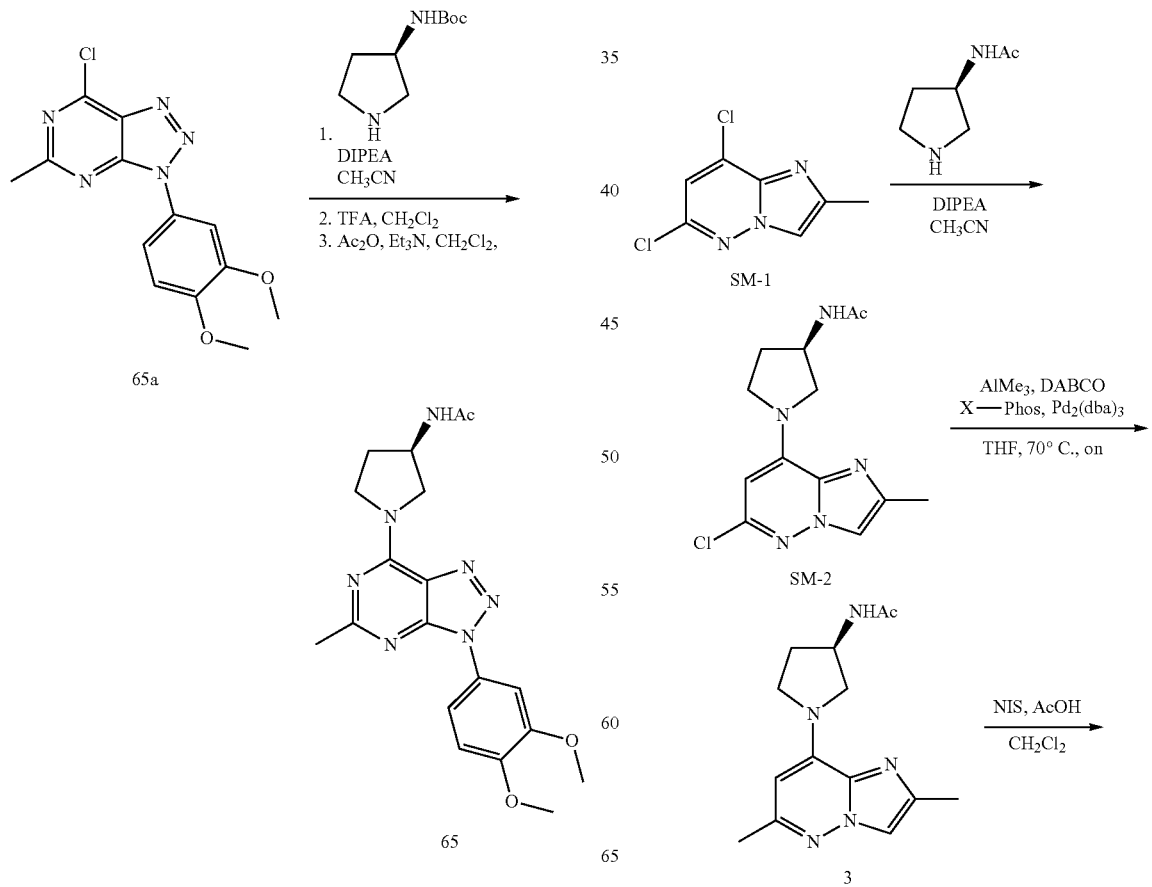

Scheme 11

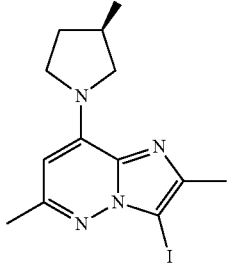

SM-4

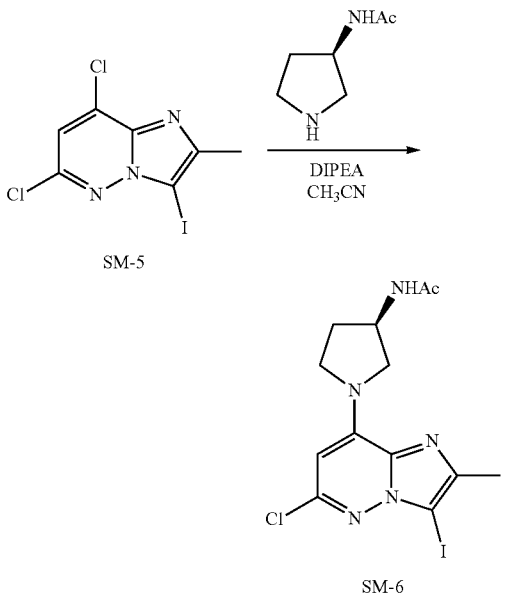

(R)—N-(1-(6-chloro-2-methylimidazo[1,2-b]pyridazin-8-yl)pyrrolidin-3-yl)acetamide (SM-2)

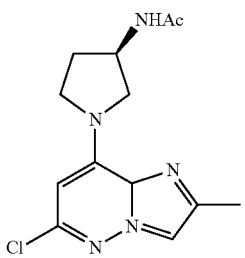

Mixture of starting material SM-1(600 mg, 2.97 mmol), (R)—N-(pyrrolidin-3-yl)acetamide (457 mg, 3.56 mmol), DIPEA (0.79 mL, 4.54 mmol) in acetonitrile (10 mL) was heated at 85° C. for 16 hours, then cooled down and evaporated. Residue was purified by column chromatography on silica gel (100 g, ethyl acetate→ethyl acetate-ethanol 7:1) to yield 864 mg (quantitative). Sample for analysis was obtained by crystallization from methanol. $^1$H NMR (400 MHz, d6-DMSO) δ 1.81 (s, 3H), 1.83-1.96 (m, 1H), 2.07-2.23 (m, 1H), 2.30 (d, J=0.9 Hz, 3H), 3.30-3.80 (br s, 1H), 3.85-4.48 (br s+m, 3H), 5.91 (s, 1H), 7.75 (d, J=0.9 Hz, 1H), 8.17 (d, J=6.5 Hz, 1H). $^{13}$C NMR (101 MHz, d6-DMSO) δ 14.5, 22.7, 92.7, 114.8, 132.0, 139.7, 142.0, 146.5, 169.4 (peaks on pyrrolidine ring were not detected). HRMS calcd for $C_{13}H_{17}ClN_5O$ m/z: 294.1116 (M+H)$^+$, found 294.1117.

(R)—N-(1-(2,6-dimethylimidazo[1,2-b]pyridazin-8-yl)pyrrolidin-3-yl)acetamide (3)

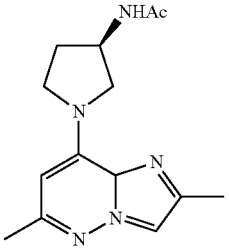

To a solution of DABCO (448 mg, 4 mmol) in 15 mL freshly distilled THF, AlMe$_3$ (2M in hexanes, 4 mL, 8 mmol) was added dropwise and the mixture was stirred at r.t. for 30 minutes under argon atmosphere. A solution of SM-2 (1.4 g, 4.77 mmol), Pd$_2$(dba)$_3$ (224 mg, 0.27 mmol) and X-Phos (234 mg, 0.49 mmol) in 80 mL freshly THF was subsequently added to the solution and the reaction mixture was stirred at 75° C. overnight under argon atmosphere. The mixture was cooled to 0° C., quenched with sat. NH$_4$Cl (16 mL), diluted with acetone and ethyl acetate and filtered through Celite. The celite pad was thoroughly washed with acetone and ethyl acetate. The filtrate was evaporated and the residue was purified by silica gel column chromatography (200 g, chloroform-ethanol 10:1) yielding compound 5 (1.42 g, 92%) as an off-white solid. Analytical sample was obtained by crystallization from ethyl acetate. $^1$H NMR (400 MHz, d6-DMSO) δ 1.81 (s, 3H), 1.84-1.93 (m, 1H), 2.08-2.19 (m, 1H), 2.27 (s, 3H), 2.28 (d, J=0.8 Hz, 3H), 3.77 (br s, 3H), 4.03 (br s, 1H), 4.27-4.37 (m, 1H), 5.71 (s, 1H), 7.62 (d, J=0.8 Hz, 1H), 8.16 (d, J=6.6 Hz, 1H). $^{13}$C NMR (101 MHz, d6-DMSO) δ 14.6, 21.6, 22.7, 30.5, 47.6, 48.8, 55.2, 93.6, 113.8, 132.6, 138.7, 141.0, 151.6, 169.4. HRMS calcd for $C_{14}H_{20}N_5O$ m/z: 274.1662 (M+H)$^+$, found 274.1663.

(R)—N-(1-(3-iodo-2,6-dimethylimidazo[1,2-b]pyridazin-8-yl)pyrrolidin-3-yl)acetamide (SM-4)

A solution of compound 3 (1.22 g, 4.5 mmol) in dichloromethane (50 mL) with acetic acid (0.19 mL) was cooled down to 0° C. then N-iodosuccinimide (1.1 g, 4.89 mmol) was added in one portion and the reaction mixture was stirred overnight (0° C.→r.t.). Reaction mixture was diluted with ethyl acetate (700 mL) and washed with sat. aq. NaHCO$_3$ (200 mL) and sat. aq. Na$_2$S$_2$O$_3$ (200 mL). Organic phase was dried over Na$_2$SO$_4$ and evaporated. The residue was purified by silica gel column chromatography (200 g, chloroform-ethyl acetate 20:1→15:1) which furnished compound SM-4 (1.53 g, 85%) as an off-white solid. Recrystallization from hot acetone yielded an analytically pure sample. $^1$H NMR (400 MHz, d6-DMSO) δ 1.81 (s, 3H), 1.83-1.93 (m, 1H), 2.09-2.19 (m, 1H), 2.31 (s, 3H), 2.34 (s, 3H), 3.77 (br s, 3H), 4.01 (br s, 1H), 4.27-4.38 (m, 1H), 5.84 (s, 1H), 8.16 (d, J=6.6 Hz, 1H). $^{13}$C NMR (101 MHz, d6-DMSO) δ 15.1, 21.5, 22.8, 30.5, 48.8, 55.3, 70.9, 94.7, 135.2, 140.8, 142.6, 152.2, 169.4 (one CH$_2$ peak was not detected). HRMS calcd for $C_{14}H_{19}IN_5O$ m/z: 400.0629 (M+H)$^+$, found 400.0630.

(R)—N-(1-(6-chloro-3-iodo-2-methylimidazo[1,2-b]pyridazin-8-yl)pyrrolidin-3-yl)acetamide (SM-6)

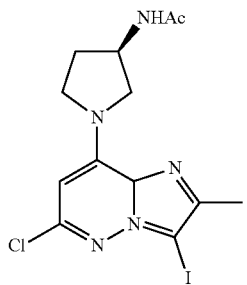

Compound SM-5 (2 g, 6.1 mmol), (R)—N-(pyrrolidin-3-yl)acetamide (860 mg, 6.71 mmol), DIPEA (1.3 mL, 7.3 mmol) was dissolved in a mixture of acetonitrile (40 mL) and ethanol (10 mL). Reaction mixture was heated at 85° C. for 16 hours and cooled down. Precipitated product was filtered-off and washed with acetonitrile (2.436 g, 96%). $^1$H NMR (400 MHz, d6-DMSO) δ 1.83 (s, 3H), 1.90-1.98 (m, 1H), 2.14-2.19 (m, 1H), 2.35 (s, 3H), 3.94-3.76 (m, 3H), 4.09 (br s, 1H), 4.35-4.44 (m, 1H), 5.99 (s, 1H), 7.91 (br s, 1H). $^{13}$C NMR (101 MHz, d6-DMSO) δ 14.6, 22.3, 30.1, 47.9, 48.4, 55.1, 71.1, 93.5, 134.6, 141.8, 143.4, 146.8, 169.0. HRMS calcd for $C_{13}H_{16}ClIN_5O$ m/z: 420.0083 (M+H)$^+$, found 420.0082.

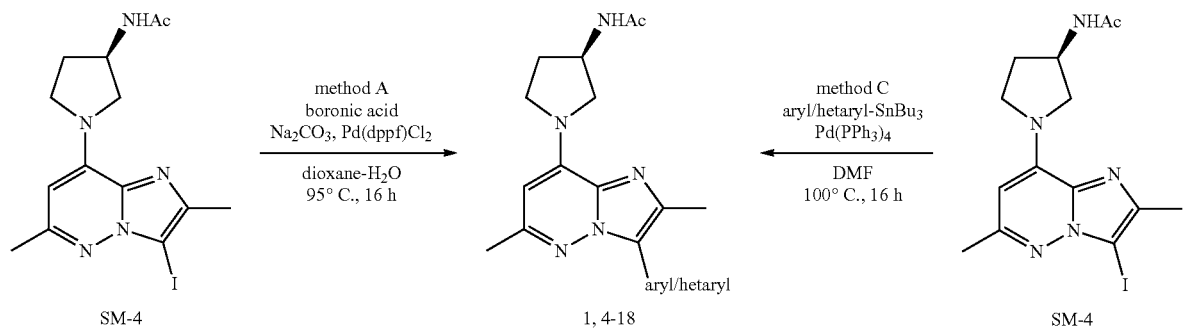

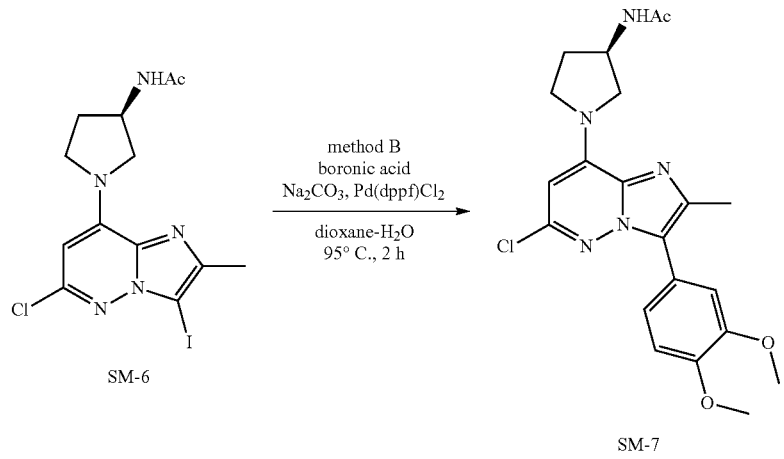

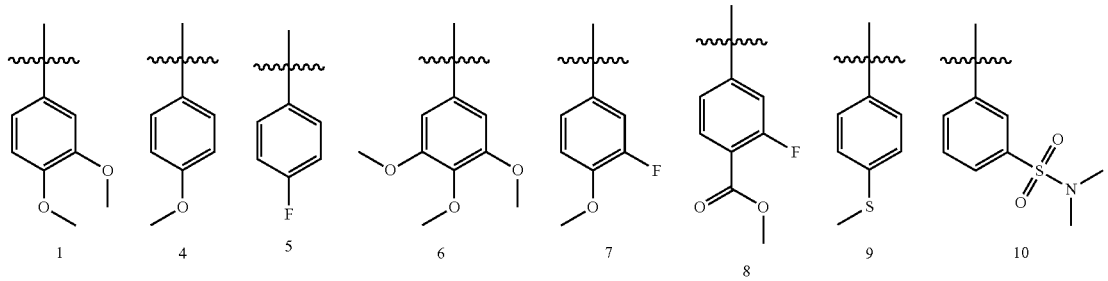

-continued

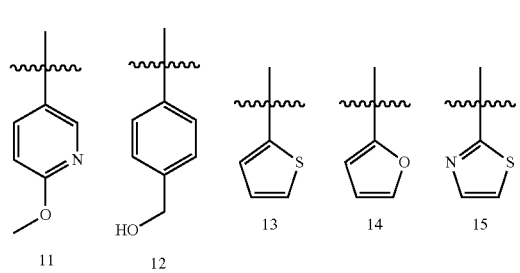
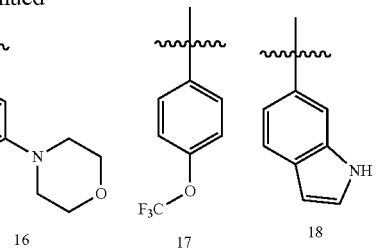

General Procedure for Suzuki Coupling with Compound SM-4 (Method A)

Suspension of starting material SM-4 (1 mmol), appropriate boronic acid (1.5 mmol), sodium carbonate (2 mmol) in dioxane-water (10 mL, 4:1) was three times purged argon. Then Pd(dppf)$_2$Cl$_2$ (0.1 mmol) was added and again flask was purged with argon. Reaction mixture was then heated to 95° C. overnight, cooled down and diluted with ethyl acetate or chloroform (300 mL). The suspension was dried over Na$_2$SO$_4$ and evaporated. Final compound was isolated by column chromatography and then crystallized.

General Procedure for Suzuki Coupling with Compound SM-6 (Method B)

Suspension of starting material SM-6 (1 mmol), appropriate boronic acid (1.2 mmol), sodium carbonate (1.5 mmol) in dioxane-water (10 mL, 4:1) was three times purged argon. Then Pd(dppf)$_2$Cl$_2$ (0.05-0.1 mmol) was added and again flask was purged with argon. Reaction mixture was then heated to 95° C. for 2 hours, cooled down and diluted with ethyl acetate or chloroform (300 mL). The mixture was dried over Na$_2$SO$_4$ and evaporated. Product was isolated by column chromatography and then crystallized.

General Procedure for Stille Coupling with Compound SM-4 (Method C)

Mixture of compound SM-4 (0.5 mmol) and tributyltin reagent (0.65 mmol) in DMF (10 ml) was degassed and purged with argon. To this mixture Pd(PPh$_3$)$_4$ (58 mg, 10%) was added and reaction mixture was purged with argon and then heated to 100° C. for 16 hours. Reaction mixture was cooled down, diluted with ethyl acetate (300 mL), dried over Na$_2$SO$_4$ and evaporated. Product was isolated by column chromatography and then crystallized.

(R)—N-(1-(3-(3,4-dimethoxyphenyl)-2,6-dimethylimidazo[1,2-b]pyridazin-8-yl)pyrrolidin-3-yl)acetamide (1)

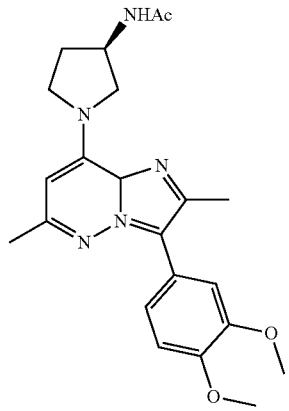

Prepared by method A from 3,4-dimethoxyphenylboronic acid in 64%. Chromatography:CHCl$_3$-ethanol 15:1, crystallization from methanol). [α]$_D^{20}$=+6.5 (c 0.245, CHCl$_3$). $^1$H NMR (400 MHz, d6-DMSO) δ 1.84 (s, 3H), 1.90-1.98 (m, 1H), 2.16-2.24 (m, 1H,), 2.30 (s, 3H), 2.41 (s, 3H), 3.76-3.86 (m, 8H), 3.93 (m, 1H), 4.12 (m, 1H), 4.35-4.41 (m, 1H, H-3), 5.78 (s, 1H, H-7'), 7.07 (d, J=8.3 Hz, 1H), 7.19 (dd, J=2.0, J=8.3 Hz, 1H), 7.32 (d, J=2.0 Hz, 1H), 7.94 (d, J=6.1 Hz, 1H). $^{13}$C NMR (101 MHz, d6-DMSO) δ 14.6, 21.2, 22.3, 30.3, 47.4, 48.5, 54.8, 55.7, 55.8, 93.6, 112.3, 113.9, 121.9, 122.4, 123.6, 131.7, 136.3, 141.0, 148.4, 148.5, 151.0, 169.0. HRMS calcd for C$_{22}$H$_{27}$N$_5$O$_3$ m/z: 410.2187 (M+H)$^+$, found 410.2186.

(S)—N-(1-(3-(3,4-dimethoxyphenyl)-2,6-dimethylimidazo[1,2-b]pyridazin-8-yl)pyrrolidin-3-yl)acetamide (2)

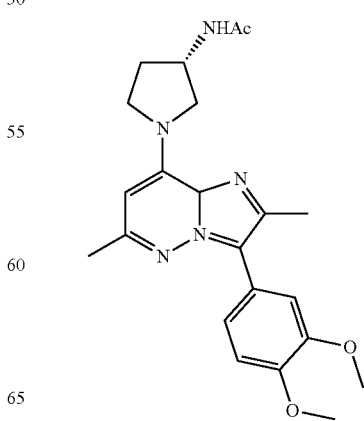

(S)-Enantiomer was prepared following the same reaction sequence as for compound 1. As an amine was used commercially available (S)—N-(pyrrolidin-3-yl)acetamide. All the spectra were identical to those for (R)-enantiomers. $[\alpha]_D^{90}=-2.0$ (c 0.245, CHCl$_3$).

(R)—N-(1-(3-(4-methoxyphenyl)-2,6-dimethylimidazo[1,2-b]pyridazin-8-yl)pyrrolidin-3-yl)acetamide (4)

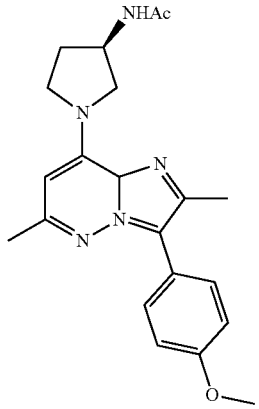

Prepared by method A from 4-methoxybenzeneboronic acid in 64%. Chromatography:CHCl$_3$-ethanol 15:1, crystallization from ethyl acetate). $[\alpha]_D^{20}=+2.5$ (c 0.258, CHCl$_3$). $^1$H NMR (400 MHz, d6-DMSO) δ 1.82 (s, 3H), 1.86-1.95 (m, 1H), 2.10-2.22 (m, 1H), 2.27 (s, 1H), 2.36 (s, 1H), 3.63-3.97 (br s, 3H), 3.81 (s, 3H), 4.06 (br s, 1H), 4.35 (m, 1H), 5.79 (s, 1H), 7.06 (d, J=8.4 Hz, 1H), 7.56 (d, J=8.4 Hz, 1H), 8.17 (d, J=6.6 Hz, 1H). $^{13}$C NMR (101 MHz, d6-DMSO) δ 14.8, 21.7, 22.8, 30.5, 47.7, 48.8, 55.2, 55.3, 93.9, 113.9, 122.0, 123.8, 130.7, 131.9, 136.4, 141.1, 151.4, 158.6, 169.4. HRMS calcd for C$_{21}$H$_{26}$N$_5$O$_2$ m/z: 380.2081 (M+H)$^+$, found 380.3083.

(R)—N-(1-(3-(4-fluorophenyl)-2,6-dimethylimidazo[1,2-b]pyridazin-8-yl)pyrrolidin-3-yl)acetamide (5)

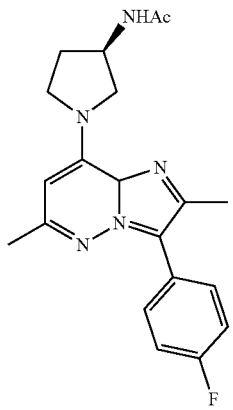

Prepared by method A 4-fluorobenzeneboronic acid in 55% yield. Chromatography:CHCl$_3$-ethanol 15:1, crystallization from acetone. $[\alpha]_D^{20}=+9.3$ (c 0.259, CHCl$_3$). $^1$H NMR (400 MHz, d6-DMSO) δ 1.82 (s, 1H), 1.86-1.96 (m, 1H), 2.11-2.23 (m, 1H), 2.28 (s, 1H), 2.37 (s, 1H), 4.31-4.39 (m, 1H), 5.82 (s, 1H), 7.39-7.25 (m, 1H), 7.77-7.62 (m, 1H), 8.17 (d, J=6.6 Hz, 1H). $^{13}$C NMR (101 MHz, d6-DMSO) δ 14.8, 21.7, 22.8, 30.5, 47.7, 48.8, 55.3, 94.2, 115.3 (d, J=21.4 Hz), 123.00, 126.1 (d, J=3.2 Hz), 131.4 (d, J=8.1 Hz), 132.2, 137.0, 141.1, 151.6, 161.4 (d, J=244.7 Hz), 169.4. HRMS calcd for C$_{20}$H$_{23}$N$_5$OF m/z: 368.1881 (M+H)$^+$, found 368.1882.

(R)—N-(1-(2,6-dimethyl-3-(3,4,5-trimethoxyphenyl)imidazo[1,2-b]pyridazin-8-yl)pyrrolidin-3-yl)acetamide (6)

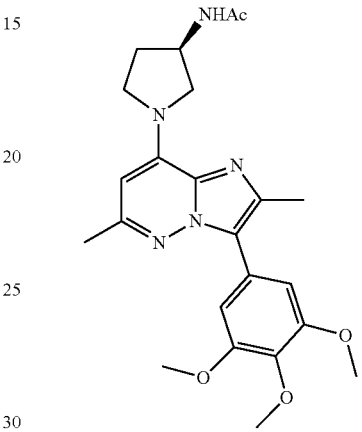

Prepared by method A from 3,4,5-trimethoxybenzeneboronic acid in 65% yield. Chromatography:CHCl$_3$-ethanol 15:1, crystallization from ethyl acetate. $[\alpha]_D^{20}=+12.5$ (c 0.240, CHCl$_3$). $^1$H NMR (400 MHz, d6-DMSO) δ 1.82 (s, 1H), 1.86-1.95 (m, 1H), 2.23-2.12 (m, 1H), 2.30 (s, 1H), 2.43 (s, 1H), 3.73 (s, 3H), 3.81 (s+br s, 9H), 4.08 (br s, 1H), 4.30-4.39 (m, 1H), 5.81 (s, 1H), 6.99 (s, 1H), 8.17 (d, J=6.6 Hz, 1H). $^{13}$C NMR (101 MHz, d6-DMSO) δ 15.2, 21.7, 22.8, 30.4, 48.8, 47.7*, 55.3, 56.1, 60.3, 94.0, 106.9, 123.8, 125.1, 132.1, 136.9, 137.0 141.2, 151.5, 152.8, 169.4. HRMS calcd for C$_{23}$H$_{30}$N$_5$O$_4$ m/z: 440.2292 (M+H)$^+$, found 440.2291.

(R)—N-(1-(3-(3-fluoro-4-methoxyphenyl)-2,6-dimethylimidazo[1,2-b]pyridazin-8-yl)pyrrolidin-3-yl)acetamide (7)

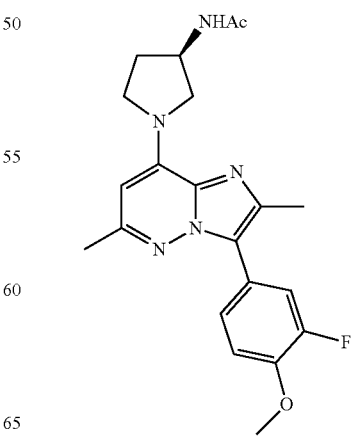

Prepared by method A from 3-fluoro-4-methoxybenzeneboronic acid in 49% yield. Chromatography:CHCl$_3$-ethanol 15:1, crystallization from ethanol. [α]$_D^{20}$=+8.1 (c 0.247, CHCl$_3$). $^1$H NMR (400 MHz, d6-DMSO) δ 1.85-1.96 (m, 1H), 1.82 (s, 3H), 2.10-2.21 (m, 1H), 2.29 (s, 3H), 2.38 (s, 3H), 3.81 (br s, 3H), 3.90 (s, 3H), 4.06 (br s, 1H), 4.29-4.38 (m, 1H), 5.81 (s, 1H), 7.28 (t, J~8.9, J~9 Hz, 1H), 7.42 (ddd, J=8.5, 2.1, 1.1 Hz, 1H), 7.54 (dd, J=12.9, 2.1 Hz, 1H), 8.17 (d, J=6.6 Hz, 1H). $^{13}$C NMR (101 MHz, d6-DMSO) δ 14.9, 21.7, 22.8, 30.5, 40.5, 47.5*, 48.8, 55.3, 56.2, 94.2, 113.8 (d, J=2.3 Hz), 116.5 (d, J=19.0 Hz), 122.5 (d, J=7.5 Hz), 122.6 (d, J=1.0 Hz), 125.7 (d, J=3.3 Hz), 132.1, 137.0, 141.1, 146.4 (d, J=10.6 Hz), 151.2 (d, J=243 Hz), 151.6, 169.4. HRMS calcd for C$_{21}$H$_{25}$N$_5$O$_2$F m/z: 398.1987 (M+H)$^+$, found 398.1988.

methyl (R)-4-(8-(3-acetamidopyrrolidin-1-yl)-2,6-dimethylimidazo[1,2-b]pyridazin-3-yl)-2-fluorobenzoate (8)

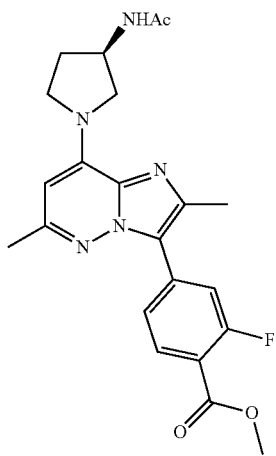 [SMILES: COC(=O)c1ccc(-c2c(C)nc3c(N4CC[C@@H](NC(C)=O)C4)cc(C)nn23)cc1F]

Prepared by method A from 3-fluoro-4-methoxycarbonyl-benzeneboronic acid in 41% yield. Chromatography: CHCl$_3$— ethanol 20:1, crystallization from ethyl acetate. [α]$_D^{20}$=+13.2 (c 0.227, CHCl$_3$). $^1$H NMR (400 MHz, d6-DMSO) δ 1.82 (s, 3H), 1.86-1.97 (m, 1H), 2.11-2.23 (m, 1H), 2.33 (s, 3H), 2.47 (s, 4H), 3.63-4.15 (br s+s, 6H), 4.31-4.41 (m, 1H), 5.91 (s, 1H), 7.64-7.74 (m, 1H), 7.73-7.83 (m, 1H), 7.99 (t, J=8.1 Hz, 1H), 8.17 (d, J=6.6 Hz, 1H). $^{13}$C NMR (101 MHz, d6-DMSO) δ 15.5, 21.6, 22.7, 30.4, 48.5, 52.5, 55.3, 95.0, 116.3 (d, J=24.1 Hz), 121.5, 124.5 (d, J=3.1 Hz), 128.6, 128.7, 130.8, 130.9, 131.7, 136.5 (d, J=10.1 Hz), 133.11, 139.1, 141.1, 152.1, 160.9 (d, J=256.4 Hz), 163.9, 169.4. HRMS calcd for C$_{22}$H$_{25}$N$_5$O$_3$F m/z: 426.1936 (M+H)$^+$, found 426.1848.

(R)—N-(1-(2,6-dimethyl-3-(4-(methylthio)phenyl)imidazo[1,2-b]pyridazin-8-yl)pyrrolidin-3-yl)acetamide (9)

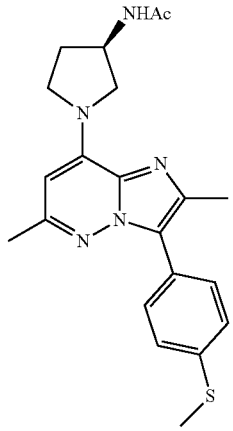 [SMILES: CSc1ccc(-c2c(C)nc3c(N4CC[C@@H](NC(C)=O)C4)cc(C)nn23)cc1]

Prepared by method A from 4-(methylthio)benzeneboronic acid in 61% yield. Chromatography:CHCl$_3$-acetone 4:1, crystallization from ethyl acetate. [α]$_D^{20}$=+6.1 (c 0.231, CHCl$_3$). $^1$H NMR (400 MHz, d6-DMSO) δ 1.82 (s, 3H), 1.97-1.86 (m, 1H), 2.10-2.21 (m, 1H), 2.28 (s, 3H), 2.38 (s, 3H), 2.53 (s, 3H), 3.81 (br s, 3H), 4.05 (br s, 1H), 4.30-4.39 (m, 1H), 5.81 (s, 1H), 7.37 (d, J=8.5 Hz, 1H), 7.60 (d, J=8.5 Hz, 1H), 8.16 (d, J=6.6 Hz, 1H). $^{13}$C NMR (101 MHz, d6-DMSO) δ 14.8, 14.9, 21.6, 22.7, 30.5, 39.9, 47.7, 48.8, 55.2, 94.1, 123.5, 125.8, 126.2, 129.7, 132.2, 136.9, 137.3, 141.1, 151.5, 169.4. HRMS calcd for C$_{21}$H$_{25}$N$_5$OSNa m/z: 418.1672 (M+Na)$^+$, found 418.1673.

(R)—N-(1-(3-(3-(N,N-dimethylsulfamoyl)phenyl)-2,6-dimethylimidazo[1,2-b]pyridazin-8-yl)pyrrolidin-3-yl)acetamide (10)

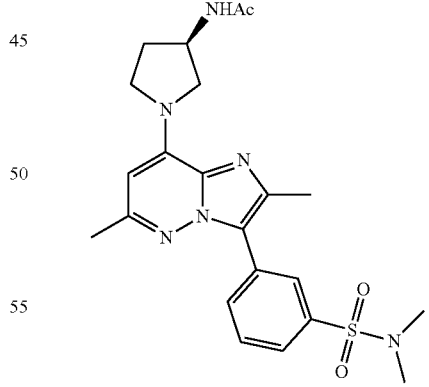

Prepared by method A (3-(N,N-dimethylsulfamoyl)phenyl)boronic acid in 50% yield. Chromatography:CHCl$_3$-ethanol 15:1, crystallization from ethyl acetate (freezer). [α]$_D^{20}$=+18.0 (c 0.239, CHCl$_3$). $^1$H NMR (400 MHz, d6-DMSO) δ 1.82 (s, 3H), 1.87-1.96 (m, 1H), 2.11-2.22 (m, 1H), 2.27 (s, 3H), 2.46 (s, 3H), 2.70 (s, 6H), 3.83 (br s, 3H), 4.07 (br s, 1H), 4.31-4.40 (m, 1H) 5.88 (s, 1H), 7.72 (dt, J=7.9, 1.5 Hz, 1H), 7.80-7.74 (m, 1H), 7.99 (dt, J=7.7, 1.5

Hz, 1H), 8.14 (dt, J=1.8, 1.0 Hz, 1H), 8.17 (d, J=6.6 Hz, 1H). $^{13}$C NMR (101 MHz, d6-DMSO) δ 15.0, 21.5, 22.7, 30.5*, 37.8, 47.8*, 48.7, 55.1*, 94.7, 122.1, 126.0, 127.7, 129.5, 130.7, 132.7, 133.1, 134.6, 138.0, 141.2, 151.9, 169.4. HRMS calcd for $C_{22}H_{28}N_6O_3SNa$ m/z: 479.1836 (M+Na)$^+$, found 479.1835.

(R)—N-(1-(3-(6-methoxypyridin-3-yl)-2,6-dimethylimidazo[1,2-b]pyridazin-8-yl)pyrrolidin-3-yl)acetamide (11)

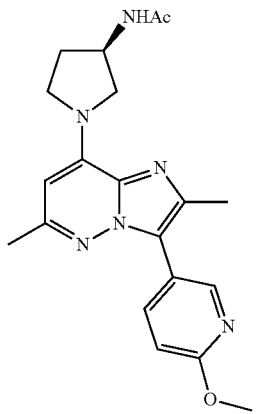

Prepared by method A from 2-methoxy-5-pyridineboronic acid in 45% yield. Chromatography: 1. CHCl$_3$-ethanol 20:1→15:1, 2. CHCl$_3$-acetone 1:1, crystallization from ethyl acetate (freezer). $[α]_D^{20}$=+15.8 (c 0.291, DMSO). $^1$H NMR (400 MHz, d6-DMSO) δ 1.82 (s, 3H), 1.86-1.97 (m, 1H), 2.10-2.22 (m, 1H), 2.27 (s, 3H), 2.37 (s, 3H), 3.81 (br s, 3H), 3.91 (s, 3H), 4.07 (br s, 1H), 4.29-4.40 (m, 1H), 5.81 (s, 1H), 6.96 (dd, J=8.6, 0.8 Hz, 1H), 7.98 (dd, J=8.6, 2.4 Hz, 1H), 8.18 (d, J=6.6 Hz, 1H), 8.48-8.34 (m, 1H). $^{13}$C NMR (101 MHz, d6-DMSO) δ 14.7, 21.6, 22.8, 30.5, 39.9, 48.0*, 48.8, 53.5, 55.3, 94.3, 110.3, 119.4, 121.0, 132.4, 137.1, 140.0, 141.2, 147.1, 151.7, 162.7, 169.5. HRMS calcd for $C_{20}H_{25}N_6O_2$ m/z: 381.2034 (M+H)$^+$, found 381.2036.

(R)—N-(1-(3-(4-(hydroxymethyl)phenyl)-2,6-dimethylimidazo[1,2-b]pyridazin-8-yl)pyrrolidin-3-yl)acetamide (12)

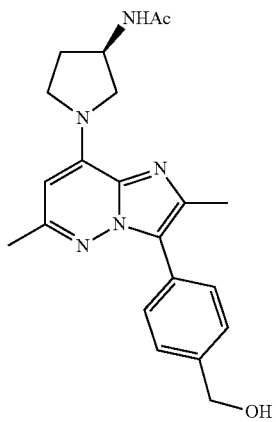 [SMILES: CC(=O)N[C@@H]1CCN(c2cc(C)nn3c(-c4ccc(CO)cc4)c(C)nc23)C1]

Prepared by method A with 4-formylbenzeneboronic acid followed by reduction with NaBH$_4$ in CH$_2$Cl$_2$—CH$_3$OH. Intermediate was chromatographed in CHCl$_3$-acetone 3:2 and was immediately used for reduction. Total yield: 54%, Chromatography: 1. CHCl$_3$-ethanol 15:1, 2. CHCl$_3$-acetone 1:1, crystallization from ethyl acetate. $[α]_D^{20}$=+14.5 (c 0.221, DMSO). $^1$H NMR (400 MHz, d6-DMSO) δ 1.82 (s, 3H), 1.86-1.95 (m, 1H), 2.23-2.11 (m, 1H), 2.27 (s, 3H), 2.38 (s, 3H), 3.82 (br s, 3H), 4.08 (br s, 1H), 4.30-4.39 (m, J=5.7 Hz, 1H), 4.56 (s, 2H), 5.81 (s, 1H), 7.33-7.49 (m, 2H), 7.50-7.67 (m, 2H), 8.18 (d, J=6.7 Hz, 1H). $^{13}$C NMR (101 MHz, d6-DMSO) δ 14.8, 21.7, 22.8, 30.5, 48.8, 47.7.*, 55.3*, 63.00, 94.1, 124.0, 128.1, 129.1, 132.1, 136.9, 141.2, 141.8, 151.5, 169.4. HRMS calcd for $C_{21}H_{26}N_5O_2$ m/z: 380.2081 (M+H)$^+$, found 380.2054.

(R)—N-(1-(2,6-dimethyl-3-(thiophen-2-yl)imidazo[1,2-b]pyridazin-8-yl)pyrrolidin-3-yl)acetamide (13)

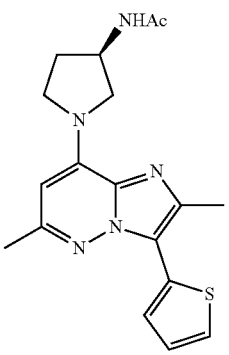

Prepared by method C from 2-(tributylstannyl)thiophene in 68% yield. Chromatography:CHCl$_3$-acetone 3:2, crystallization from ethyl acetate. $[α]_D^{28}$=+6.7 (c 0.210, CHCl$_3$). $^1$H NMR (400 MHz, d6-DMSO) δ 1.82 (s, 3H), 1.86-1.96 (m, 1H), 2.11-2.22 (m, 1H), 2.39 (s, 3H), 2.54 (s, 3H), 3.82 (br s, 3H), 4.06 (br s, 1H), 4.36 (h, J=5.6 Hz, 1H), 5.87 (s, 1H), 7.21 (dd, J=5.2, 3.7 Hz, 1H), 7.60 (dd, J=5.2, 1.2 Hz, 1H), 7.63 (dd, J=3.7, 1.2 Hz, 1H), 8.17 (d, J=6.7 Hz, 1H). $^{13}$C NMR (101 MHz, d6-DMSO) δ 16.3, 21.6, 22.7, 30.4, 47.8, 48.8, 55.3, 94.2, 119.4, 125.3, 124.9, 126.9, 130.6, 131.9, 136.9, 141.0, 151.7, 169.4. HRMS calcd for $C_{18}H_{22}N_5OS$ m/z: 356.1540 (M+H)$^+$, found 356.1536.

(R)—N-(1-(3-(furan-2-yl)-2,6-dimethylimidazo[1,2-b]pyridazin-8-yl)pyrrolidin-3-yl)acetamide (14)

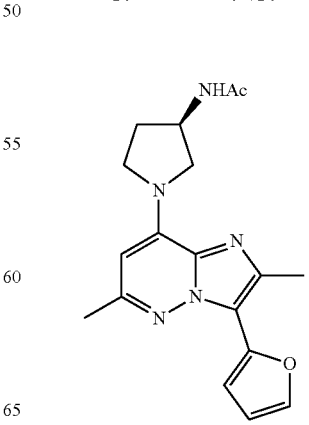

Prepared by method C from 2-(tributylstannyl)furane in 52% yield. Chromatography:CHCl$_3$-acetone 3:2, prior to crystallization, product was decolorized with active carbon, crystallization from ethyl acetate. [α]$_D^{22}$=+3.0 (c 0.234, CHCl$_3$). $^1$H NMR (400 MHz, d6-DMSO) δ 1.82 (s, 2H), 1.91 (ddt, J=12.6, 7.4, 5.2 Hz, 1H), 2.16 (dtd, J=13.5, 7.7, 6.0 Hz, 1H), 2.58 (s, 2H), 2.38 (s, 2H), 3.45-4.25 (2×br s, 4H), 4.35 (h, J=5.7 Hz, 1H), 5.86 (s, 1H), 6.66 (dd, J=3.3, 1.8 Hz, 1H), 7.21 (dd, J=3.3, 0.9 Hz, 1H), 7.80 (dd, J=1.8, 0.9 Hz, 1H), 8.17 (d, J=6.7 Hz, 1H). $^{13}$C NMR (101 MHz, d6-DMSO) δ 15.6, 21.7, 22.7, 30.5, 48.8, 55.3, 94.3, 107.7, 111.4, 116.7, 132.5, 136.8, 140.9, 141.9, 145.0, 152.0, 169.4 (one CH$_2$ was not detected). HRMS calcd for C$_{18}$H$_{22}$N$_5$O$_2$ m/z: 340.1768 (M+H)$^+$, found 340.1743.

(R)—N-(1-(2,6-dimethyl-3-(thiazol-2-yl)imidazo[1,2-b]pyridazin-8-yl)pyrrolidin-3-yl)acetamide (15)

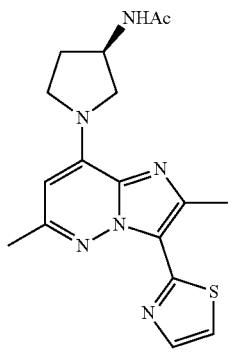

Prepared by method C from 2-tributylstannylthiazole in 62% yield. Chromatography: 1. CHCl$_3$-acetone 3:2, 2, toluene-acetone 1:1, crystallization from acetone-ethanol. [α]$_D^{20}$=+11.3 (c 0.266, DMSO). $^1$H NMR (400 MHz, d6-DMSO) δ 1.82 (s, 1H), 2.00-1.85 (m, 1H), 2.25-2.11 (m, 1H), 2.46 (s, 1H), 2.76 (s, 1H), 3.39-4.28 (2×br s, 4H), 4.37 (h, J=5.6 Hz, 1H), 5.98 (s, 1H), 7.73 (d, J=3.3 Hz, 1H), 7.99 (d, J=3.3 Hz, 1H), 8.18 (d, J=6.6 Hz, 1H). $^{13}$C NMR (101 MHz, d6-DMSO) δ 16.5, 21.5, 22.7, 95.1, 118.5, 119.7, 132.5, 140.2, 141.0, 142.3, 152.0, 155.5, 169.4 (carbons on pyrrolidine ring were not detected). HRMS calcd for C$_{17}$H$_{21}$N$_6$OS m/z: 357.1492 (M+H)$^+$, found 357.1469.

(R)—N-(1-(2,6-dimethyl-3-(3-morpholinophenyl)imidazo[1,2-b]pyridazin-8-yl)pyrrolidin-3-yl)acetamide (16)

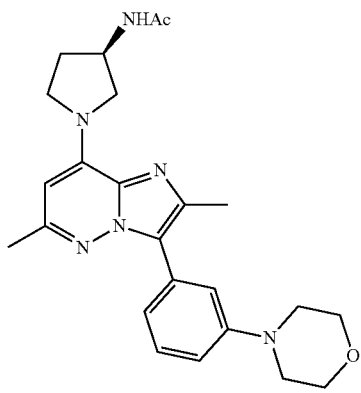 [SMILES: CC(=O)N[C@@H]1CCN(c2cc(C)nn3c(-c4cccc(N5CCOCC5)c4)c(C)nc23)C1]

Prepared by method A from (3-morpholinophenyl)boronic acid in 82% yield. Chromatography: 1. CHCl$_3$-acetone 1:1, 2, toluene-acetone 1:2, crystallization from ethyl acetate. [α]$_D^{20}$=+6.6 (c 0.334, CHCl$_3$). $^1$H NMR (400 MHz, d6-DMSO) δ 1.83 (s, 1H), 1.95-1.86 (m, 1H), 2.24-2.11 (m, 1H), 2.29 (s, 1H), 2.39 (s, 1H), 3.20-3.09 (m, 1H), 3.81-3.73 (m, 2H), 3.82 and 4.08 (2×br s, 4H), 4.35 (m, 1H), 5.80 (s, 1H), 6.96 (ddd, J=8.4, 2.6, 0.9 Hz, 1H), 7.14-7.07 (m, 1H), 7.21 (dd, J=2.6, 1.5 Hz, 1H), 7.34 (dd, J=8.4, 7.6 Hz, 1H), 8.18 (d, J=6.7 Hz, 1H). $^{13}$C NMR (101 MHz, d6-DMSO) δ 15.0, 21.7, 22.8, 30.5, 47.7, 48.8, 55.3, 66.3, 94.0, 114.5, 116.2, 120.5, 124.4, 128.9, 130.3, 132.1, 137.0, 141.1, 151.1, 151.4, 169.4 (CH on pyrrolidine ring was not detected). HRMS calcd for C$_{24}$H$_{31}$N$_6$O$_2$ m/z: 435.2503 (M+H)$^+$, found 435.2480.

(R)—N-(1-(2,6-dimethyl-3-(4-(trifluoromethoxy)phenyl)imidazo[1,2-b]pyridazin-8-yl)pyrrolidin-3-yl)acetamide (17)

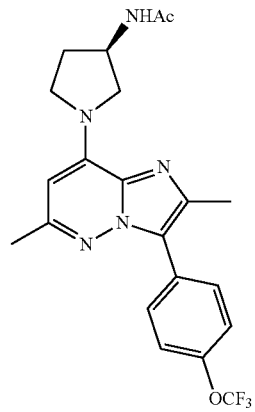 [SMILES: CC(=O)N[C@@H]1CCN(c2cc(C)nn3c(-c4ccc(OC(F)(F)F)cc4)c(C)nc23)C1]

Prepared by method A from 4-(trifluoromethoxy)benzeneboronic acid in 84% yield. Chromatography: 1. CHCl$_3$-acetone 2:1, 2, toluene-acetone 2:3, crystallization from ethyl acetate. [α]$_D^{20}$=+6.7 (c 0.237, CHCl$_3$). $^1$H NMR (400 MHz, d6-DMSO) δ 1.86-1.98 (m, 1H), 1.82 (s, 1H), 2.10-2.23 (m, 1H), 2.29 (s, 3H), 2.40 (s, 3H), 3.83 (br s, 3H), 4.08 (br s, 1H), 4.31-4.40 (m, 1H), 5.85 (s, 1H), 7.49 (d, J=8.3 Hz, 1H), 7.81 (d, J=8.3 Hz, 1H), 8.17 (d, J=6.5 Hz, 1H). $^{13}$C NMR (101 MHz, d6-DMSO) δ 14.9, 21.6, 22.8, 30.4, 48.8, 55.2, 94.5, 120.3 (d, J=255.4 Hz), 122.5, 129.1, 131.0, 132.5, 137.5, 141.2, 147.3, 151.8, 169.4. HRMS calcd for C$_{21}$H$_{23}$F$_3$N$_5$O$_2$ m/z: 434.1798 (M+H)$^+$, found 434.1799.

(R)—N-(1-(3-(1H-indol-6-yl)-2,6-dimethylimidazo[1,2-b]pyridazin-8-yl)pyrrolidin-3-yl)acetamide (18)

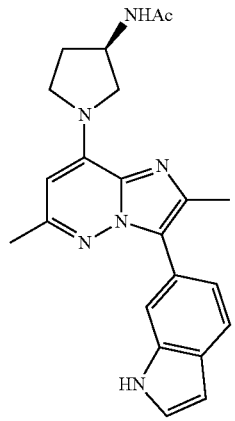 [SMILES: CC(=O)N[C@@H]1CCN(c2cc(C)nn3c(-c4ccc5cc[nH]c5c4)c(C)nc23)C1]

Prepared by method A from indole-6-boronic acid in 40% yield. Chromatography: 1. CHCl$_3$-acetone 1:1, 2, toluene:acetone 1:2, 3, flash chromatography on RP column (C18, H$_2$O:acetonitrile+0.5% HCOOH, 30% to 50%). $[\alpha]_D^{20}$=+16.8 (c 0.262, CHCl$_3$). $^1$H NMR (400 MHz, d6-DMSO) δ 1.83 (s, 3H), 1.87-1.98 (m, 1H), 2.13-2.23 (m, 1H), 2.28 (s, 3H), 2.40 (s, 3H), 3.84 (br s, 3H), 4.10 (br s, 1H), 4.31-4.41 (m, 1H), 5.80 (s, 1H), 6.47 (ddd, J=3.0, 2.0, 1.0 Hz, 1H), 7.22 (dd, J=8.2, 1.5 Hz, 1H), 7.41 (dd, J=3.0, 2.4 Hz, 1H), 7.63 (d, J=8.2 Hz, 1H), 7.68 (dt, J=1.6, 0.8 Hz, 1H), 8.18 (d, J=6.7 Hz, 1H), 11.17 (br s, 1H). $^{13}$C NMR (101 MHz, d6-DMSO) δ 14.9, 21.7, 22.8, 30.5, 47.7, 48.8, 55.3, 93.8, 101.2, 112.7, 119.7, 120.9, 122.1, 125.4, 126.3, 127.1, 131.8, 135.9, 136.4, 141.2, 151.3, 169.4. HRMS calcd for C$_{22}$H$_{25}$N$_6$O m/z: 389.2084 (M+H)$^+$, found. 389.2124.

(R)—N-(1-(6-chloro-3-(3,4-dimethoxyphenyl)-2-methylimidazo[1,2-b]pyridazin-8-yl)pyrrolidin-3-yl)acetamide (SM-7)

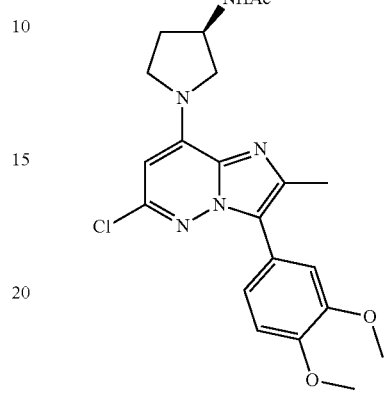

Prepared by method B from 3,4-dimethoxyphenylboronic acid. Yield: 83%. Chromatography:CHCl$_3$-ethanol 20:1, crystallization from methanol). $^1$H NMR (400 MHz, d6-DMSO) δ 1.84 (s, 3H), 1.92-1.98 (m, 1H), 2.16-2.25 (m, 1H), 2.41 (s, 3H), 3.81 (s, 3H), 3.85 (s, 3H), 3.86, 3.98 (m, 3H), 4.15 (br s, 1H), 4.40 (m, 1H), 5.94 (s, 1H), 7.10 (d, J=8.3 Hz, 1H), 7.17 (dd, J=2.0, J=8.3 Hz, 1H), 7.23 (d, J=2.0 Hz, 1H), 7.96 (d, J=6.2 Hz, 1H). $^{13}$C NMR (101 MHz, d6-DMSO) δ 14.4, 22.3, 30.2, 47.8, 48.5, 55.1, 55.7, 55.9, 92.6, 112.4, 113.9, 121.2, 122.1, 124.5, 131.1, 137.1, 142.0, 146.2, 148.7, 148.9, 169.1. HRMS calcd for C$_{21}$H$_{25}$ClN$_5$O$_3$ m/z: 430.1640 (M+H)+, found 430.1640.

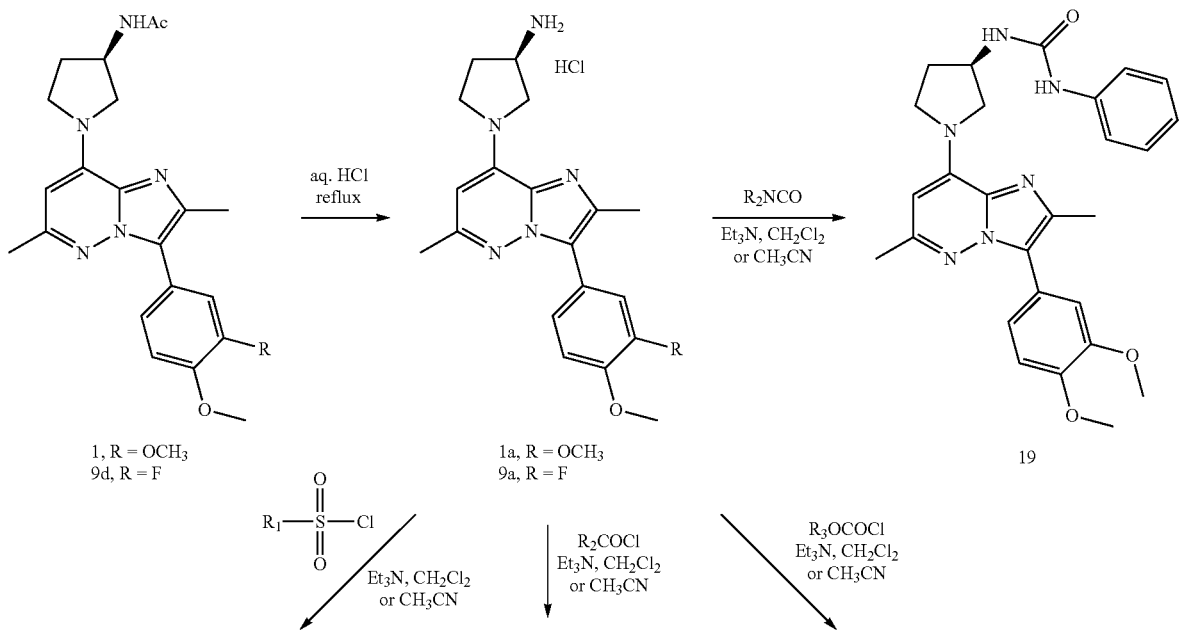

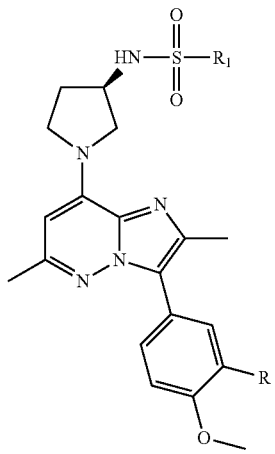 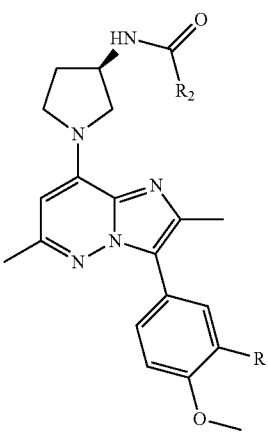 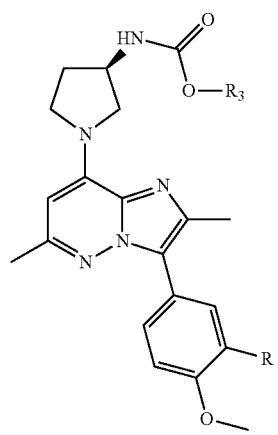

20-30

20, R = OCH₃, R₁ = CH₃
21, R = F, R₁ = CH₃,
22, R = OCH₃, R₁ = p-tolyl,
23, R = OCH₃, R₁ = 4-acetylphenyl,
24, R = OCH₃, R₁ = cyclopropyl,
25, R = OCH₃, R₁ = 2-thienyl,
26, R = OCH₃, R₁ = NH₂,
27, R = OCH₃, R₁ = isopropyl,
28, R = OCH₃, R₁ = phenyl,
29, R = OCH₃, R₁ = 4-chlorophenyl,
30, R = OCH₃, R₁ = 4-trifluoromethylphenyl 31-37

31, R = H, R₂ = cyclohexyl,
32, R = OCH₃, R₂ = pentyl,
33, R = OCH₃, R₂ = benzyl,
34, R = OCH₃, R₂ = CH₂OPh,
35, R = OCH₃, R₂ = CF₃,
36, R = OCH₃, R₂ =

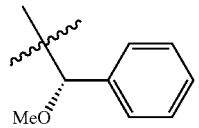

37, R = OCH₃, R₂ = CF₂Ph, 38-43

38, R = OCH₃, R₃ = Ph,
39, R = OCH₃, R₃ = benzyl,
40, R = F, R₃ = Ph,
41, R = OCH₃, R₃ = cyclohexyl,
42, R = OCH₃, R₃ = m-tolyl,
43, R = OCH₃, R₃ = 2-naphtyl, (R)-1-(3-(3,4-dimethoxyphenyl)-2,6-dimethylimidazo[1,2-b]pyridazin-8-yl)pyrrolidin-3-amine hydrochloride (1a)

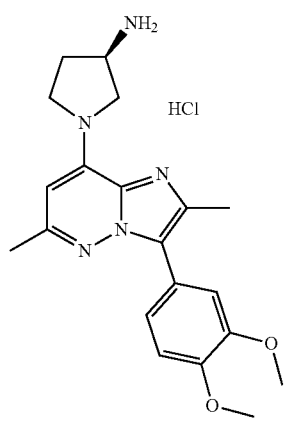

(R)-1-(3-(3-fluoro-4-methoxyphenyl)-2,6-dimethylimidazo[1,2-b]pyridazin-8-yl)pyrrolidin-3-amine hydrochloride (9a)

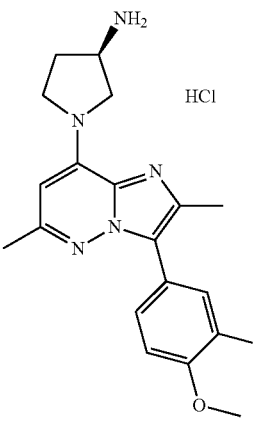

Acetamide 1 (2.87 g, 7 mmol) was heated to reflux overnight in a mixture of conc. HCl (40 mL) and water (40 mL). Reaction mixture was evaporated to dryness, co-evaporated with ethanol (2×100 mL) and then triturated with isopropanol (with heating and sonication). Precipitated solid was filtered-off, washed with isopropanol and diethyl ether and was directly used without further purification. It was obtained 2.19 g of the hydrochloride salt. UPLC-MS: t=3.08 (M+H, 368.3).

Acetamide 9 (410 mg, 1.03 mmol) was heated to reflux overnight in a mixture of conc. HCl (6.5 mL) and water (6.5 mL). Reaction mixture was evaporated to dryness, co-evaporated with ethanol (2×20 mL) and ethyl acetate (2×20 mL). It was obtained off white solid which was used without further purification. UPLC-MS: t=3.11 (M+H, 356.3).

(R)-1-(1-(3-(3,4-dimethoxyphenyl)-2,6-dimethylimidazo[1,2-b]pyridazin-8-yl)pyrrolidin-3-yl)-3-phenylurea (19)

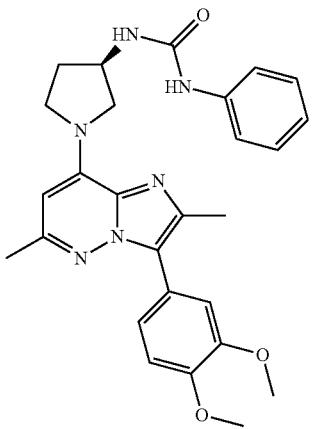 [SMILES: COc1ccc(-c2c(C)nc3c(N4CC[C@@H](NC(=O)Nc5ccccc5)C4)cc(C)nn23)cc1OC]

To a mixture of hydrochloride 1a (200 mg, 0.5 mmol), Et$_3$N (0.14 ml, 1 mmol) in dichloromethane (7 mL) was added phenylisocyanate (81 μL, 0.74 mmol) and mixture was stirred overnight at r.t. and then quenched with few drops of methanol. Reaction mixture was evaporated and chromatographed on silica gel column (150 g, CHCl$_3$-EtOH 25:1). Fractions containing product were evaporated and re-chromatographed (80 g, CHCl$_3$-acetone 4:1). It was obtained 120 mg (49%) of the product as off-white solid. $[\alpha]_D^{22}$=+4.02 (c 0.235, DMSO). $^1$H NMR (400 MHz, d6-DMSO) δ 1.91-2.04 (m, 1H), 2.16-2.28 (m, 1H), 2.23 (s, 3H), 2.40 (s, 3H), 3.78 (s) and 3.81 (s) and 3.85 (br s, 9H) 4.28-4.38 (m, 1H), 5.84 (s, 1H), 6.55 (d, J=6.8 Hz, 1H), 6.90 (tt, J=7.3, 1.2 Hz, 1H), 7.07 (d, J=8.4 Hz, 1H), 7.17 (dd, J=8.3, 2.0 Hz, 1H), 7.25-7.19 (m, 2H), 7.28 (d, J=2.0 Hz, 1H), 7.42-7.33 (m, 2H), 8.31 (s, 1H). $^{13}$C NMR (101 MHz, d6-DMSO) δ 15.0, 21.7, 30.8, 49.3, 55.7, 93.9, 111.8, 113.2, 117.8, 121.4, 122.0, 122.2, 123.9, 128.9, 131.9, 136.6, 140.4, 141.2, 148.3, 148.4, 151.4, 155.1. HRMS calcd for C$_{27}$H$_{31}$N$_6$O$_3$ m/z: 487.2452 (M+H)$^+$, found 487.2437.

General Procedure for Preparation of the Sulfonates 20-30

Hydrochloride 1a or 9a (160 mg, 0.4 mmol) was suspended in dry CH$_2$Cl$_2$ (10 mL) and sequentially was added Et$_3$N (0.3 mL, 2.2 mmol) and DMAP (cat.) at r.t. Corresponding sulfonyl chloride was then added dropwise and reaction mixture was stirred at r.t. overnight. Reaction mixture was evaporated and residue was purified by silica gel chromatography (80 g) and product was then crystallized.

(R)—N-(1-(3-(3,4-dimethoxyphenyl)-2,6-dimethylimidazo[1,2-b]pyridazin-8-yl)pyrrolidin-3-yl)methanesulfonamide (20)

Yield: 110 mg (67%).

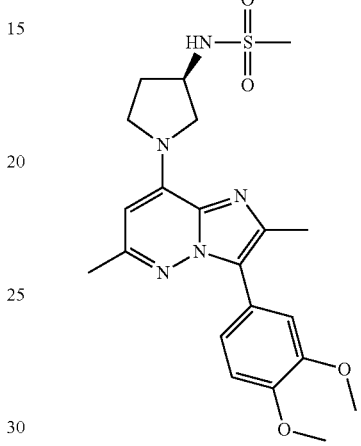

Chromatography: CHCl$_3$-ethanol 20:1, crystallization from acetone. $[\alpha]_D^{20}$=−11.8 (c 0.263, CHCl$_3$). $^1$H NMR (400 MHz, d6-DMSO) δ 7.48 (d, J=5.1 Hz, 1H), 7.29 (d, J=2.0 Hz, 1H), 7.18 (dd, J=8.3, 2.0 Hz, 1H), 7.08 (d, J=8.5 Hz, 1H), 5.82 (s, 1H), 4.11 (br s, 1H), 4.08 (m, 1H), 3.82 (s, 3H), 3.81 (br s, 3H), 3.79 (s, 2H), 3.01 (s, 3H), 2.40 (s, 3H), 2.30 (s, 3H), 2.20-2.29 (m, 1H), 1.94-2.05 (m, 1H). $^{13}$C NMR (101 MHz, d6-DMSO) δ 15.0, 21.7, 31.4, 47.8, 55.4, 93.9, 111.8, 113.2, 122.0, 122.2, 123.9, 131.9, 136.6, 141.0, 148.3, 148.4, 151.4. HRMS calcd for C$_{21}$H$_{28}$N$_5$O$_4$S m/z: 446.1857 (M+H)$^+$, found 446.1857.

(R)—N-(1-(3-(3-fluoro-4-methoxyphenyl)-2,6-dimethylimidazo[1,2-b]pyridazin-8-yl)pyrrolidin-3-yl)methanesulfonamide (21)

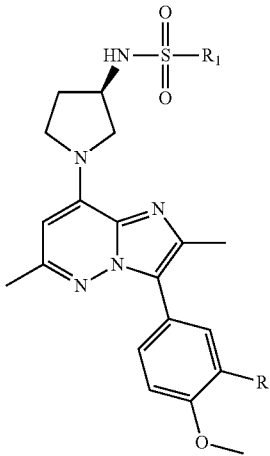

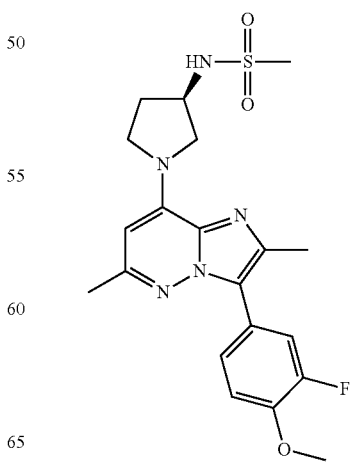

Yield: 135 mg (78%). Chromatography:CHCl₃-acetone 3:1, crystallization from ethyl acetate. [α]$_D^{20}$=−5.9 (c 0.221, CHCl₃). ¹H NMR (400 MHz, d6-DMSO) δ 1.92-2.07 (m, 1H), 2.19-2.28 (m, 1H), 2.29 (s, 3H), 2.39 (s, 3H), 3.00 (s, 3H), 3.69-4.20 (2×br s and m, 5H) 3.90 (s, 3H), 5.83 (s, 1H), 7.28 (t, J=8.9 Hz, 1H), 7.42 (ddd, J=8.6, 2.1, 1.1 Hz, 1H), 7.47 (s, 1H), 7.54 (dd, J=12.9, 2.1 Hz, 1H). ¹³C NMR (101 MHz, d6-DMSO) δ 14.9, 21.7, 31.4, 40.5, 47.7, 52.3, 55.4, 56.2, 94.2, 113.8 (d, J=2.3 Hz), 116.5 (d, J=19.0 Hz), 122.5 (d, J=7.5 Hz), 122.6 (d, J=1.9 Hz), 125.7 (d, J=3.3 Hz), 132.0, 137.0, 141.0, 146.4, 146.5, 151.2 (d, J=244 Hz), 151.6. HRMS calcd for C₂₃H₂₄N₅O₂S m/z: 434.1645 (M−H)⁺, found 434.1656.

(R)—N-(1-(3-(3,4-dimethoxyphenyl)-2,6-dimethyl-imidazo[1,2-b]pyridazin-8-yl)pyrrolidin-3-yl)-4-methylbenzenesulfonamide (22)

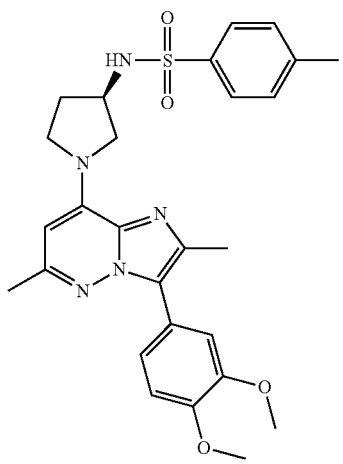

Yield: 175 mg (82%). Chromatography:CHCl₃-acetone 5:1, crystallization from ethyl acetate. [α]$_D^{20}$=+42.4 (c 0.245, CHCl₃). ¹H NMR (400 MHz, d6-DMSO) δ 1.94-2.05 (m, 1H), 2.20-2.29 (m, 1H), 2.30 (s, 3H), 2.40 (s, 3H), 3.01 (s, 3H), 3.79 (s, 2H), 3.81 (br s, 3H), 3.82 (s, 3H), 4.08 (m, 1H), 4.11 (br s, 1H), 5.82 (s, 1H), 7.08 (d, J=8.5 Hz, 1H), 7.18 (dd, J=8.3, 2.0 Hz, 1H), 7.29 (d, J=2.0 Hz, 1H), 7.48 (d, J=5.1 Hz, 1H). ¹³C NMR (101 MHz, d6-DMSO) δ 1.79-1.90 (m, 1H), 1.96-2.06 (m, 1H), 2.27 (s, 3H), 2.37 (s, 3H), 2.38 (s, 3H), 3.63 and 3.97 (2×br s and m, 5H), 3.78 (s, 3H), 3.81 (s, 3H), 7.07 (d, J=8.3 Hz, 1H), 7.16 (dd, J=8.3, 2.0 Hz, 1H), 7.27 (d, J=2.0 Hz, 1H), 7.35-7.42 (m, 2H), 7.68-7.72 (m, 2H), 7.99 (d, J=5.1 Hz, 1H). ¹³C NMR (101 MHz, d6-DMSO) δ 15.0, 21.2, 21.7, 30.7, 40.3, 47.3, 52.5, 55.1, 55.7, 93.8, 122.2, 123.8, 131.7, 136.5, 138.4, 140.9, 142.8, 148.3, 148.4, 151.3. HRMS calcd for C₂₇H₃₂N₅O₄S m/z: 522.2170 (M+H)⁺, found 522.2170.

(R)-4-acetyl-N-(1-(3-(3,4-dimethoxyphenyl)-2,6-dimethylimidazo[1,2-b]pyridazin-8-yl)pyrrolidin-3-yl)benzenesulfonamide (23)

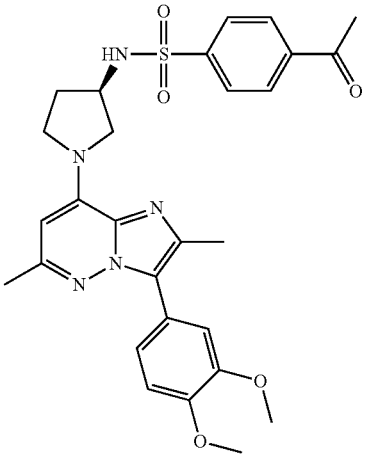 [SMILES: COc1ccc(-c2c(C)nc3c(N4CC[C@@H](NS(=O)(=O)c5ccc(C(C)=O)cc5)C4)cc(C)nn23)cc1OC]

Yield: 167 mg (76%). Chromatography:CHCl₃-acetone 21:4, crystallization from ethyl acetate. [α]$_D^{20}$=+34.2 (c 0.263, CHCl₃). ¹H NMR (400 MHz, d6-DMSO) δ 1.83-1.94 (m, 1H), 2.00-2.12 (m, 1H), 2.27 (s, 3H), 2.34 (s, 3H), 2.60 (s, 3H), 3.57-3.99 (2×br s and m, 5H), 3.79 (s, 3H), 3.82 (s, 3H), 5.71 (s, 1H), 7.07 (d, J=8.4 Hz, 1H), 7.15 (dd, J=8.3, 2.0 Hz, 1H), 7.27 (d, J=2.0 Hz, 1H), 7.86-8.01 (m, 1H), 8.06-8.16 (m, 1H), 8.30 (s, 1H). ¹³C NMR (101 MHz, d6-DMSO) δ 14.9, 21.7, 27.1, 30.7, 40.1, 47.2, 52.7, 54.9, 93.8, 111.8, 113.2, 121.9, 122.1, 123.8, 126.9, 129.2, 131.7, 136.5, 139.5, 140.8, 145.1, 148.3, 148.4, 151.3, 197.3. HRMS calcd for C₂₈H₃₁N₅O₅SNa m/z: 572.1938 (M+Na)⁺, found 572.1939.

(R)—N-(1-(3-(3,4-dimethoxyphenyl)-2,6-dimethyl-imidazo[1,2-b]pyridazin-8-yl)pyrrolidin-3-yl)cyclopropanesulfonamide (24)

Yield: 131 mg (69%). Chromatography:CHCl₃-acetone 21:4, crystallization from ethyl acetate. [α]$_D^{20}$=~0 (c 0.242, CHCl₃). ¹H NMR (400 MHz, d6-DMSO) δ 1.06-0.95 (m, 4H), 1.95-2.07 (m, 1H), 2.19-2.29 (m, 1H), 2.30 (s, 3H), 2.40 (s, 3H), 2.66 (tt, J=7.8, 5.0 Hz, 1H), 3.79 (s, 3H), 3.82 (s, 3H), 3.85 (br s, 1H), 4.05-4.17 (m, 1H), 4.20 (br s, 1H), 5.81 (s, 1H), 7.08 (d, J=8.3 Hz, 1H), 7.18 (dd, J=8.3, 2.0 Hz, 1H), 7.29 (d, J=2.0 Hz, 1H), 7.52 (d, J=7.1 Hz, 1H). ¹³C NMR (101 MHz, d6-DMSO) δ 5.5, 5.6, 15.3, 22.0, 30.5, 31.9, 48.0, 52.6, 55.8, 56.0, 94.2, 112.2, 113.6, 122.3, 122.5, 124.2, 132.2, 136.9, 141.3, 148.6, 148.7, 151.7. HRMS calcd for $C_{23}H_{30}N_5O_4S$ m/z: 472.2013 (M+H)$^+$, found 472.2014.

(R)—N-(1-(3-(3,4-dimethoxyphenyl)-2,6-dimethyl-imidazo[1,2-b]pyridazin-8-yl)pyrrolidin-3-yl)thiophene-2-sulfonamide (25)

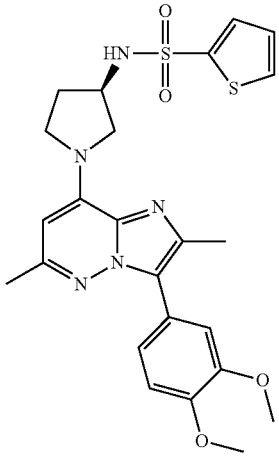 [SMILES: COc1ccc(-c2c(C)nc3c(N4CC[C@@H](NS(=O)(=O)c5cccs5)C4)cc(C)nn23)cc1OC]

Yield: 143 mg (70%). Chromatography:CHCl$_3$-acetone 21:3, crystallization from ethyl acetate. $^1$H NMR (400 MHz, d6-DMSO) δ 1.83-1.94 (m, 1H), 2.03-2.14 (m, 1H), 2.28 (s, 3H), 2.38 (s, 3H), 3.78 (s and br s, 6H), 3.81 (s, 3H), 3.90-3.98 (m, 1H), 4.04 (br s, 1H), 5.74 (s, 1H), 7.07 (d, J=8.5 Hz, 1H), 7.16 (dd, J=8.5, 2.0 Hz, 1H), 7.21 (dd, J=5.0, 3.7 Hz, 1H), 7.27 (d, J=2.0 Hz, 1H), 7.67 (dd, J=3.7, 1.3 Hz, 1H), 7.97 (dd, J=5.0, 1.3 Hz, 1H), 8.26-8.33 (m, 1H). $^{13}$C NMR (101 MHz, d6-DMSO) δ 15.0, 21.7, 30.7, 47.3, 52.8, 55.1, 55.7, 93.8, 111.8, 113.2, 122.0, 122.2, 123.9, 127.9, 131.8, 132.0, 132.9, 136.6, 140.9, 142.0, 148.3, 148.4, 151.3. HRMS calcd for $C_{24}H_{28}N_5O_4S_2$ m/z: 514.1577 (M+H)$^+$, found 514.1578.

(R)—N-[1-(3-(3,4-dimethoxyphenyl)-2,6-dimethyl-imidazo[1,2-b]pyridazin-8-yl)pyrrolidin-3-yl]sulfuric diamide (26)

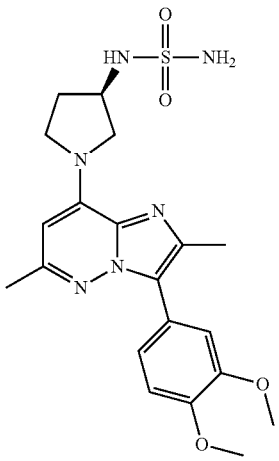

To a mixture of chlorosulfonyl isocyanate (105 μL, 1.2 mmol) in dry dichloromethane (3 mL) was added t-butanol (116 μL, 1.2 mmol) at r.t. and resulting solution was stirred for 30 minutes. This solution was then transferred to a mixture of 1a (160 mg, 0.4 mmol) and triethylamine (0.28 mL, 2 mmol) in dichloromethane (5 mL) and reaction mixture was stirred overnight at r.t. and then evaporated. Residue was absorbed on silica gel (from chloroform) and filtrate through plug of silica gel (50 g, chloroform-ethanol 20:1). Bocylated intermediate was dissolved in mixture H$_2$O/DMF (13 mL, 10:3) and heated to 100° C. for one hour. Reaction mixture was evaporated and product was isolated by column chromatography (100 g, chloroform-ethanol 10:1). It was obtained 89 mg (50%) of the product which was re-crystalized from acetone. $[α]_D^{20}$=+19.8 (c 0.325, DMSO). $^1$H NMR (400 MHz, d6-DMSO) δ 1.94-2.08 (m, 1H), 2.16-2.27 (m, 1H), 2.29 (s, 3H), 2.39 (s, 3H), 3.78 (s, 3H), 3.81 (s and br s, 6H), 3.94-4.03 (m, 1H), 4.13 (br s, 1H), 5.77 (s, 1H), 6.68 (s, 2H), 6.98 (d, J=6.4 Hz, 1H), 7.07 (d, J=8.4 Hz, 1H), 7.17 (dd, J=8.4, 2.0 Hz, 1H), 7.27 (d, J=2.0 Hz, 1H). $^{13}$C NMR (101 MHz, d6-DMSO) δ 15.0, 21.7, 31.1, 47.8, 52.3, 55.1, 55.7, 93.8, 111.8, 113.3, 122.0, 122.2, 123.9, 131.9, 136.6, 141.1, 148.3, 148.4, 151.4. HRMS calcd for $C_{20}H_{27}N_6O_4S$ m/z: 447.1809 (M+H)$^+$, found 447.1811.

(R)—N-(1-(3-(3,4-dimethoxyphenyl)-2,6-dimethyl-imidazo[1,2-b]pyridazin-8-yl)pyrrolidin-3-yl)propane-2-sulfonamide (27)

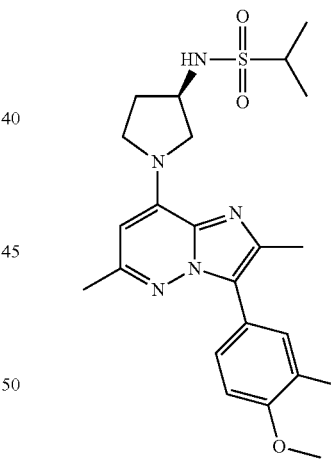

Yield: 66 mg (35%). Chromatography:CHCl$_3$-acetone 21:3, crystallization from ethyl acetate. $^1$H NMR (400 MHz, d6-DMSO) δ 1.26 (dd, J=6.8, 2.5 Hz, 1H), 1.92-2.03 (m, 1H), 2.15-2.27 (m, 1H), 2.28 (s, 3H), 2.40 (s, 3H), 3.26 (p, J=6.8 Hz, 1H), 3.78 (s, 3H) and 3.80 (br s, 3H), 3.81 (s, 3H), 4.00-4.10 (m, 1H), 4.15 (br s, 1H), 5.81 (s, 1H), 7.07 (d, J=8.4 Hz, 1H), 7.17 (dd, J=8.4, 2.0 Hz, 1H), 7.28 (d, J=2.0 Hz, 1H), 7.46 (d, J=7.1 Hz, 1H). $^{13}$C NMR (101 MHz, d6-DMSO) δ 15.0, 16.5, 16.6, 21.7, 31.6, 47.7, 52.0, 52.4, 55.5, 55.7, 93.9, 111.8, 113.3, 122.0, 122.2, 123.9, 131.8, 136.6, 141.0, 148.3, 148.4, 151.4. HRMS calcd for $C_{23}H_{32}N_5O_4S$ m/z: 474.217 (M+H)$^+$, found 474.2169.

(R)—N-(1-(3-(3,4-dimethoxyphenyl)-2,6-dimethyl-imidazo[1,2-b]pyridazin-8-yl)pyrrolidin-3-yl)benzenesulfonamide (28)

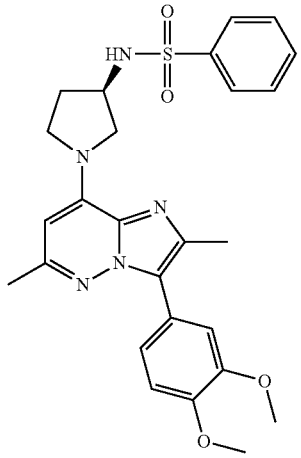 [SMILES: COc1ccc(-c2c(C)nc3c(N4CC[C@@H](NS(=O)(=O)c5ccccc5)C4)cc(C)nn23)cc1OC]

Yield: 157 mg (77%). Chromatography:CHCl$_3$-acetone 21:3, crystallization from ethyl acetate-acetone. $[\alpha]_D^{20}$=+33.1 (c 0.296, CHCl$_3$). $^1$H NMR (400 MHz, d6-DMSO) δ 1.78-1.89 (m, 1H), 1.96-2.09 (m, 1H), 2.27 (s, 3H), 2.37 (s, 3H), 3.62-4.03 (2×br s and m, 5H), 3.78 (s, 3H), 3.81 (s, 3H), 5.71 (s, 1H), 7.07 (d, J=8.4 Hz, 1H), 7.16 (dd, J=8.4, 2.0 Hz, 1H), 7.27 (d, J=2.0 Hz, 1H), 7.70-7.55 (m, 3H), 7.91-7.81 (m, 2H), 8.09 (s, 1H). $^{13}$C NMR (101 MHz, d6-DMSO) δ 14.5, 21.7, 30.8, 47.3, 52.5, 55.1, 55.7, 93.8, 111.8, 113.2, 122.0, 122.2, 123.8, 126.6, 129.4, 131.7, 132.7, 136.6, 140.9, 141.2, 148.3, 148.4, 151.3. HRMS calcd for C$_{26}$H$_{30}$N$_5$O$_4$S m/z: 508.2013 (M+H)$^+$, found 508.2019.

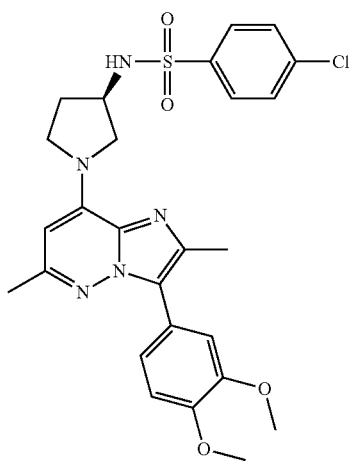 [SMILES: COc1ccc(-c2c(C)nc3c(N4CC[C@@H](NS(=O)(=O)c5ccc(Cl)cc5)C4)cc(C)nn23)cc1OC]

(R)-4-chloro-N-(1-(3-(3,4-dimethoxyphenyl)-2,6-dimethylimidazo[1,2-b]pyridazin-8-yl)pyrrolidin-3-yl)benzenesulfonamide (29) Yield: 173 mg (80%). Chromatography: CHCl$_3$-acetone 22:3, crystallization from ethyl acetate-acetone. $^1$H NMR (400 MHz, d6-DMSO) δ 1.80-1.92 (m, 1H), 2.00-2.11 (m, 1H), 2.27 (s, 3H), 2.37 (s, 3H), 3.50-4.05 (2×br s and m, 5H), 3.78 (s, 3H), 3.81 (s, 3H), 7.07 (d, J=8.5 Hz, 1H), 7.16 (dd, J=8.3, 2.0 Hz, 1H), 7.27 (d, J=2.0 Hz, 1H), 7.72-7.63 (m, 2H), 7.90-7.77 (m, 2H), 8.20 (s, 1H). $^{13}$C NMR (101 MHz, d6-DMSO) δ 15.0, 21.7, 30.7, 47.2, 52.6, 55.0, 55.7, 55.7, 93.8, 111.8, 113.2, 122.0, 122.2, 123.9, 128.6, 129.7, 131.7, 136.5, 137.5, 140.2, 140.9, 148.3, 148.4, 151.3. HRMS calcd for C$_{26}$H$_{29}$ClN$_5$O$_4$S m/z: 542.1623 (M+H)$^+$, found 542.1608.

(R)—N-(1-(3-(3,4-dimethoxyphenyl)-2,6-dimethyl-imidazo[1,2-b]pyridazin-8-yl)pyrrolidin-3-yl)-4-(trifluoromethyl)benzenesulfonamide (30)

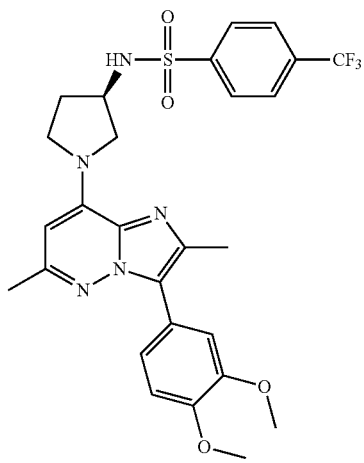 [SMILES: COc1ccc(-c2c(C)nc3c(N4CC[C@@H](NS(=O)(=O)c5ccc(C(F)(F)F)cc5)C4)cc(C)nn23)cc1OC]

Yield: 173 mg (75%) Chromatography:CHCl$_3$-acetone 8:1, crystallization from ethyl acetate. $[\alpha]_D^{20}$=+27.9 (c 0.208, CHCl$_3$). $^1$H NMR (400 MHz, d6-DMSO) δ 1.83-1.93 (m, 1H), 2.00-2.12 (m, 1H), 2.26 (s, 3H), 2.35 (s, 3H), 3.52-4.04 (2×br s and m, 5H), 3.78 (s, 3H), 3.81 (s, 3H), 5.72 (s, 1H), 7.07 (d, J=8.4 Hz, 1H), 7.15 (dd, J=8.3, 2.0 Hz, 1H), 7.26 (d, J=2.0 Hz, 1H), 7.97-8.01 (m, 2H), 8.04-8.13 (m, 2H), 8.38 (s, 1H). $^{13}$C NMR (101 MHz, d6-DMSO) δ 14.9, 21.6, 30.8, 47.3, 52.6, 55.0, 55.7, 93.8, 111.8, 113.2, 122.0, 122.2, 123.7 (q, J=273 Hz), 123.9, 126.7 (q, J=32 Hz), 131.7, 132.4 (q, J=3.8 Hz), 136.5, 140.9, 145.3, 148.3, 148.4, 151.3. HRMS calcd for C$_{27}$H$_{29}$F$_3$N$_5$O$_4$S m/z: 576.1877 (M+H)$^+$, found 542.1859.

Procedure for Synthesis of Amides 31-37

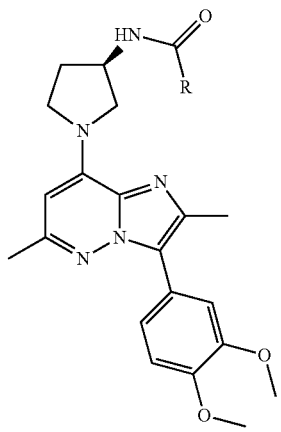

(R)—N-(1-(3-(4-methoxyphenyl)-2,6-dimethylimidazo[1,2-b]pyridazin-8-yl)pyrrolidin-3-yl)cyclohexanecarboxamide (31)

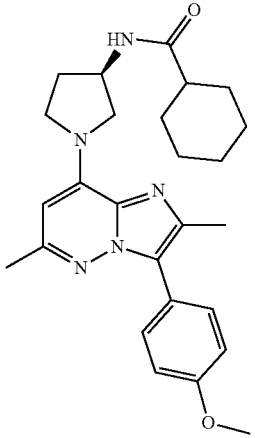

Compound 4 (100 mg, 0.26 mmol) was heated to reflux overnight in a mixture of conc. HCl (3 mL) and water (3 mL). Reaction mixture was evaporated to dryness, co-evaporated with ethanol (3×20 mL) and then with ethyl acetate. Resulting solid was suspended in dichloromethane (10 mL) and sequentially was added triethylamine (182 µL, 1.3 mmol), DMAP (cat. amount) and cyclohexanecarbonyl chloride (53 µL, 0.39 mmol). Reaction mixture was stirred at r.t. for three hours and then evaporated. Product was purified by column chromatography (75 g, toluene:ethyl acetate 1:1). Obtained solid was triturated with ether and filtered off. It was obtained 47 mg (41%) of the product. $[\alpha]_D^{20}$=−11.8 (c 0.263, CHCl$_3$). $^1$H NMR (400 MHz, d6-DMSO) δ 1.08-1.26 (m, 4H), 1.27-1.40 (m, 2H), 1.55-1.76 (m, 6H), 1.83-1.94 (m, 1H), 2.04-2.20 (m, 2H), 2.27 (s, 3H), 2.36 (s, 3H), 3.81 (s+br s, 6H), 4.06 (br s, 1H), 4.29-4.40 (m, 1H), 5.79 (s, 1H), 6.89-7.17 (m, 2H), 7.42-7.60 (m, 2H), 8.00 (d, J=6.7 Hz, 1H). $^{13}$C NMR (101 MHz, d6-DMSO) δ 14.8, 21.7, 25.4, 25.5, 25.6, 29.3, 29.4, 30.6, 44.0, 48.5, 55.2, 55.3, 93.9, 113.9, 122.0, 123.8, 130.7, 131.9, 136.4, 141.2, 151.4, 158.6, 175.5. HRMS calcd for C$_{26}$H$_{23}$N$_5$O$_2$ m/z: 448.27070 (M+H)$^+$, found 448.27064.

(R)—N-(1-(3-(3,4-dimethoxyphenyl)-2,6-dimethylimidazo[1,2-b]pyridazin-8-yl)pyrrolidin-3-yl)hexanamide hydrochloride (32)

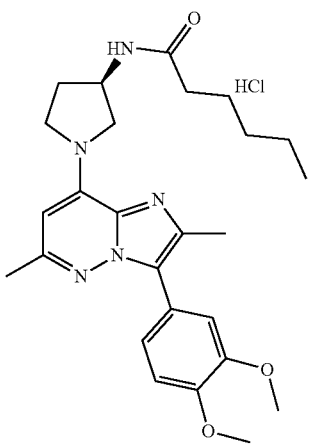 [SMILES: CCCCCC(=O)N[C@@H]1CCN(c2cc(C)nn3c(-c4ccc(OC)c(OC)c4)c(C)nc23)C1 ; Cl]

Hydrochloride 1a (200 mg, 0.5 mmol) was suspended in dichloromethane (10 mL) and triethylamine (350 µL, 0.25 mmol) and hexanoyl chloride (105 µl, 0.75 mmol) were added and reaction mixture was stirred for 16 h and evaporated. Residue was chromatographed on silica gel column (100 g, CHCl$_3$:acetone 5:1) and obtained semisolid was treated with HCl in ether (4M) to form white solid (149 mg, 59%). $[\alpha]_D^{20}$=+48.5 (c 0.344, DMSO). $^1$H NMR (400 MHz, d6-DMSO) δ 0.84 (t, J=7.0 Hz, 3H), 1.16-1.32 (m, 4H), 1.46-1.55 (m, 2H), 1.93-2.04 (m, 1H), 2.05-2.15 (m, 2H), 2.16-2.27 (m, 1H), 2.36 (s, 3H), 3.71 (br s, 1H), 3.79 (s, 3H), 3.84 (s, 3H), 3.88 (br s, 2H), 4.06 (br s, 2H), 4.38-4.46 (m, 1H), 6.22 (s, 1H), 7.12 (d, J=8.4 Hz, 1H), 7.19 (dd, J=8.3, 1.9 Hz, 1H), 7.25 (d, J=1.9 Hz, 1H), 8.23 (d, J=6.7 Hz, 1H). HRMS calcd for C$_{26}$H$_{35}$N$_5$O$_3$Na m/z: 488.2632 (M+Na)$^+$, found 488.2629.

(R)—N-(1-(3-(3,4-dimethoxyphenyl)-2,6-dimethylimidazo[1,2-b]pyridazin-8-yl)pyrrolidin-3-yl)-2-phenylacetamide (33)

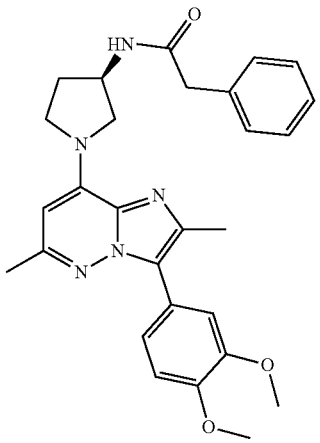 [SMILES: COc1ccc(-c2c(C)nc3c(N4CC[C@@H](NC(=O)Cc5ccccc5)C4)cc(C)nn23)cc1OC]

Hydrochloride 1a (200 mg, 0.5 mmol) was suspended in dichloromethane (10 mL) and triethylamine (350 µL, 0.25 mmol) and 2-phenylacetyl chloride (100 µL, 0.75 mmol) were added and reaction mixture was stirred for 16 h and evaporated. Residue was chromatographed on silica gel column (100 g, CHCl$_3$:acetone 5:1) to afford 179 mg (74%) of the product. Analytical sample was obtained after crystallization from ethyl acetate. $[\alpha]_D^{20}$=−39.2 (c 0.278, CHCl$_3$). $^1$H NMR (400 MHz, d6-DMSO) δ 1.87-1.97 (m, 1H), 2.12-2.24 (m, 1H), 2.29 (s, 3H), 2.39 (s, 3H), 3.42 (s, 2H), 3.78 (s) and 3.81 (s) and 3.83 (br s, 9H), 4.07 (br s, 1H), 4.33-4.41 (m, 1H), 5.81 (s, 1H), 7.18-7.19 (m, 5H), 8.43 (d, J=6.6 Hz, 1H). $^{13}$C NMR (101 MHz, d6-DMSO) δ 15.0, 21.7, 30.6, 42.3, 47.8, 48.9, 55.2, 55.7, 94.0, 111.8, 113.2, 122.0, 122.2, 123.9, 126.5, 128.4, 129.1, 131.9, 136.5, 136.6, 141.2, 148.3, 148.4, 151.4, 170.3. HRMS calcd for C$_{28}$H$_{32}$N$_5$O$_3$ m/z: 486.2500 (M+H)$^+$, found 486.2449.

(R)—N-(1-(3-(3,4-dimethoxyphenyl)-2,6-dimethyl-imidazo[1,2-b]pyridazin-8-yl)pyrrolidin-3-yl)-2-phenoxyacetamide (34)

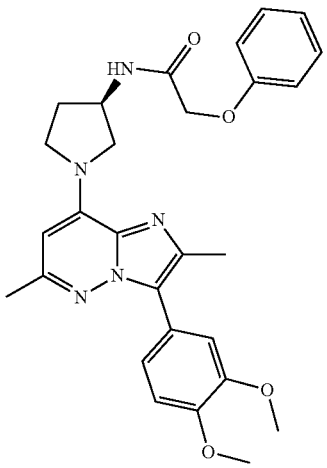

Hydrochloride 1a (200 mg, 0.5 mmol) was suspended in dichloromethane (10 mL) and triethylamine (350 µL, 0.25 mmol) and 2-phenoxyacetyl chloride (104 µL, 0.75 mmol) were added and reaction mixture was stirred for 16 h and evaporated. Residue was chromatographed on silica gel column (100 g, toluene:acetone 4:1). Product (172 mg, 69%) was isolated as foam. $[\alpha]_D^{20}=-38.3$ (c 0.243, CHCl$_3$). $^1$H NMR (400 MHz, d6-DMSO) δ 1.96-2.06 (m, 1H), 2.16-2.24 (m, 1H), 2.29 (s, 3H), 2.39 (s, 3H), 3.66-3.96 (m, 9H), 4.13 (br s, 1H), 4.43-4.55 (m, 3H), 5.80 (s, 1H), 6.89-7.00 (m, 3H), 7.07 (d, J=8.4 Hz, 1H), 7.17 (dd, J=8.3, 2.0 Hz, 1H), 7.23-7.33 (m, 3H), 8.40 (d, J=6.9 Hz, 1H). $^{13}$C NMR (101 MHz, d6-DMSO) δ 15.0, 21.7, 30.3, 47.6, 48.7, 54.8, 55.7, 67.0, 93.9, 111.8, 113.2, 114.8, 121.3, 122.0, 122.2, 123.9, 129.6, 131.9, 136.6, 141.1, 148.3, 148.4, 151.4, 158.0, 168.0. HRMS calcd for $C_{28}H_{32}N_5O_4$ m/z: 502.2449 (M+H)$^+$, found 502.2406.

(R)—N-(1-(3-(3,4-dimethoxyphenyl)-2,6-dimethyl-imidazo[1,2-b]pyridazin-8-yl)pyrrolidin-3-yl)-2,2,2-trifluoroacetamide (35)

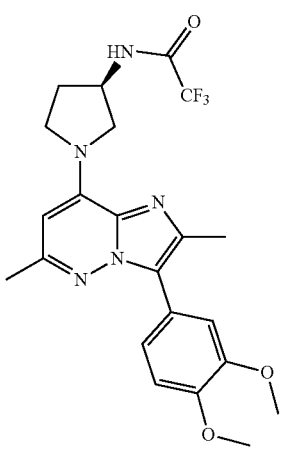

Hydrochloride 1a (160 mg, 0.4 mmol) was suspended in dichloromethane (10 mL) and triethylamine (300 µL, 0.2 mmol) and trifluoroacetic anhydride (83 µL, 0.6 mmol) were added and reaction mixture was stirred for 16 h and evaporated. Residue was chromatographed on silica gel column (100 g, CHCl$_3$:acetone 8:1) and it was obtained 120 mg (65%) of the product as foam. $[\alpha]_D^{20}=-5.5$ (c 0.234, CHCl$_3$). $^1$H NMR (400 MHz, d6-DMSO) δ 2.01-2.11 (m, 1H), 2.22-2.29 (m, 1H), 2.29 (s, 3H), 2.40 (s, 3H), 3.78 (s, 3H), 3.81 (s, 3H), 3.87 (br s, 3H), 4.18 (br s, 1H), 4.44-4.55 (m, 1H), 5.83 (s, 1H), 7.07 (d, J=8.4 Hz, 1H), 7.17 (dd, J=8.3, 2.0 Hz, 1H), 7.28 (d, J=2.0 Hz, 1H), 9.72 (d, J=6.1 Hz, 1H). $^{13}$C NMR (101 MHz, d6-DMSO) δ 15.0, 21.7, 30.0, 47.6, 49.8, 54.1, 55.7, 94.1, 111.8, 113.3, 116.0 (q, J=288 Hz), 122.0, 122.2, 123.9, 131.9, 136.6, 141.1, 148.3, 148.4, 151.4, 156.5 (q, J=36.4 Hz). HRMS calcd for $C_{22}H_{25}F_3N_5O_3$ m/z: 464.1904 (M+H)$^+$, found 464.1906.

(S)—N—((R)-1-(3-(3,4-dimethoxyphenyl)-2,6-dimethylimidazo[1,2-b]pyridazin-8-yl)pyrrolidin-3-yl)-2-methoxy-2-phenylacetamide (36)

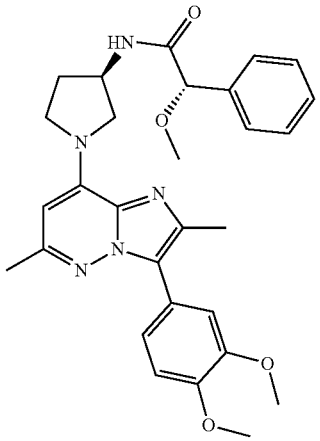 [SMILES: COc1ccc(-c2c(C)nc3c(N4CC[C@@H](NC(=O)[C@@H](OC)c5ccccc5)C4)cc(C)nn23)cc1OC]

To a solution of 1a (160 mg, 0.4 mmol), DIPEA (0.3 mL, 2 mmol) and (S)-2-methoxy-2-phenylacetic acid (100 mg, 0.6 mmol) in DMF (5 mL) was added HATU (182.5 mg, 0.48 mmol) and reaction mixture was stirred for 14 h and then solvent was evaporated. Residue was chromatographed on silica gel column (75 g, toluene:acetone 3:1) to afford product (154 mg, 75%) as foam. $[\alpha]_D^{28}=+97.5$ (c 0.279, CHCl$_3$). $^1$H NMR (400 MHz, d6-DMSO) δ 1.93-2.04 (m, 1H), 2.11-2.22 (m, 1H), 2.29 (s, 3H), 2.39 (s, 3H), 3.28 (s, 3H), 3.78 (s) and 3.81 (s) and 3.82 (br s, 9H), 4.07 (br s, 1H), 4.36-4.46 (m, 1H), 4.66 (s, 1H), 5.80 (s, 1H), 7.07 (d, J=8.4 Hz, 1H), 7.17 (dd, J=8.3, 2.0 Hz, 1H), 7.47-7.25 (m, 6H), 8.44 (d, J=7.1 Hz, 1H). $^{13}$C NMR (101 MHz, d6-DMSO) δ 15.0, 21.7, 30.5, 48.6, 54.5, 55.7, 56.9, 83.3, 94.0, 111.8, 113.2, 122.0, 122.2, 123.9, 127.2, 128.2, 128.4, 131.9, 136.6, 138.1, 141.2, 148.3, 148.4, 151.4, 170.1. HRMS calcd for $C_{29}H_{34}N_5O_4$ m/z: 516.2605 (M+H)$^+$, found 516.2562.

(R)—N-(1-(3-(3,4-dimethoxyphenyl)-2,6-dimethyl-imidazo[1,2-b]pyridazin-8-yl)pyrrolidin-3-yl)-2,2-difluoro-2-phenylacetamide (37)

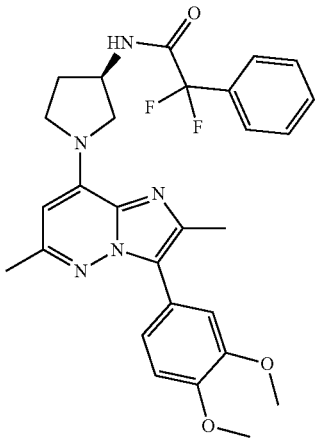 [SMILES: COc1ccc(-c2c(C)nc3c(N4CC[C@@H](NC(=O)C(F)(F)c5ccccc5)C4)cc(C)nn23)cc1OC]

To a solution of 1a (320 mg, 0.8 mmol), DIPEA (0.6 mL, 4 mmol) and 2,2-difluoro-2-phenylacetic acid (206 mg, 1.2 mmol) in DMF (10 mL) was added HATU (365 mg, 0.96 mmol) and reaction mixture was stirred for 24 h and then solvent was evaporated. Residue was chromatographed on silica gel column (150 g, toluene:ethyl acetate 2:1). Fractions containing product were evaporated and re-chromatographed (120 g, toluene:acetone 8:1) to afford product (202 mg, 48%). Solids were re-crystalized from ethyl acetate in freezer. $[\alpha]_D^{20}=\sim 0$ (c 0.224, CHCl$_3$). $^1$H NMR (400 MHz, d6-DMSO) δ 1.95-2.08 (m, 1H), 2.16-2.27 (m, 1H), 2.29 (s, 3H), 2.39 (s, 3H), 3.78 (s, 3H), 3.81 (s, 3H), 3.89 (br s, 3H), 4.14 (br s, 1H), 4.41-4.51 (m, 1H), 5.81 (s, 1H), 7.07 (d, J=8.5 Hz, 1H), 7.17 (dd, J=8.3, 2.0 Hz, 1H), 7.28 (d, J=2.0 Hz, 1H), 7.66-7.45 (m, 5H), 9.29 (d, J=6.8 Hz, 1H). $^{13}$C NMR (101 MHz, d6-DMSO) δ 15.0, 21.7, 30.2, 47.8, 49.4, 54.1, 55.7, 94.1, 111.8, 113.2, 114.9 (t, J=250.8 Hz), 122.0, 123.9, 125.4 (t, J=5.9 Hz), 129.0, 133.4 (t, J=25.6 Hz), 131.18, 136.6, 141.1, 148.3, 148.4, 163.6 (t, J=31.3 Hz), 163.31. HRMS calcd for C$_{28}$H$_{30}$F$_2$N$_5$O$_3$ m/z: 522.2311 (M+H)$^+$, found 522.2203.

Procedure for Carbamates 38-40

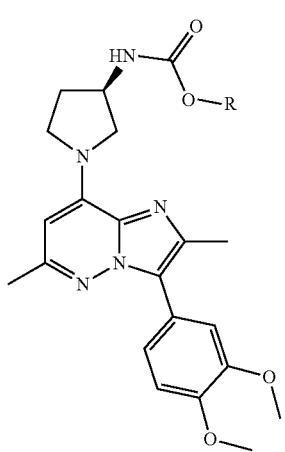

Hydrochloride 1a or 1b (160 mg, 0.4 mmol) was suspended in dry CH$_2$Cl$_2$ (10 mL) and mixture was cooled down to 0° C. To this suspension was sequentially added Et$_3$N (0.3 mL, 2.2 mmol) and DMAP (cat.). Appropriate chloroformate (0.6 mmol) was then added dropwise at 0° C. and reaction mixture slowly warmed to r.t. and was stirred overnight. Reaction mixture was evaporated and residue was purified by silica gel chromatography (100 g) and product was then crystallized.

Phenyl (R)-(1-(3-(3,4-dimethoxyphenyl)-2,6-dimethylimidazo[1,2-b]pyridazin-8-yl)pyrrolidin-3-yl)carbamate (38)

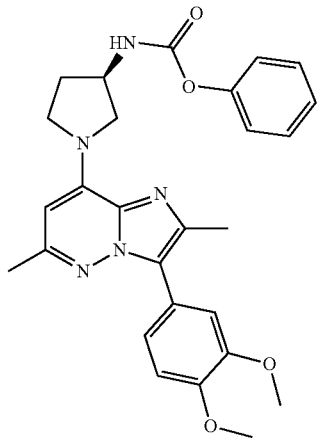 [SMILES: COc1ccc(-c2c(C)nc3c(N4CC[C@@H](NC(=O)Oc5ccccc5)C4)cc(C)nn23)cc1OC]

Yield: 140 mg (72%). Chromatography:toluene:ethyl acetate 3:1. Crystallization: ethyl acetate (freezer). $[\alpha]_D^{20}=+11.5$ (c 0.234, CHCl$_3$). $^1$H NMR (400 MHz, d6-DMSO) δ 2.00-2.09 (m, 1H), 2.19-2.28 (m, 1H), 2.30 (s, 3H), 2.40 (s, 3H), 3.79 (s, 3H), 3.81 (s, 3H), 3.92 (br s, 3H), 4.15 (br s, 1H) 4.23-4.31 (m, 1H), 5.82 (s, 1H), 7.07 (d, J=8.4 Hz, 1H), 7.10-7.25 (m, 4H), 7.28 (d, J=2.0 Hz, 1H), 7.34-7.43 (m, 2H), 8.19 (d, J=6.5 Hz, 1H). $^{13}$C NMR (101 MHz, d6-DMSO) δ 14.8, 21.5, 30.2, 50.5, 55.1*, 55.2*, 55.6, 93.8, 111.6, 113.1, 121.1, 121.8, 122.0, 123.7, 125.0, 129.3, 131.7, 136.4, 141.0, 148.1, 148.2, 150.9, 151.2, 154.5. HRMS calcd for C$_{27}$H$_{30}$N$_5$O$_4$ m/z: 488.2292 (M+H)$^+$, found 488.2267.

Benzyl (R)-(1-(3-(3,4-dimethoxyphenyl)-2,6-dimethylimidazo[1,2-b]pyridazin-8-yl)pyrrolidin-3-yl)carbamate (39)

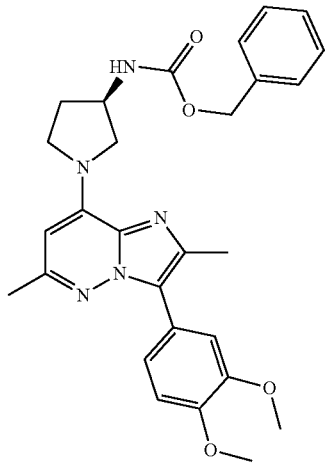 [SMILES: COc1ccc(-c2c(C)nc3c(N4CC[C@@H](NC(=O)OCc5ccccc5)C4)cc(C)nn23)cc1OC]

Yield: 82 mg (41%). Chromatography:toluene:acetone 1:1. Crystallization: ethyl acetate. $[\alpha]_D^{20}=-18.1$ (c 0.238, CHCl$_3$). $^1$H NMR (400 MHz, d6-DMSO) δ 1.89-1.99 (m, 1H), 2.13-2.22 (m, 1H), 2.28 (s, 3H), 2.39 (s, 3H), 3.70-3.97 (br s and 2×s, 9H), 4.10 (m, 1H), 5.04 (s, 2H), 5.79 (s, 1H), 7.07 (d, J=8.5 Hz, 1H), 7.17 (dd, J=8.3, 2.0 Hz, 1H), 7.28 (d, J=2.0 Hz, 1H), 7.31-7.42 (m, 5H), 7.69 (d, J=6.6 Hz, 1H). $^{13}$C NMR (101 MHz, d6-DMSO) δ 15.0, 21.7, 30.4, 47.7, 50.5, 55.2, 55.7, 65.6, 93.9, 111.8, 113.3, 122.0, 122.2, 123.9, 128.0, 128.5, 131.9, 136.6, 137.2, 141.1, 148.3, 148.4, 151.4, 156.0. HRMS calcd for C$_{28}$H$_{32}$N$_5$O$_4$ m/z: 502.2449 (M+H)$^+$, found 502.2414.

Phenyl (R)-(1-(3-(3-fluoro-4-methoxyphenyl)-2,6-dimethylimidazo[1,2-b]pyridazin-8-yl)pyrrolidin-3-yl)carbamate (40)

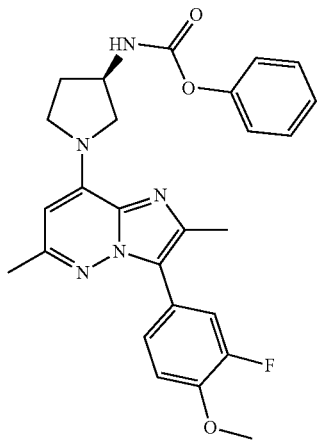 [SMILES: COc1ccc(-c2c(C)nc3c(N4CC[C@@H](NC(=O)Oc5ccccc5)C4)cc(C)nn23)cc1F]

Yield: 104 mg (55%). Chromatography: 1, toluene:ethyl acetate 3:1, 2, reverse-phase flash chromatography (C18, 50 g, water/acetonitrile 40% to 100%). Product was lyophilized. $[\alpha]_D^{20}=+10.6$ (c 0.245, CHCl$_3$). $^1$H NMR (400 MHz, d6-DMSO) δ 1.98-2.09 (m, 1H), 2.12-2.29 (m, 1H), 2.30 (s, 3H), 2.40 (s, 3H), 3.90 (s+br s, 6H), 4.13 (br s, 1H), 4.22-4.31 (m, 1H), 5.85 (s, 1H), 7.13 (dd, J=8.6, 1.2 Hz, 1H), 7.17-7.24 (m, 1H), 7.29 (t, J=8.9 Hz, 1H), 7.34-7.47 (m, 3H), 7.55 (dd, J=12.9, 2.1 Hz, 1H), 8.19 (d, J=6.5 Hz, 1H). $^{13}$C NMR (101 MHz, d6-DMSO) δ 15.0, 21.7, 50.7, 56.3, 94.3, 113.8, 113.8, 116.5 (d, J=18.8 Hz). 122.5 (d, J=7.5 Hz), 122.7 (d, J=1.9 Hz), 125.2, 125.7, 125.8 (d, J=3.2 Hz), 129.5, 132.1, 137.0, 141.1, 146.4, 146.5, 151.1, 151.6, 152.2 (d, J=243 Hz), 154.3 (2×CH2 peaks, were not detected). HRMS calcd for C$_{26}$H$_{27}$FN$_5$O$_3$ m/z: 476.2092 (M+H)$^+$, found 476.2116.

Procedure for Preparation of Carbamates (41-43)

Hydrochloride 1a (320 mg, 0.79 mmol) was suspended in dry acetonitrile (20 mL) and mixture was cooled down to 0° C. To this suspension were sequentially added Et$_3$N (0.68 mL, 3.95 mmol) and DMAP (cat.), p-Nitrophenyl chloroformate (221 mg, 1.1 mmol) was then added in one portion at 0° C. and reaction mixture was stirred for 2 hours at 0° C. Then was sequentially added triethylamine (0.4 mL, 2.4 mmol) and an appropriate alcohol (4 mmol) and reaction mixture was heated to 85° C. (bath) overnight. After evaporation the residue was chromatographed on silica gel column (150 g) followed by purification on reverse-phase flash chromatography (C18, 50 g, water/acetonitrile 40% to 100%). Compounds were then lyophilized from dioxane.

Cyclohexyl (R)-(1-(3-(3,4-dimethoxyphenyl)-2,6-dimethylimidazo[1,2-b]pyridazin-8-yl)pyrrolidin-3-yl)carbamate (41)

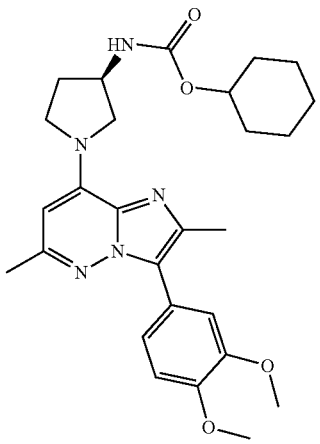 [SMILES: COc1ccc(-c2c(C)nc3c(N4CC[C@@H](NC(=O)OC5CCCCC5)C4)cc(C)nn23)cc1OC]

Yield: 139 mg (36%). Chromatography: 1. toluene:ethyl acetate 2:1, 2. reverse-phase flash chromatography (C18, 50 g, water/acetonitrile 40% to 100%). Product was lyophilized. $[\alpha]_D^{20}=-2.7$ (c 0.255, CHCl$_3$). $^1$H NMR (400 MHz, d6-DMSO) δ 1.13-1.24 (m, 1H), 1.25-1.38 (m, 4H), 1.44-1.54 (br m, 1H), 1.59-1.73 (br m, 2H), 1.75-1.87 (br m, 2H), 1.88-1.99 (m, 1H), 2.10-2.21 (m, 1H), 2.28 (s, 3H), 2.39 (s, 3H), 3.82 (2×s and br s, 9H), 4.01-4.22 (m and br s, 2H), 4.43-4.58 (br s, 1H), 5.78 (s, 1H), 7.07 (d, J=8.4 Hz, 1H), 7.16 (dd, J=8.4, 2.0 Hz, 1H), 7.27 (d, J=2.0 Hz, 1H), 7.47 (d, J=6.4 Hz, 1H). $^{13}$C NMR (101 MHz, d6-DMSO) δ 15.0, 21.7, 21.7, 23.7, 25.1, 30.4, 32.0, 47.6, 50.3, 55.2, 55.7, 55.8, 72.0, 93.8, 111.8, 113.2, 122.0, 122.2, 123.9, 131.9, 136.6, 141.1, 148.3, 148.4, 151.4, 155.7. HRMS calcd for C$_{27}$H$_{36}$N$_5$O$_4$ m/z: 494.2762 (M+H)$^+$, found 494.2786.

m-tolyl (R)-(1-(3-(3,4-dimethoxyphenyl)-2,6-dimethylimidazo[1,2-b]pyridazin-8-yl)pyrrolidin-3-yl)carbamate (42)

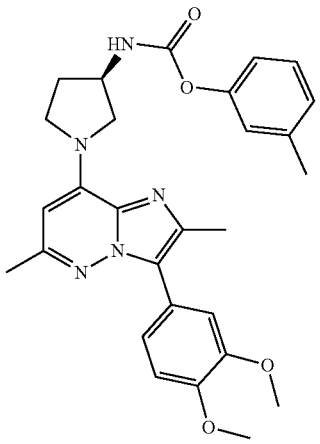 [SMILES: COc1ccc(-c2c(C)nc3c(N4CC[C@@H](NC(=O)Oc5cccc(C)c5)C4)cc(C)nn23)cc1OC]

Yield: 192 mg (49%). Chromatography: 1. toluene:ethyl acetate 3:1→2:1, 2. reverse-phase flash chromatography (C18, 50 g, water/acetonitrile 40% to 100%). Product was lyophilized. $[\alpha]_D^{20}$=+11.6 (c 0.259, $CHCl_3$). $^1H$ NMR (400 MHz, d6-DMSO) δ 1.98-2.09 (m, 1H), 2.18-2.27 (m, 2H), 2.30 (s, 3H), 2.31 (s, 3H), 2.40 (s, 3H), 3.79 (s, 3H), 3.82 (s, 3H), 3.87 (br s, 3H), 4.14 (br s, 1H), 4.22-4.30 (m, 1H), 5.82 (s, 1H), 6.91 (d, J=8.4 Hz, 1H), 6.95 (d, J=2.6 Hz, 1H), 7.04-7.00 (m, 1H), 7.08 (d, J=8.5 Hz, 1H), 7.17 (dd, J=8.3, 2.0 Hz, 1H), 7.25 (t, J=7.8 Hz, 1H), 7.28 (d, J=2.0 Hz, 1H), 8.16 (d, J=6.5 Hz, 1H). $^{13}C$ NMR (101 MHz, d6-DMSO) δ 15.0, 21.0, 21.7, 30.4, 47.7, 50.7, 55.2, 55.7, 94.0, 111.8, 113.3, 119.0, 122.2, 123.9, 131.9, 136.6, 139.1, 141.1, 148.3, 148.4, 151.0, 151.4, 154.3. HRMS calcd for $C_{28}H_{32}N_5O_4$ m/z: 502.2449 $(M+H)^+$, found 502.2498.

naphthalen-2-yl (R)-(1-(3-(3,4-dimethoxyphenyl)-2,6-dimethylimidazo[1,2-b]pyridazin-8-yl)pyrrolidin-3-yl)carbamate (43)

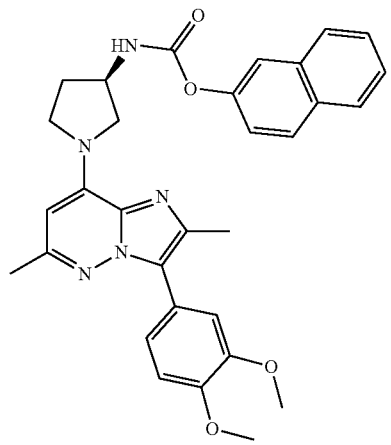 [SMILES: COc1ccc(-c2c(C)nc3c(N4CC[C@@H](NC(=O)Oc5ccc6ccccc6c5)C4)cc(C)nn23)cc1OC]

Yield: 242 mg (45%). Chromatography: 1. toluene:ethyl acetate 3:1→2:1, 2. reverse-phase flash chromatography (C18, 50 g, water/acetonitrile 30% to 100%). Product was lyophilized. $[\alpha]_D^{20}$=+23.4 (c 0.222, $CHCl_3$). $^1H$ NMR (400 MHz, d6-DMSO) δ 2.02-2.12 (m, 1H), 2.22-2.30 (m, 1H), 2.31 (s, 3H), 2.41 (s, 3H), 3.79 (s, 3H), 3.82 (s, 2H), 3.95 (br s, 3H), 4.17 (br s, 1H), 4.26-4.35 (m, 1H), 5.84 (s, 1H), 7.08 (d, J=8.5 Hz, 1H), 7.18 (dd, J=8.3, 2.0 Hz, 1H), 7.29 (d, J=2.0 Hz, 1H), 7.33 (dd, J=8.8, 2.4 Hz, 1H), 7.51 (dddd, J=14.5, 8.3, 6.9, 1.5 Hz, 2H), 7.68 (d, J=2.3 Hz, 1H), 7.97-7.87 (m, 3H), 8.30 (d, J=6.5 Hz, 1H). $^{13}C$ NMR (101 MHz, d6-DMSO) δ 15.0, 21.7, 50.7, 94.0, 111.8, 113.3, 122.0, 122.1, 122.2, 123.9, 125.6, 126.7, 127.5, 127.8, 129.2, 130.8, 131.9, 133.6, 136.6, 141.1, 148.3, 148.4, 148.8, 151.4, 154.4 ($CH_2$ peaks on pyrrolidine ring were not detected). HRMS calcd for $C_{31}H_{32}N_5O_4$ m/z: 538.2449 $(M+H)^+$, found 538.2511.

Procedure for Different Substituents in Position 8 (44-53)

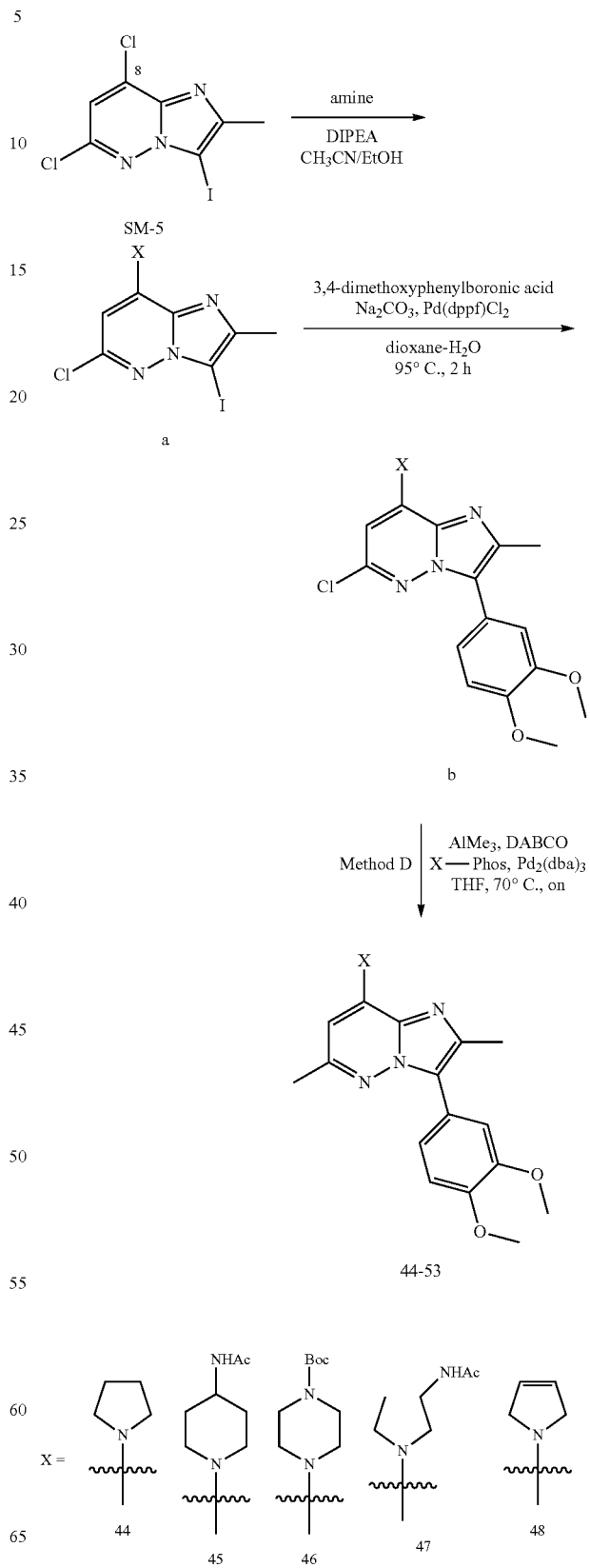

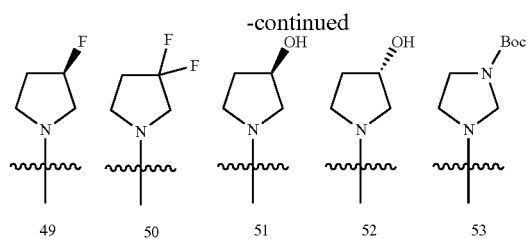

49  50  51  52  53

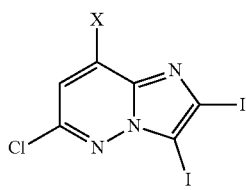

Compound SM-5 (500 mg, 1.53 mmol), appropriate amine (2 mmol), DIPEA (3 mmol for amines, 4 mmol for amine hydrochlorides) was dissolved in acetonitrile (10 mL). Reaction mixture was heated at 85° C. for 16 hours and cooled down. Products were separated by column chromatography or directly as precipitated solids were filtered-off and washed with acetonitrile.

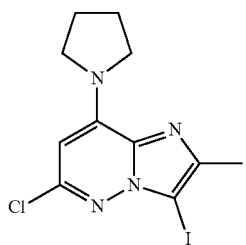 [SMILES: Cc1nc2c(N3CCCC3)cc(Cl)nn2c1I]

6-chloro-3-iodo-2-methyl-8-(pyrrolidin-1-yl)imidazo[1,2-b]pyridazine (44a)

Yield: 79%. Chromatography:toluene:ethyl acetate 20:1. UPLC-MS: t=5.28 (M+H, 363.1/365.1).

N-(1-(6-chloro-3-iodo-2-methylimidazo[1,2-b]pyridazin-8-yl)piperidin-4-yl)acetamide (45a)

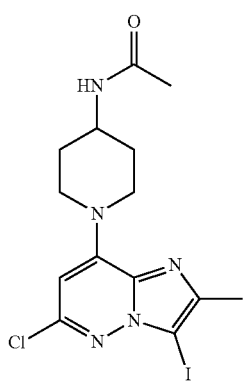 [SMILES: CC(=O)NC1CCN(c2cc(Cl)nn3c(I)c(C)nc23)CC1]

Yield: 90%, precipitated solid was filtered-off and used without further purification. UPLC-MS: t=4.26 (M+H, 434.2/436.1).

tert-butyl 4-(6-chloro-3-iodo-2-methylimidazo[1,2-b]pyridazin-8-yl)piperazine-1-carboxylate (46a)

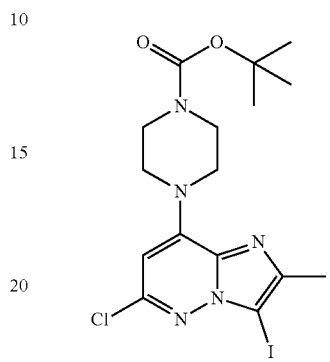

Yield: 92%. Chromatography: toluene:ethyl acetate 10:1. UPLC-MS: t=5.46 (M+H, 478.2/480.2).

N-(2-((6-chloro-3-iodo-2-methylimidazo[1,2-b]pyridazin-8-yl)(ethyl)amino)ethyl)acetamide (47a)

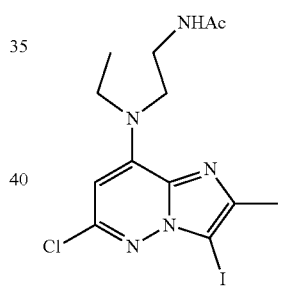

Yield: 73%. Chromatography: CHCl$_3$:acetone 7:1. UPLC-MS: t=4.46 (M+H, 422.2/424.1).

6-chloro-8-(2,5-dihydro-1H-pyrrol-1-yl)-3-iodo-2-methylimidazo[1,2-b]pyridazine (48a)

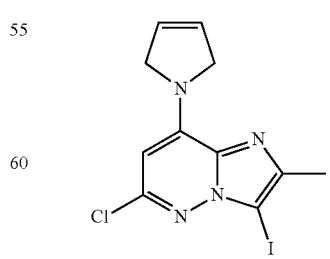

Yield: 94%. Chromatography: toluene:ethyl acetate 40:1. UPLC-MS: t=5.23 (M+H, 361.1/363.0).

147

(R)-6-chloro-8-(3-fluoropyrrolidin-1-yl)-3-iodo-2-methylimidazo[1,2-b]pyridazine (49a)

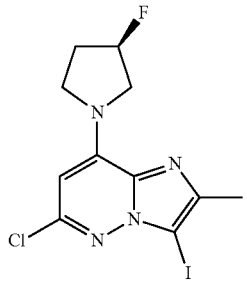 [SMILES: Cc1nc2c(N3CC[C@@H](F)C3)cc(Cl)nn2c1I]

Yield: 97%. Chromatography: toluene:ethyl acetate 15:1. UPLC-MS: t=4.95 (M+H, 381.1/383.3).

6-chloro-8-(3,3-difluoropyrrolidin-1-yl)-3-iodo-2-methylimidazo[1,2-b]pyridazine (50a)

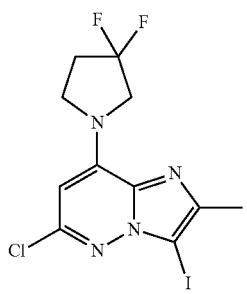 [SMILES: Cc1nc2c(N3CCC(F)(F)C3)cc(Cl)nn2c1I]

Yield: 88%. Chromatography: cyclohexane:ethyl acetate 15:1. UPLC-MS: t=5.15 (M+H, 399.1/401.3).

(R)-1-(6-chloro-3-iodo-2-methylimidazo[1,2-b]pyridazin-8-yl)pyrrolidin-3-ol (51a)

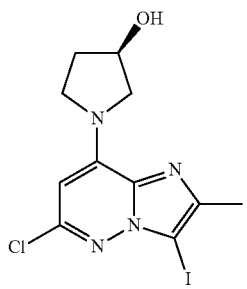 [SMILES: Cc1nc2c(N3CC[C@@H](O)C3)cc(Cl)nn2c1I]

Yield: 93%, precipitated solid was filtered-off and used without further purification. UPLC-MS: t=4.26 (M+H, 379.0/381.0).

148

(S)-1-(6-chloro-3-iodo-2-methylimidazo[1,2-b]pyridazin-8-yl)pyrrolidin-3-ol (52a)

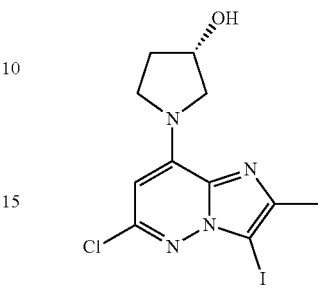

Yield: 89%, precipitated solid was filtered-off and used without further purification. UPLC-MS: t=4.26 (M+H, 379.0/381.0).

tert-butyl 3-(6-chloro-3-iodo-2-methylimidazo[1,2-b]pyridazin-8-yl)imidazolidine-1-carboxylate (53a)

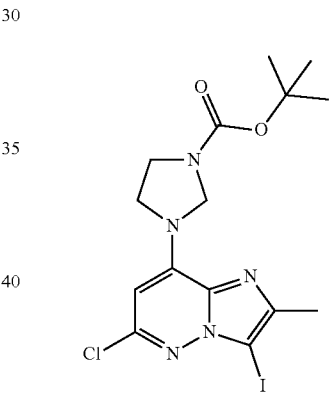

Yield: 64%. Chromatography: cyclohexane:ethyl acetate 3:1. UPLC-MS: t=5.43 (M+H, 463.3/466.2).

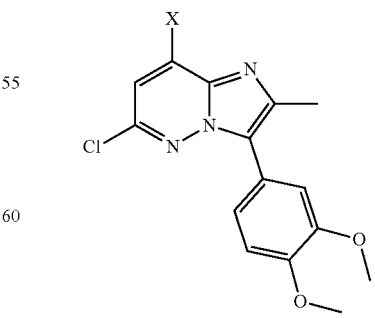

General method B with 3,4-dimethoxyphenyl boronic acid as a coupling agent was used.

6-chloro-3-(3,4-dimethoxyphenyl)-2-methyl-8-(pyrrolidin-1-yl)imidazo[1,2-b]pyridazine (44b)

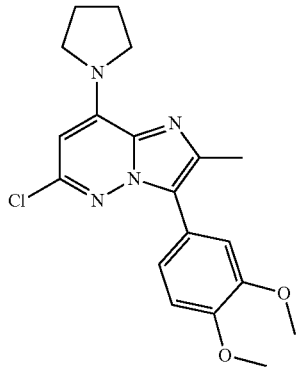 [SMILES: COc1ccc(-c2c(C)nc3c(N4CCCC4)cc(Cl)nn23)cc1OC]

Yield: 65%. Chromatography: CHCl$_3$:acetone 40:1. UPLC-MS: t=5.03 (M+H, 373.2/375.2). $^1$H NMR (400 MHz, d6-DMSO): δ 1.95 (4H, m), 2.32 (s, 3H), 3.41 (br s, 2H), 4.15 (br s, 2H), 5.97 (s, 1H). $^{13}$C NMR (101 MHz, d6-DMSO) δ 15.1, 72.4, 93.6, 134.7, 141.8, 143.5, 147.1 (CH$_2$ peaks were not detected).

N-(1-(6-chloro-3-(3,4-dimethoxyphenyl)-2-methylimidazo[1,2-b]pyridazin-8-yl)piperidin-4-yl)acetamide (45b)

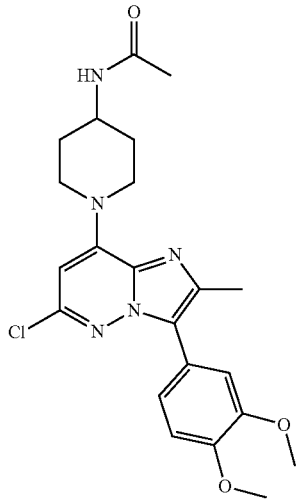 [SMILES: COc1ccc(-c2c(C)nc3c(N4CCC(NC(C)=O)CC4)cc(Cl)nn23)cc1OC]

Yield: 85%. Chromatography: CHCl$_3$:ethanol 20:1. UPLC-MS: t=4.14 (M+H, 444.3/446.3). $^1$H NMR (400 MHz, CDCl$_3$): δ 1.48-1.68 (m, 1H), 2.00 (s, 3H), 2.05-2.23 (m, 2H), 3.13-3.36 (m, 2H), 3.92 (s, 3H), 3.94 (s, 3H), 4.07-4.17 (m, 1H), 4.90 (d, J=13.5 Hz, 2H), 5.39 (d, J=8.0 Hz, 1H), 6.09 (s, 1H), 6.99 (d, J=8.3 Hz, 1H), 7.15-7.21 (m, 1H), 7.23 (d, J=2.0 Hz, 1H).

tert-butyl 4-(6-chloro-3-(3,4-dimethoxyphenyl)-2-methylimidazo[1,2-b]pyridazin-8-yl)piperazine-1-carboxylate (46b)

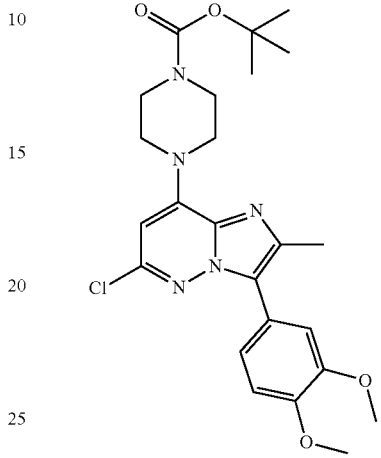

Yield: 88%. Chromatography: CHCl$_3$:aceton 20:1. UPLC-MS: t=5.30 (M+H, 484.3/490.4). $^1$H NMR (400 MHz, CDCl$_3$): 1.43 (s, 9H), 2.40 (s, 3H), 3.51 (t, J=5.2 Hz, 4H), 3.78 (s, 3H), 3.82 (s, 3H), 4.09 (t, J=5.0 Hz, 4H), 6.41 (s, 1H), 7.10 (d, J=8.4 Hz, 1H), 7.15 (dd, J=8.3, 1.9 Hz, 1H), 7.18 (d, J=1.9 Hz, 1H).

N-(2-((6-chloro-3-(3,4-dimethoxyphenyl)-2-methylimidazo[1,2-b]pyridazin-8-yl)(ethyl)amino)ethyl)acetamide (47b)

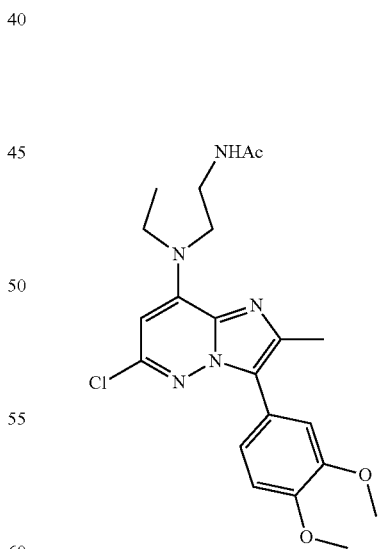

Yield: 65%. Chromatography: CH$_2$Cl$_2$:ethanol 25:1. UPLC-MS: t=4.34 (M+H, 432.4/434.3). $^1$H NMR (400 MHz, d6-DMSO): δ 1.21 (t, J=6.9 Hz, 3H), 1.80 (s, 3H), 2.40 (s, 3H), 3.40-3.33 (m, 2H), 3.68 (2×br m+2×s, 10H), 6.26 (s, 1H), 6.96-7.31 (m, 3H), 8.06 (t, J=5.8 Hz, 1H).

6-chloro-8-(2,5-dihydro-1H-pyrrol-1-yl)-3-(3,4-dimethoxyphenyl)-2-methylimidazo[1,2-b]pyridazine (48b)

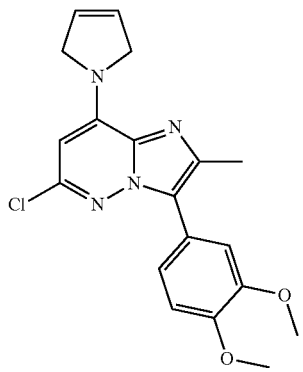 [SMILES: COc1ccc(-c2c(C)nc3c(N4CC=CC4)cc(Cl)nn23)cc1OC]

Yield: 65% (85% purity). Chromatography: CHCl₃:acetone 40:1. UPLC-MS: t=4.85 (M+H, 370.2/372.1).

(R)-6-chloro-3-(3,4-dimethoxyphenyl)-8-(3-fluoropyrrolidin-1-yl)-2-methylimidazo[1,2-b]pyridazine (49b)

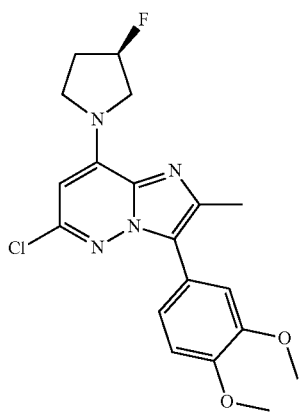 [SMILES: COc1ccc(-c2c(C)nc3c(N4CC[C@@H](F)C4)cc(Cl)nn23)cc1OC]

Yield: 92%. Chromatography: CHCl₃:ethyl acetate 15:1. UPLC-MS: t=4.85 (M+H, 390.1/393.2). $^1$H NMR (400 MHz, d6-DMSO): δ 2.08-2.36 (m, 3H), 2.41 (s, 3H), 3.56-4.20 (br s+2×s, 9H) 5.50 (dt, J=53.0, 3.4 Hz, 1H), 6.05 (s, 1H), 7.08-7.26 (m, 3H).

6-chloro-8-(3,3-difluoropyrrolidin-1-yl)-3-(3,4-dimethoxyphenyl)-2-methylimidazo[1,2-b]pyridazine (50b)

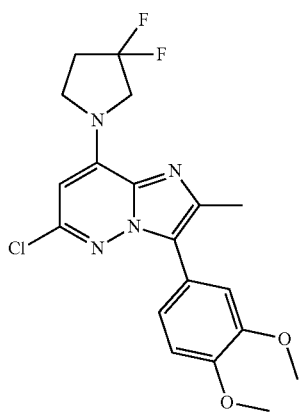 [SMILES: COc1ccc(-c2c(C)nc3c(N4CCC(F)(F)C4)cc(Cl)nn23)cc1OC]

Yield: 87%. Chromatography: cyclohexane:ethyl acetate 4:1. UPLC-MS: t=5.05 (M+H, 409.3/411.2). $^1$H NMR (400 MHz, d6-DMSO): δ 2.41 (s, 3H), 2.53-2.66 (m, 2H), 3.78 (s, 3H), 3.82 (s, 3H), 4.08 (br s, 2H), 4.40 (br s, 2H), 6.13 (s, 1H), 7.07-7.23 (m, 3H).

(R)-1-(6-chloro-3-(3,4-dimethoxyphenyl)-2-methyl-imidazo[1,2-b]pyridazin-8-yl)pyrrolidin-3-yl acetate (51b)

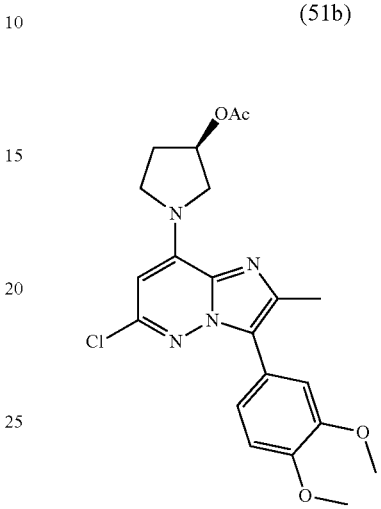

Residue after Suzuki coupling was not purified on silica gel column but was immediately acetylated (Ac₂O (1.2 eq), Et₃N (2 eq.), DMAP (cat.), CH₃CN) to afford acetyl derivative. Yield: 89% (two steps). Chromatography: toluene:ethyl acetate 3:1. UPLC-MS: t=4.77 (M+H, 431.3/433.3). $^1$H NMR (400 MHz, d6-DMSO): δ 2.03 (s, 3H), 2.11-2.19 (m, 1H), 2.20-2.32 (m, 1H), 2.40 (s, 3H), 3.48-4.91 (2×br s, 4H), 3.79 (s, 3H), 3.83 (s, 3H), 5.38 (tt, J=4.4, 2.0 Hz, 1H), 6.03 (s, 1H), 7.11 (d, J=8.4 Hz, 1H), 7.16 (dd, J=8.3, 2.0 Hz, 1H), 7.20 (d, J=1.9 Hz, 1H).

(S)-1-(6-chloro-3-(3,4-dimethoxyphenyl)-2-methyl-imidazo[1,2-b]pyridazin-8-yl)pyrrolidin-3-yl acetate (52b)

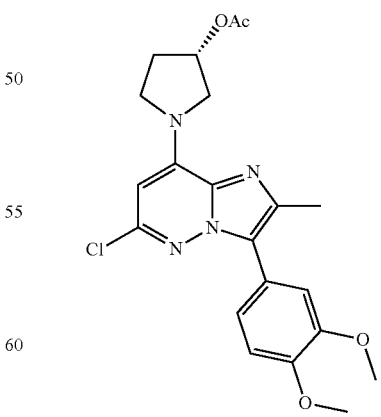

Residue after Suzuki coupling was not purified on silica gel column but was immediately acetylated (Ac₂O (1.2 eq), Et₃N (2 eq.), DMAP (cat.), CH₃CN) to afford acetyl derivative. Yield: 89% (two steps). Chromatography: toluene:ethyl acetate 3:1. UPLC-MS: t=4.77 (M+H, 431.3/433.3). NMR spectra identical.

tert-butyl 3-(6-chloro-3-(3,4-dimethoxyphenyl)-2-methylimidazo[1,2-b]pyridazin-8-yl)imidazolidine-1-carboxylate (53b)

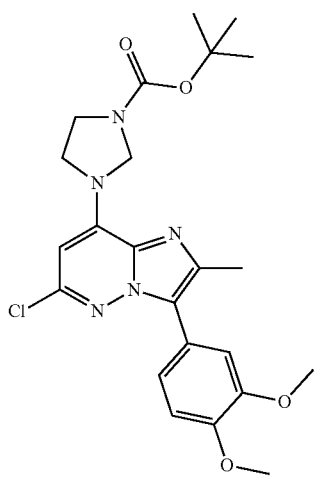 [SMILES: COc1ccc(-c2c(C)nc3c(N4CCN(C(=O)OC(C)(C)C)C4)cc(Cl)nn23)cc1OC]

Yield: 92%. Chromatography: cyclohexane:ethyl acetate 2:1. UPLC-MS: t=5.30 (M+H, 474.4/476.5). $^1$H NMR (400 MHz, d6-DMSO): δ 1.46 (s, 9H), 2.41 (s, 3H), 3.66 (dd, J=7.6, 6.0 Hz, 2H), 3.79 (s, 3H), 3.82 (s, 3H), 3.99 (br s, 2H), 5.24 (br s, 2H), 6.12 (s, 1H), 7.10 (d, J=8.4 Hz, 1H), 7.16 (dd, J=8.3, 1.9 Hz, 1H), 7.20 (d, J=1.9 Hz 1H).

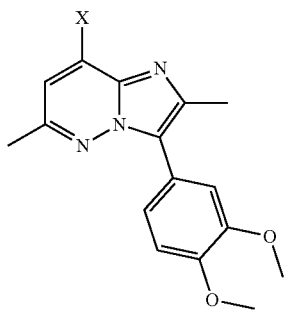

General Procedure for Methylation of Position 6 (Method D)

To a solution of DABCO (98 mg, 0.88 mmol) in 3 mL freshly distilled THF, AlMe$_3$ (2M in hexanes, 0.89 mL, 1.78 mmol) was added dropwise and the mixture was stirred at r.t. for 30 minutes under argon atmosphere. A solution of chloro derivative (1 mmol), Pd$_2$(dba)$_3$ (50 mg, 0.06 mmol) and X-Phos (57 mg, 0.12 mmol) in 15 mL freshly THF was subsequently added to the solution and the reaction mixture was stirred at 75° C. overnight under argon atmosphere. The mixture was cooled to 0° C. and quenched with sat. NH$_4$Cl (4 mL), diluted with acetone and ethyl acetate and filtered through Celite. The Celite pad was thoroughly washed with acetone and ethyl acetate. The filtrate was evaporated and the residue was purified by silica gel column chromatography (120 g). Solids were then crystalized from appropriate solvent.

3-(3,4-dimethoxyphenyl)-2,6-dimethyl-8-(pyrrolidin-1-yl)imidazo[1,2-b]pyridazine (MS 842) (44)

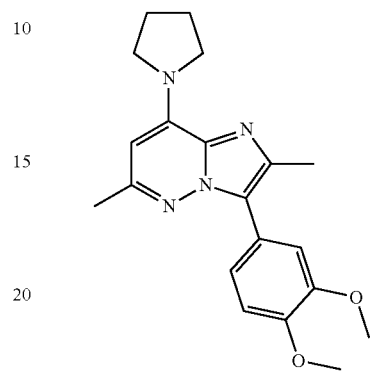

Yield: 73%. Chromatography: CHCl$_3$-acetone 30:1. Crystallization: ethyl acetate. $^1$H NMR (400 MHz, d6-DMSO) δ 1.91-2.01 (m, 4H), 2.39 (s, 3H), 2.28 (s, 3H), 3.78 (s, 3H), 3.80 (br s, 4H), 3.81 (s, 3H), 5.76 (s, 1H), 7.29 (d, J=2.0 Hz, 1H), 7.17 (dd, J=8.3, 2.0 Hz, 1H), 7.07 (d, J=8.4 Hz, 1H). $^{13}$C NMR (101 MHz, d6-DMSO) δ 15.0, 21.7, 25.1, 49.6, 55.7, 55.7, 93.7, 111.8, 113.3, 122.0, 122.3, 123.8, 132.0, 136.4, 141.1, 148.2, 151.3. HRMS calcd for C$_{20}$H$_{25}$N$_4$O$_2$ m/z: 353.1972 (M+H)$^+$, found 353.1972.

N-(1-(3-(3,4-dimethoxyphenyl)-2,6-dimethylimidazo[1,2-b]pyridazin-8-yl)piperidin-4-yl)acetamide (45)

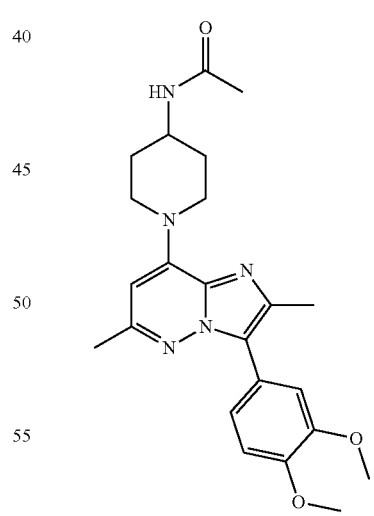

Yield: 82%. Chromatography: CHCl$_3$-ethanol 15:1. Crystallization: acetone. $^1$H NMR (400 MHz, d6-DMSO) δ 1.39-1.54 (m, 2H), 1.79-1.89 (m, 3H), 1.81 (s, 3H), 3.23 (ddd, J=13.8, 11.5, 2.6 Hz, 2H), 4.77 (d, J=13.8 Hz, 2H), 6.24 (s, 1H), 7.07 (d, J=8.4 Hz, 1H), 7.16 (dd, J=8.4, 2.0 Hz, 1H), 7.26 (d, J=2.0 Hz, 1H), 7.83 (d, J=8.4 Hz, 1H). $^{13}$C NMR (101 MHz, d6-DMSO) δ 15.2, 22.0, 23.3, 31.6, 47.0, 56.0, 97.4, 112.1, 113.7, 122.3, 122.4, 124.2, 132.4, 136.5, 143.3, 148.7, 148.6, 151.7, 168.8. HRMS calcd for C$_{23}$H$_{29}$N$_5$O$_3$Na m/z: 446.2163 (M+Na)$^+$, found 446.2161.

tert-butyl 4-(3-(3,4-dimethoxyphenyl)-2,6-dimethyl-imidazo[1,2-b]pyridazin-8-yl)piperazine-1-carboxylate (46)

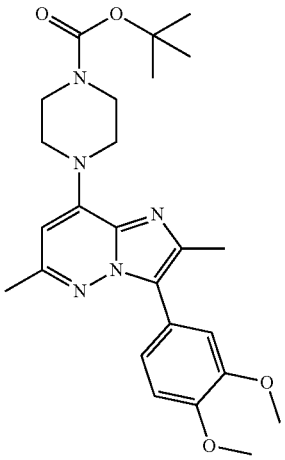

Yield: 85%. Chromatography: CHCl$_3$-acetone 10:1. Crystallization: ethyl acetate. $^1$H NMR (400 MHz, CDCl$_3$) δ 1.50 (s, 9H), 2.41 (s, 3H), 2.51 (s, 3H), 3.63-3.70 (m, 4H), 3.79-4.03 (br m, 2×s 10H), 5.96 (s, 1H), 6.99 (d, J=8.4 Hz, 1H), 7.22 (dd, J=8.3, 2.0 Hz, 1H), 7.30 (d, J=2.0 Hz, 1H). $^{13}$C NMR (101 MHz, CDCl$_3$) δ 15.0, 22.3, 28.6, 47.9, 56.1, 80.2, 97.8, 111.2, 113.1, 122.4, 122.5, 124.7, 132.8, 137.5, 144.1, 148.7, 148.8, 151.6, 154.9. HRMS calcd for C$_{25}$H$_{34}$N$_5$O$_4$ m/z: 468.2605 (M+H)$^+$, found 468.2599.

N-(2-((3-(3,4-dimethoxyphenyl)-2,6-dimethylimidazo[1,2-b]pyridazin-8-yl)(ethyl)amino)ethyl)acetamide (47)

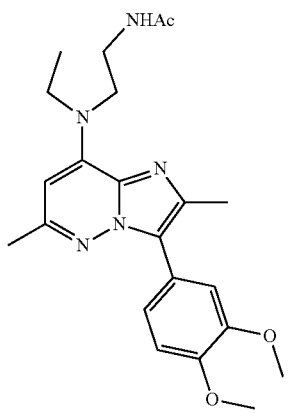

Yield: 86%. Chromatography: 1. CH$_2$Cl$_2$-ethanol 25:1, 2. CH$_2$Cl$_2$— acetone 2:1. Crystallization: product was isolated as foam. $^1$H NMR (400 MHz, d6-DMSO) δ 1.19 (t, J=6.9 Hz, 1H), 1.80 (s, 1H), 2.0 (s, 1H), 2.40 (s, 1H), 3.33-3.40 (m, 1H), 3.81 (s, 1H), 3.78 (s, 1H), 3.85 (t, J=6.5 Hz, 1H), 3.97 (q, J=6.5 Hz, 1H), 6.08 (s, 1H), 7.07 (d, J=8.4 Hz, 1H), 7.16 (dd, J=8.4, 1.9 Hz, 1H), 7.27 (d, J=1.9 Hz, 1H), 8.09 (t, J=5.7 Hz, 1H). $^{13}$C NMR (101 MHz, d6-DMSO) δ 13.4, 15.3, 22.0, 23.0, 37.4, 46.1, 49.6, 56.0, 94.9, 112.1, 113.7, 122.4, 131.9, 136.5, 142.0, 148.6, 148.7, 151.5, 170.0. HRMS calcd for C$_{22}$H$_{30}$N$_5$O$_3$ m/z: 412.2343 (M+H)$^+$, found 412.2327.

8-(2,5-dihydro-1H-pyrrol-1-yl)-3-(3,4-dimethoxyphenyl)-2,6-dimethylimidazo[1,2-b]pyridazine (48)

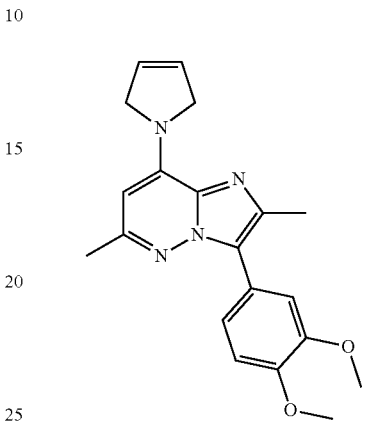

Yield: 40%. Chromatography: 1. CHCl$_3$-acetone 30:1, 2. Reverse phase flash chromatography (C18, 50 g, water/methanol 30% to 100%). Crystallization: ethyl acetate. $^1$H NMR (400 MHz, d6-DMSO) δ 2.30 (s, 3H), 2.40 (s, 3H), 4.60 (br s, 4H), 5.77 (s, 1H), 6.07 (s, 2H), 7.08 (d, J=8.4 Hz, 1H), 7.18 (dd, J=8.3, 2.0 Hz, 1H), 7.29 (d, J=2.0 Hz, 1H). $^{13}$C NMR (101 MHz, d6-DMSO) δ 15.0, 21.7, 55.7, 56.5*, 93.8, 111.8, 113.3, 122.2, 124.0, 125.9*, 131.8, 136.8, 140.5, 148.3, 148.4, 151.5. HRMS calcd for C$_{20}$H$_{24}$N$_4$O$_2$ m/z: 351.1816 (M+H)$^+$, found 351.1813.

(R)-3-(3,4-dimethoxyphenyl)-8-(3-fluoropyrrolidin-1-yl)-2,6-dimethylimidazo[1,2-b]pyridazine (49)

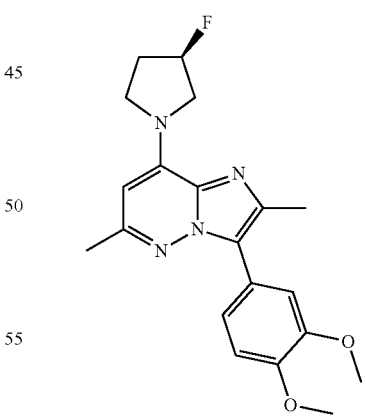

Yield: 68%. Chromatography: CHCl$_3$-acetone 15:1. Crystallization: ethyl acetate. [α]$_D^{20}$=−19.5 (c 0.303, CHCl$_3$). $^1$H NMR (400 MHz, d6-DMSO) δ 2.08-2.35 (m, 5H), 2.40 (s, 3H), 3.63-3.85 (m, 7H), 3.86-4.15 (m, 2H), 4.23-4.52 (br s, 1H), 5.48 (dt, J=53.4, 3.6 Hz, 1H), 5.86 (s, 1H), 7.08 (d, J=8.4 Hz, 1H), 7.17 (dd, J=8.3, 2.0 Hz, 1H), 7.28 (d, J=2.0 Hz, 1H). $^{13}$C NMR (101 MHz, d6-DMSO) δ 15.0, 21.7, 31.4 (d, J=20.8 Hz), 47.1, 55.7, 56.3 (d, J=23.2 Hz), 93.0 (d, J=172.0 Hz), 94.3, 111.8, 113.3, 122.0, 122.1, 124.0, 131.8, 136.7, 141.0, 148.3, 148.4, 151.4. HRMS calcd for C$_{20}$H$_{24}$FN$_4$O$_2$ m/z: 371.1878 (M+H)$^+$, found 371.1895.

8-(3,3-difluoropyrrolidin-1-yl)-3-(3,4-dimethoxyphenyl)-2,6-dimethylimidazo[1,2-b]pyridazine (50)

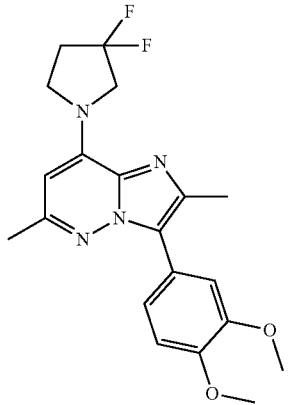

Yield: 60%. Chromatography: cyclohexane-ethyl acetate 5:2. Crystallization: ethyl acetate (freezer). [α]$_D^{20}$=+2.4 (c 0.333, CHCl$_3$). $^1$H NMR (400 MHz, d6-DMSO) δ 2.32 (s, 3H), 2.41 (s, 3H), 2.51-2.68 (m, 2H), 3.79 (s, 3H), 3.82 (s, 3H), 3.94-4.05 (m, 2H), 4.37 (t, J=13.1 Hz, 2H), 5.94 (s, 1H), 7.08 (d, J=8.4 Hz, 1H), 7.17 (dd, J=8.3, 2.0 Hz, 1H), 7.28 (d, J=2.0 Hz, 1H). $^{13}$C NMR (101 MHz, d6-DMSO) δ 15.0, 21.7, 32.9 (t, J=23.3 Hz), 47.2, 55.7, 56.0 (t, J=32.4 Hz), 94.8, 111.8, 113.2, 121.9, 122.0, 124.1, 128.5 (t, J=245.7 Hz), 131.5, 137.0, 140.7, 148.4, 148.5, 151.5. HRMS calcd for C$_{20}$H$_{23}$F$_2$N$_4$O$_2$ m/z: 389.1784 (M+H)$^+$, found 389.1720.

(R)-1-(3-(3,4-dimethoxyphenyl)-2,6-dimethylimidazo[1,2-b]pyridazin-8-yl)pyrrolidin-3-ol (51)

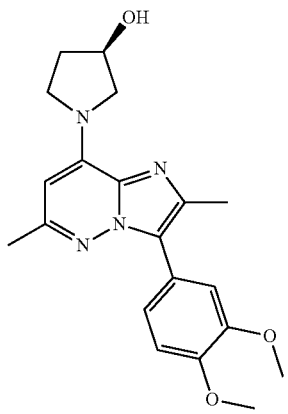

During methylation step, partially deacetylation occurred. Residue after filtration through Celite was then completely deacetylated by potassium carbonate (1 eq.) in methanol. Yield: 79%. Chromatography: CHCl$_3$-ethanol 20:1. Crystallization: ethyl acetate. [α]$_D^{20}$=−11.2 (c 0.277, DMSO). $^1$H NMR (400 MHz, d6-DMSO) δ 1.88-1.96 (m, 1H), 1.98-2.09 (m, 1H), 2.28 (s, 3H), 2.39 (s, 3H), 3.58-4.13 (br s+2×s, 10H) 4.38-4.45 (m, 1H), 5.01 (d, J=3.4 Hz, 1H), 5.77 (s, 1H), 7.07 (d, J=8.4 Hz, 1H), 7.17 (dd, J=8.3, 2.0 Hz, 1H), 7.29 (d, J=2.0 Hz, 1H). $^{13}$C NMR (101 MHz, d6-DMSO) δ 15.0, 21.7, 33.3, 47.5, 55.7, 58.2, 69.1, 93.6, 111.8, 113.3, 122.0, 122.3, 123.8, 132.0, 136.5, 141.3, 148.2, 148.4, 151.3. HRMS calcd for C$_{20}$H$_{25}$N$_4$O$_3$ m/z: 369.1921 (M+H)$^+$, found 369.1932.

(S)-1-(3-(3,4-dimethoxyphenyl)-2,6-dimethylimidazo[1,2-b]pyridazin-8-yl)pyrrolidin-3-ol (52)

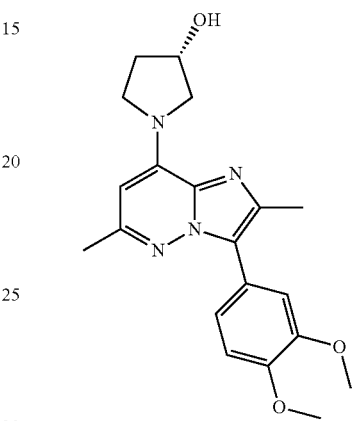

During methylation step, partially deacetylation occurred. Residue after filtration through Celite was then completely deacetylated by potassium carbonate (1 eq.) in methanol. Yield: 74%. Chromatography: CHCl$_3$-ethanol 20:1. Crystallization: ethyl acetate. Physical and spectral properties are identical to those for compound 18h. [α]$_D^{20}$=+13.5 (c 0.325, DMSO). HRMS calcd for C$_{20}$H$_{25}$N$_4$O$_3$ m/z: 369.1921 (M+H)$^+$, found 369.1932.

tert-butyl 3-(3-(3,4-dimethoxyphenyl)-2,6-dimethylimidazo[1,2-b]pyridazin-8-yl)imidazolidine-1-carboxylate (53)

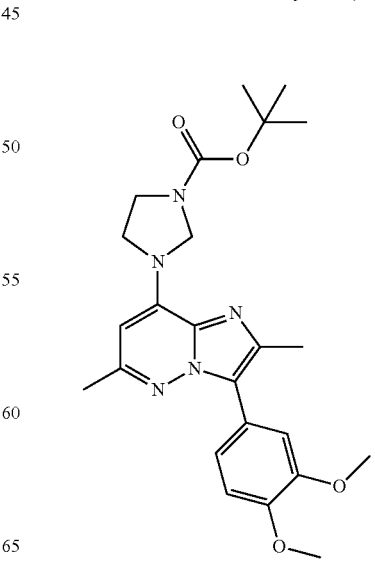

Yield: 75%. Chromatography: cyclohexane:ethyl acetate 1:1. Crystallization: ethyl acetate. ¹H NMR (400 MHz, d6-DMSO) δ 1.47 (s, 9H), 2.32 (s, 3H), 2.41 (s, 3H), 3.65 (dd, J=7.6, 6.0 Hz, 2H), 3.79 (s, 3H), 3.82 (s, 3H), 3.97 (br s, 2H), 5.17 (br s, 2H), 5.95 (s, 1H), 7.08 (d, J=8.4 Hz, 1H), 7.17 (dd, J=8.3, 2.0 Hz, 1H), 7.28 (d, J=2.0 Hz, 1H). ¹³C NMR (101 MHz, d6-DMSO) δ 15.0, 21.6, 28.2, 43.6, 55.7, 79.8, 95.4, 111.8, 113.2, 121.9, 122.0, 124.2, 131.4, 137.1, 139.6, 148.4, 148.5, 151.6, 152.6 (one $CH_2$ carbon and $C(CH_3)_3$ carbon were not detected). HRMS calcd for $C_{24}H_{32}N_5O_4$ m/z: 454.2449 (M+H)⁺, found 454.2491.

(R)—N-(1-(3-(3,4-dimethoxyphenyl)-2-methyl-6-phenylimidazo[1,2-b]pyridazin-8-yl)pyrrolidin-3-yl)acetamide (54)

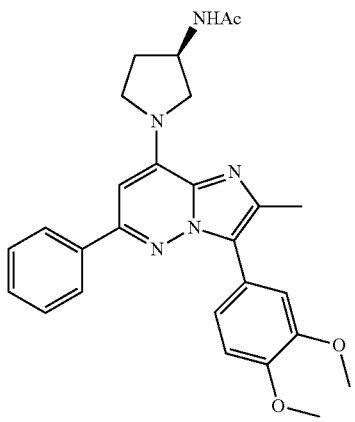 [SMILES: COc1ccc(-c2c(C)nc3c(N4CC[C@@H](NC(C)=O)C4)cc(-c4ccccc4)nn23)cc1OC]

Solution of starting material SM-7 (200 mg, 0.47 mmol), $K_3PO_4$ (143 mg, 0.94 mmol) and phenyl boronic acid (115 mg, 0.94 mmol) in DMF-water (5.5 ml, 5:1) was degassed and purged with argon. Pd(dppf)Cl₂ (39 mg, 0.05 mmol) was added and mixture was heated to 95° C. for 24 h. Then, same amounts of reagents were added and heating continued for another 12 h after which second addition of the same reagents followed. Reaction mixture was heated for additional 12 h and then cooled down and diluted with ethyl acetate (250 ml). Organic phase was dried over $Na_2SO_4$ and evaporated. The residue was purified by silica gel column chromatography (200 g, chloroform-ethanol 20:1→15:1) to obtain brownish solid which was re-crystalized from ethyl acetate to yield 55 mg (25%) of the product. $[α]_D^{20}$=+7.0 (c 0.230, CHCl₃). ¹H NMR (400 MHz, d6-DMSO) δ 1.84 (s, 3H), 1.89-2.01 (m, 1H), 2.21 (dq, J=13.6, 7.3 Hz, 1H), 2.46 (s, 3H), 3.82 (s, 3H), 3.83 (s, 4H), 3.93 (br s, 3H), 4.18 (br s, 1H), 4.40 (q, J=5.7 Hz, 1H), 6.36 (s, 1H), 7.11 (d, J=8.5 Hz, 1H), 7.25 (dd, J=8.5, 2.0 Hz, 1H), 7.35-7.61 (m, 4H), 7.79-8.08 (m, 2H), 8.22 (d, J=6.7 Hz, 1H). ¹³C NMR (101 MHz, d6-DMSO) δ 15.2, 22.8, 30.5*, 48.2*, 48.8, 51.6, 55.2*, 55.7, 59.9, 91.1, 111.8, 113.0, 121.9, 122.0, 124.3, 126.7, 128.8, 129.4, 132.1, 137.1, 137.5, 141.7, 148.3, 148.4, 151.0, 169.4.

(R)—N-(1-(3-(3,4-dimethoxyphenyl)-6-(ethylthio)-2-methylimidazo[1,2-b]pyridazin-8-yl)pyrrolidin-3-yl)acetamide (55)

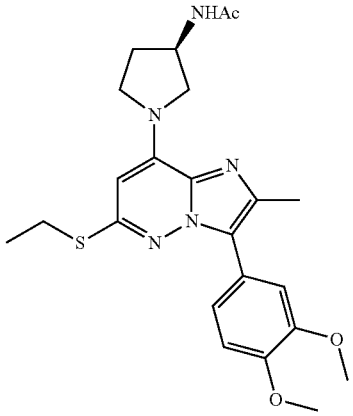 [SMILES: CCSc1cc(N2CC[C@@H](NC(C)=O)C2)c2nc(C)c(-c3ccc(OC)c(OC)c3)n2n1]

To a solution of ethanthiol (173 µL, 2.35 mmol) in NMP (5 mL) was added NaH (93 mg, 2.35 mmol, 60% in mineral oil) at r.t. and reaction mixture was stirred for 20 minutes. Then starting material SM-7 (200 mg, 0.47 mmol) was added in one portion (solid) and flask was immersed to an oil bath (100° C.) and reaction mixture was heated for 16 h. Reaction mixture was poured to an aq. NH₄Cl (50 mL) and extracted with ethyl acetate (2×100 mL). Combined organic phases were dried over $Na_2SO_4$ and evaporated. Residue was passed through short column with silica gel (CHCl₃-ethanol 10:1) and fractions with intermediate were evaporated. It was obtained 120 mg of mixture of partially demethylated derivatives. This intermediate was dissolved in acetone (7 ml), $K_2CO_3$ (75 mg) and CH₃I (40 µL) was added and reaction mixture was stirred overnight, filtered through Celite and filtrate was evaporated. Residue was chromatographed on silica gel column (50 g, CHCl₃→CHCl₃-acetone 3:1) to obtain 100 mg (47%) of the product as a white solid. $[α]_D^{20}$=+3.2 (c 0.250, CHCl₃). ¹H NMR (400 MHz, d6-DMSO) δ 1.27 (t, J=7.3 Hz, 3H), 1.82 (s, 3H), 1.85-1.95 (m, 1H), 2.20-2.26 (m, 1H), 2.40 (s, 3H), 3.05 (q, J=7.3 Hz, 2H), 3.79 (s, 3H), 3.81 (s, 3H), 3.85 (br s, 3H), 4.08 (br s 1H), 4.35 (m, 1H), 5.75 (s, 1H), 7.07 (d, J=8.4 Hz, 1H), 7.18 (dd, J=8.4, 2.0 Hz, 1H), 7.29 (d, J=2.0 Hz, 1H), 8.17 (d, J=6.7 Hz, 1H). ¹³C NMR (101 MHz, d6-DMSO) δ 14.9, 15.0, 22.8, 24.2, 30.3*, 48.8*, 55.7, 55.7, 92.1, 111.7, 113.0, 121.8, 122.0, 124.3, 131.5, 136.5, 140.8, 148.4, 148.4, 152.3, 169.4 (2×CH₂ not detected). HRMS calcd for $C_{23}H_{30}N_5O_3S$ m/z: 456.2064 (M+H)⁺, found 456.2052.

(R)—S-(1-(3-(3,4-dimethoxyphenyl)-2,6-dimethyl-imidazo[1,2-b]pyridazin-8-yl)pyrrolidin-3-yl) ethanethioate (56)

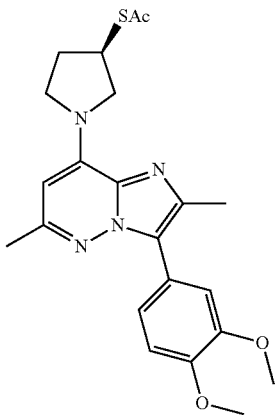

Solution of the starting material 52 (500 mg, 1.36 mmol), triphenylphosphine (712 mg, 2.72 mmol) in THF (14 mL) was cooled to 0° C. and DIAD (0.54 mL, 2.72 mmol) was dropwise added followed by dropwise addition of thioacetic acid (194 µL, 2.72 mL). Reaction mixture was allowed to warm to r.t. and stirred overnight. Reaction mixture was cooled to 0° C. and same amount of the reagents was added again and reaction mixture was stirred at r.t. overnight and evaporated. Residue was chromatographed on silica gel (200 g, CHCl$_3$-acetone 30:1). Fractions containing the product were evaporated and subjected to reverse-phase flash chromatography (C18, 100 g, water/acetonitrile 10% to 100%). It was obtained 156 mg (27%) of the product. $[\alpha]_D^{20}$=+46.88 (c 0.265, CHCl$_3$). $^1$H NMR (400 MHz, d6-DMSO) δ 1.95-2.05 (m, 1H), 2.29 (s, 3H), 2.37 (s, 3H), 2.39-2.47 (m, 1H), 2.39 (s, 3H), 3.74 (m, 9H), 4.03-4.14 (m, 1H), 4.32 (br s, 1H), 5.82 (s, 1H), 7.07 (d, J=8.3 Hz, 1H), 7.16 (dd, J=8.3, 2.0 Hz, 1H), 7.27 (d, J=2.0 Hz, 1H). $^{13}$C NMR (101 MHz, d6-DMSO) δ 15.0, 21.6, 30.7, 30.8, 41.1, 48.3, 55.4, 55.7, 94.2, 111.9, 113.3, 122.0, 122.1, 124.0, 131.7, 136.7, 140.8, 148.3, 148.4, 151.4, 195.4. HRMS calcd for C$_{22}$H$_{27}$N$_4$O$_3$S m/z: 427.1798 (M+H)$^+$, found 427.1824.

(R)-4-(1-(3-(3,4-dimethoxyphenyl)-2,6-dimethylimidazo[1,2-b]pyridazin-8-yl)pyrrolidin-3-yl)morpholine (57)

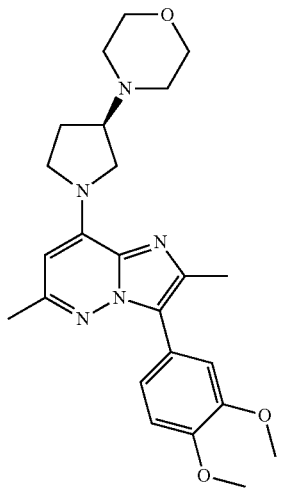

Hydrochloride 1a (320 mg, 0.73 mmol) was combined with sodium iodide (55 m, 0.36 mmol), DIPEA (1 mL, 5.8 mmol), 2,2'-bischlorodiethyl ether (130 µL, 1.1 mmol) in DMF (4 mL) at r.t. and resulting mixture was heated to 100° C. for 24 h. Reaction mixture was cooled down, DIPEA (0.5 mL, 2.9 mmol) and 2,2'-bischlorodiethyl ether (130 µL, 1.1 mmol) and then heating was continued for 5 h at 110° C. Solvents were evaporated and residue was chromatographed on silica gel (150 g, CHCl$_3$-acetone 1:1). Final purification of the product (101 mg, 31%) was achieved by reverse-phase flash chromatography (C18, 50 g, water/acetonitrile 10% to 100%). $[\alpha]_D^{20}$=+28.8 (c 0.250, CHCl$_3$). $^1$H NMR (400 MHz, d6-DMSO) δ 1.76-1.92 (m, 1H), 2.14-2.23 (m, 1H), 2.28 (s, 3H), 2.39 (s, 3H), 2.40-2.50 (m, 4H), 2.87-2.97 (m, 1H), 3.55 (br s, 1H), 3.61 (t, J=4.6 Hz, 4H), 3.70 (br s, 1H), 3.78 (s, 1H), 3.81 (s, 1H), 4.12 (br s, 2H), 5.80 (s, 1H), 7.07 (d, J=8.4 Hz, 1H), 7.16 (dd, J=8.4, 2.0 Hz, 1H), 7.27 (d, J=2.0 Hz, 1H). $^{13}$C NMR (101 MHz, d6-DMSO) δ 15.0, 21.7, 51.9, 53.1, 55.7, 63.9, 66.3, 66.5, 93.8, 111.8, 113.3, 122.2, 123.9, 131.8, 136.6, 141.0, 148.3, 148.4, 151.4. HRMS calcd for C$_{24}$H$_{32}$N$_5$O$_3$ m/z: 438.2500 (M+H)$^+$, found 438.2503.

(R)-8-(3-azidopyrrolidin-1-yl)-3-(3,4-dimethoxyphenyl)-2,6-dimethylimidazo[1,2-b]pyridazine (58)

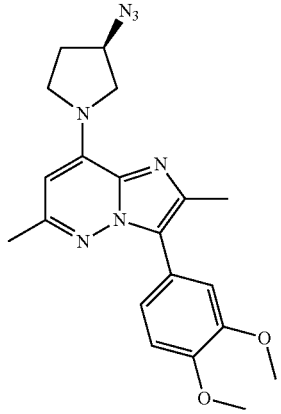

To a solution of compound 52 (500 mg, 1.37 mmol), triphenylphosphine (538 mg, 2.05 mmol) in THF (20 mL) was added DIAD (0.4 mL, 2.05 mmol) at 0° C. followed by dropwise addition of diphenyl phosphoryl azide (0.59 mL, 2.72 mmol) at 0° C. Reaction mixture was slowly allowed to r.t. and stirred overnight and evaporated. Residue was purified on flash chromatography (120 g, CHCl$_3$:ethyl acetate 10:1). Fractions containing the product were evaporated and subjected to reverse-phase flash chromatography (C18, 100 g, water/acetonitrile 10% to 100%). It was obtained 425 mg (79%) of the product. $[\alpha]_D^{20}$=−53.5 (c 0.325, CHCl$_3$). $^1$H NMR (400 MHz, d6-DMSO) δ 2.06-2.15 (m, 1H), 2.19-2.28 (m, 1H), 2.29 (s, 3H), 2.40 (s, 3H), 3.65 (m, 8H), 3.99 (br s, 1H), 4.20 (br s, 1H), 4.49-4.56 (m, 1H), 5.84 (s, 1H), 7.07 (d, J=8.4 Hz, 1H), 7.17 (dd, J=8.3, 2.0 Hz, 1H), 7.28 (d, J=2.0 Hz, 1H). $^{13}$C NMR (101 MHz, d6-DMSO) δ 15.0, 21.7, 30.3, 47.4, 54.7, 55.7, 60.2, 94.2, 111.8, 113.3, 122.0, 122.1, 124.0, 131.7, 136.7, 140.8, 148.3, 148.4, 151.4. HRMS calcd for C$_{20}$H$_{24}$N$_7$O$_2$ m/z: 394.1986 (M+H)$^+$, found 394.2022.

(R)-3-(3,4-dimethoxyphenyl)-2,6-dimethyl-8-(3-(4-phenyl-1H-1,2,3-triazol-1-yl)pyrrolidin-1-yl)imidazo[1,2-b]pyridazine (59)

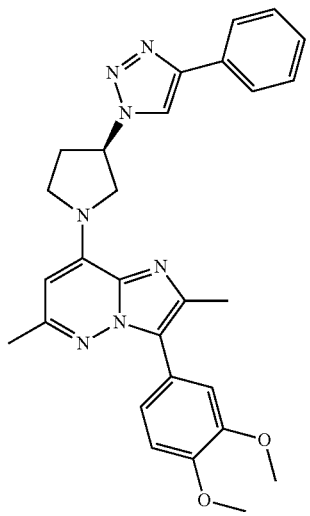 [SMILES: COc1ccc(-c2c(C)nc3c(N4CC[C@@H](n5cc(-c6ccccc6)nn5)C4)cc(C)nn23)cc1OC]

To a solution of azide 58 (200 mg, 0.56 mmol) and phenylacetylene (92 µl, 0.84 mmol) in THF/H$_2$O (9 mL, 2:1) was added CuSO$_4$.5H$_2$O (7 mg, 0.03 mmol) and sodium ascorbate (11 mg, 0.06 mmol) at r.t. under an argon atmosphere. Reaction mixture was heated at 55° C. for 14 hours. Resulting solution was evaporated and chromatographed on silica gel (150 mg, CHCl$_3$-acetone 8:1). It was obtained 191 mg (69%) of the solid which was re-crystalized from ethyl acetate/acetone. [α]$_D^{20}$=−106.3 (c 0.223, CHCl$_3$). $^1$H NMR (400 MHz, d6-DMSO) δ 2.31 (s, 3H), 2.39 (s, 3H), 2.54-2.71 (m, 2H), 3.78 (s, 3H), 3.81 (s, 3H), 3.99 (br s, 2H), 4.45 (br s, 1H), 4.59 (br s, 1H), 5.32-5.55 (m, 1H), 5.91 (s, 1H), 7.07 (d, J=8.4 Hz, 1H), 7.17 (dd, J=8.3, 2.0 Hz, 1H), 7.28 (d, J=2.0 Hz, 1H), 7.29-7.37 (m, 1H), 7.44 (t, J=7.6 Hz, 2H), 7.75-7.92 (m, 2H), 8.74 (s, 1H). $^{13}$C NMR (101 MHz, d6-DMSO) δ 14.9, 21.7, 30.8, 47.9, 55.3, 55.7, 59.2, 94.5, 111.8, 113.3, 120.7, 122.0, 122.1, 124.0, 125.3, 128.1, 129.0, 130.8, 131.8, 136.7, 140.8, 146.7, 148.3, 148.4, 151.5. HRMS calcd for C$_{28}$H$_{30}$N$_7$O$_2$ m/z: 496.2455 (M+H)$^+$, found 496.2461.

(R)-1-(3-(3,4-dimethoxyphenyl)-2,6-dimethylimidazo[1,2-b]pyridazin-8-yl)pyrrolidin-3-yl acetate (60)

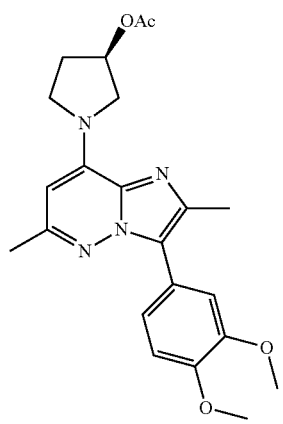

To a mixture of starting material 51 (221 mg, 0.6 mmol), triethylamine (0.22 mL, 1.6 mmol) and DMAP (cat. amount) was added acetanhydride (0.1 mL, 1.1 mmol) at r.t. and reaction mixture was stirred for 2 h and then evaporated. Residue was chromatographed on silica gel column (50 g, toluene:ethyl acetate 3:1) to afford 220 mg (89%) of the product. Analytical sample was then re-crystalized from ethyl acetate. [α]$_D^{20}$=−8.7 (c 0.333, CHCl$_3$). $^1$H NMR (400 MHz, d6-DMSO) δ 2.01 (s, 3H), 2.07-2.18 (m, 1H), 2.18-2.28 (m, 1H), 2.29 (s, 3H), 2.39 (s, 3H), 3.63-4.28 (m, 10H), 5.32-5.40 (m, 1H), 5.84 (s, 1H), 7.07 (d, J=8.4 Hz, 1H), 7.17 (dd, J=8.3, 2.0 Hz, 1H), 7.27 (d, J=2.0 Hz, 1H). $^{13}$C NMR (101 MHz, d6-DMSO) δ 15.0, 21.1, 21.7, 30.5, 47.4, 55.5, 55.8, 73.4, 94.2, 111.8, 113.3, 122.0, 122.2, 124.0, 131.8, 136.7, 141.0, 148.3, 148.4, 151.5, 170.4. HRMS calcd for C$_{27}$H$_{27}$N$_4$O$_4$ m/z: 411.2027 (M+H)$^+$, found 411.2029.

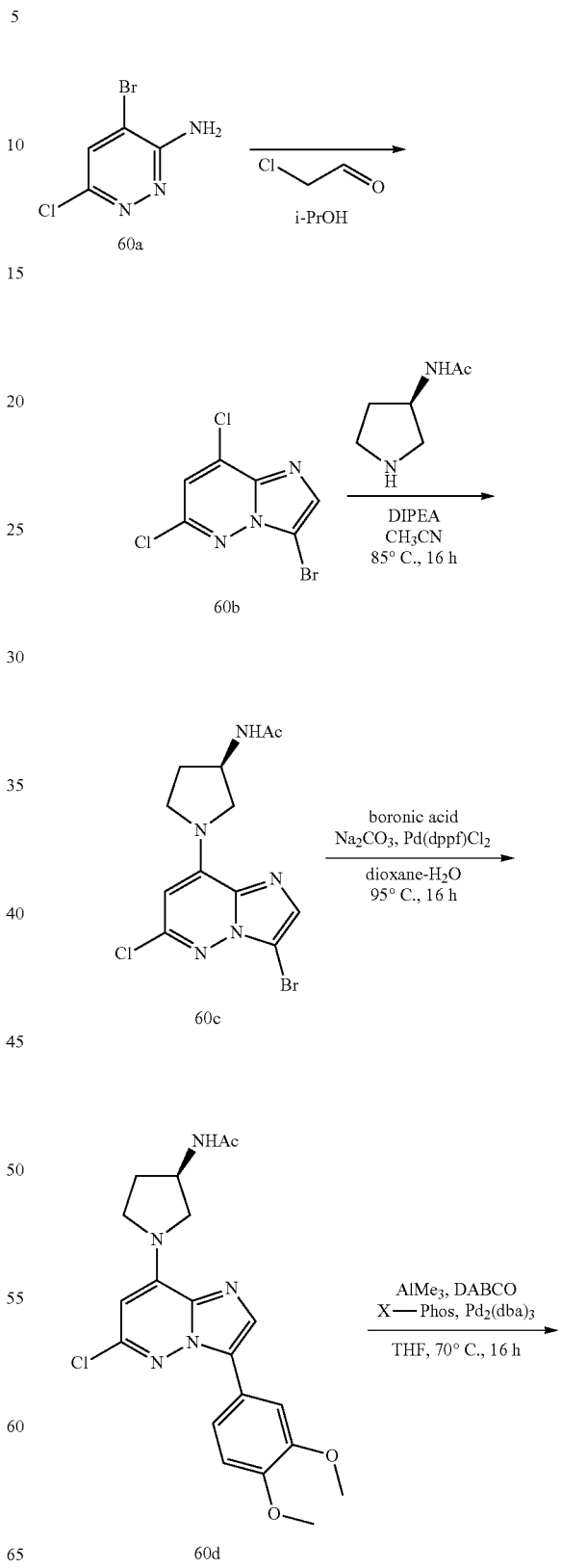

3-bromo-6,8-dichloroimidazo[1,2-b]pyridazine (60b)

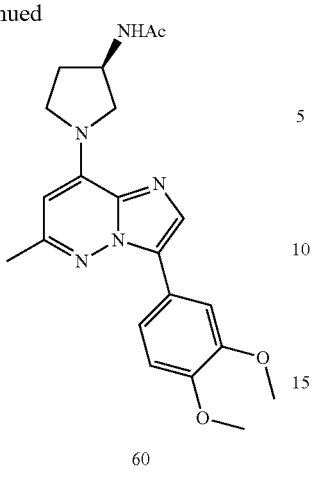

Mixture of pyridazine 60a (2 g, 3.9 mmol), aq. chloroacetaldehyde (4 mL, 50% sol.) was heated to 80° C. in isopropanol (20 mL) for 16 h. Reaction mixture was cooled down, evaporated and extracted between ethyl acetate (400 mL) and satd. sodium bicarbonate (150 mL). Organic phases were dried over sodium sulphate and evaporated. Residue was passed through small pad of silica gel (toluene:ethyl acetate 3:1) and obtained solid (1.77 g) was used without further purification. UPLC-MS: t=4.11 (M+H, 266/268/270), t=4.18 (310/312/314. Product is a mixture with its 8-Br derivative.

(R)—N-(1-(3-bromo-6-chloroimidazo[1,2-b]pyridazin-8-yl)pyrrolidin-3-yl)acetamide (60c)

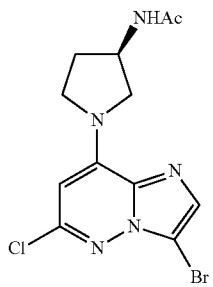 [SMILES: CC(=O)N[C@@H]1CCN(c2cc(Cl)nn3c(Br)cnc23)C1]

Mixture of starting material 60b (400 mg, 1.5 mmol), (R)—N-(pyrrolidin-3-yl)acetamide (211 mg, 1.65 mmol), DIPEA (0.35 mL, 1.95 mmol) in acetonitrile (10 mL) was heated at 85° C. overnight, cooled down and evaporated. Residue was purified by column chromatography on silica gel (100 g, ethyl acetate→ethyl acetate-ethanol 10:1) to yield 520 mg (97%). UPLC-MS: t=3.86 (M+H, 358/360). $^1$H NMR (400 MHz, d6-DMSO) δ 1.80 (s, 3H), 1.87-1.98 (m, 1H), 2.12-2.22 (m, 1H), 3.35-4.55 (4×br s, 5H), 6.08 (s, 1H), 7.69 (s, 1H), 8.17 (s, 1H). $^{13}$C NMR (101 MHz, d6-DMSO) δ 22.7, 93.5, 100.9, 131.0, 133.6, 142.6, 148.3, 169.4 (carbons on pyrrolidine ring were not detected).

(R)—N-(1-(6-chloro-3-(3,4-dimethoxyphenyl)imidazo[1,2-b]pyridazin-8-yl)pyrrolidin-3-yl)acetamide (60d)

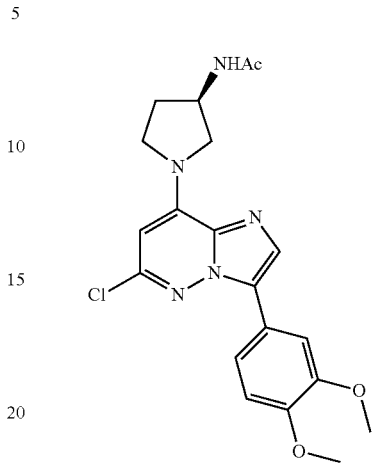

Using general method B, product was prepared in 86% yield. Chromatography: CH$_2$Cl$_2$:ethanol 15:1. $^1$H NMR (400 MHz, d6-DMSO) δ 1.82 (s, 3H), 1.89-1.99 (m, 1H), 2.08-2.28 (m, 1H), 3.55 (br s, 2H), 3.81 (s, 3H), 3.83 (s, 3H), 4.05-4.55 (br s+m, 3H), 6.04 (s, 1H), 7.09 (d, J=8.5 Hz, 1H), 7.61 (d, J=2.1 Hz, 1H), 7.65 (dd, J=8.4, 2.1 Hz, 1H), 7.93 (s, 1H), 8.19 (d, J=6.4 Hz, 1H). $^{13}$C NMR (101 MHz, d6-DMSO) δ 22.7, 55.8, 92.8, 110.7, 112.1, 119.4, 121.2, 127.9, 129.3, 133.5, 142.8, 147.1, 148.8, 169.4 (carbons on pyrrolidine ring were not detected).

(R)—N-(1-(3-(3,4-dimethoxyphenyl)-6-methylimidazo[1,2-b]pyridazin-8-yl)pyrrolidin-3-yl)acetamide (60)

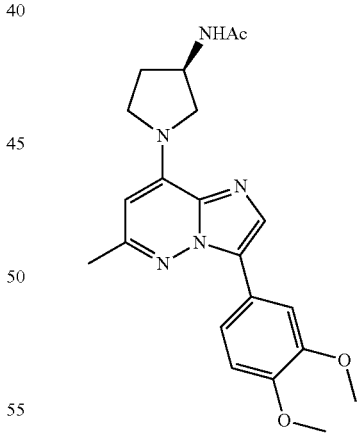

Using general method D, product was prepared in 90% yield. Chromatography: CHCl$_3$:ethanol 15:1. Crystallization: ethyl acetate. $[\alpha]_D^{20}$=+11.2 (c 0.303, CHCl$_3$). $^1$H NMR (400 MHz, d6-DMSO) δ 1.82 (s, 3H), 1.87-1.96 (m, 1H), 2.12-2.21 (m, 1H), 2.38 (s, 3H), 3.51-4.20 (m, 10H), 4.30-4.40 (m, 1H), 5.85 (s, 1H), 7.05 (d, J=8.5 Hz, 1H), 7.71 (dd, J=8.4, 2.1 Hz, 1H), 7.78 (d, J=2.0 Hz, 1H), 7.85 (s, 1H), 8.19 (d, J=6.5 Hz, 1H). $^{13}$C NMR (101 MHz, d6-DMSO) δ 21.9, 22.8, 30.5, 48.8, 55.3, 55.7, 93.7, 110.5, 112.0, 119.1, 122.4, 127.1, 128.7, 134.1, 141.8, 148.3, 148.7, 152.2, 169.4.

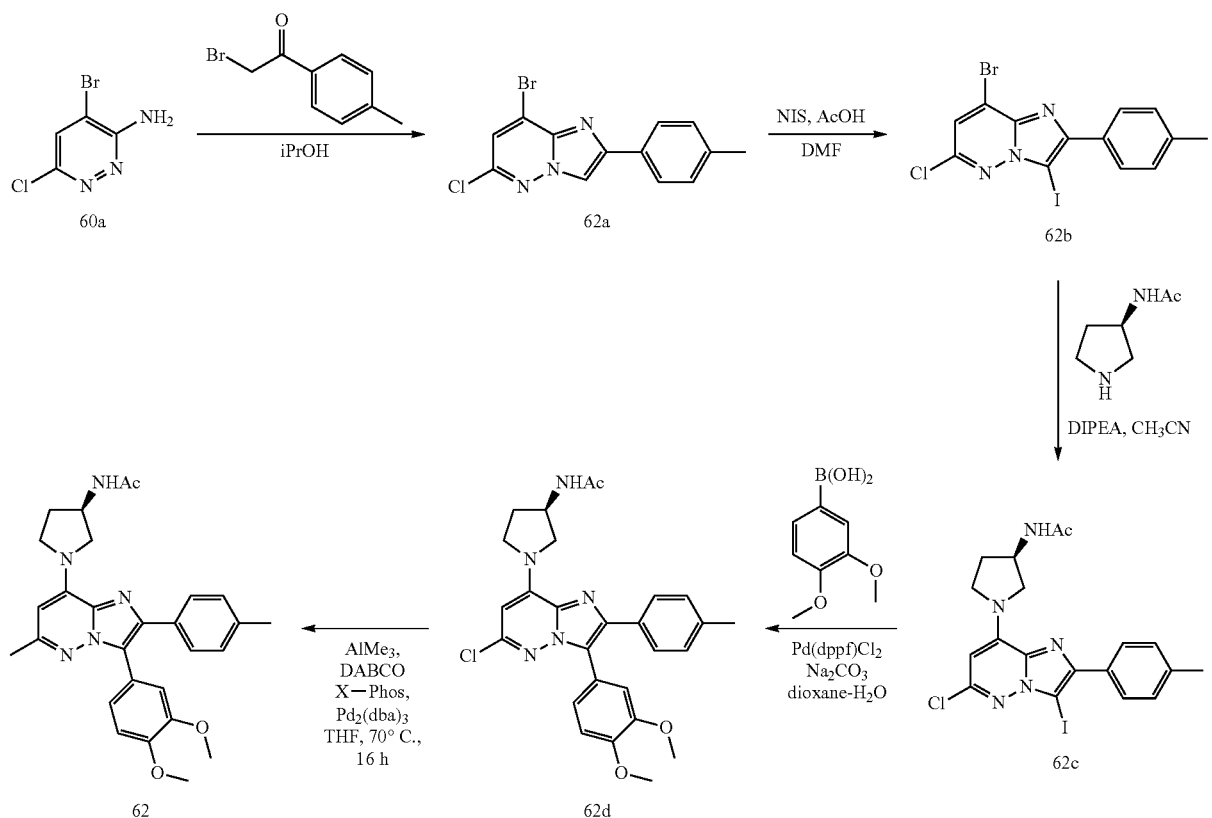

8-bromo-6-chloro-2-(p-tolyl)imidazo[1,2-b]pyridazine (62a)

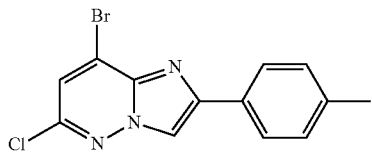 [SMILES: Cc1ccc(-c2cn3nc(Cl)cc(Br)c3n2)cc1]

Mixture of pyridazine 60a (800 mg, 3.9 mmol), 2-bromo-1-(p-tolyl)ethan-1-one (850 mg, 4.29 mmol) was heated to 90° C. in isopropanol (20 mL) for 16 h. Reaction mixture was cooled down and precipitated solid was filtered off, washed with isopropanol and diethyl ether. The obtained solid (950 mg, 76%) was immediately used without further purification. UPLC-MS: t=5.19 (M+H, 322/324).

8-bromo-6-chloro-3-iodo-2-(p-tolyl)imidazo[1,2-b]pyridazine (62b)

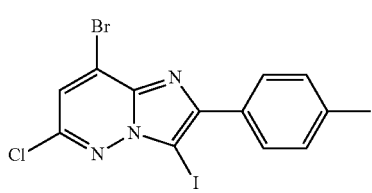 [SMILES: Cc1ccc(-c2nc3c(Br)cc(Cl)nn3c2I)cc1]

To a stirred solution of compound 62a (450 mg, 1.39 mmol) in DMF (3 mL) was added acetic acid (0.13 mL) and NIS (353 mg, 1.57 mmol) at r.t. Reaction mixture was heated overnight at 65° C., cooled down and diluted with ethyl acetate (150 mL). Organic phase was washed aq. NaHCO$_3$ (50 mL) and aq. Na$_2$S$_2$O$_3$ (50 mL). Organic phase was dried over Na$_2$SO$_4$ and evaporated. Residue was chromatographed on silica gel column (50 g, CH$_2$Cl$_2$) to obtain 345 mg (52%). UPLC-MS: t=5.43 (M+H, 448/450).

(R)—N-(1-(6-chloro-3-iodo-2-(p-tolyl)imidazo[1,2-b]pyridazin-8-yl)pyrrolidin-3-yl)acetamide (62c)

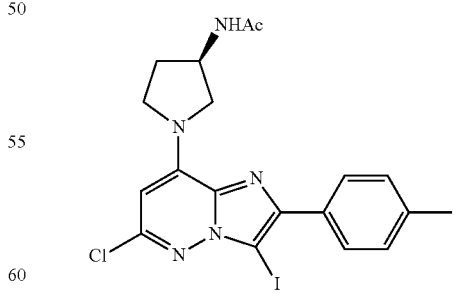

Iodo derivative 62b (345 mg, 0.77 mmol), (R)—N-(pyrrolidin-3-yl)acetamide (109 mg, 0.85 mmol), DIPEA (0.16 mL, 0.92 mmol) was dissolved in acetonitrile (8 mL). Reaction mixture was heated at 85° C. for 16 hours and cooled down. After cooling, precipitated product (327 mg, 86%) was filtered off, washed with acetonitrile and ether. UPLC-MS: t=5.0 (M+H, 496.3/498.3).

(R)—N-(1-(6-chloro-3-(3,4-dimethoxyphenyl)-2-(p-tolyl)imidazo[1,2-b]pyridazin-8-yl)pyrrolidin-3-yl)acetamide (62d)

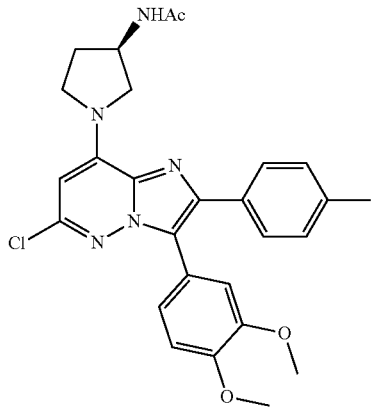 [SMILES: COc1ccc(-c2c(-c3ccc(C)cc3)nc3c(N4CC[C@@H](NC(C)=O)C4)cc(Cl)nn23)cc1OC]

General method B with 3,4-dimethoxyphenyl boronic acid as a coupling agent was used. Yield: 86%. Chromatography: CHCl₃:acetone 5:1. UPLC-MS: t=4.82 (M+H, 506.2).

(R)—N-(1-(3-(3,4-dimethoxyphenyl)-6-methyl-2-(p-tolyl)imidazo[1,2-b]pyridazin-8-yl)pyrrolidin-3-yl)acetamide (62)

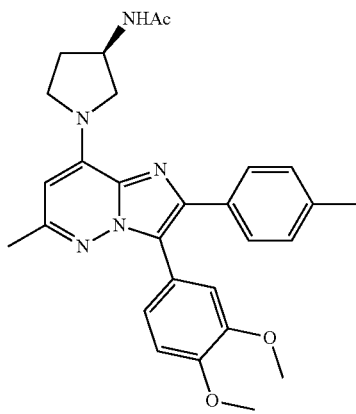

Product was prepared according to general method D. Yield: 65%. Chromatography: CHCl₃:ethanol 25:1. Crystallization: ethyl acetate. $[\alpha]_D^{20}$=+1.4 (c 0.292, DMSO). ¹H NMR (400 MHz, d6-DMSO) δ 1.83 (s, 3H), 1.88-1.98 (m, 1H), 2.14-2.24 (m, 1H), 2.27 (s, 3H), 2.28 (s, 3H), 3.66 (s, 3H), 3.82 (s, 3H), 3.95 (br m, 4H), 5.84 (s, 1H), 7.00 (dd, J=8.2, 1.9 Hz, 1H), 7.02-7.08 (m, 2H), 7.09-7.14 (m, 2H), 7.46-7.53 (m, 2H), 8.19 (d, J=6.6 Hz, 1H). ¹³C NMR (101 MHz, d6-DMSO) δ 21.0, 21.7, 22.8, 30.6, 40.1, 47.9, 48.7, 55.3, 55.6, 94.2, 111.9, 114.5, 122.3, 123.5, 124.0, 128.9, 129.1, 132.1, 132.8, 136.4, 138.2, 141.4, 148.6, 148.9, 152.1, 169.4. HRMS calcd for C₂₈H₃₂N₅O₃ m/z: 486.2500 (M+H)⁺, found 486.2449.

cyclohexyl(4-(3-(3,4-dimethoxyphenyl)-2,6-dimethylimidazo[1,2-b]pyridazin-8-yl)piperazin-1-yl)methanone (63)

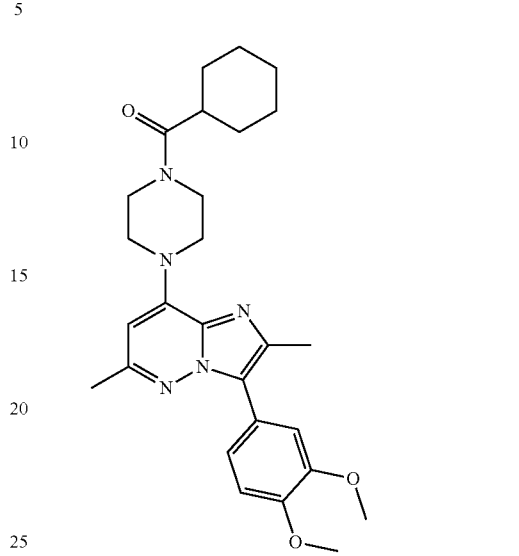

Compound 46 (200 mg, 0.43 mmol) was dissolved in CH₂Cl₂/TFA (8 mL, 7:1) and stirred at r.t. overnight. Reaction mixture was evaporated and co-evaporated with acetonitrile (2×15 mL). Residue was dissolved in acetonitrile (15 mL) and subsequently triethylamine (0.3 mL, 2.15 mmol) and cyclohexanoyl chloride (88 μl, 0.66 mmol) was added. Reaction mixture was stirred overnight and evaporated. Product was isolated by column chromatography on silica gel (75 g, CHCl₃:acetone 5:1) and obtained solid (173 mg, 84%) was crystalized from ethyl acetate. ¹H NMR (400 MHz, d6-DMSO) δ 1.09-1.27 (m, 2H), 1.27-1.40 (m, 4H), 1.63-1.73 (m, 4H), 2.33 (s, 3H), 2.40 (s, 3H), 2.58-2.68 (m, 1H), 3.57-3.74 (m, 4H), 3.78 (s, 3H), 3.80-3.89 (s, 5H), 4.05 (br s, 2H), 6.24 (s, 1H), 7.08 (d, J=8.5 Hz, 1H), 7.16 (dd, J=8.3, 2.0 Hz, 1H), 7.26 (d, J=2.0 Hz, 1H). ¹³C NMR (101 MHz, d6-DMSO) δ 15.0, 21.8, 25.3, 29.3, 39.2, 40.7, 44.5, 47.1, 48.0, 97.3, 111.8, 113.3, 121.9, 122.1, 124.0, 131.9, 136.4, 143.0, 148.4, 148.5, 151.5, 173.8. HRMS calcd for C₂₇H₃₆N₅O₃ m/z: 478.2813 (M+H)⁺, found 478.2815.

(R)—N-(1-(2,6-dimethyl-3-(1-methyl-1H-indol-6-yl)imidazo[1,2-b]pyridazin-8-yl)pyrrolidin-3-yl)acetamide (64)

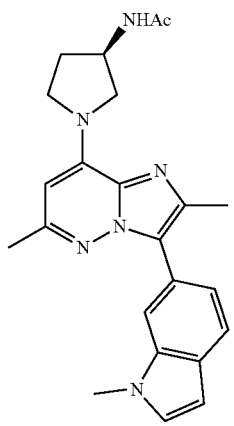 [SMILES: CC(=O)N[C@@H]1CCN(c2cc(C)nn3c(-c4ccc5ccn(C)c5c4)c(C)nc23)C1]

To a solution of compound 18 (241 mg, 0.6 mmol) in DMF (5 mL) was added sodium hydride (29 mg, 0.72 mmol, 60% in mineral oil) and reaction mixture was stirred for 20 mins. Then, methyl iodide (69 μL, 0.72 mmol) was added and stirring continued for 12 h. Reaction mixture was diluted with ethyl acetate (40 mL) and filtrated. Filtrate was evaporated and residue was chromatographed on silica gel column (150 g, toluene: acetone 2:3). It was obtained 180 mg (75%) of the product as foam. $[\alpha]_D^{20}=+16.3$ (c 0.343, DMSO). $^1$H NMR (400 MHz, d6-DMSO) δ 1.83 (s, 3H), 1.88-1.97 (m, 1H), 2.13-2.21 (m, 1H), 2.27 (s, 3H), 2.41 (s, 3H), 3.75-3.90 (s+br s, 6H), 4.33-4.40 (m, 1H), 5.80 (s, 1H), 6.47 (dd, J=3.1, 0.9 Hz, 1H), 7.27 (dd, J=8.2, 1.4 Hz, 1H), 7.39 (d, J=3.0 Hz, 1H), 7.63 (dd, J=8.3, 0.7 Hz, 1H), 7.66 (dt, J=1.5, 0.8 Hz, 1H), 8.18 (d, J=6.7 Hz, 1H). $^{13}$C NMR (101 MHz, DMSO) δ 14.9, 21.7, 22.8, 30.5, 32.7, 40.1, 47.7, 48.8, 55.2, 93.8, 100.5, 110.9, 120.0, 121.0, 122.4, 125.3, 127.5, 130.6, 131.8, 136.4, 136.6, 141.1, 151.3, 169.4. HRMS calcd for $C_{23}H_{27}N_6O$ m/z: 403.2241 (M+H)$^+$, found 403.2164.

N-{(3R)-1-[3-(3,4-dimethoxyphenyl)-3H-[1,2,3]triazolo[4,5-d]pyrimidin-7-yl]pyrrolidin-3-yl}acetamide (65)

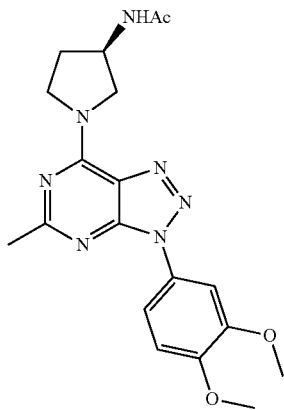

To a mixture of 7-chloro-3-(3,4-dimethoxyphenyl)-5-methyl-3H-[1,2,3]triazolo[4,5-d]pyrimidine 65a (961 mg, 3.14 mmol), DIPEA (0.855 mL, 4.91 mmol) in acetonitrile (15 mL) was added tert-butyl (3R)-pyrrolidin-3-ylcarbamate (651 mg, 3.45 mmol) at r.t. and reaction mixture was heated at 85° C. for 2 hours, cooled down and evaporated. The residue was chromatographed on silica gel column (100 g, toluene-ethyl acetate 1:1). Fractions containing product were evaporated and dissolved in a mixture of trifluoroacetic acid and dichloromethane (44 mL, 1:10, v/v). Reaction mixture was stirred at r.t. for 16 hours, evaporated, two times co-evaporated with acetonitrile (2×40 mL) and redissolved in acetonitrile. To this solution was sequentially added Et$_3$N (1.96 mL, 14 mmol), catalytic amount of DMAP and acetic anhydride (0.49 mL, 5.2 mmol). Reaction mixture was stirred at r.t. for 2 hours and then methanol (1 mL) was added and mixture was evaporated. Residue was purified by column chromatography (200 g, toluene-acetone 1:2) to obtain 1.1 g (91%) of the product. Obtained solid was recrystallized from ethyl acetate. $[\alpha]_D^{20}=+2.3$ (c 0.258, CHCl$_3$). NMR spectrum showed signals of two rotamers. $^1$H NMR (400 MHz, d6-DMSO) δ 1.83 (2×s, 3H), 1.87-1.98 and 2.00-2.10 (2×m, 1H), 2.12-2.24 and 2.24-2.37 (2×m, 1H), 2.50* (s, 3H, covered by DMSO, observed in HSQC), 3.62-3.70 (m, 0.5H), 3.73-3.89 (m and 2×s, 7.5H), 4.01-4.09 (m, 0.5H), 4.18-4.24 (m, 1H), 4.24-4.31 (m, 0.5H), 4.32-4.39 (m, 0.5H), 4.43-4.50 (m, 0.5H), 7.15-7.25 (m, 1H), 7.59-7.69 (m, 2H), 8.22 and 8.26 (2×d, J=6.5 Hz, 1H). $^{13}$C NMR (101 MHz, d6-DMSO) δ 22.8, 26.4, 26.5, 29.5 and 31.2, 45.7 and 47.6, 47.7 and 49.4, 52.9 and 54.5, 56.00, 106.2 and 106.3, 112.1, 114.1 and 114.2, 124.1 and 124.2, 129.1 and 129.2, 148.9 (2×), 149.3, 149.8 and 149.9, 152.2 and 152.3, 166.4 (2×), 169.6 (2×). HRMS calcd for $C_{19}H_{27}N_7O_3$ m/z: 398.1935 (M+H)$^+$, found 398.1900.

Example 3

Human nSMase2 Activity Assay

Methods

The fluorescence based assay to monitor the activity of human nSMase2 in the presence or absence of potential inhibitors has been described recently. Figuera-Losada, et al. Lysate of cells expressing recombinant nSMase2 is used to catalyze the hydrolysis of sphingomyelin (SM) to ceramide and phosphorylcholine. Phosphorylcholine undergoes dephosphorylation in a reaction catalyzed by alkaline phosphatase (4 U/mL) to produce choline which in turn is oxidized by choline oxidase (0.1 U/mL) to betaine and hydrogen peroxide ($H_2O_2$). Hydrogen peroxide is made to react with Amplex red (50 μM) in the presence of horseradish peroxidase (HRP, 1 U/mL) to generate the fluorescent molecule resorufin. Generation of fluorescence is monitored by measuring relative florescence units (RFU) with excitation at 530 nm and emission at 590 nm. Extent of fluorescence is directly proportional to the extent of SM hydrolysis. Substrate stock solution is prepared in 2% Triton X-100 and sonicated for 1 min. Reactions are carried out for 1 h at 37° C. in 100 mM Tris-HCl pH 7.4, 10 mM MgCl2, 0.2% Triton X-100. This assay has been optimized in 384-well format (50 μL total volume per well) under conditions where nSMase2-catalyzed hydrolysis of SM is linear with respect to nSMase2 concentration, time of incubation and SM concentration (FIGS. 3A-3C). The assay has high reliability (Z'=0.8-0.9). It is used for compound screening, IC$_{50}$ determinations and mode of inhibition studies. IC$_{50}$ determinations are carried out in duplicate eight-point dose response curves. A counter screen is concomitantly carried out to identify false positives resulting from inhibition of the coupling enzymes. For the counter screen, the alkaline phosphatase, choline oxidase and HRP reactions are carried out in the absence of human nSMase2 and initiated by the addition of phosphorylcholine (2 μM), the alkaline phosphatase substrate. Compounds that show inhibition of the coupling enzymes are considered false positives and are not used further. Data analysis and non-linear least squares curve fitting are carried out with GraphPad Prism 5.

Referring now to FIG. 3A, FIG. 3B, and FIG. 3C, plots show the dependence of enzyme activity with respect to protein concentration (left panel, FIG. 3A), sphingomyelin (SM) concentration (middle panel. FIG. 3B) and time of incubation (right panel. FIG. 3C). K$_m$ and V$_{max}$ in middle panel were obtained from a non-linear least squares fit to the Michaelis-Menten equation.

Example 4

Inhibition of Extracellular Vesicle/Exosome Release by Selected nSMase2 Inhibitors Methods The effect of nSMase2 inhibitors on the manufacturing and release of ceramide rich exosomes from primary astrocytes was investigated as previously described. Dickens, et al. Briefly, rat astrocytes are seeded onto 6-well plates at a density of 20,000 cells/well. Twenty-four hours after seeding, astrocytes are washed with PBS and the medium changed to media without FBS. Absence of FBS mimics a trophic factor withdrawal stimulus causing the release of exosomes via a nSMase2-dependent pathway. Astrocytes are then treated with nSMase2 inhibitors at concentrations in the range 0.03-30 µM. DMSO (0.02%) is used as control. Two hours after treatment, media is collected and centrifuged at 2700 g for 15 min (4° C.). Supernatant is further centrifuged at 10,000 g for 15 min (4° C.) to remove large particles such as apoptotic bodies. Astrocyte-derived extracellular vesicles (EVs) are isolated via ultracentrifugation at 100,000 g for 3 h at 4° C. Fractions containing EV are washed twice with 5 ml PBS and the final pellet resuspended in PBS. This isolation procedure results in the isolation of EVs with a narrow size range and protein markers consistent with exosomes. Dickens, et al. The number of EVs is quantified using ZetaView Nanoparticle Tracker (Particle Metrix GmBH, Meerbusch, Germany) and the corresponding ZetaVeiw software (8.03.04.01). Nanosphere size standard 100 nm (Thermo Scientific) is used to calibrate the instrument prior to sample readings. For each sample 1 mL of the supernatant is injected into the sample-carrier cell and the particle count measured at 5 positions, with 2 cycles of reading per position. Cells are washed with PBS after every sample. Mean concentration of EVs/mL (±SEM) is calculated from 6 replicates. This screening assay is reliable with a Z'=0.75.

Referring now to FIG. 4A and FIG. 4B, the ability of compound 38 and several of its analogs to inhibit exosome release in vitro was evaluated as previously described. Dickens, et al. Primary astrocytes were treated with compound of interest including the closely related inactive analog 65 at different concentrations (0.3-10 µM) with DMSO (0.02%) as control. Two hours after treatment, exosomes were isolated from the media and quantified using ZetaView Nanoparticle Tracker. The mean concentration of exosomes (EVs/mL±SEM) was calculated from 6 replicate experiments (see FIG. 4). Compounds 38, 30, 62 and 44 decreased the number of exosomes released from astrocytes in a dose dependent manner. In contrast, compound 65, the closely related inactive analog, had no effect on exosome release. Baseline exosome release can be variable between experiments; as a result, inhibition is always compared relative to vehicle treatment within the same experiment. Structures of compounds with their corresponding $IC_{50}$s are provided in the second row of FIG. 4.

Example 5

Metabolic Stability of Selected nSMase2 Inhibitors

Methods

Phase I metabolic stability in both mouse and human liver microsomes was performed as described previously. Rais et al. Briefly, compounds are spiked in liver microsomes (mouse, human) and incubated in an orbital shaker at 37° C. At predetermined times (0, 30 and 60 min) aliquots of the mixture in triplicate are removed and the reaction quenched by addition of three times the volume of ice cold acetonitrile spiked with internal standard. Compound disappearance is monitored over time using LC/MS/MS. See Table 2 and FIG. 5.

TABLE 2

Phase I metabolic stability of nSMase2 inhibitors

| Compound # | Mouse Liver Microsome (+) NADPH* % Remaining at 60 min | Human Liver Microsome (+) NADPH* Remaining at 60 min |
| --- | --- | --- |
| 22 | 2 ± 1 | 29 ± 1 |
| 44 | 1 ± 0 | 58 ± 4 |
| 23 | 5 ± 1 | 12 ± 3 |
| 62 | 53 ± 6 | 28 ± 5 |
| 28 | 20 ± 1 | 43 ± 6 |
| 29 | 7 ± 2 | 32 ± 6 |
| 30 | 15 ± 5 | 61 ± 3 |
| 35 | 117 ± 8 | 113 ± 8 |
| 38 | 63 ± 6 | 103 ± 14 |
| 13 | 28 ± 2 | 50 ± 4 |
| 17 | 72 ± 6 | 114 ± 4 |
| 37 | 6 ± 1 | 20 ± 2 |

*Negative controls without NADPH > 95% remaining

Example 6

Further Characterization of Compound 38

6.A. Compound 38 is a Noncompetitive Inhibitor of nSMase2

Methods

Mode of inhibition of compound 38 was determined using the fluorescence-based assay detailed above. Lysate of cells expressing recombinant nSMase2 (1.9 µg protein/50 µL) was incubated with different SM concentrations in the presence of different concentrations of 38 for 3 h. Rate of change of fluorescence vs. sphinghomyelin concentration in the presence of increasing concentrations of 38 were plotted in GraphPad Prism and $V_{max}$ and $K_m$ were obtained by a least-squares fit to the Michaelis-Menten equation using non-linear regression.

Referring now to compound 38 exhibited non-competitive inhibition. Maximal rate of SM hydrolysis ($V_{max}$) decreased with increasing concentrations of 38 while the binding constant ($K_m$) remained the same (top panel). $V_{max}$ in RFU (Relative Fluorescent Units) per hour and $K_m$ at each inhibitor concentration were obtained from non-linear least squares fitting to the Michaelis-Menten equation. (middle panel).

6.B Compound 38 Shows Excellent Exposure and Brain Penetration in Mice

Methods

Compound 38 was dosed at 10 mg/kg (IP or peroral) at a dosing volume of 10 mL/kg. Blood was obtained via cardiac puncture and brain tissue was dissected at 0.25, 0.5, 1, 2, 4, 6 and 8 h post dose (n=3 per gender and time point). Plasma was harvested from blood by centrifugation. Subsequently, samples were extracted from plasma and brain by a one-step protein precipitation using acetonitrile followed by vortexing for 30 min and centrifugation (10,000 g for 10 min) as we have described previously. Rais, et al. Once extracted, the samples were reconstituted into a mobile phase and analyzed via LC/MS/MS. Plasma concentrations (nM) as well as tissue concentrations (pmol/g) were determined and plots of mean plasma concentration vs. time were constructed for PK analysis. Non-compartmental-analysis modules in WinNonlin® (version 5.3) were used to assess pharmacokinetic parameters including maximal concentration ($C_{max}$), time to $C_{max}$ ($T_{max}$), area under the curve extrapolated to infinity ($AUC_{0-\infty}$) and brain-to-plasma (B/P) ratios.

Referring now to FIG. 7A and FIG. 7B, plasma and brain levels of 38 were measured at 0.25, 0.50, 1, 2, 4, 6 and 8 h post dose (n=3 per time point). Following i.p. administration compound 38 showed high systemic exposures and excellent brain penetration (0.6). Brain levels at 8 h post dose were >2.5-fold higher than the $IC_{50}$ value of 38 for inhibition of nSMase2 (300 nM). Similarly, following oral administration, 38 showed high plasma exposures suggesting 38 to be orally available. In addition, 38 also achieved high brain exposures with a brain to plasma ratio of 0.67.

6. C Compound 38 Shows Inhibition of Exosome Release In Vivo

Methods

Striatal injections of IL-1β and exosome measurements are performed as previously described by our group in adult (2-3 month) male GFAP-GFP mice (Jackson Laboratories). Dickens, et al.; McCluskey, et al. Mice are anesthetized with 3% Isoflourane (Baxter) in oxygen (Airgas), and placed in a stereotaxic frame (Stoelting Co.). A small burr hole is drilled in the skull over the left striatum using a dental drill (Fine Scientific Tools). IL1β (0.1 ng/3 µl) is injected (total volume of 3 µl) at the rate 0.5 µl/min via a pulled glass capillary tip diameter <50 µm using the stereotaxic coordinates: A/P+1; M/L-2; -3 D/V. Following infusion, the capillary is held in place for 5 min to allow for solution to diffuse into the tissue. Animals are sacrificed at 2, 12 or 24 h by an overdose of anesthetic, and transcardially perfused with ice-cold saline containing heparin (20 µl per 100 ml, Sigma). Blood is rapidly isolated and flash frozen. Brains are rapidly extracted and flash frozen or post fixed in 4% PFA followed by cryoprotection in a 30% sucrose solution and frozen at −80° C.

Quantitation of Plasma EVs:

GFAP-GFP mice that release green EVs from astrocytes into the systemic circulation were used so that exosome release from astrocytes in plasma can be followed. Dickens, et al. Blood is collected via cardiac puncture using a heparin (Sigma Aldrich) coated syringe and EDTA tubes (BD) 2 h following striatal injections. Blood is immediately centrifuged at 2700 g for 15 min (20° C.) to obtain plasma. Plasma is further centrifuged at 10,000 g for 15 min (4° C.) to generate platelet free plasma. This procedure removes large particles such as apoptotic bodies. Plasma-derived EVs are isolated via ultracentrifugation at 100,000 g for 3 h (4° C.). Fractions containing EVs are washed twice with 5 ml saline and the final pellet resuspended in saline. This isolation procedure results in the isolation of EVs with a narrow size range and protein markers consistent with exosomes. For isolation of GFP+ EVs from plasma collected from GFAP-GFP mice, Dynabeads M-450 Epoxy (Invitrogen) is coupled with anti-GFP antibody (Thermo Fisher) at a ratio of 200 µg antibody per 4×10⁸ beads. Plasma from GFAP-GFP mouse (50 µL) is incubated with 2×10⁷ anti-GFP antibody-coupled Dynabeads at 4° C. overnight. The beads are washed and placed on a magnet to separate EVs bound to anti-GFP antibody-coupled Dynabeads. The precipitated EVs are eluted using 0.1M glycine, pH=3.0. The concentration of immunoprecipitated GFP+ EVs is quantified using ZetaView nanoparticle tracking analysis (Particle Metrix) as described in the cell-based exosome release.

Referring now to FIG. 8A and FIG. 8B, the ability of compound 38 to inhibit exosome release in vivo was evaluate as previously described. Dickens, et al. Striatal injection of IL-1β in mice triggers a release of brain exosomes which is measurable in plasma. Administration of 38 (10 mg/kg IP) 30 min before IL-1β injection significantly reduced the increased exosomes 2 h after IL-1β administration. The closely related inactive analog, 65, had no effect. Similar results were observed at 12 and 24 h (data not shown). Taken together, both, in vitro and in vivo results indicate 38 inhibits exosome release; the fact that 65, a closely related nSMase2 inactive analog, had no effect suggests that the effect of 38 is through nSMase2 inhibition. FIG. 8 Left Panel: Total number of extracellular vesicles in plasma. FIG. 8 Right Panel: Total number of GFP labeled EVs known to be released from brain. * p<0.05, ** p<0.001 when comparing IL1-1β and IL-1β+65 vs. Saline. ##p<0.01, ###p<0.001 when comparing IL-1β+38 vs. IL-1β.

6.D. Compound 38 Shows Selectivity in Eurofins Tox SafetyScreen44 Selectivity Screen In addition to compound 38 not inhibiting the related enzymes alkaline phosphatase (a phosphomonoesterase) or acid sphinghomyelinase (a phosphodiesterase), compound 38 was evaluated in Eurofins SafetyScreen44, a panel of 44 selected targets recommended by major pharmaceutical companies to establish undesirable off target activity profiles. Bowes, et al. There were 4/44 positive hits at 10 µM ($\alpha_{1A}$ adrenergic receptor, $Ca^{2+}$ and $Na^+$ channels and dopamine transporter). All positive hits however, were significantly less than 100% inhibition indicating that there is at least a 20-fold segregation in potency between inhibition of these off targets and inhibition of nSMase2. Of note, compound 38 was negative against hERG and two additional phosphodiesterases (3A and 4D2).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Bowes, J., Brown, A. J., Hamon, J., Jarolimek, W., Sridhar, A., Waldron, G., and Whitebread, S. (2012) Reducing safety-related drug attrition: the use of in vitro pharmacological profiling, Nat Rev Drug Discov 11, 909-922.

Dickens, A. M., Tovar, Y. R. L. B., Yoo, S. W., Trout, A. L., Bae, M., Kanmogne, M., Megra, B., Williams, D. W., Witwer, K. W., Gacias, M., Tabatadze, N., Cole, R. N., Casaccia, P., Berman, J. W., Anthony, D. C., and Haughey, N. J. (2017) Astrocyte-shed extracellular vesicles regulate the peripheral leukocyte response to inflammatory brain lesions, Sci Signal 10.

Figuera-Losada, M., Stathis, M., Dorskind, J. M., Thomas, A. G., Bandaru, V. V., Yoo, S. W., Westwood, N. J., Rogers, G. W., McArthur, J. C., Haughey, N. J., Slusher, B. S., and Rojas, C. (2015) Cambinol, a novel inhibitor of neutral sphingomyelinase 2 shows neuroprotective properties, PLoS One 10, e0124481.

McCluskey, L., Campbell, S., Anthony, D., and Allan, S. M. (2008) Inflammatory responses in the rat brain in response to different methods of intra-cerebral administration, J Neuroimmunol 194, 27-33.

Rais, R., Jancarik, A., Tenora, L., Nedelcovych, M., Alt, J., Englert, J., Rojas, C., Le, A., Elgogary, A., Tan, J., Monincova, L., Pate, K., Adams, R., Ferraris, D., Powell, J., Majer, P., and Slusher, B. S. (2016) Discovery of 6-Diazo-5-oxo-1-norleucine (DON) Prodrugs with Enhanced CSF Delivery in Monkeys: A Potential Treatment for Glioblastoma, J Med Chem 59, 8621-8633.

Loberto, C., Hasslere, D. F., Signorelli, P., Okamoto, Y., Sawai, H., Boros, E., Hazen-Martin, D. J., Obeid, L. M., Hannun, Y. A., and Smith, G. K., "Inibition of Tumor Necrosis Factor-induced Cell Death in MCF7 by a Novel Inhibitor of Neutral Sphingomyelinase" J Biol Chem Vol. 277, 41128-41139 (2002).

Figuera-Losada, M., Stathis, M., Dorskind, J. M., Thomas, A. G., Bandaru, V. Yoo, S.-W., Westwood, N. J., Rogers, G. W., McArthur, J. C., Haughey, N. J., Slusher, B. S., and Rojas, C., Cambinol, a Novel Inhibitor of Neutral Sphingomyelinase 2 Shows Neuroprotective Properties, PLOS ONE, 26 May 2015.

Asai, H., Ikezu, S., Tsunoda, S., Medalla, M., Luebke, J., Haydar, T., Wolozin, B., Butovsky, O., Kugler, S., Ikezu, T., "Depletion of Microglia and Inhibition of Exosome Synthesis Halt Tau Propagation" Nat Neurosci Vol. 18, 1584-1593 (2015).

Van Echten-Deckert, G. and Walter, J. "Sphingolipids: Critical Players in Alzheimer's Disease" Progress in Lipid Research Vol. 51, 378-393 (2012).

Jana, A. and Pahan, K., "Fibrillar Amyloid-Beta-Activated Human Astroglia Kill Primary Human Neurons Via Neutral Sphingomyelinase: Implications for Alzheimer's Disease" J Neurosci Vol. 30, 12676-12689 (2010).

Jana, A. and Pahan, K., "Sphingolipids in Multiple Sclerosis" Neuromol Med Vol. 12, 351-361 (2010).

Jana, A., Hogan, E. L., Pahan, K., "Ceramide and Neurodegeneration: Susceptibility of Neurons and Oligodendrocytes to Cell Damage and Death" Journal of the Neurological Sciences Vol. 278, 5-15 (2009).

Cutler, R. G., Pedersen, W. A., Camandola, S., Rothstein, J. D., Mattson, M. P. "Evidence that Accumulation of Ceramides and Cholesterol Esters Mediates Oxidative Stree-Induced Death of Motor Neurons in Amyotrophic Lateral Sclerosis" Ann Neurol Vol. 52, 448-457 (2002).

Jana, A. and Pahan, K., "Human Immunodeficiency Virus Type 1 gp120 Induces Apoptosis in Human Primary Neurons through Redox-Regulated Activation of Neutral Sphingomyelinase" J Neurosci Vol. 24, 9531-9540 (2004).

Haughey, N. J., Cutler, R. G., Tamara, A., McArthur, J. C., Vargas, D. L., Pardo, C. A., Turchan, J., Nath, A., Mattson, M. P. "Perturbation of Sphingolipid Metabolism and Ceramide Production in HIV-Dementia" Ann Neurol Vol. 55, 257-267 (2004).

Kosaka, N., Iguchi, H., Hagiwara, K., Yoshioka, Y., Takeshita, F., Ochiya, T., "Neutral Sphingomyelinase 2 (nSMase2)-dependent Exosomal Transfer of Angiogenic MicroRNAs Regulate Cancer Cell Metastasis" J Biol Chem Vol. 288, 10849-10859 (2013).

Horres, C. R. and Hannun, Y. A., "The Roles of Neutral Spingomyelinases in Neurological Pathologies" Neurochem Res Vol. 37, 1137-1149 (2012).

Mejdrova, I., Chalupska, D., Kogler, M., Sala, M., Plackova, P., Baumlova, A., Hrebabecky, H., Prochazkova, E., Dejmek, M., Guillon, R., Strunin, D., Weber. J., Lee, G., Birkus, G., Mertlikova-Kalserova, H., Boura, E., Nencka, R. "Highly Selective Phosphatidylinositol 4-Kinase III-Beta Inhibitors and Structural Insight Into Their Mode of Action" J. Med. Chem., Vol. 58, 3767-3793 (2015).

Sala, M., Kogler, M., Plackova, P., Mejdrova, I., Hrebabecky, H., Prochazkova, E., Strunin, D., Lee, G., Birkus, G., Weber, J., Mertlikova-Kaiserova, H., Nencka, R., "Purine Analogs as Phosphatidylinositol 4-Kinase IIIBeta Inhibitors" Bioorg. Med. Chem. Lett., Vol. 26, 2706-2712 (2016).

U.S. Patent Application Publication No. US20120220581A1 for imidazo[1,2-b]pyridazine Derivatives and their use as PDE10 Inhibitors, to Pastor-Fernández, published Aug. 30, 2012.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I):

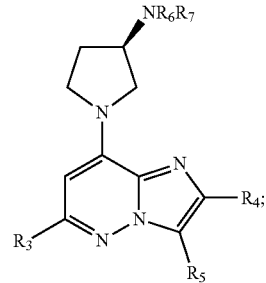

$R_3$ is selected from the group consisting of H, substituted or unsubstituted alkyl, substituted or unsubstituted alkoxyl, substituted or unsubstituted thioalkyl, substituted or unsubstituted aryl, and halogen;

$R_4$ is selected from the group consisting of H, substituted or unsubstituted alkyl, and substituted or unsubstituted aryl;

$R_5$ is selected from the group consisting of H, halogen, substituted or unsubstituted alkyl, substituted or unsubstituted aryl, substituted or unsubstituted heteroaryl, and a substituted or unsubstituted multicyclic aryl or multicyclic heteroaryl ring;

$R_6$ is selected from the group consisting of H or substituted or unsubstituted $C_{1-6}$ alkyl; and $R_7$ is selected from the group consisting of —C(=O)—$(CR_yR_z)_m$—$R_8$, —C(=O)—$(CR_yR_z)_m$—O—$R_8$, —C(=O)—O—$(CR_yR_z)_m$—$R_8$, and —S(=O)$_2$—$R_9$, wherein each m is an integer selected from the group consisting of 0, 1, 2, 3, 4, 5, and 6, $R_y$ and $R_z$ are each independently H, alkoxyl, or halogen, $R_8$ and $R_9$ are each independently selected from the group consisting of substituted or unsubstituted alkyl, —$CF_3$, substituted or unsubstituted cycloalkyl, substituted or unsubstituted aryl, substituted or unsubstituted cycloheteroaryl, substituted or unsubstituted multicyclic aryl or heteroaryl ring, and $NR_{10}R_{11}$, wherein $R_{10}$ and $R_{11}$ are each independently selected from the group consisting of H, substituted or unsubstituted $C_{1-6}$ alkyl, and substituted or unsubstituted aryl; and pharmaceutically acceptable salts thereof.

2. The compound of claim 1, wherein the compound of formula (I) is:

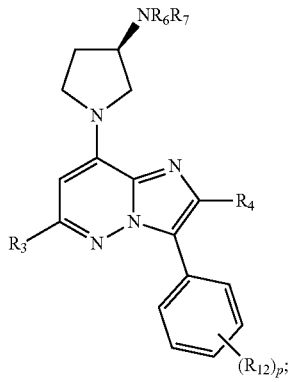

wherein:
p is an integer selected from the group consisting of 0, 1, 2, 3, 4, and 5;
each $R_{12}$ is independently selected from the group consisting of substituted or unsubstituted alkyl, hydroxyl, alkoxyl, halogen, cyano, amino, —$CF_3$, —O—$CF_3$, substituted or unsubstituted cycloheteroalkyl, —$NR_{13}$(C=O)$R_{14}$, —S(=O)$_2$—$R_{15}$, —S(=O)$_2$—$NR_{15}R_{16}$, —C(=O)—$R_{17}$, —C(=O)—O—$R_{18}$, and —C(=O)—$NR_{19}R_{20}$, wherein $R_{13}$ is selected from the group consisting of H or substituted or unsubstituted $C_{1-6}$ alkyl, $R_{14}$ is substituted or unsubstituted $C_{1-6}$ alkyl or —O—$R_{21}$, and $R_{15}$, $R_{16}$, $R_{17}$, $R_{18}$, $R_{19}$, $R_{20}$, $R_{21}$ are each independently H or substituted or unsubstituted $C_{1-6}$ alkyl.

3. The compound of claim 2, wherein $R_6$ is H and $R_7$ is —C(=O)—(CR$_y$R$_z$)$_m$—$R_8$, wherein m is 0 and $R_8$ is $C_{1-6}$ alkyl.

4. The compound of claim 3, wherein the compound of formula (I) is selected from the group consisting of:

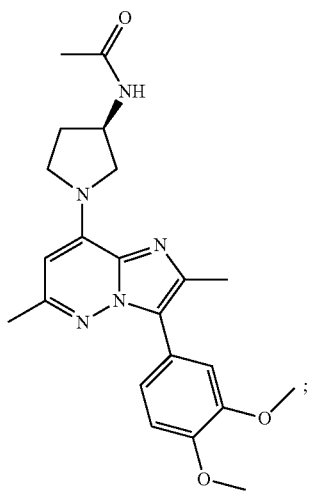

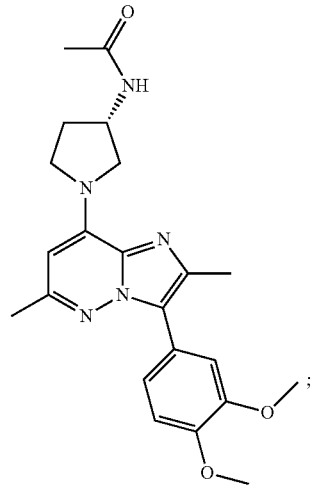

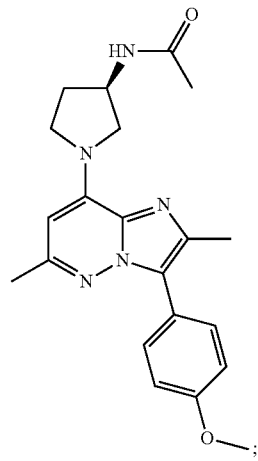

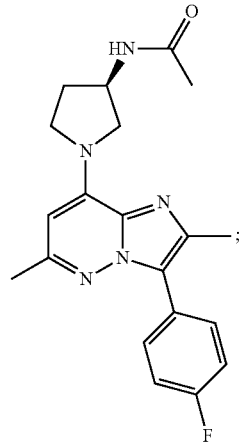

181
-continued
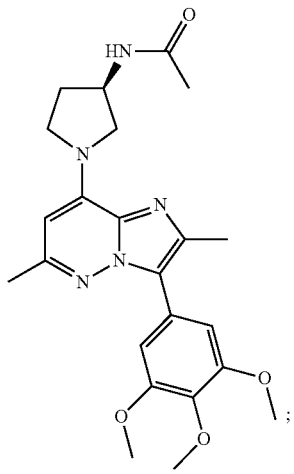
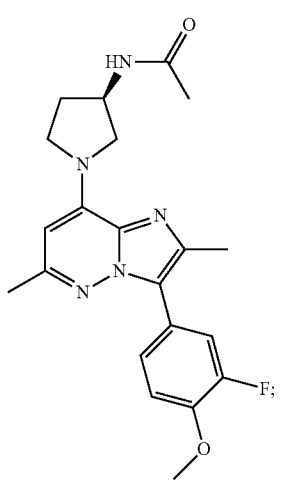
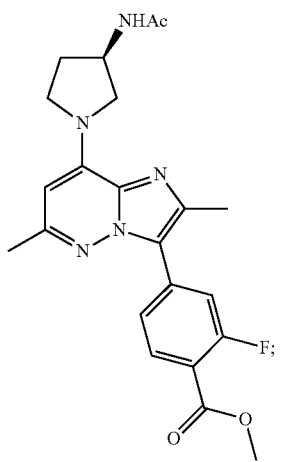
182
-continued
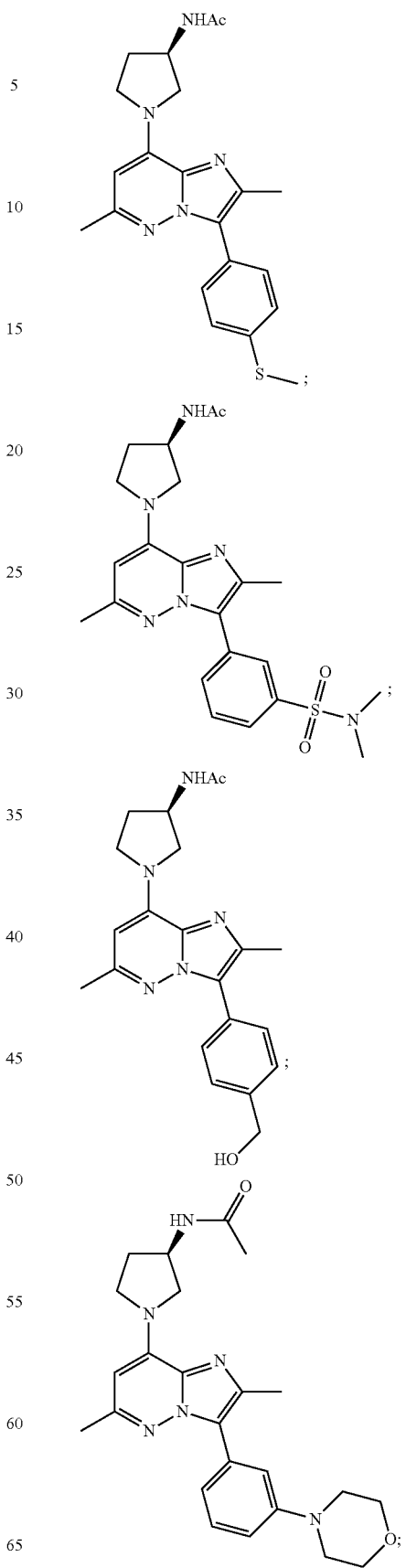

183
-continued
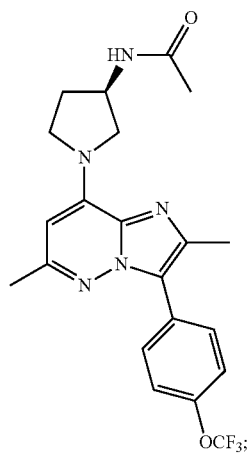
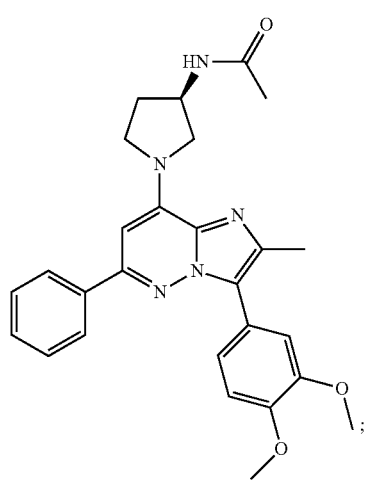
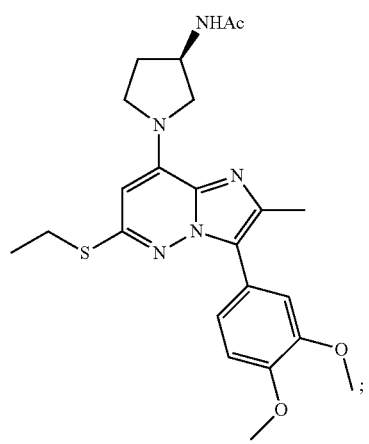
184
-continued
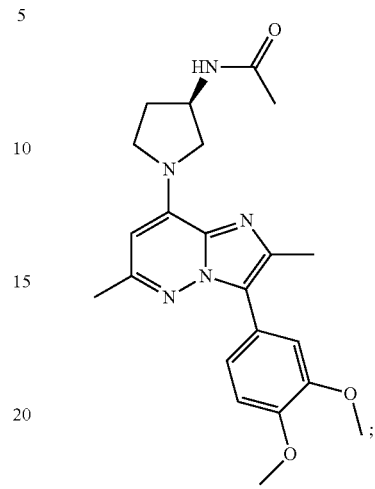
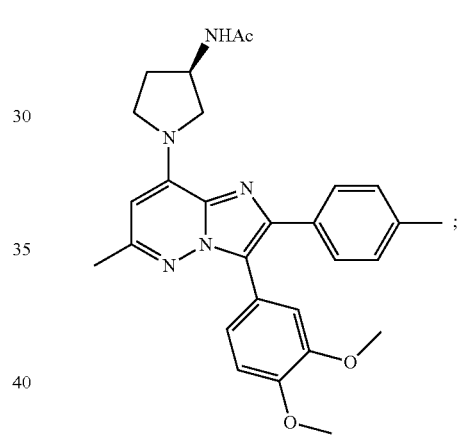
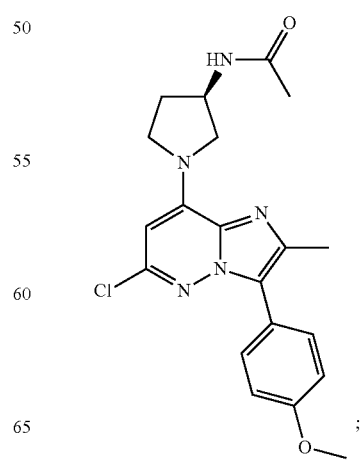

185
-continued
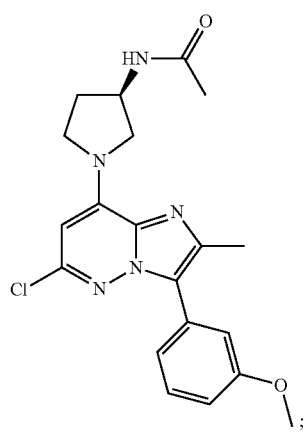
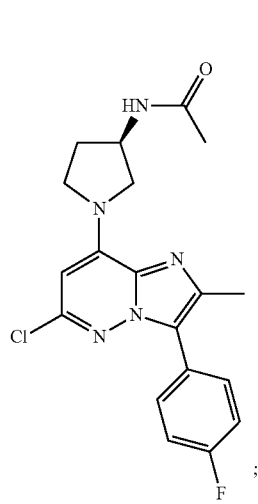
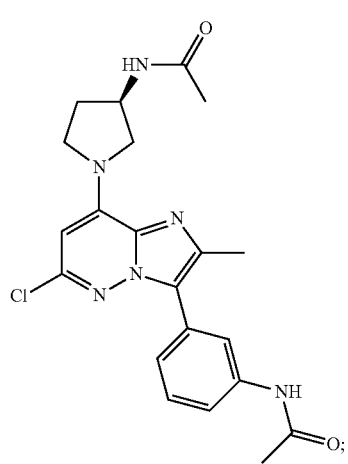
186
-continued
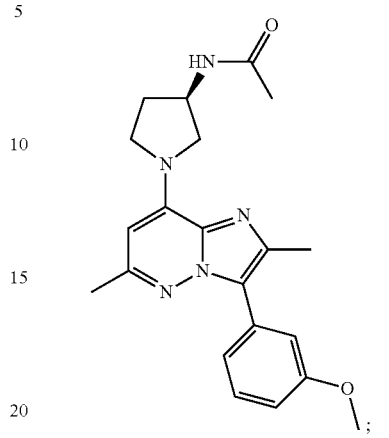
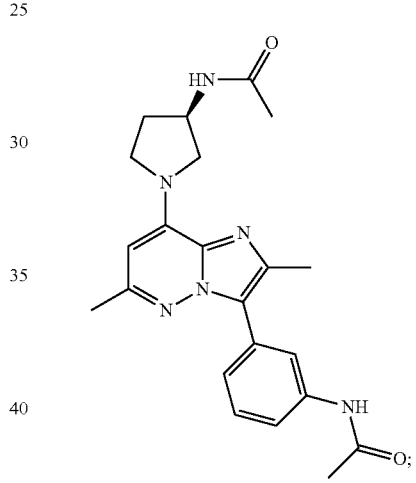
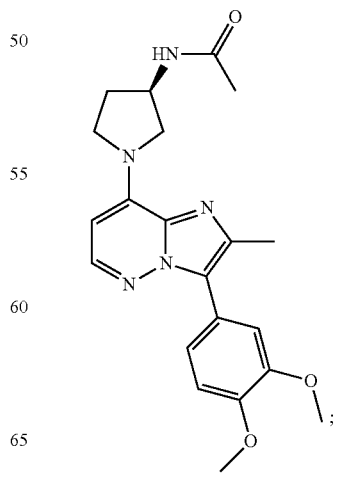

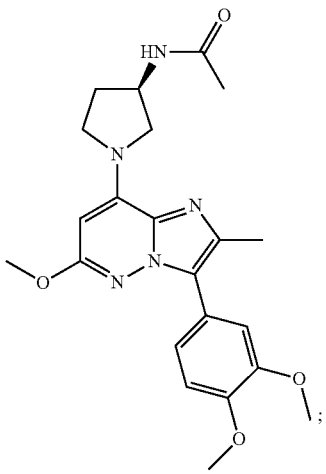

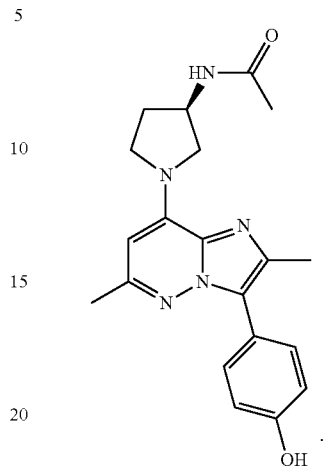

5. The compound of claim 2, wherein $R_6$ is H and $R_7$ is selected from the group consisting of —C(=O)—$(CR_yR_z)_m$—$R_8$, —C(=O)—$(CR_yR_z)_m$—O—$R_8$, —C(=O)—O—$(CR_yR_z)_m$—$R_8$, wherein each m is an integer selected from the group consisting of 0, 1, 2, 3, 4, 5, and 6, $R_y$ and $R_z$ are each independently H, alkoxyl, or halogen, $R_8$ is selected from the group consisting of substituted or unsubstituted alkyl, —$CF_3$, substituted or unsubstituted cycloalkyl, substituted or unsubstituted aryl, substituted or unsubstituted cycloheteroaryl, substituted or unsubstituted multicyclic aryl or heteroaryl ring, and $NR_{10}R_{11}$, wherein $R_{10}$ and $R_{11}$ are each independently selected from the group consisting of H, substituted or unsubstituted $C_{1-6}$ alkyl, and substituted or unsubstituted aryl.

6. The compound of claim 5, wherein the compound of formula (I) is selected from the group consisting of:

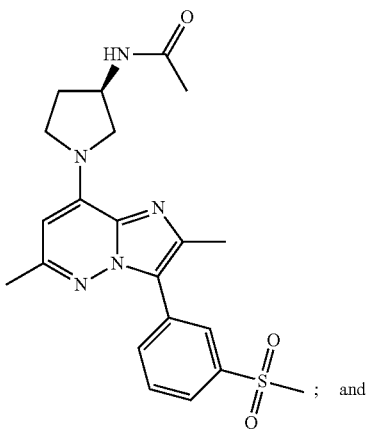 ; and

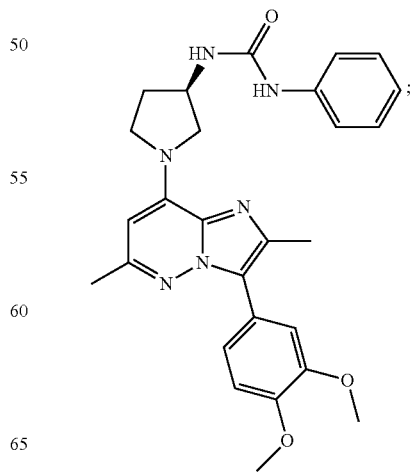

189
-continued
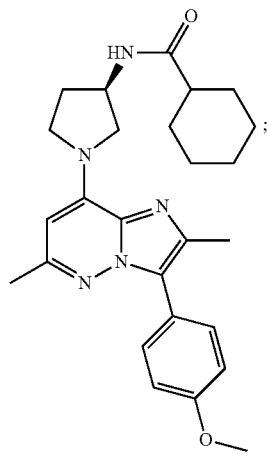
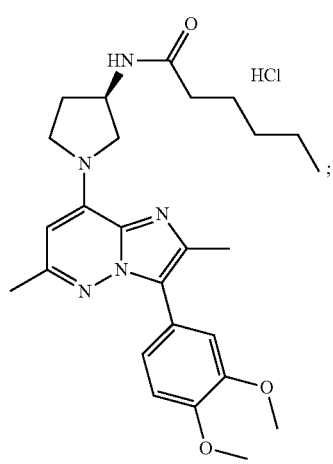
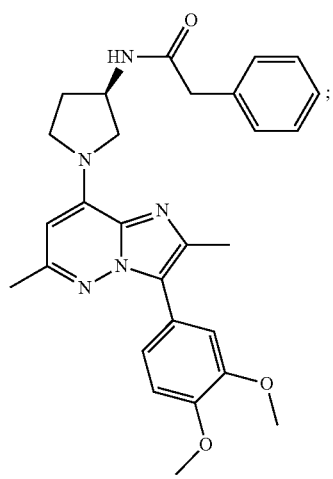
190
-continued
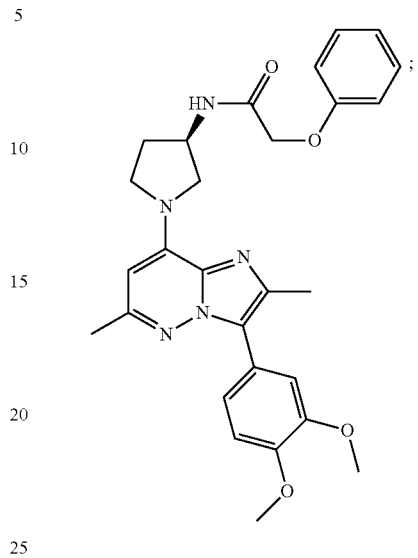
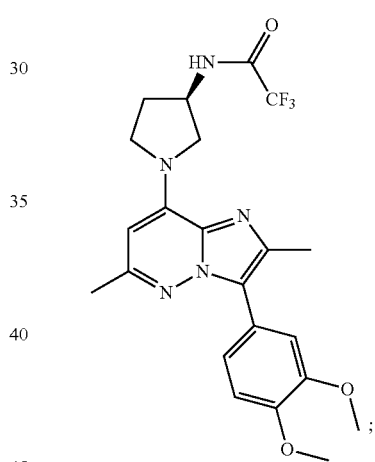
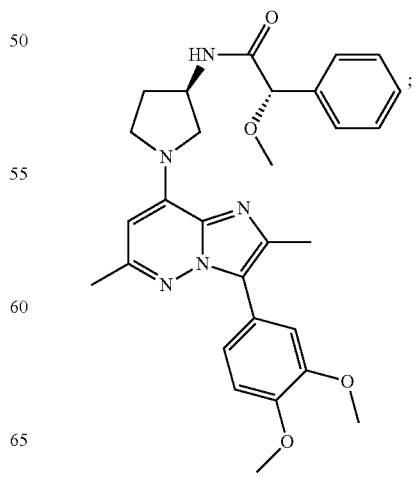

191
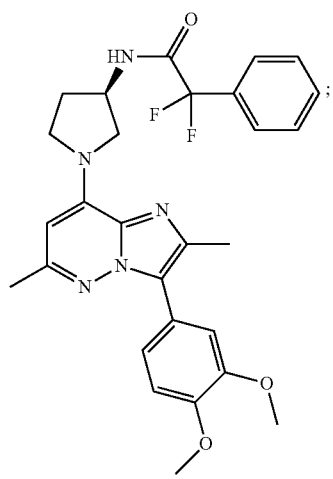
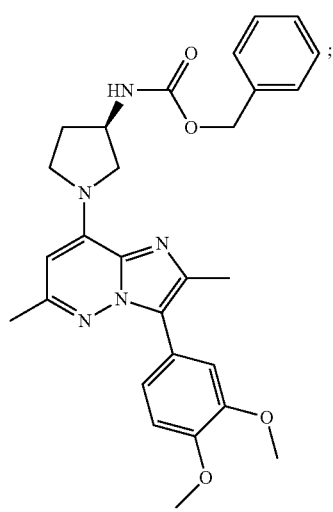
192
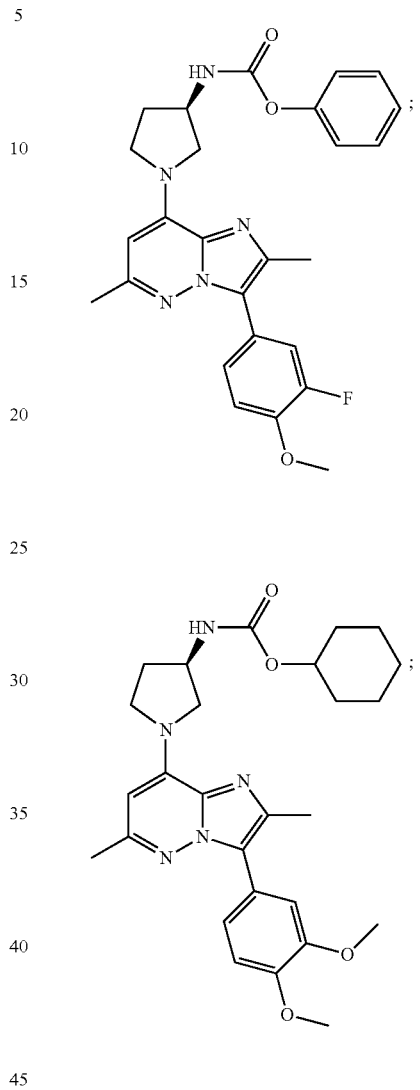

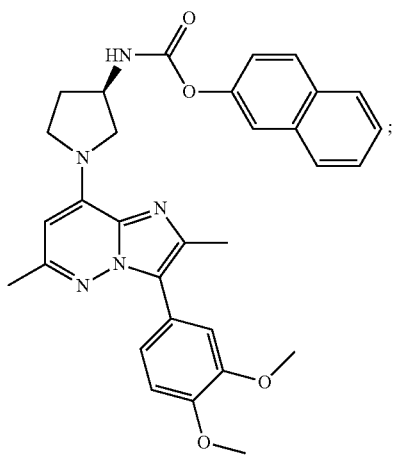
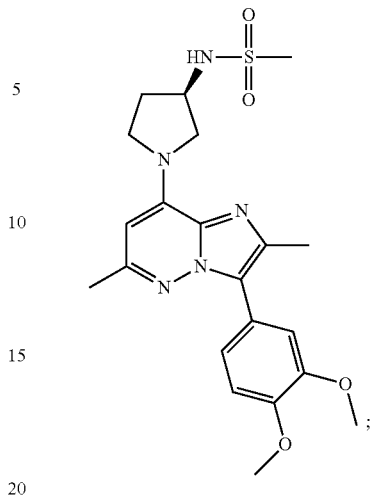
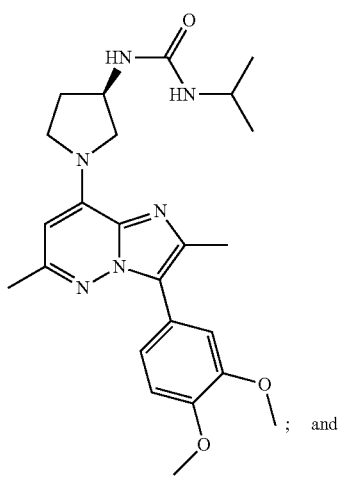
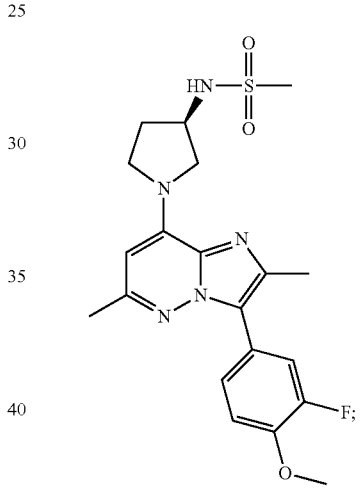
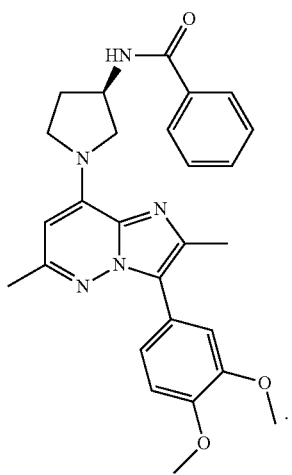
; and
.
7. The compound of claim 2, wherein $R_6$ is H and $R_7$ is —S(=O)$_2$—R$_9$.
8. The compound of claim 5, wherein the compound of formula (I) is selected from the group consisting of:
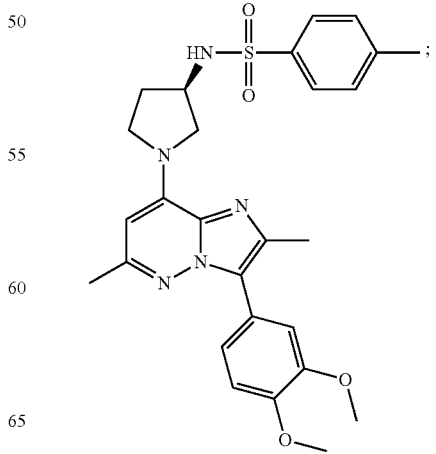

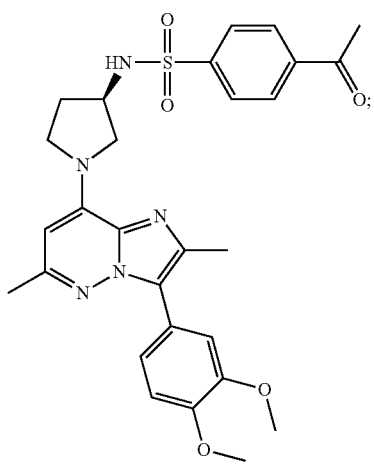
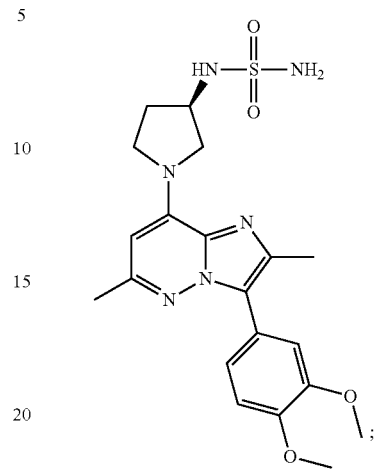
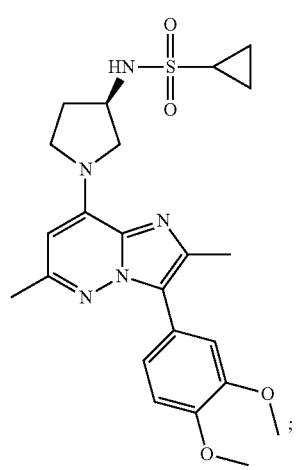
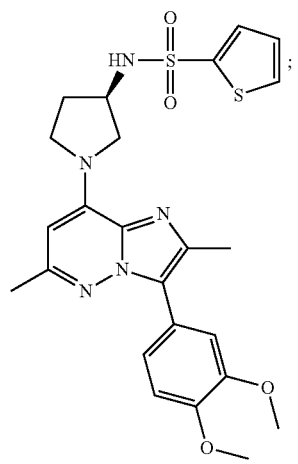

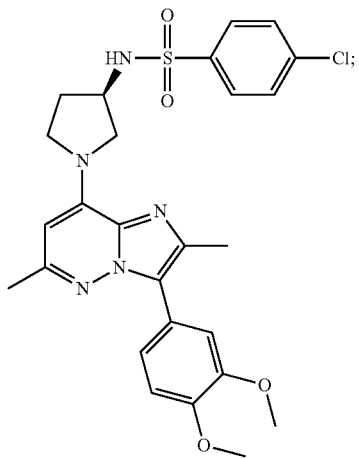

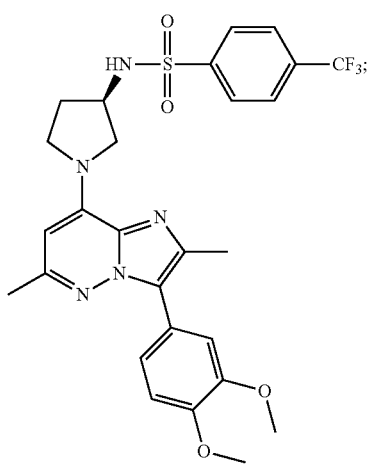

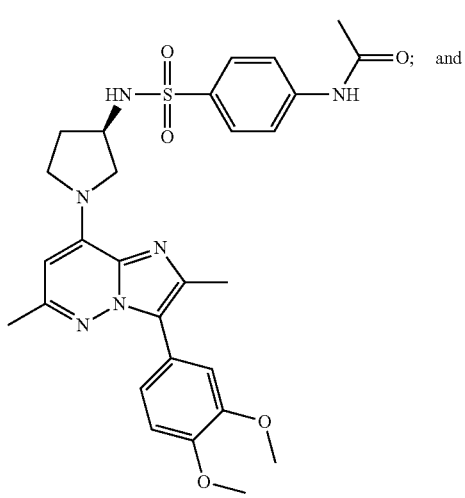

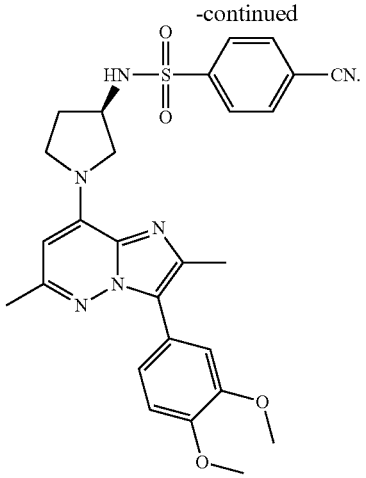

9. The compound of claim 1, wherein R$_5$ is selected from the group consisting of H, halogen, and substituted or unsubstituted alkyl.

10. The compound of claim 9, wherein the compound of formula (I) is selected from the group consisting of:

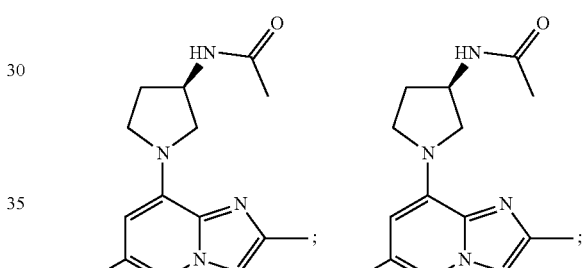

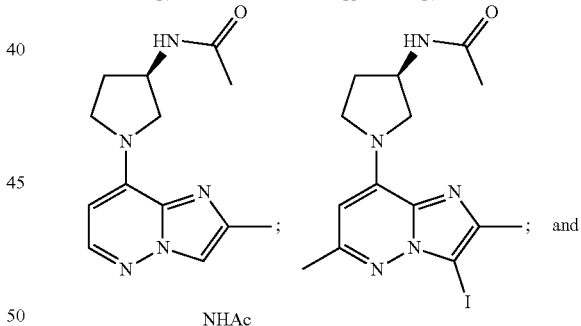

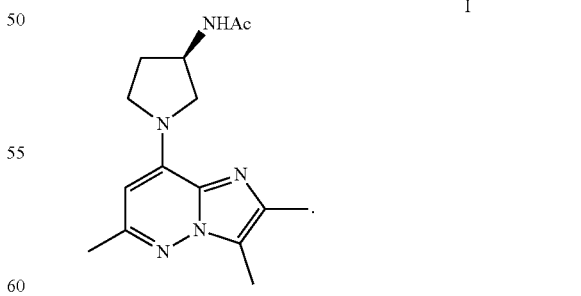

11. The compound of claim 1, wherein R$_5$ is a substituted or unsubstituted multicyclic aryl or multicyclic heteroaryl ring.

12. The compound of claim 11, wherein the compound of formula (I) is selected from the group consisting of:

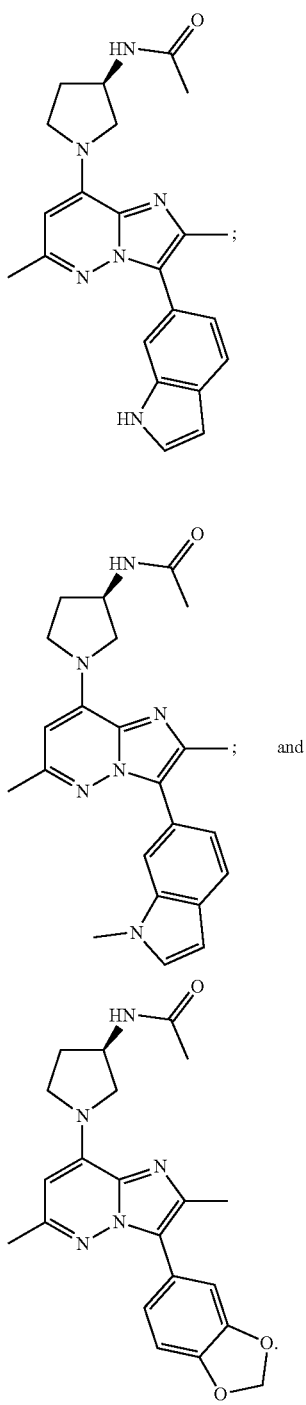

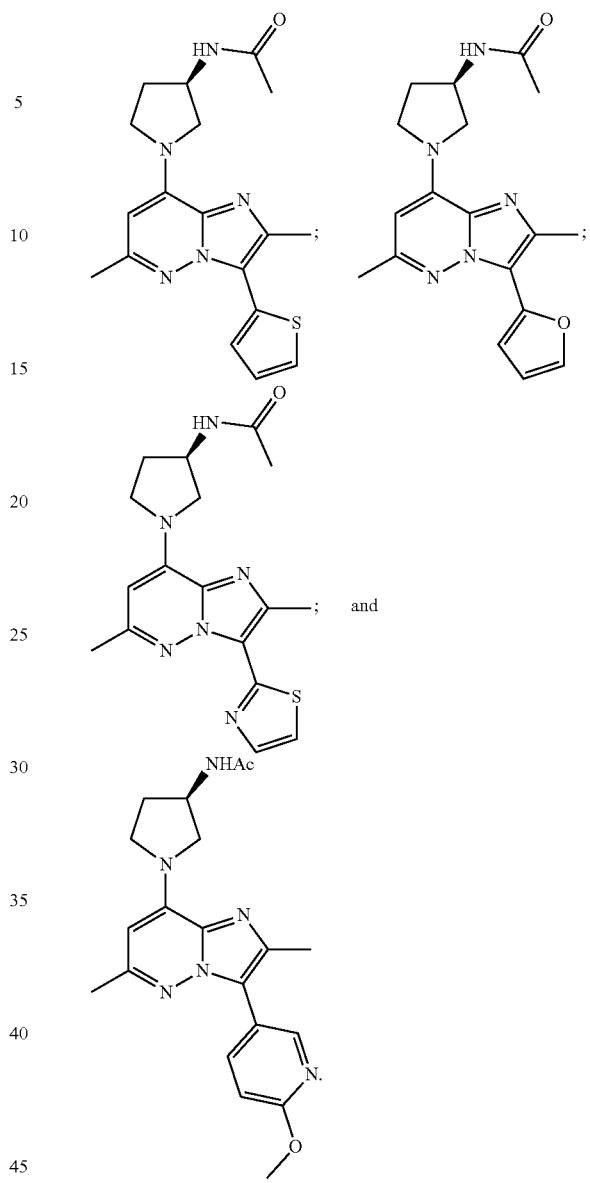

13. The compound of claim 1, wherein $R_5$ is a substituted or unsubstituted heteroaryl.

14. The compound of claim 13, wherein the compound of formula (I) is selected from the group consisting of:

15. A method for treating a subject afflicted with Alzheimer's disease, the method comprising administering to a subject in need of treatment thereof an effective amount of compound of claim 1.

16. The method of claim 15, wherein the administration of an effective amount of a compound of formula (I) to the subject decreases a neutral sphingomyelinase 2 (nSMase2) activity or expression or decreases a level of ceramide in the subject.

17. A method for inhibiting neutral sphingomyelinase 2 (nSMase2), the method comprising administering to a subject, cell, or tissue an amount of a compound of claim 1.

* * * * *